(12) United States Patent
Kaizawa et al.

(10) Patent No.: US 8,822,448 B2
(45) Date of Patent: Sep. 2, 2014

(54) PYRAZOLOQUINOLINE COMPOUND

(71) Applicant: Astellas Pharma Inc., Chuo-ku (JP)

(72) Inventors: Hiroyuki Kaizawa, Tokyo (JP);
Hirofumi Yamamoto, Tokyo (JP);
Kazunori Kamijo, Tokyo (JP); Mari Sugita, Tokyo (JP); Ryushi Seo, Tokyo (JP); Satoshi Yamamoto, Tokyo (JP);
Atsushi Ukai, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/788,907

(22) Filed: Mar. 7, 2013

(65) Prior Publication Data

US 2013/0225553 A1 Aug. 29, 2013

Related U.S. Application Data

(63) Continuation-in-part of application No. PCT/JP2011/070410, filed on Sep. 7, 2011.

(30) Foreign Application Priority Data

Sep. 7, 2010 (JP) ................................ 2010-200403

(51) Int. Cl.
C07D 471/04 (2006.01)
C07D 471/10 (2006.01)
C07D 487/04 (2006.01)
C07D 487/08 (2006.01)
C07D 491/107 (2006.01)

(52) U.S. Cl.
USPC ............ 514/210.18; 514/210.21; 514/217.07; 514/232.8; 514/245; 514/249; 514/252.02; 514/252.11; 514/252.18; 514/253.03; 514/274; 514/278; 514/293; 540/597; 544/121; 544/126; 544/212; 544/238; 544/295; 544/316; 544/349; 544/357; 544/361; 546/16; 546/17; 546/82

(58) Field of Classification Search
None
See application file for complete search history.

(56) References Cited

U.S. PATENT DOCUMENTS

| 2009/0203703 A1 | 8/2009 | Gotanda et al. |
| 2009/0318478 A1 | 12/2009 | Asagarasu et al. |
| 2010/0048556 A1 | 2/2010 | Okada et al. |
| 2010/0113484 A1 | 5/2010 | Gotanda et al. |

FOREIGN PATENT DOCUMENTS

| EP | 0 476 544 A1 | 3/1992 |
| EP | 2 103 613 A1 | 9/2009 |
| JP | 5-132484 A | 5/1993 |
| JP | 2006-45118 A | 2/2006 |
| WO | WO 03/037432 A1 | 5/2003 |
| WO | WO 03/037899 A1 | 5/2003 |
| WO | WO 2004/018474 A1 | 3/2004 |
| WO | 2005/028474 | 3/2005 |
| WO | WO 2005/028474 A2 | 3/2005 |
| WO | WO 2006/135080 A1 | 12/2006 |
| WO | WO 2007/115232 A2 | 10/2007 |
| WO | WO 2008/018306 A1 | 2/2008 |
| WO | WO 2008/072778 A1 | 6/2008 |
| WO | WO 2008/072779 A1 | 6/2008 |
| WO | WO 2008/139293 A1 | 11/2008 |
| WO | WO 2009/068617 A1 | 6/2009 |
| WO | WO 2009/121919 A1 | 10/2009 |
| WO | WO 2010/026214 A1 | 3/2010 |
| WO | WO 2010/084434 A1 | 7/2010 |

OTHER PUBLICATIONS

Extended European Search Report issued Dec. 4, 2013 in European Patent Application No. 11823618.1.
International Search Report and Written Opinion of the International Searching Authority Issued Nov. 15, 2011 in PCT/JP2011/070410 (with English translations).
International Preliminary Report on Patentability Issued Apr. 9, 2013 in PCT/JP2011/070410.
M. Thiyagarajan, "α-Adrenoceptor Antagonists in the Treatment of Benign Prostate Hyperplasia", Pharmacology, vol. 65, 2002, pp. 119-128.
P.J.R. Shah et al., "Distigmine Bromide and Pots-Prostatectomy Voiding", British Journal of Urology, vol. 55, 1983, pp. 229-232.
Alex E. Finkbeiner, "Is bethanechol chloride clinically effective in promoting bladder emptying? A literature review", The Journal of Urology, vol. 134, 1985, pp. 443-449.
Wilhelm Bloch et al., "Distribution of Nitric Oxide Synthase Implies a Regulation of Circulation, Smooth Muscle Tone, and Secretory Function in the Human Prostate by Nitric Oxide", The Prostate, vol. 33, 1997, pp. 1-8.
M. Toprakçi et al., "Age-associated changes in nitric oxide metabolites nitrite and nitrate", Int J Clin Lab Res, vol. 30, 2000, pp. 83-82.
Douglas A. Fisher et al., "Isolation and Characterization of PDE9A, a Novel Human cGMP-specific Phosphodiesterase", The Journal of Biological Chemistry, vol. 273, No. 25, Jun. 19, 1998, pp. 15559-15564.
Carles Rentero et al., "Identification and distribution of different mRNA variants produced by differential splicing in the human phosphodiesterase 9A gene", Biochemical and Biophysical Research Communications, vol. 301, 2003, pp. 686-692.
Hourani et al, "Characterization and ontogeny of $P_1$-purinoceptors on rat vas deferens", Br. J. Pharmacol. (1993), vol. 108, pp. 754-758.
Nicholls et al, "Characterization of $P_1$-purinoceptors on rat isolated duodenum longitudinal muscle and muscularis mucosae", Br. J. Pharmacol.(1996), vol. 117, pp. 170-174.
Office Action issued Apr. 29, 2014, in Eurasian Patent Application No. 201390353 (w/English translation).

Primary Examiner — Janet L Andres
Assistant Examiner — Timothy R Rozof
(74) Attorney, Agent, or Firm — Oblon, Spivak, McClelland, Maier & Neustadt, L.L.P.

(57) ABSTRACT

The present inventors have investigated a compound which has a PDE9-inhibiting action and is useful as an active ingredient for an agent for treating and/or preventing storage dysfunction, voiding dysfunction, bladder/urethral diseases, and the like, and thus, have found that a pyrazoloquinoline compound has a PDE9-inhibiting action, thereby completing the present invention.

19 Claims, No Drawings

PYRAZOLOQUINOLINE COMPOUND

CROSS REFERENCES TO RELATED APPLICATIONS

This application is a Continuation-in-Part of International Patent Application No. PCT/JP2011/070410, filed on Sep. 7, 2011, and claims priority to Japanese Patent Application No. 2010-200403, filed on Sep. 7, 2010.

TECHNICAL FIELD

The present invention relates to a pyrazoloquinoline compound which is useful as an active ingredient for a pharmaceutical composition, in particular, a pharmaceutical composition for treating storage dysfunction, voiding dysfunction, bladder/urethral diseases, and the like.

BACKGROUND ART

The important roles of voiding function are urine storage and voiding, which are regulated by a coordinated action of the bladder and the urethra. That is, during the urine storage, the bladder smooth muscle is relaxed and the urethra sphincter is contracted, whereby a state in which urethral resistance is high is maintained, and urinary continence is also maintained. On the other hand, during the voiding, the bladder smooth muscle is contracted while the urethra smooth muscle is relaxed, and the contraction of the external urethral sphincter is also inhibited. Examples of voiding dysfunction include a storage dysfunction such as overactive bladder and the like in which urine cannot be retained during urine storage and a voiding dysfunction in which urine cannot be drained sufficiently due to increase in the urethral resistance and decrease in the bladder contractile force. These two dysfunctions may be expressed simultaneously.

In treatment of a storage dysfunction such as overactive bladder and the like, anticholinergic agents have been used frequently. However, these agents cannot provide a sufficient therapeutic effect, and further, side effects based on the anticholinergic action (dry mouth, gastrointestinal symptoms, eye symptoms, arrhythmias, or the like) appear, and accordingly, administration of the agents may be often interrupted. Further, the anticholinergic agents reduce the bladder contractile force, and are therefore contraindicated for urinary frequency/incontinence accompanying urethral obstruction such as benign prostatic hyperplasia and the like.

Voiding dysfunction is caused by an increase in urethral resistance during the voiding or a decrease in the bladder contractile force. As a disease causing an increase in urethral resistance, voiding dysfunction accompanying benign prostatic hyperplasia is well known, which is characterized by urethral obstruction due to nodular hypertrophy of the prostate tissues. An $\alpha_1$ receptor antagonist has now been used for the purpose of treating voiding dysfunction accompanying benign prostatic hyperplasia (see, for example, Non-Patent Document 1). Other causes of the increase in urethral resistance include functional obstructions such as urethra relaxation failure during voiding or detrusor-external urethral sphincter dyssynergia and the like due to neurological disorders such as diabetes, aging, bone marrow damage, pelvic surgery, and the like,. With patients with these diseases, there exists many cases in which the $\alpha_1$ receptor antagonist is ineffective. On the other hand, a decrease in the bladder contractile force during the voiding, referred to as underactive bladder, acontractile bladder, neurogenic bladder, or the like, also causes voiding dysfunction. Known factors for decreasing the bladder contractile force include aging, neurological diseases such as diabetes, Parkinson's disease, multiple sclerosis and the like, bone marrow damage, and neurological disorders due to pelvic surgery. Examples of an agent for treating a decrease in the bladder contractile force during voiding include bethanechol chloride which is a muscarinic receptor agonist and distigmine bromide which is a cholinesterase inhibitor. Both of these drugs have side effects, and thus, their satisfactoriness is low (see, for example, Non-Patent Documents 2 and 3). In voiding dysfunction caused by an increase in the urethral resistance or a decrease in the bladder contractile force as described above, residual urine after voiding is observed. Increased residual urine may cause a decrease in effective bladder capacity, and thus, cause overactive bladder symptoms such as urinary frequency and the like, or severe symptoms, such as hydronephrosis in some cases, and in this regard, there is a demand for a therapeutic agent which is more effective than a current therapeutic agent.

It is known that a relaxation system due to nitric oxide (NO) is present in the smooth muscle, and NO produced in the nerve terminals or locally activates soluble guanylate cyclase present in the smooth muscle cells. The activated guanylate cyclase increases cyclic guanosine monophosphate (cGMP) in the cells. On the other hand, the cGMP is degraded into 5'-GMP by phosphodiesterase (PDE) which is an enzyme degrading the cGMP. An increase in the intracellular cGMP concentration is considered to contribute significantly to the smooth muscle relaxation. Therefore, the decrease of the NO-cGMP system causes relaxation failure of the smooth muscle. For example, in patients showing urethral obstruction in benign prostatic hyperplasia or in the elderly as described above, it is reported that NO production is significantly decreased (Non-Patent Documents 4 and 5).

As a subtype of PDE which specifically degrades cGMP, PDE5, PDE6 and PDE9 are known, and among these, PDE9 has a higher substrate affinity than PDE5 and PDE6 (Non-Patent Document 6). Further, from the viewpoint that in the distribution of expression in various tissues, PDE9 is observed at its highest expression in the human prostate (Non-Patent Document 7), it plays an important role in smooth muscle relaxation in lower urethra smooth muscle and a PDE9 inhibitor enhances the relaxation of the urethra via the elevation of cGMP in the tissue. Therefore, it is considered that the PDE9 inhibitor exhibits an effect against voiding dysfunction due to an increase in the urethral resistance. Since the PDE9 inhibitor decreases the urethral resistance, an effect against voiding dysfunction in which the bladder contractile forces are decreased can be expected. In addition, the decrease in residual urine due to an improvement of the voiding dysfunction will lead to the improvement of overactive bladder symptoms such as urinary frequency and the like or avoidance of renal disorders. Therefore, it is considered that the PDE9 inhibitor is useful as an agent for preventing and/or treating storage dysfunction, voiding dysfunction, and bladder/urethral diseases.

For example, as a compound having a PDE5- and/or PDE9-inhibitory action(s), in Patent Documents 1 and 2, there are disclosed quinoxaline derivatives represented by the following formulae (A) and (B), respectively. Further, in Patent Documents 3 and 4, there are disclosed a thienopyrimidine derivative and a quinazoline derivative as compounds having a PDE5- and/or PDE9-inhibitory action(s), respectively. In addition, in Patent Documents 5 to 12, there is disclosed a pyrazolopyridine derivative which has a PDE9-inhibitory action.

Furthermore, in Patent Documents 13 to 17, there are disclosed compounds represented by the following formulae (C)

to (G), but there is no specific disclosure of the compounds of the present invention. In addition, there is no description that the compound has a PDE9-inhibitory action and can be used for treating disorders in voiding function.

[Chem. 1]

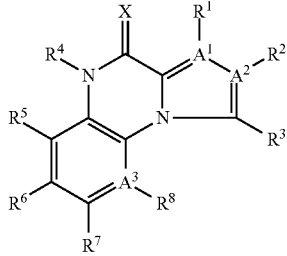

[Chem. 2]

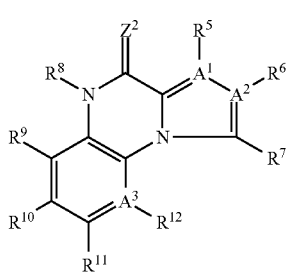

[Chem. 3]

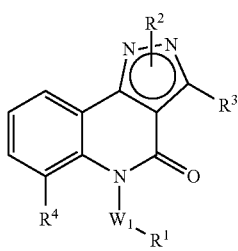

[Chem. 4]

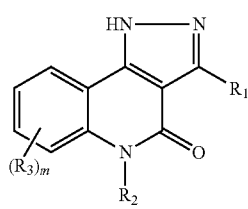

[Chem. 5]

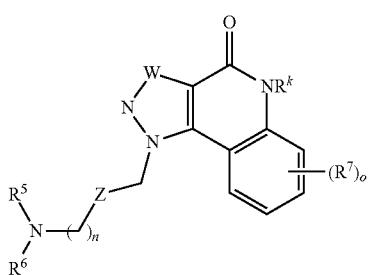

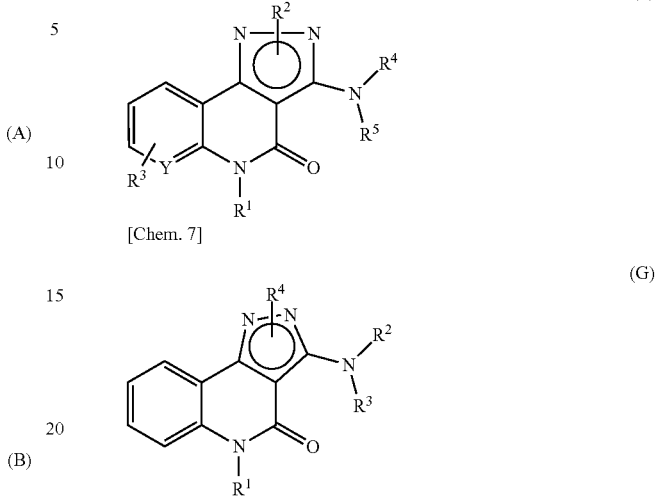

(For the symbols in the formulae, refer to each of the corresponding patent publications.)

RELATED ART

Patent Document

[Patent Document 1] Pamphlet of International Publication WO 2008/072779
[Patent Document 2] Pamphlet of International Publication WO 2008/072778
[Patent Document 3] Pamphlet of International Publication WO 2006/135080
[Patent Document 4] Pamphlet of International Publication WO 2008/018306
[Patent Document 5] Pamphlet of International Publication WO 2010/026214
[Patent Document 6] Pamphlet of International Publication WO 2010/084438
[Patent Document 7] Pamphlet of International Publication WO 2009/068617
[Patent Document 8] Pamphlet of International Publication WO 2009/121919
[Patent Document 9] Pamphlet of International Publication WO 2008/139293
[Patent Document 10] Pamphlet of International Publication WO 2004/018474
[Patent Document 11] Pamphlet of International Publication WO 2003/037432
[Patent Document 12] Pamphlet of International Publication WO 2003/037899
[Patent Document 13] Pamphlet of International Publication WO 2005/028474
[Patent Document 14] JP-A-2006-45118
[Patent Document 15] Pamphlet of International Publication WO 2007/115232
[Patent Document 16] JP-A-5-132484
[Patent Document 17] European Patent Publication No. 476544

Non-Patent Document

[Non-Patent Document 1] Thiyagarajan, M., Pharmacology, 65:pp. 119-128 (2002)

[Non-Patent Document 2] Shah, P. J. R., et al., Br. J. Urol., 55:pp. 229-232 (1983)

[Non-Patent Document 3] Finkbeiner, A. E., J. Urol., 134: pp. 443-449 (1985)

[Non-Patent Document 4] Bloch, W., et al., Prostate, 33:pp. 1-8 (1997)

[Non-Patent Document 5] Toprakqi, M., et al., Int. J. Clin. Lab. Res., 30:pp. 83-85 (2000)

[Non-Patent Document 6] Fisher, D.A., et al., J. Biol. Chem., 273:pp. 15559-15564 (1998)

[Non-Patent Document 7] Rentero, C., et al., Biochem. Biophys. Res. Commun., 301:pp. 686-692 (2003)

SUMMARY OF INVENTION

Problems to Be Solved by the Invention

The present inventors aim to provide a compound which has a PDE9-inhibitory action and is useful as an active ingredient for a pharmaceutical composition for preventing and treating storage dysfunction, voiding dysfunction, bladder/urethral diseases, and the like.

Means for Solving the Problems

The present inventors have extensively investigated a compound which has a PDE9-inhibitory action, and as a result, they have found that a compound of the formula (I) is useful as a compound having a PDE9-inhibitory action, thereby completing the present invention.

That is, the present invention relates to a compound of the formula (I) or a salt thereof, and a pharmaceutical composition including the compound of the formula (I) or a salt thereof, and an excipient.

[Chem. 8]

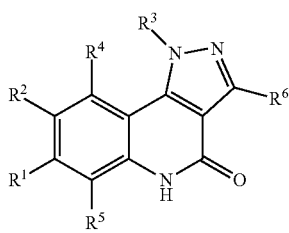

(I)

(wherein
one of $R^1$ and $R^2$ is hydrogen, halogen, halogeno-lower alkyl, or lower alkyl, —O-lower alkyl or cycloalkyl, each of which may be substituted, and the other is a group of the formula (II):

[Chem. 9]

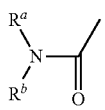

(II)

$R^3$ is lower alkyl, cycloalkyl or a saturated hetero ring, each of which may be substituted, $R^4$, $R^5$ and $R^6$ are the same as or different from each other, and each is hydrogen or lower alkyl, and $R^a$ and $R^b$ are the same as or different from each other, and each is hydrogen, or lower alkyl, cycloalkyl, aryl or a hetero ring, each of which may be substituted, or $R^a$ and $R^b$ are combined with the adjacent nitrogen atom to form a monocyclic nitrogen-containing hetero ring or a polycyclic nitrogen-containing hetero ring, each of which may be substituted).

Furthermore, the present invention relates to a compound of the formula (I-1) or a salt thereof, and a pharmaceutical composition including the compound of the formula (I-1) or a salt thereof, and an excipient.

A compound of the formula (I-1) or a salt thereof:

[Chem. 10]

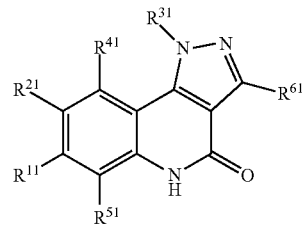

(I-1)

(wherein
one of $R^{11}$ and $R^{21}$ is hydrogen, halogen, or lower alkyl, —O-lower alkyl or cycloalkyl, each of which may be substituted, and the other is a group of the formula (II-1):

[Chem. 11]

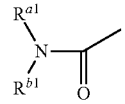

(II-1)

$R^{31}$ is lower alkyl, cycloalkyl or saturated hetero ring, each of which may be substituted, $R^{41}$, $R^{51}$ and $R^{61}$ are the same as or different from each other, and each is hydrogen or lower alkyl, and $R^{a1}$ and $R^{b1}$ are the same as or different from each other, and each is hydrogen, or lower alkyl, cycloalkyl, aryl or a hetero ring, each of which may be substituted, or $R^{a1}$ and $R^{b1}$ are combined with the adjacent nitrogen atom to form a monocyclic nitrogen-containing hetero ring or a polycyclic nitrogen-containing hetero ring, each of which may be substituted).

Furthermore, unless specifically described otherwise, in the case where the symbols in any of the formulae in the present specification are also used in other formulae, the same symbols denote the same meanings.

Furthermore, the present invention relates to a pharmaceutical composition for preventing or treating storage dysfunction, voiding dysfunction, and bladder/urethral diseases, and the like, which includes a compound of the formula (I) or a salt thereof, or a compound of the formula (I-1) or a salt thereof. Further, the pharmaceutical composition includes an agent for preventing or treating storage dysfunction, voiding dysfunction, and bladder/urethral diseases, and the like, which includes a compound of the formula (I) or a salt thereof, or a compound of the formula (I-1) or a salt thereof.

The present invention further relates to use of the compound of the formula (I) or a salt thereof, or the compound of the formula (I-1) or a salt thereof for the manufacture of a pharmaceutical composition for preventing or treating storage dysfunction, voiding dysfunction, bladder/urethral diseases, and the like; use of the compound of the formula (I) or a salt thereof, or the compound of the formula (I-1) or a salt thereof for preventing or treating storage dysfunction, voiding dysfunction, bladder/urethral diseases, and the like; the compound of the formula (I) or a salt thereof, or the compound of the formula (I-1) or a salt thereof for treating storage dysfunction, voiding dysfunction, bladder/urethral diseases, and the like; and a method for preventing or treating storage dysfunction, voiding dysfunction, bladder/urethral diseases, and the like, which includes administering to a subject an effective amount of the compound of the formula (I) or a salt thereof, or the compound of the formula (I-1) or a salt thereof. Further, the "subject" is a human or another animal in need of such prevention or treatment, and in a certain embodiment, a human in need of such prevention or treatment.

Moreover, the compound of the formula (I-1) or a salt thereof is included in the compound of the formula (I) or a salt thereof. Accordingly, in the present specification, the description of the compound of the formula (I) also includes the description of the compound of the formula (I-1).

In the present specification, the "storage dysfunction" refers to "storage function disorder (storage dysfunction)" with which urine cannot be held during storage, and the "voiding dysfunction" refers to "voiding function disorder (voiding dysfunction)" with which urine cannot be discharged sufficiently during voiding due to increased urethral resistance and decreased bladder contraction (Neurourol Urodynam, 21: pp. 167-178 (2002)).

As used in the present specification, the "bladder/urethral diseases" include "lower urinary tract dysfunction", and "lower urinary tract symptoms (LUTS)" (Neurourol Urodynam, 21: pp. 167-178 (2002)), which are symptoms derived from the lower urinary tract dysfunction. Accordingly, "bladder/urethral diseases" as used herein include "storage dysfunction" and "voiding dysfunction".

In the present invention, examples of the bladder/urethral diseases include, in a certain embodiment, underactive bladder, hypotonic bladder, acontractile bladder, detrusor underactivity, neurogenic bladder, urethra relaxation failure or detrusor-external urethral sphincter dyssynergia, overactive bladder, and lower urinary tract symptoms thereof, and benign prostatic hyperplasia, interstitial cystitis, chronic prostatitis, urethra calculus, and lower urinary tract symptoms accompanying them, and the like.

In another embodiment, examples of the bladder/urethral diseases include underactive bladder, hypotonic bladder, acontractile bladder, detrusor underactivity, neurogenic bladder, urethra relaxation failure or detrusor-external urethral sphincter dyssynergia, and lower urinary tract symptoms thereof, and benign prostatic hyperplasia, interstitial cystitis, chronic prostatitis, urethra calculus, and lower urinary tract symptoms accompanying them, and the like.

In a further embodiment, examples of the bladder/urethral diseases include underactive bladder, hypotonic bladder, acontractile bladder, detrusor underactivity, neurogenic bladder, urethra relaxation failure or detrusor-external urethral sphincter dyssynergia, and lower urinary tract symptoms thereof, benign prostatic hyperplasia and lower urinary tract symptoms accompanying them, and the like.

In a still further embodiment, examples of the bladder/urethral diseases include underactive bladder, hypotonic bladder, acontractile bladder, detrusor underactivity, urethra relaxation failure or detrusor-external urethral sphincter dyssynergia, lower urinary tract symptoms thereof, benign prostatic hyperplasia and lower urinary tract symptoms accompanying them, and the like.

In the present invention, specific examples of the storage dysfunction include overactive bladder, and overactive bladder symptoms such as urinary urgency, urinary frequency, urge incontinence, nocturia, and the like.

In the present invention, examples of the voiding dysfunction include voiding dysfunction due to an increase in urethral resistance and voiding dysfunction due to a decrease in the bladder contractile force. In a certain embodiment, specific examples thereof include voiding dysfunction in the underactive bladder, voiding dysfunction in the hypotonic bladder, voiding dysfunction in the acontractile bladder, voiding dysfunction in the neurogenic bladder, voiding dysfunction in the detrusor underactivity, voiding dysfunction in the urethra relaxation failure or detrusor-external urethral sphincter dyssynergia, voiding dysfunction accompanying benign prostatic hyperplasia, voiding dysfunction accompanying chronic prostatitis, voiding dysfunction accompanying urethra calculus, voiding dysfunction accompanying interstitial cystitis, voiding dysfunction accompanying detrusor underactivity, and the like.

In a further embodiment, examples of the voiding dysfunction include voiding dysfunction in the underactive bladder, voiding dysfunction in the hypotonic bladder, voiding dysfunction in the acontractile bladder, voiding dysfunction in the detrusor underactivity, voiding dysfunction in the urethra relaxation failure or detrusor-external urethral sphincter dyssynergia, voiding dysfunction accompanying benign prostatic hyperplasia, and the like.

Effect of the Invention

The compound of the formula (I) or a salt thereof has a PDE9-inhibitory action, and can be used as an agent for preventing and/or treating diseases related to degradation of cGMP by PDE9, for example, storage dysfunction, voiding dysfunction, and bladder/urethral diseases, in another embodiment, diseases such as underactive bladder, hypotonic bladder, acontractile bladder, detrusor underactivity, neurogenic bladder, urethra relaxation failure or detrusor-external urethral sphincter dyssynergia, overactive bladder, and lower urinary tract symptoms thereof, and benign prostatic hyperplasia, interstitial cystitis, chronic prostatitis, urethra calculus, and lower urinary tract symptoms accompanying them, and the like, and in a further embodiment, diseases such as underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis, urethra calculus, and the like.

EMBODIMENTS FOR CARRYING OUT THE INVENTION

The "lower alkyl" is straight or branched chain alkyl having 1 to 6 carbon atoms (hereinafter simply referred to as $C_{1-6}$), for example, methyl, ethyl, n-propyl, isopropyl, n-butyl, isobutyl, sec-butyl, tert-butyl, n-pentyl, sec-pentyl, n-hexyl, or the like, and in another embodiment, $C_{1-4}$ alkyl, and in a further embodiment, methyl, ethyl, n-propyl, isopropyl, n-butyl, sec-butyl or tert-butyl.

The "lower alkylene" is linear or branched chain $C_{1-6}$ alkylene, for example, methylene, ethylene, trimethylene, tetramethylene, pentamethylene, hexamethylene, propylene, methylmethylene, ethylethylene, 1,2-dimethylethylene or 1,1,2,2-tetramethylethylene.

The "halogen" means F, Cl, Br or I.

The "halogeno-lower alkyl" is $C_{1-6}$ alkyl substituted with one or more halogen atoms, in another embodiment, lower alkyl substituted with 1 to 5 halogen atoms, and in a further embodiment, trifluoromethyl.

The "cycloalkyl" is a $C_{3-10}$ saturated hydrocarbon ring group, which may have a bridge. It is, for example, cyclopropyl, cyclobutyl, cyclopentyl, cyclohexyl, cycloheptyl, cyclooctyl, adamantyl, or the like, in another embodiment, $C_{3-8}$ cycloalkyl, in a further embodiment, $C_{3-6}$ cycloalkyl, and in a still further embodiment, cyclopropyl, cyclobutyl, cyclopentyl or cyclohexyl.

The "aryl" refers to a $C_{6-14}$ monocyclic to tricyclic aromatic hydrocarbon ring group, and includes a ring group fused with $C_{5-8}$ cycloalkene at its double bond site. It is, for example, phenyl, naphthyl, 5-tetrahydronaphthyl, 1-tetrahydronaphthyl, 4-indenyl, 1-fluorenyl, or the like. In another embodiment, it is phenyl or 1-tetrahydronaphthyl.

The "hetero ring" means a ring group containing i) a monocyclic 3- to 8-membered hetero ring, and in another embodiment, 5- to 7-membered hetero ring, each containing 1 to 4 hetero atoms selected from oxygen, sulfur and nitrogen, and ii) a bi- to tricyclic hetero ring containing 1 to 5 hetero atoms selected from oxygen, sulfur and nitrogen, formed by ring fusion of monocyclic hetero ring with one or two rings selected from the group consisting of a monocyclic hetero ring, a benzene ring, $C_{5-8}$ cycloalkane, and $C_{5-8}$ cycloalkene, and it includes a Spiro ring group. The ring atom, sulfur or nitrogen, may be oxidized to form an oxide or a dioxide.

Examples of the "hetero ring" include the following embodiments:

(1) Monocyclic saturated hetero rings (a) those containing 1 to 4 nitrogen atoms, for example, azepanyl, diazepanyl, aziridinyl, azetidinyl, pyrrolidinyl, imidazolidinyl, piperidyl, pyrazolidinyl, piperazinyl, azocanyl, and the like;

(b) those containing 1 to 3 nitrogen atoms and 1 to 2 sulfur atoms and/or 1 to 2 oxygen atoms, for example, thiomorpholinyl, thiazolidinyl, isothiazolidinyl, oxazolidinyl, morpholinyl, and the like;

(c) those containing 1 to 2 sulfur atoms, for example, tetrahydrothiopyranyl, tetrahydrothiophenyl, and the like;

(d) those containing 1 to 2 sulfur atoms and 1 to 2 oxygen atoms, for example, oxathiolanyl and the like;

(e) those containing 1 to 2 oxygen atoms, for example, oxiranyl, oxetanyl, dioxiranyl, tetrahydrofuranyl, tetrahydropyranyl, 1,4-dioxanyl, and the like;

(2) Monocyclic unsaturated hetero ring groups (a) those containing 1 to 4 nitrogen atoms, for example, pyrrolyl, imidazolyl, pyrazolyl, pyridyl, dihydropyridyl, tetrahydropyridinyl, pyrimidinyl, pyrazinyl, pyridazinyl, triazolyl, tetrazolyl, triazinyl, dihydrotriazinyl, azepinyl, and the like;

(b) those containing 1 to 3 nitrogen atoms and 1 to 2 sulfur atoms and/or 1 to 2 oxygen atoms, for example, thiazolyl, isothiazolyl, thiadiazolyl, dihydrothiazinyl, oxazolyl, isoxazolyl, oxadiazolyl, oxazinyl, and the like;

(c) those containing 1 to 2 sulfur atoms, for example, thienyl, thiepinyl, dihydrodithiopyranyl, dihydrodithionyl, and the like;

(d) those containing 1 to 2 sulfur atoms and 1 to 2 oxygen atoms, for example, dihydroxathiopyranyl and the like;

(e) those containing 1 to 2 oxygen atoms, for example, furyl, pyranyl, oxepinyl, dioxolyl, and the like;

(3) Fused polycyclic saturated hetero ring groups (a) those containing 1 to 5 nitrogen atoms, for example, quinuclidinyl, azabicyclo [2.2.1 ]heptyl, diazabicyclo [2.2.1 ]heptyl, azabicyclo[3.2.1]octyl, diazabicyclo[3.2.1]octyl, diazabicyclo[3.3.1]nonyl, octahydropyrrolopyrazinyl, octahydropyrrolopyrrolyl, and the like;

(b) those containing 1 to 4 nitrogen atoms and 1 to 3 sulfur atoms and/or 1 to 3 oxygen atoms, for example, trithiadiazaindenyl, dioxoloimidazolidinyl, 2-oxa-5-azabicyclo[2.2.1] heptyl, and the like;

(c) those containing 1 to 3 sulfur atoms and/or 1 to 3 oxygen atoms, for example, 2,6-dioxabicyclo[3.2.2]oct-7-yl and the like;

(4) Fused polycyclic unsaturated hetero ring groups (a) those containing 1 to 5 nitrogen atoms, for example, indolyl, isoindolyl, indolinyl(2,3-dihydroindolyl), isoindolinyl(1,3-dihydroisoindolyl), indolidinyl, benzoimidazolyl, dihydrobenzoimidazolyl, tetrahydrobenzoimidazolyl, dihydropyrrolopyridyl, dihydropyrrolopyrimidinyl, quinolyl, dihydroquinolyl, tetrahydroquinolyl, isoquinolyl, tetrahydroisoquinolyl, indazolyl, imidazopyridyl, benzotriazolyl, tetrazolopyridazinyl, carbazolyl, acridinyl, quinoxalinyl, dihydroquinoxalinyl, tetrahydroquinoxalinyl, phthalazinyl, dihydroindazolyl, benzopyrimidinyl, naphthyridinyl, quinazolinyl, cinnolinyl, tetrahydronaphthyridinyl, tetrahydropyridopyrimidinyl, tetrahydropyrazolopyridyl, tetrahydropyrrolopyrazinyl, hexahydropyrrolopyrazinyl, tetrahydroimidazopyrazinyl, tetrahydrobenzoazepinyl, tetrahydropyridonaphthyridinyl, tetrahydropyridoindolyl, hexahydropyridoindolyl, tetrahydropyrrolopyridyl, tetrahydroimidazopyridyl, tetrahydrocarbolinyl, tetrahydrotriazolopyrazinyl, and the like;

(b) those containing 1 to 4 nitrogen atoms and 1 to 3 sulfur atoms and/or 1 to 3 oxygen atoms, for example, benzothiazolyl, dihydrobenzothiazolyl, benzothiadiazolyl, imidazothiazolyl, imidazothiadiazolyl, benzoxazolyl, dihydrobenzoxazolyl, dihydrobenzoxazinyl, dihydropyridoxazinyl, benzoxadiazolyl, benzoisothiazolyl, benzoisoxazolyl, tetrahydrothienopyridyl, tetrahydroxazolopyridyl, tetrahydrothiazolopyridyl, tetrahydroisoquixazolopyridyl, and the like;

(c) those containing 1 to 3 sulfur atoms, for example, benzothienyl, benzodithiopyranyl, dibenzothienyl, and the like;

(d) those containing 1 to 3 sulfur atoms and 1 to 3 oxygen atoms, for example, benzoxathiopyranyl, phenoxazinyl, and the like;

(e) those containing 1 to 3 oxygen atoms, for example, benzodioxolyl, benzofuranyl, dihydrobenzofuranyl, isobenzofuranyl, chromanyl, chromenyl, dibenzofuranyl, methylenedioxyphenyl, ethylenedioxyphenyl, and the like; and (5) Spiro ring groups (a) those containing only a saturated bond, for example, azaspiro[4,4]nonyl, azaspiro[4,5]decyl, diazaspiro[4,5]decyl, triazaspiro[4,5]decyl, azaspiro[5,5]undecyl, diazaspiro[5,5]undecyl, oxazaspiro[4,5]decyl, and the like; and (b) those containing an unsaturated bond, for example, 3H-spiro[2-benzofuran-1,4'-piperidyl], spiro[1-benzofuran-3,4'-piperidyl], 2,3-dihydrospiro[indene-1,4'-piperidyl], 3,4-dihydro-2H-spiro[naphthalene-1,3'-piperidyl], 1,2-dihydrospiro[indole-3,4'-piperidyl], and the like.

Specific examples of the "hetero ring" in the substituent for the polycyclic nitrogen-containing hetero ring formed by $R^a$ and $R^b$ which are combined with the adjacent nitrogen atom, or the "hetero ring" in the "hetero ring which may be substituted" in $R^a$ and $R^b$ include pyridyl, azethidinyl, pyrrolidinyl, piperidyl, piperazinyl, morpholinyl, and the like.

Specific examples of the "hetero ring" in the substituent for the monocyclic nitrogen-containing hetero ring formed by $R^a$ and $R^b$ which are combined with the adjacent nitrogen atom include azethidinyl, pyrrolidinyl, piperidyl, piperazinyl, azepanyl, morpholinyl, pyrrolyl, imidazolyl, pyrazolyl, pyridyl, pyrimidinyl, pyridazinyl, pyrazinyl, triazinyl, thiazolyl, thiadiazolyl, oxazolyl, isooxazolyl, furanyl, thienyl, tetrahydrofuranyl, tetrahydropyranyl, tetrahydrothiopyranyl, tetrahydrothiophenyl, indolinyl(2,3-dihydroindolyl), dihydroquinolyl, and the like, and in another embodiment, pyridyl.

The "saturated hetero ring" in $R^3$ means a group described in (1) Monocyclic saturated hetero rings and (3) Fused polycyclic saturated hetero rings of the "hetero ring" above. The ring atom, sulfur or nitrogen, may be oxidized to form an oxide or a dioxide. In another embodiment, the saturated hetero ring is a monocyclic saturated hetero ring, and in another embodiment, oxetanyl, tetrahydrofuranyl, tetrahydropyranyl, tetrahydrothiopyranyl, pyrrolidinyl or piperidyl.

Specific examples of the "saturated hetero ring" in $R^3$ include "oxygen-containing saturated hetero rings", and "monocyclic nitrogen-containing saturated hetero rings".

The "oxygen-containing saturated hetero ring" as an example of the "saturated hetero ring" in $R^3$ means a saturated hetero ring which contains at least one oxygen atom, among (1)(b), (1)(d), (1)(e), (3)(b), (3)(c), and the like of the "hetero ring" above, and in another embodiment, the oxygen-containing saturated hetero ring is a monocyclic saturated hetero ring containing 1 to 2 oxygen atoms, for example, oxiranyl, oxetanyl, dioxolanyl, tetrahydrofuranyl, tetrahydropyranyl, 1,4-dioxanyl, and the like.

Specific examples of the "oxygen-containing saturated hetero ring" as an example of the "saturated hetero ring" in $R^3$ include tetrahydropyranyl and tetrahydrofuranyl, in another embodiment, tetrahydropyranyl, and in a further embodiment, tetrahydrofuranyl.

The "monocyclic nitrogen-containing saturated hetero ring" as an example of the "saturated hetero ring" in $R^3$ means a monocyclic saturated hetero ring which contains at least one nitrogen atom and may further contain a heteroatom selected from oxygen and sulfur, as the group described in (1)(a), (1)(b), and the like of the "hetero ring" above. The ring atom, sulfur or nitrogen, may be oxidized to form an oxide or a dioxide. In another embodiment, the monocyclic nitrogen-containing saturated hetero ring is azethidinyl, pyrrolidinyl, piperidyl, piperazinyl, morpholinyl, thiomorpholinyl, azepanyl, or diazepanyl.

Specific examples of the "monocyclic nitrogen-containing saturated hetero ring" as an example of the "saturated hetero ring" in $R^3$ include azethidinyl, pyrrolidinyl, piperidyl and piperazinyl, and in another embodiment, pyrrolidinyl and piperidyl.

The "monocyclic nitrogen-containing hetero ring" formed by $R^a$ and $R^b$ which are combined with the adjacent nitrogen atom means a monocyclic saturated hetero ring or a monocyclic unsaturated hetero ring, which contains at least one nitrogen atom and may further contain a heteroatom selected from oxygen and sulfur, as the group described in (1)(a), (1)(b), (2)(a), (2)(b), and the like of the "hetero ring" above, which is a group having a binding arm on a nitrogen atom. The ring atom, sulfur or nitrogen, may be oxidized to form an oxide or a dioxide. In another embodiment, the monocyclic nitrogen-containing hetero ring is azethidinyl, pyrrolidinyl, piperidyl, piperazinyl, morpholinyl, thiomorpholinyl, azepanyl or diazepanyl.

Specific examples of the "monocyclic nitrogen-containing hetero ring" formed by $R^a$ and $R^b$ which are combined with the adjacent nitrogen atom include azethidinyl, pyrrolidinyl, piperidyl, piperazinyl and morpholinyl, in another embodiment, piperidyl and piperazinyl, in a further embodiment, piperidyl, and in a still further embodiment, piperazinyl.

The "polycyclic nitrogen-containing hetero ring" formed by $R^a$ and $R^b$ which are combined with the adjacent nitrogen atom means a bi- to tricyclic fused polycyclic saturated hetero ring or a bi- to tricyclic fused polycyclic unsaturated hetero ring, which contains at least one nitrogen atom and may further contain a heteroatom selected from oxygen and sulfur, as the group described in (3)(a), (3)(b), (4)(a), (4)(b), and the like of the "hetero ring" above, which is a group having a binding arm on a nitrogen atom. Further, the polycyclic nitrogen-containing hetero ring also includes groups having one or more nitrogen atoms among the groups described in (5) Spiro ring groups of the "hetero rings" above. The ring atom, sulfur or nitrogen, may be oxidized to form an oxide or a dioxide. In another embodiment, the polycyclic nitrogen-containing hetero ring is indolinyl, isoindolinyl, dihydropyrrolopyridyl, dihydropyrrolopyrimidinyl, tetrahydroquinolyl, tetrahydroisoquinolyl, dihydrobenzoxadinyl, dihydropyridoxadinyl, tetrahydronaphthyridinyl, tetrahydropyridopyrimidinyl, tetrahydrothienopyridyl, tetrahydroxazolopyridyl, tetrahydropyrazolopyridyl, tetrahydropyrrolopyrazinyl, hexahydropyrrolopyrazinyl, hexahydropyrrolopyrrolyl, octahydropyrrolopyrrolyl, octahydropyrrolopyrazinyl, tetrahydroimidazopyrazinyl, tetrahydrothiazolopyridyl, tetrahydrobenzoazepinyl, tetrahydropyridonaphthyridinyl, hexahydropyridoindolyl, tetrahydroisoquixazolopyridyl, tetrahydropyrrolopyridyl, tetrahydroimidazopyridyl, tetrahydropyridoindolyl, tetrahydrotriazolopyrazinyl, diazabicyclo[2.2.1]heptyl, diazabicyclo[3.2.1]octyl, 3H-spiro[2-benzofuran-1,4'-piperidyl], 1H-spiro[1-benzofuran-3,4'-piperidyl], 2,3-dihydrospiro[indene-1,4'-piperidyl], diazaspiro[4,5]decyl, and diazaspiro[5,5]undecyl.

Specific examples of the "polycyclic hetero ring" formed by $R^a$ and $R^b$ which are combined with the adjacent nitrogen atom include indolinyl(2,3-dihydroindolyl), isoindolinyl(1,3-dihydroisoindolyl), dihydropyrrolopyridyl, hexahydropyrrolopyrazinyl, octahydropyrrolopyrazinyl, diazabicyclo[2.2.1]heptyl, diazabicyclo[3.2.1]octyl, 3H-spiro[2-benzofuran-1,4'-piperidyl], spiro[1-benzofuran-3,4'-piperidyl], diazaspiro[4,5]decyl, diazaspiro[5,5]undecyl, oxazaspiro[4,5]decyl and octahydropyrrolopyrrolyl;

in another embodiment, indolinyl(2,3-dihydroindolyl), isoindolinyl(1,3-dihydroisoindolyl), dihydropyrrolopyridyl, diazabicyclo[2.2.1]heptyl, diazaspiro[5,5]undecyl, 3H-spiro[2-benzofuran-1,4'-piperidyl], spiro[1-benzofuran-3,4'-piperidyl], oxazaspiro[4,5]decyl, octahydropyrrolopyrazinyl and octahydropyrrolopyrrolyl; and in a further embodiment, diazabicyclo[2.2.1]heptyl.

The "protected carboxyl" group may include the following groups.

(1) Ester groups. Specific examples thereof include —CO—O-lower alkyl, —CO—O-lower alkylene-O-lower alkyl, —CO—O-lower alkylene-aryl, —CO—O-lower alkylene-O-aryl, and the like, and in another embodiment, —CO—O-lower alkyl.

(2) Carbamoyl groups. Specific examples thereof include —CO—NH$_2$, —CO—NH-lower alkyl, —CO—N(lower alkyl)$_2$, —CO—N(lower alkyl)-aryl, —CO—N(lower alkyl)-hetero ring, —CO—N(lower alkyl)-(lower alkylene-aryl), —CO—NH-lower alkylene-OH, —CO—NH-hetero ring, and the like, and in another embodiment, —CO–NH$_2$, —CO—NH-lower alkyl, —CO—N(lower alkyl)$_2$, and —CO—NH-hetero ring.

In the present specification, the expression "which may be substituted" represents "which is not substituted" or "which is substituted with 1 to 5 substituents". Further, if it has a plurality of substituents, the substituents may be the same as or different from each other.

Examples of the substituent for "lower alkyl, —O-lower alkyl or cycloalkyl, each of which may be substituted" in $R^1$ and $R^2$ include —OH, —O-lower alkyl, —NH$_2$, —NH-lower alkyl, —N(lower alkyl)$_2$, and a monocyclic nitrogen-containing hetero ring which may be substituted with lower alkyl. The substituent for the "lower alkyl which may be substituted" is, in another embodiment, —O-lower alkyl.

Examples of the substituent for the "lower alkyl, cycloalkyl or a saturated hetero ring, each of which may be substituted" in $R^3$ include cycloalkyl which may be substituted with halogen or —O-lower alkyl, halogen, lower alkyl, an oxygen-containing saturated hetero ring, —OH, oxo(=O), —O-lower alkyl, lower alkylene-aryl, and —CO-lower alkylene-O-lower alkyl.

Examples of the substituent for the "lower alkyl which may be substituted" in $R^3$ include, in another embodiment, cycloalkyl which may be substituted with halogen or —O-lower alkyl, and an oxygen-containing saturated hetero ring, in a further embodiment, cyclopropyl and cyclobutyl, in a still further embodiment, cycloalkyl substituted with halogen, in a still further embodiment, cyclobutyl substituted with halogen, and in a still further embodiment, tetrahydropyranyl.

Examples of the substituent for the "cycloalkyl which may be substituted" in $R^3$ include, in another embodiment, halogen and —O-lower alkyl,
in a further embodiment, halogen, and
in a still further embodiment, —O-lower alkyl.

Examples of the substituent for the "saturated hetero ring which may be substituted" in $R^3$ include, in another embodiment, lower alkyl, lower alkylene-aryl, and —CO-lower alkylene-O-lower alkyl, and in a further embodiment, lower alkyl.

Examples of the substituent for the "lower alkyl, cycloalkyl, aryl or a hetero ring, each of which may be substituted" in $R^a$ and $R^b$ include halogen; —OH; lower alkyl; —O-lower alkyl; halogeno-lower alkyl; cycloalkyl which may be substituted with a group selected from the group consisting of a hetero ring which may be substituted with —O-lower alkyl, and —N(lower alkyl)$_2$; —NH$_2$; —NH-lower alkyl; —N(lower alkyl)$_2$; —N(lower alkyl)(cycloalkyl); —N(lower alkyl)(aryl); aryl which may be substituted with a group selected from a group $G_1$; a hetero ring which may be substituted with a group selected from a group $G_2$; lower alkylene-(aryl which may be substituted with a group selected from a group $G_1$); lower alkylene-(hetero ring which may be substituted with a group selected from a group $G_2$); —CO-(aryl which may be substituted with a group selected from a group $G_1$); —CO-(hetero ring which may be substituted with a group selected from a group $G_2$); and —CO—N(lower alkyl)(hetero ring).

Examples of the substituent for the "lower alkyl which may be substituted" in $R^a$ and $R^b$ include, in another embodiment, —OH; —O-lower alkyl; cycloalkyl which may be substituted with a group selected from the group consisting of a hetero ring which may be substituted with —O-lower alkyl, and —N(lower alkyl)$_2$; —NH$_2$; —NH-lower alkyl; —N(lower alkyl)$_2$; —N(lower alkyl)(cycloalkyl); —N(lower alkyl) (aryl); aryl which may be substituted with a group selected from a group $G_1$; a hetero ring which may be substituted with a group selected from a group $G_2$; —CO-(hetero ring which may be substituted with a group selected from a group $G_2$); and —CO—N(lower alkyl)(hetero ring).

Examples of the substituent for the "cycloalkyl which may be substituted" in $R^a$ and $R^b$ include, in another embodiment, a hetero ring which may be substituted with a group selected from a group $G_2$, and in a further embodiment, a hetero ring.

Examples of the substituent for the "hetero ring which may be substituted" in $R^a$ and $R^b$ include, in another embodiment, lower alkylene-(aryl which may be substituted with a group selected from a group $G_1$), and in a substituent embodiment, lower alkylene-aryl.

Examples of the substituent for the "the monocyclic nitrogen-containing hetero ring or the polycyclic nitrogen-containing hetero ring, each of which may be substituted", formed by $R^a$ and $R^b$ which are each combined with the adjacent nitrogen atom, include halogen; —OH; oxo(=O); —O-lower alkyl which may be substituted with one or more groups selected from the group consisting of halogen, halogeno-lower alkyl, —O-lower alkyl, cycloalkyl and aryl; cyano; halogeno-lower alkyl; cycloalkyl which may be substituted with a substituent selected from the group consisting of halogen, —OH, lower alkyl, —O-lower alkyl and lower alkylene-O-lower alkyl; aryl which may be substituted with a group selected from a group $G_1$; a hetero ring which may be substituted with a group selected from a group $G_2$; lower alkylene-N(lower alkyl)$_2$; lower alkylene-(aryl which may be substituted with a group selected from a group $G_1$); lower alkylene-(hetero ring which may be substituted with a group selected from a group $G_2$); lower alkylene-(cycloalkyl which may be substituted with a group selected from a group $G_1$); lower alkylene-O-(aryl which may be substituted with a group selected from a group $G_1$); lower alkylene-O-(hetero ring which may be substituted with a group selected from a group $G_2$) ; lower alkylene-O-(cycloalkyl which may be substituted with a group selected from a group $G_1$); lower alkyl which may be substituted with one or more groups selected from the group consisting of halogen, halogeno-lower alkyl, —OH, —COOH, protected carboxy, cyano, aryl, hetero ring, —O-aryl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl and cycloalkyl; —COOH; protected carboxy; —NH$_2$; —NH-lower alkyl; —N(lower alkyl which may be substituted with halogeno-lower alkyl or —O-lower alkyl)$_2$; —O-(aryl which may be substituted with a group selected from a group $G_1$); —O-(hetero ring which may be substituted with a group selected from a group $G_2$); —O-cycloalkyl; —CO-lower alkyl; —CO-(aryl which may be substituted with a group selected from a group $G_1$); —CO-(hetero ring which may be substituted with a group selected from a group $G_2$); and —CO—NH-hetero ring.

Examples of the substituent for the "monocyclic nitrogen-containing hetero ring which may be substituted" formed by $R^a$ and $R^b$ which are each combined with the adjacent nitrogen atom include, in another embodiment, —OH; oxo(=O); —O-lower alkyl; cycloalkyl; aryl which may be substituted with a group selected from a group $G_1$; a hetero ring which may be substituted with a group selected from a group $G_2$; lower alkylene-(aryl which may be substituted with a group selected from a group $G_1$); lower alkylene-(hetero ring which may be substituted with a group selected from a group $G_2$); and lower alkyl which may be substituted with —OH, —O-lower alkyl or cyano.

Examples of the substituent for the "monocyclic nitrogen-containing hetero ring which may be substituted" formed by $R^a$ and $R^b$ which are each combined with the adjacent nitrogen atom include, in another embodiment, halogen; —OH; oxo(=O); halogeno-lower alkyl; —O-lower alkyl which may be substituted with a group selected from the group consisting of halogen, halogeno-lower alkyl, —O-lower alkyl, cycloalkyl and aryl; cycloalkyl which may be substituted with a group selected from the group consisting of halogen, —OH, lower alkyl, —O-lower alkyl, and lower alkylene-O-lower alkyl; —COOH; protected carboxy; aryl which may be substituted with a group selected from a group $G_1$; a hetero ring which may be substituted with a group selected from a group $G_2$; lower alkylene-N(lower alkyl)$_2$; lower alkylene-(aryl which may be substituted with a group selected from a group $G_1$); lower alkylene-(hetero ring which may be substituted with a group selected from a group $G_2$); lower alkylene-(cycloalkyl which may be substituted with a group selected from a group $G_1$); lower alkylene-O-(aryl which may be substituted with a group selected from a group $G_1$); lower alkylene-O-(hetero ring which may be substituted with a group selected from a group $G_2$); lower alkylene-O-(cycloalkyl which may be substituted with a group selected from a group $G_1$); —N(lower alkyl which may be substituted with halogeno-lower alkyl or —O-lower alkyl)$_2$; —O-(aryl which may be substituted with a group selected from a group $G_1$); —O-(hetero ring which may be substituted with a group selected from a group $G_2$); —O-cycloalkyl; —CO-(hetero ring which may be substituted with a group selected from a group $G_2$); —CO—NH-hetero ring; lower alkyl which may be substituted with one or more groups selected from the group consisting of halogen, halogeno-lower alkyl, —OH, —COOH, protected carboxy, cyano, aryl, hetero ring, —O-aryl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl.

Examples of the substituent for the "monocyclic nitrogen-containing hetero ring which may be substituted" formed by $R^a$ and $R^b$ which are combined with the adjacent nitrogen atom include, in another embodiment, halogen; —OH; oxo (=O); halogeno-lower alkyl; —O-lower alkyl which may be substituted with a group selected from the group consisting of halogen, halogeno-lower alkyl, —O-lower alkyl, cycloalkyl and aryl; cycloalkyl which may be substituted with a group selected from the group consisting of halogen, —OH, lower alkyl, —O-lower alkyl, and lower alkylene-O-lower alkyl; —COOH; aryl which may be substituted with a group selected from a group $G_1$; a hetero ring which may be substituted with a group selected from a group $G_2$; lower alkylene-N(lower alkyl)$_2$; lower alkylene-(aryl which may be substituted with a group selected from a group $G_1$); lower alkylene-(hetero ring which may be substituted with a group selected from a group $G_2$); lower alkylene-(cycloalkyl which may be substituted with lower alkylene-O-lower alkyl); lower alkylene-O-(aryl); lower alkylene-O-(hetero ring); lower alkylene-O-(cycloalkyl); —N(lower alkyl which may be substituted with halogeno-lower alkyl or –O-lower alkyl)$_2$; —O-(aryl which may be substituted with —COOH); —O-(hetero ring which may be substituted with halogen or lower alkyl); —O-cycloalkyl; —CO-(hetero ring which may be substituted with lower alkyl); —CO—NH-hetero ring; lower alkyl which may be substituted with one or more groups selected from the group consisting of halogen, halogeno-lower alkyl, —OH, —COOH, cyano, aryl, a hetero ring, —O-aryl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl.

Examples of the substituent for the "monocyclic nitrogen-containing hetero ring which may be substituted" formed by $R^a$ and $R^b$ which are each combined with the adjacent nitrogen atom include, in another embodiment, —OH; halogeno-lower alkyl; —O-lower alkyl which may be substituted with 1 to 3 groups selected from the group consisting of halogen, halogeno-lower alkyl, and cycloalkyl; aryl which may be substituted with a group selected from a group $G_1$; a hetero ring which may be substituted with a group selected from a group $G_2$; lower alkylene-O-cycloalkyl; —O-cycloalkyl; —O-(hetero ring which may be substituted with a group selected from a group $G_2$); lower alkyl which may be substituted with one or more groups selected from the group consisting of halogen, halogeno-lower alkyl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl.

Examples of the substituent for the "monocyclic nitrogen-containing hetero ring which may be substituted" formed by $R^a$ and $R^b$ which are each combined with the adjacent nitrogen atom include, in another embodiment, —OH; halogeno-lower alkyl; —O-lower alkyl which may be substituted with 1 to 3 groups selected from the group consisting of halogen, halogeno-lower alkyl, and cycloalkyl; aryl; pyridyl which may be substituted with 1 to 3 groups selected from the group consisting of halogen and lower alkyl; lower alkylene-O-cycloalkyl; —O-cycloalkyl; —O-(pyridyl which may be substituted with lower alkyl); lower alkyl which may be substituted with one or more groups selected from the group consisting of halogen, halogeno-lower alkyl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl.

Examples of the substituent for the "monocyclic nitrogen-containing hetero ring which may be substituted" formed by $R^a$ and $R^b$ which are each combined with the adjacent nitrogen atom include, in another embodiment, —O-lower alkyl which may be substituted with 1 to 3 groups selected from halogen and cycloalkyl; lower alkylene-O-cycloalkyl; —O-cycloalkyl; lower alkyl which may be substituted with one or more groups selected from the group consisting of halogen, halogeno-lower alkyl, and —O-lower alkyl; and lower alkylene-O-lower alkyl.

Examples of the substituent for the "monocyclic nitrogen-containing hetero ring which may be substituted" formed by $R^a$ and $R^b$ which are each combined with the adjacent nitrogen atom include, in another embodiment, —O-lower alkyl which may be substituted with 1 to 3 halogen atoms; lower alkyl which may be substituted with one or more groups selected from the group consisting of halogen, halogeno-lower alkyl, and —O-lower alkyl; and lower alkylene-O-lower alkyl.

Examples of the substituent for the "polycyclic nitrogen-containing hetero ring which may be substituted" formed by $R^a$ and $R^b$ which are each combined with the adjacent nitrogen atom include, in another embodiment, halogen; —OH; oxo(=O); —O-lower alkyl; cyano; halogeno-lower alkyl; cycloalkyl; aryl which may be substituted with a group selected from a group $G_1$; a hetero ring which may be substituted with a group selected from a group $G_2$; and lower alkyl which may be substituted with —OH, —O-lower alkyl, or cyano, in a further embodiment, halogen; —OH; oxo(=O); —O-lower alkyl; cyano; halogeno-lower alkyl; cycloalkyl; aryl which may be substituted with a group selected from a group $G_1$; a hetero ring which may be substituted with a group selected from a group $G_2$; lower alkylene-(aryl which may be substituted with a group selected from a group $G_1$); lower alkylene-(hetero ring which may be substituted with a group selected from a group $G_2$); lower alkylene-cycloalkyl; and lower alkyl which may be substituted with —OH, —O-lower alkyl, or cyano.

Examples of the substituent for the "polycyclic nitrogen-containing hetero ring which may be substituted" formed by $R^a$ and $R^b$ which are each combined with the adjacent nitrogen atom include, in another embodiment, a hetero ring which may be substituted with a group selected from a group $G_2$; lower alkylene-(aryl which may be substituted with a group selected from a group $G_1$); and lower alkylene-O-lower alkyl.

Examples of the substituent for the "polycyclic nitrogen-containing hetero ring which may be substituted" formed by $R^a$ and $R^b$ which are each combined with the adjacent nitrogen atom include, in another embodiment, halogen, lower alkyl, and —O-lower alkyl.

The group $G_1$ consists of halogen, lower alkyl, halogeno-lower alkyl, —OH, —O-lower alkyl, —O-hetero ring, —O-lower alkylene-aryl, —O-lower alkylene-hetero ring, —O-halogeno-lower alkyl, —N(lower alkyl)$_2$, lower alkylene-N(lower alkyl)$_2$, lower alkylene-hetero ring, aryl which may be substituted with lower alkyl, a hetero ring which may be substituted with lower alkyl, —COOH, and protected carboxy.

In another embodiment, the group $G_1$ consists of —O-hetero ring, —O-lower alkylene-hetero ring, —N(lower alkyl)$_2$, lower alkylene-N(lower alkyl)$_2$, lower alkylene-hetero ring, lower alkylene-N(lower alkyl)$_2$, and a hetero ring.

In a further embodiment, the group $G_1$ consists of halogen, lower alkyl, —O-lower alkyl, —COOH, and protected carboxy.

The group $G_2$ consists of halogen, lower alkyl, halogeno-lower alkyl, —OH, —O-lower alkyl, —O-lower alkylene-aryl, —O-lower alkylene-hetero ring, —O-halogeno-lower alkyl, cyano, —N(lower alkyl)$_2$, —NH—CO-lower alkyl, lower alkylene-O-lower alkyl, lower alkylene-hetero ring, aryl, a hetero ring which may be substituted with lower alkyl, —COOH, and protected carboxy.

In another embodiment, the group $G_2$ consists of lower alkyl, —O-lower alkyl, aryl, and a hetero ring.

In a further embodiment, the group $G_2$ consists of halogen, lower alkyl, halogeno-lower alkyl, —OH, —O-lower alkyl, cyano, —N(lower alkyl)$_2$, —NH—CO-lower alkyl, lower alkylene-O-lower alkyl, lower alkylene-hetero ring, and a hetero ring, and in a still further embodiment, halogen and lower alkyl.

Certain embodiments of the compound of the formula (I) or a salt thereof are presented below.

(1)

(1-1) The compound or a salt thereof, wherein $R^1$ is a group of the formula (II).

(1-2) The compound or a salt thereof, wherein $R^1$ is hydrogen, halogen, halogeno-lower alkyl, or lower alkyl, —O-lower alkyl or cycloalkyl, each of which may be substituted;

in another embodiment, the compound or a salt thereof, wherein $R^1$ is hydrogen, halogen, halogeno-lower alkyl, lower alkyl, —O-lower alkyl, or lower alkylene-O-lower alkyl;

in a further embodiment, the compound or a salt thereof, wherein $R^1$ is halogeno-lower alkyl, lower alkyl, or —O-lower alkyl;

in a still further embodiment, the compound or a salt thereof, wherein $R^1$ is lower alkyl; and in a still further embodiment, the compound or a salt thereof, wherein $R^1$ is methyl.

(2)

(2-1) The compound or a salt thereof, wherein $R^2$ is a group of the formula (II).

(2-2) The compound or a salt thereof, wherein $R^2$ is hydrogen, halogen, halogeno-lower alkyl, or lower alkyl, —O-lower alkyl or cycloalkyl, each of which may be substituted; and in another embodiment, the compound or a salt thereof, wherein $R^2$ is hydrogen, halogen, halogeno-lower alkyl, lower alkyl, —O-lower alkyl, or lower alkylene-O-lower alkyl.

(3)

(3-1) The compound or a salt thereof, wherein $R^3$ is lower alkyl which may be substituted;

in another embodiment, the compound or a salt thereof, wherein $R^3$ is lower alkylene-(cycloalkyl which may be substituted with halogen or —O-lower alkyl), or lower alkylene-oxygen-containing saturated hetero ring;

in a further embodiment, the compound or a salt thereof, wherein $R^3$ is lower alkylene-cyclopropyl or lower alkylene-cyclobutyl;

in a still further embodiment, the compound or a salt thereof, wherein $R^3$ is lower alkylene-(cyclobutyl substituted with two halogen atoms); and in a still further embodiment, the compound or a salt thereof, wherein $R^3$ is lower alkylene-tetrahydropyranyl.

(3-2) The compound or a salt thereof, wherein $R^3$ is cycloalkyl which may be substituted;

in another embodiment, the compound or a salt thereof, wherein $R^3$ is cycloalkyl which may be substituted with halogen or —O-lower alkyl;

in a further embodiment, the compound or a salt thereof, wherein $R^3$ is cyclobutyl or cyclopentyl; and in a still further embodiment, the compound or a salt thereof, wherein $R^3$ is cyclohexyl substituted with two halogen atoms.

(3-3) The compound or a salt thereof, wherein $R^3$ is a saturated hetero ring which may be substituted;

in another embodiment, the compound or a salt thereof, wherein $R^3$ is a saturated hetero ring which may be substituted with lower alkyl, lower alkylene-aryl, or —CO-lower alkylene-O-lower alkyl;

in a further embodiment, the compound or a salt thereof, wherein $R^3$ is an oxygen-containing saturated hetero ring, or a monocyclic nitrogen-containing saturated hetero ring substituted with lower alkyl;

in a still further embodiment, the compound or a salt thereof, wherein $R^3$ is piperidyl substituted with lower alkyl or pyrrolidinyl substituted with lower alkyl; and in a still further embodiment, the compound or a salt thereof, wherein $R^3$ is tetrahydrofuranyl or tetrahydropyranyl.

(3-4) The compound or a salt thereof, wherein $R^3$ is lower alkylene-(cycloalkyl), lower alkylene-(cycloalkyl substituted with two halogen atoms), cycloalkyl, cycloalkyl substituted with two halogen atoms, an oxygen-containing saturated hetero ring, or a monocyclic nitrogen-containing saturated hetero ring substituted with lower alkyl;

in another embodiment, the compound or a salt thereof, wherein $R^3$ is cyclopropylmethyl, cyclobutylmethyl, difluorocyclobutylmethyl, cyclobutyl, cyclopentyl, cyclohexyl substituted with difluoro, tetrahydro-2H-pyran-4-yl, tetrahydrofuran-3-yl, piperidyl substituted with methyl, or pyrrolidinyl substituted with methyl;

in a further embodiment, the compound or a salt thereof, wherein $R^3$ is cycloalkyl or oxygen-containing saturated hetero ring;

in a still further embodiment, the compound or a salt thereof, wherein $R^3$ is cyclobutyl, cyclopentyl, tetrahydrofuran-3-yl, or tetrahydro-2H-pyran-4-yl; and in a still further embodiment, the compound or a salt thereof, wherein $R^3$ is tetrahydro-2H-pyran-4-yl or cyclobutyl.

(4) The compound or a salt thereof, wherein $R^4$ is hydrogen; and in another embodiment, the compound or a salt thereof, wherein $R^4$ is lower alkyl.

(5) The compound or a salt thereof, wherein $R^5$ is hydrogen; and in another embodiment, the compound or a salt thereof, wherein $R^5$ is lower alkyl.

(6) The compound or a salt thereof, wherein $R^6$ is hydrogen; and in another embodiment, the compound or a salt thereof, wherein $R^6$ is lower alkyl.

(7)

(7-1) The compound or a salt thereof, wherein $R^a$ is lower alkyl which may be substituted; and in another embodiment, the compound or a salt thereof, wherein $R^a$ is lower alkyl which may be substituted with a group selected from the group consisting of —OH; —O-lower alkyl; cycloalkyl which may be substituted with a group selected from the group consisting of a hetero ring which may be substituted with —O-lower alkyl, and —N(lower alkyl)$_2$; —NH$_2$; —NH-lower alkyl; —N(lower alkyl)$_2$; —N(lower alkyl)(cycloalkyl); —N(lower alkyl)(aryl); aryl which may be substituted with a group selected from a group $G_1$; a hetero ring which may be substituted with a group selected from a group $G_2$; —CO-(hetero ring which may be substituted with a group selected from a group $G_2$); and —CO—N(lower alkyl)(hetero ring).

(7-2) The compound or a salt thereof, wherein $R^a$ is cycloalkyl which may be substituted;

in another embodiment, the compound or a salt thereof, wherein $R^a$ is cycloalkyl which may be substituted with a hetero ring which may be substituted with a group selected from a group $G_2$; and in a further embodiment, the compound or a salt thereof, wherein $R^a$ is cycloalkyl which may be substituted with a hetero ring.

(7-3) The compound or a salt thereof, wherein $R^a$ is aryl which may be substituted.

(7-4) The compound or a salt thereof, wherein $R^a$ is a hetero ring which may be substituted;

in another embodiment, the compound or a salt thereof, wherein $R^a$ is a hetero ring which may be substituted with lower alkylene-(aryl which may be substituted with a group selected from a group $G_1$); and in a further embodiment, the compound or a salt thereof, wherein $R^a$ is a hetero ring which may be substituted with lower alkylene-aryl.

(8) The compound or a salt thereof, wherein $R^b$ is hydrogen or lower alkyl; and in another embodiment, the compound or a salt thereof, wherein $R^b$ is hydrogen.

(9) The compound or a salt thereof, wherein $R^a$ and $R^b$ are combined with the adjacent nitrogen atom to form a monocyclic nitrogen-containing hetero ring which may be substituted;

in another embodiment, the compound or a salt thereof, wherein $R^a$ and $R^b$ each combined with the adjacent nitrogen atom to form a monocyclic nitrogen-containing hetero ring which may be substituted, which may be substituted with a group selected from the group consisting of halogen; —OH; oxo(=O); halogeno-lower alkyl; —O-lower alkyl which may be substituted with a group selected from the group consisting of halogen, halogeno-lower alkyl, —O-lower alkyl, cycloalkyl and aryl; cycloalkyl which may be substituted with a group selected from the group consisting of halogen, —OH, lower alkyl, —O-lower alkyl, and lower alkylene-O-lower alkyl; —COOH; protected carboxy; aryl which may be substituted with a group selected from a group $G_1$; a hetero ring which may be substituted with a group selected from a group $G_2$; lower alkylene-N(lower alkyl)$_2$; lower alkylene-(aryl which may be substituted with a group selected from a group $G_1$); lower alkylene-(hetero ring which may be substituted with a group selected from a group $G_2$); lower alkylene-(cycloalkyl which may be substituted with a group selected from a group $G_1$); lower alkylene-O-(aryl which may be substituted with a group selected from a group $G_1$); lower alkylene-O-(hetero ring which may be substituted with a group selected from a group $G_2$); lower alkylene-O-(cycloalkyl which may be substituted with a group selected from a group $G_1$); —N(lower alkyl which may be substituted with halogeno-lower alkyl or —O-lower alkyl)$_2$; —O-(aryl which may be substituted with a group selected from a group $G_1$); —O-(hetero ring which may be substituted with a group selected from a group $G_2$); —O-cycloalkyl; —CO-(hetero ring which may be substituted with a group selected from a group $G_2$); —CO—NH-hetero ring; lower alkyl which may be substituted with one or more groups selected from the group consisting of halogen, halogeno-lower alkyl, —OH, —COOH, protected carboxy, cyano, aryl, hetero ring, —O-aryl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl; and in a further embodiment, the compound or a salt thereof, wherein $R^a$ and $R^b$ are combined with the adjacent nitrogen atom to form a monocyclic nitrogen-containing hetero ring which may be substituted, which may be substituted with a group selected from the group consisting of —OH; halogeno-lower alkyl; —O-lower alkyl which may be substituted with 1 to 3 groups selected from the group consisting of halogen, halogeno-lower alkyl, and cycloalkyl; aryl which may be substituted with a group selected from a group $G_1$; a hetero ring which may be substituted with a group selected from a group $G_2$; lower alkylene-O-cycloalkyl; —O-cycloalkyl; —O-(hetero ring which may be substituted with a group selected from a group $G_2$); lower alkyl which may be substituted with one or more groups selected from the group consisting of halogen, halogeno-lower alkyl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl.

(10-1) The compound or a salt thereof, wherein $R^a$ and $R^b$ are each combined with the adjacent nitrogen atom to form azethidinyl which may be substituted; and in another embodiment, the compound or a salt thereof, wherein $R^a$ and $R^b$ are combined with the adjacent nitrogen atom to form azethidinyl which may be substituted, which may be substituted with a group selected from the group consisting of —O-lower alkyl; a hetero ring which may be substituted with a group selected from halogen and lower alkyl; —N(lower alkyl which may be substituted with halogeno-lower alkyl or —O-lower alkyl)$_2$—O-(aryl); lower alkyl; and lower alkylene-O-lower alkyl.

(10-2) The compound or a salt thereof, wherein $R^a$ and $R^b$ are combined with the adjacent nitrogen atom to form morpholinyl which may be substituted; and in another embodiment, the compound or a salt thereof, wherein $R^a$ and $R^b$ are combined with the adjacent nitrogen atom to form morpholinyl which may be substituted, which may be substituted with a group selected from the group consisting of aryl which may be substituted with —O-lower alkyl; a hetero ring; and lower alkylene-N(lower alkyl)$_2$.

(10-3) The compound or a salt thereof, wherein $R^a$ and $R^b$ are combined with the adjacent nitrogen atom to form pyrrolidinyl which may be substituted; and in another embodiment, the compound or a salt thereof, wherein $R^a$ and $R^b$ are combined with the adjacent nitrogen atom to form pyrrolidinyl which may be substituted, which may be substituted with a group selected from the group consisting of —OH; —O-lower alkyl which may be substituted with aryl; —O-aryl; a hetero ring which may be substituted with halogen or lower alkyl; and lower alkylene-O-lower alkyl.

(10-4) The compound or a salt thereof, wherein $R^a$ and $R^b$ are combined with the adjacent nitrogen atom to form piperidyl which may be substituted;

in another embodiment, the compound or a salt thereof, wherein $R^a$ and $R^b$ are combined with the adjacent nitrogen atom to form piperidyl which may be substituted, which may be substituted with a group selected from the group consisting of halogen; —OH; halogeno-lower alkyl; —O-lower alkyl which may be substituted with a group selected from the group consisting of halogen, halogeno-lower alkyl, —O-lower alkyl, cycloalkyl and aryl; —COOH; protected carboxy; aryl which may be substituted with —COOH or protected carboxy; a hetero ring which may be substituted with halogen, lower alkyl, or lower alkylene-O-lower alkyl; lower alkylene-(aryl which may be substituted with —COOH); lower alkylene-hetero ring; lower alkylene-O-hetero ring; lower alkylene-O-cycloalkyl; —N(lower alkyl)$_2$; —O-(aryl which may be substituted with —COOH); —O-(hetero ring which may be substituted with halogen or lower alkyl); —O-cycloalkyl; —CO-(hetero ring which may be substituted with lower alkyl); —CO—NH-hetero ring; lower alkyl which may be substituted with one or more groups selected from the group consisting of —OH, —COOH, protected carboxy, —O-cycloalkyl, and a hetero ring; and lower alkylene-O-lower alkyl which may be substituted with one or more groups selected from the group consisting of halogen, halogeno-lower alkyl, and cycloalkyl; and in a further embodiment, the compound or a salt thereof, wherein $R^a$ and $R^b$ are combined with the adjacent nitrogen atom to form piperidyl which may be substituted, which may be substituted with a group selected from the group consisting of —OH; halogeno-lower alkyl; —O-lower alkyl which may be substituted with 1 to 3 groups selected from the group consisting of halogen, halogeno-lower alkyl, and cycloalkyl; lower alkylene-O-cycloalkyl; —O-cycloalkyl; —O-(hetero ring which may be substituted with lower alkyl); and lower alkylene-O-lower alkyl.

(10-5) The compound or a salt thereof, wherein $R^a$ and $R^b$ are combined with the adjacent nitrogen atom to form piperazinyl which may be substituted;

in another embodiment, the compound or a salt thereof, wherein $R^a$ and $R^b$ are combined with the adjacent nitrogen atom to form piperazinyl which may be substituted, which may be substituted with a group selected from the group consisting of oxo(=O); cycloalkyl which may be substituted with a group selected from the group consisting of halogen, —OH, lower alkyl, —O-lower alkyl, and lower alkylene-O-lower alkyl; aryl which may be substituted with halogen or —COOH; a hetero ring which may be substituted with a group selected from a group G$_2$; lower alkylene-(aryl which may be substituted with halogen or —O-lower alkyl); lower alkylene-(hetero ring which may be substituted with a group selected from a group G$_2$); lower alkylene-(cycloalkyl which may be substituted with lower alkylene-O-lower alkyl); lower alkylene-O-aryl; lower alkylene-O-cycloalkyl; lower alkyl which may be substituted with one or more groups selected from the group consisting of halogen, halogeno-lower alkyl, —OH, —COOH, protected carboxy, cyano, aryl, hetero ring, —O-aryl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl; and in a further embodiment, the compound or a salt thereof, wherein $R^a$ and $R^b$ are combined with the adjacent nitrogen atom to form piperazinyl which may be substituted, which may be substituted with a group selected from the group consisting of aryl which may be substituted with a group selected from a group G$_1$; a hetero ring which may be substituted with a group selected from lower alkyl and halogen; lower alkylene-O-cycloalkyl; lower alkyl which may be substituted with one or more groups selected from the group consisting of halogen, halogeno-lower alkyl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl.

(10-6) The compound or a salt thereof, wherein $R^a$ and $R^b$ are combined with the adjacent nitrogen atom to form piperidyl or piperazinyl, each of which may be substituted; and in another embodiment, the compound or a salt thereof, wherein $R^a$ and $R^b$ are combined with the adjacent nitrogen atom to form piperidyl or piperazinyl, which may be substituted, which may be substituted with a group selected from the group consisting of —O-lower alkyl which may be substituted with 1 to 3 groups selected from halogen and cycloalkyl; lower alkylene-O-cycloalkyl; —O-cycloalkyl; lower alkyl which may be substituted with one or more groups selected from the group consisting of halogen, halogeno-lower alkyl, and —O-lower alkyl; and lower alkylene-O-lower alkyl.

(11) The compound or a salt thereof, wherein $R^a$ and $R^b$ are combined with the adjacent nitrogen atom to form a polycyclic nitrogen-containing hetero which may be substituted;

in another embodiment, the compound or a salt thereof, wherein $R^a$ and $R^b$ are combined with the adjacent nitrogen atom, and may be substituted with a substituent selected from halogen; —OH; oxo(=O); —O-lower alkyl; cyano; halogeno-lower alkyl; cycloalkyl; aryl which may be substituted with a group selected from a group G$_1$; a hetero ring which may be substituted with a group selected from a group G$_2$; and lower alkyl which may be substituted with —OH, —O-lower alkyl, or cyano;

in a further embodiment, the compound or a salt thereof, wherein the polycyclic nitrogen-containing hetero ring forms a polycyclic nitrogen-containing hetero ring which may be substituted with 1 to 3 substituents selected from the group consisting of halogen; —OH; oxo(=O); —O-lower alkyl; cyano; halogeno-lower alkyl; cycloalkyl; aryl which may be substituted with a group selected from a group G$_1$; a hetero ring which may be substituted with a group selected from a group G$_2$; lower alkylene-(aryl which may be substituted with a group selected from a group G$_1$); lower alkylene-(hetero ring which may be substituted with a group selected from a group G$_2$); lower alkylene-cycloalkyl; and lower alkyl which may be substituted with —OH, —O-lower alkyl, or cyano;

in a still further embodiment, the compound or a salt thereof, wherein $R^a$ and $R^b$ are combined with the adjacent nitrogen atom to form a polycyclic nitrogen-containing hetero ring which may be substituted with a substituent selected from the group consisting of a hetero ring which may be substituted with a group selected from a group $G_2$; lower alkylene-(aryl which may be substituted with a group selected from a group $G_1$); and lower alkylene-O-lower alkyl; and in a still further embodiment, the compound or a salt thereof, wherein $R^a$ and $R^b$ which are combined with the adjacent nitrogen atom to form a polycyclic nitrogen-containing hetero ring which may be substituted with halogen, lower alkyl, or —O-lower alkyl.

(12)

(12-1) The compound or a salt thereof, wherein $R^a$ and $R^b$ are combined with the adjacent nitrogen atom to form a bicyclic nitrogen-containing hetero ring which may be substituted, and in another embodiment, a bicyclic nitrogen-containing hetero ring having a spiro bond;

in another embodiment, the compound or a salt thereof, wherein $R^a$ and $R^b$ are combined with the adjacent nitrogen atom to form dihydroindolinyl, dihydroisoindolinyl or dihydropyrrolopyridyl, each of which may be substituted;

in a further embodiment, the compound or a salt thereof, wherein $R^a$ and $R^b$ are combined with the adjacent nitrogen atom to form diazabicyclo[2.2.1]heptyl, diazaspiro[5,5]undecyl or oxazaspiro[4,5]decyl, each of which may be substituted; and in a still further embodiment, the compound or a salt thereof, wherein $R^a$ and $R^b$ are combined with the adjacent nitrogen atom to form diazabicyclo[2.2.1]heptyl which may be substituted.

(12-2) The compound or a salt thereof, wherein $R^a$ and $R^b$ are combined with the adjacent nitrogen atom to form a tricyclic nitrogen-containing hetero ring which may be substituted, and in another embodiment, a tricyclic nitrogen-containing hetero ring having a Spiro bond, and in a further embodiment, the compound or a salt thereof, wherein $R^a$ and $R^b$ are combined with the adjacent nitrogen atom to form 3H-spiro[2-benzofuran-1,4'-piperidyl].

(13) The compound or a salt thereof, which is a combination of two or more groups of the groups described in (1) to (12) above.

The compound of the formula (I) or a salt thereof includes a compound or a salt thereof formed by one or a combination of two or more groups of the groups described in (1) to (12) above as described in (13) above, but also includes the following embodiments including specific examples thereof.

(14) The compound or a salt thereof, wherein $R^1$ is a group of the formula (II), and $R^2$ is (a) hydrogen, (b) halogen, (c) lower alkyl which may be substituted with —O-lower alkyl, —NH-lower alkyl, or —N(lower alkyl)$_2$, or (d) —O-lower alkyl, $R^a$ and $R^b$ are combined with the adjacent nitrogen atom to form a monocyclic nitrogen-containing hetero ring or a polycyclic nitrogen-containing hetero ring, each of which may be substituted.

(15) The compound or a salt thereof according to (14), wherein $R^3$ is lower alkyl, cycloalkyl or a saturated hetero ring, each of which may be substituted, and $R^4$, $R^5$ and $R^6$ are hydrogen.

(16) The compound or a salt thereof, wherein $R^1$ is a group of the formula (II), $R^2$ is hydrogen, halogen, lower alkyl which may be substituted with —O-lower alkyl, or —O-lower alkyl, $R^3$ is cycloalkyl or a saturated hetero ring, which may be substituted with one or two substituents selected from halogen, lower alkyl, —OH, oxo(=O), and —O-lower alkyl; or lower alkyl which may be substituted with cycloalkyl, $R^4$, $R^5$ and $R^6$ are hydrogen, and $R^a$ and $R^b$ are combined with the adjacent nitrogen atom to form a polycyclic nitrogen-containing hetero ring which may be substituted with 1 to 3 substituents selected from halogen; —OH; oxo(=O); —O-lower alkyl; cyano; halogeno-lower alkyl; cycloalkyl; aryl; a hetero ring; and lower alkyl which may be substituted with —OH, —O-lower alkyl, or cyano (here, aryl may be substituted with a group selected from a group $G_1$, and the hetero ring may be substituted with a group selected from a group $G_2$).

(17) The compound or a salt thereof, wherein $R^1$ is a group of the formula (II), $R^2$ is hydrogen, halogen, lower alkyl which may be substituted with —O-lower alkyl, or —O-lower alkyl, $R^3$ is cyclobutyl or cyclopentyl which may be substituted with —O-lower alkyl, or pyrrolidinyl, tetrahydrofuranyl or tetrahydropyranyl which may be substituted with lower alkyl, $R^4$, $R^5$ and $R^6$ are hydrogen, and $R^a$ and $R^b$ are combined with the adjacent nitrogen atom to form a polycyclic nitrogen-containing hetero ring selected from indolinyl, isoindolinyl and dihydropyrrolopyridyl, and the polycyclic nitrogen-containing hetero ring may be substituted with 1 to 2 substituents selected from halogen, lower alkyl and —O-lower alkyl.

(18) The compound or a salt thereof, wherein $R^1$ is a group of the formula (II), $R^2$ is (a) hydrogen, (b) halogen, (c) lower alkyl which may be substituted with —O-lower alkyl, or (d) —O-lower alkyl, $R^3$ is cycloalkyl or a saturated hetero ring, which may be substituted with 1 or 2 substituents selected from lower alkyl, —OH and —O-lower alkyl; or lower alkyl which may be substituted with cycloalkyl, $R^4$, $R^5$ and $R^6$ are hydrogen, and $R^a$ and $R^b$ are combined with the adjacent nitrogen atom to form a monocyclic nitrogen-containing hetero ring which may be substituted with 1 to 3 substituents selected from —OH; oxo(=O); —O-lower alkyl; cycloalkyl; aryl; a hetero ring; lower alkylene-aryl; lower alkylene-hetero ring; and lower alkyl which may be substituted with —OH, —O-lower alkyl, or cyano (here, aryl may be substituted with a group selected from a group $G_1$, and the hetero ring may be substituted with a group selected from a group $G_2$).

(19) The compound or a salt thereof, wherein $R^1$ is a group of the formula (II), $R^2$ is hydrogen or lower alkyl, $R^3$ is cyclobutyl or tetrahydropyranyl, $R^4$, $R^5$ and $R^6$ are hydrogen, and $R^a$ and $R^b$ are combined with the adjacent nitrogen atom to form a monocyclic nitrogen-containing hetero ring selected from piperidinyl, piperazinyl and morphoryl, and the monocyclic nitrogen-containing hetero ring may be substituted with 1 to 2 substituents selected from aryl which may be substituted with halogen, and lower alkyl.

(20) The compound or a salt thereof, wherein $R^1$ is hydrogen or lower alkyl, $R^2$ is a group of the formula (II), $R^3$ is cycloalkyl or saturated hetero group, which may be substituted with one or two substituents selected from halogen, lower alkyl, —OH, oxo(=O), and —O-lower alkyl, or lower alkyl which may be substituted with cycloalkyl, $R^4$, $R^5$ and $R^6$ are hydrogen, and $R^a$ and $R^b$ are combined with the adjacent nitrogen atom to form a monocyclic nitrogen-containing hetero ring which may be substituted with 1 to 3 substituents selected from —OH; oxo(=O); —O-lower alkyl; cycloalkyl; protected carboxy; aryl; a hetero ring; lower alkylene-N(lower alkyl)$_2$; lower alkylene-aryl; lower alkylene-hetero ring; lower alkylene-cycloalkyl; —NH-lower alkyl; —N(lower alkyl)$_2$; —O-aryl; —O-hetero ring; —CO-lower alkyl; —CO-hetero ring; or lower alkyl which may be substituted with —OH, —O-lower alkyl, or cyano (here, aryl may be substituted with a group selected from a group $G_1$, and the hetero ring may be substituted with a group selected from a group $G_2$).

(21) The compound or a salt thereof, wherein
$R^1$ is lower alkyl,
$R^2$ is a group of the formula (II),
$R^3$ is tetrahydropyranyl,
$R^4$, $R^5$ and $R^6$ are hydrogen, and
$R^a$ and $R^b$ are combined with the adjacent nitrogen atom to form a monocyclic nitrogen-containing hetero ring selected from azethidinyl, piperidyl, piperazinyl and morpholinyl, and the monocyclic nitrogen-containing hetero ring which may be substituted with 1 to 3 substituents selected from —O-lower alkyl, cycloalkyl, aryl, a hetero ring which may be substituted with lower alkyl, lower alkylene-(aryl which may be substituted with halogen), lower alkylene-hetero ring, lower alkylene-cycloalkyl, lower alkylene-O-lower alkyl, lower alkylene-N(lower alkyl)$_2$, —O-lower alkyl, —O-hetero ring, —N(lower alkyl)$_2$, —CO-(hetero ring which may be substituted with lower alkyl), and lower alkyl which may be substituted with —O-lower alkyl.

(22) The compound or a salt thereof, wherein
one of $R^1$ and $R^2$ is hydrogen, halogen, halogeno-lower alkyl, lower alkyl, —O-lower alkyl, or lower alkylene-O-lower alkyl, and
the other is a group of the formula (II),
$R^3$ is lower alkylene-(cycloalkyl which may be substituted with halogen or —O-lower alkyl); lower alkylene-oxygen-containing saturated hetero ring; cycloalkyl which may be substituted with halogen or —O-lower alkyl; an oxygen-containing saturated hetero ring; or a monocyclic nitrogen-containing saturated hetero ring which may be substituted with lower alkyl, lower alkylene-aryl, or —CO-lower alkylene-O-lower alkyl,
$R^4$ and $R^5$ are hydrogen,
$R^6$ is hydrogen or lower alkyl,
one of $R^a$ and $R^b$ is hydrogen, and the other is lower alkyl which may be substituted; cycloalkyl which may be substituted with a hetero ring which may be substituted with a group selected from a group $G_2$; or a hetero ring which may be substituted with lower alkylene-(aryl which may be substituted with a group selected from a group $G_1$), or
$R^a$ and $R^b$ are combined with the adjacent nitrogen atom to form a monocyclic nitrogen-containing hetero ring which may be substituted, or a polycyclic nitrogen-containing hetero ring which may be substituted with a group selected from the group consisting of halogen; —O-lower alkyl; a hetero ring which may be substituted with a group selected from a group $G_2$; lower alkylene-(aryl which may be substituted with a group selected from a group $G_1$); lower alkyl; and lower alkylene-O-lower alkyl.

(23) The compound or a salt thereof, wherein
$R^1$ is hydrogen, halogeno-lower alkyl, lower alkyl, or —O-lower alkyl,
$R^2$ is a group of the formula (II),
$R^3$ is lower alkylene-(cycloalkyl which may be substituted with halogen or —O-lower alkyl); lower alkylene-oxygen-containing saturated hetero ring; cycloalkyl which may be substituted with halogen or —O-lower alkyl; an oxygen-containing saturated hetero ring; or a monocyclic nitrogen-containing saturated hetero ring which may be substituted with lower alkyl, lower alkylene-aryl, or —CO-lower alkylene-O-lower alkyl,
$R^4$, $R^5$ and $R^6$ are hydrogen, and
$R^a$ and $R^b$ are combined with the adjacent nitrogen atom to form a monocyclic nitrogen-containing hetero ring, each of which may be substituted.

(24) The compound or a salt thereof according to (23) above, wherein the monocyclic nitrogen-containing hetero ring formed by $R^a$ and $R^b$ which are combined with the adjacent nitrogen atom is piperidyl or piperazinyl.

(25) The compound or a salt thereof according to (24) above, wherein piperidyl or piperazinyl, each of which may be substituted, formed by $R^a$ and $R^b$ which are combined with the adjacent nitrogen atom, may be substituted with 1 to 3 substituents selected from:
—OH; halogeno-lower alkyl; —O-lower alkyl which may be substituted with 1 to 3 groups selected from the group consisting of halogen, halogeno-lower alkyl, and cycloalkyl; aryl which may be substituted with a group selected from a group $G_1$; a hetero ring which may be substituted with a group selected from a group $G_2$; lower alkylene-O-cycloalkyl; —O-cycloalkyl; —O-(hetero ring which may be substituted with a group selected from a group $G_2$); lower alkyl which may be substituted with one or more groups selected from the group consisting of halogen, halogeno-lower alkyl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl.

(26) The compound or a salt thereof according to (25) above, wherein piperidyl or piperazinyl, each of which may be substituted, formed by $R^a$ and $R^b$ which are combined with the adjacent nitrogen atom, may be substituted with 1 to 3 groups selected from the group consisting of:
—O-lower alkyl which may be substituted with 1 to 3 groups selected from halogen and cycloalkyl; lower alkylene-O-cycloalkyl; —O-cycloalkyl; lower alkyl which may be substituted with one or more groups selected from the group consisting of halogen, halogeno-lower alkyl, and —O-lower alkyl; and lower alkylene-O-lower alkyl.

(27) The compound or a salt thereof, wherein
$R^1$ is lower alkyl,
$R^2$ is a group of the formula (II),
$R^3$ is lower alkylene-(cycloalkyl), lower alkylene-(cycloalkyl substituted with two halogen atoms), cycloalkyl, cycloalkyl substituted with two halogen atoms, an oxygen-containing saturated hetero ring, or a monocyclic nitrogen-containing saturated hetero ring substituted with lower alkyl,
$R^4$, $R^5$ and $R^6$ are hydrogen, and
$R^a$ and $R^b$ are combined with the adjacent nitrogen atom to form piperidyl or piperazinyl, each of which may be substituted, which may be substituted with 1 to 3 groups selected from the group consisting of:
—OH; halogeno-lower alkyl; —O-lower alkyl which may be substituted with 1 to 3 groups selected from the group consisting of halogen, halogeno-lower alkyl, and cycloalkyl; aryl which may be substituted with a group selected from a group $G_1$; a hetero ring which may be substituted with a group selected from a group $G_2$; lower alkylene-O-cycloalkyl; —O-cycloalkyl; —O-(hetero ring which may be substituted with a group selected from a group $G_2$); lower alkyl which may be substituted with one or more groups selected from the group consisting of halogen, halogeno-lower alkyl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl, and cycloalkyl.

(28) The compound or a salt thereof, wherein
$R^1$ is lower alkyl,
$R^2$ is a group of the formula (II),
$R^3$ is cycloalkyl or oxygen-containing saturated hetero ring,
$R^4$, $R^5$ and $R^6$ are hydrogen, and
$R^a$ and $R^b$ are combined with the adjacent nitrogen atom to form piperidyl or piperazinyl, each of which may be substituted, which may be substituted with 1 to 3 groups selected from the group consisting of:
—O-lower alkyl which may be substituted with 1 to 3 groups selected from halogen and cycloalkyl; lower alkylene-O-cycloalkyl; —O-cycloalkyl; lower alkyl which may be substituted with one or more groups selected from the group consisting of halogen, halogeno-lower alkyl, and —O-lower alkyl; and lower alkylene-O-lower alkyl.

(29) The compound or a salt thereof according to (27) above, wherein $R^3$ is cyclopropylmethyl, cyclobutylmethyl, difluorocyclobutylmethyl, cyclobutyl, cyclopentyl, cyclohexyl substituted with difluoro, tetrahydro-2H-pyran-4-yl, tetrahydrofuran-3-yl, piperidyl substituted with methyl, or pyrrolidinyl substituted with methyl.

(30) The compound or a salt thereof according to (28) above, wherein $R^3$ is cyclobutyl, cyclopentyl, tetrahydrofuran-3-yl or tetrahydro-2H-pyran-4-yl.

(31) The compound or a salt thereof, wherein
$R^1$ is lower alkyl,
$R^2$ is a group of the formula (II),
$R^3$ is tetrahydro-2H-pyran-4-yl or cyclobutyl,
$R^4$, $R^5$ and $R^6$ are hydrogen, and
$R^a$ and $R^b$ are combined with the adjacent nitrogen atom to form piperidyl or piperazinyl, each of which may be substituted, which may be substituted with 1 to 3 groups selected from the group consisting of:
—O-lower alkyl which may be substituted with 1 to 3 halogen atoms; lower alkyl which may be substituted with one or more groups selected from the group consisting of halogen, halogeno-lower alkyl, and —O-lower alkyl; and lower alkylene-O-lower alkyl.

(32) The compound or a salt thereof, wherein
$R^1$ is hydrogen or lower alkyl,
$R^2$ is a group of the formula (II),
$R^3$ is lower alkylene-(cycloalkyl which may be substituted with halogen or —O-lower alkyl); lower alkylene-oxygen-containing saturated hetero ring; cycloalkyl which may be substituted with halogen or —O-lower alkyl; an oxygen-containing saturated hetero ring; or a monocyclic nitrogen-containing saturated hetero ring which may be substituted with lower alkyl, lower alkylene-aryl, or —CO-lower alkylene-O-lower alkyl,
$R^4$, $R^5$ and $R^6$ are hydrogen, and
one of $R^a$ and $R^b$ is hydrogen, and the other is, (a) lower alkyl which may be substituted with a group selected from the group consisting of —OH; —O-lower alkyl; cycloalkyl which may be substituted with a group selected from the group consisting of a hetero ring which may be substituted with —O-lower alkyl, and —N(lower alkyl)$_2$; —NH$_2$; —NH-lower alkyl; —N(lower alkyl)$_2$; —N(lower alkyl)(cycloalkyl); —N(lower alkyl)(aryl); aryl which may be substituted with a group selected from a group $G_1$; a hetero ring which may be substituted with a group selected from a group $G_2$; —CO-(hetero ring which may be substituted with a group selected from a group $G_2$); and —CO—N(lower alkyl)(hetero ring), (b) cycloalkyl which may be substituted with a hetero ring, or (c) a hetero ring which may be substituted with lower alkylene-aryl.

(33) The compound or a salt thereof, wherein
$R^1$ is lower alkyl,
$R^2$ is a group of the formula (II),
$R^3$ is tetrahydropyranyl or cycloalkyl,
$R^4$, $R^5$ and $R^6$ are hydrogen, and
one of $R^a$ and $R^b$ is hydrogen, and the other is (a) lower alkyl which may be substituted with a group selected from the group consisting of —OH; —O-lower alkyl; cycloalkyl which may be substituted with a group selected from the group consisting of a hetero ring which may be substituted with —O-lower alkyl, and —N(lower alkyl)$_2$; —NH$_2$; —NH-lower alkyl; —N(lower alkyl)$_2$; —N(lower alkyl)(cycloalkyl); —N(lower alkyl)(aryl); aryl which may be substituted with a group selected from a group $G_1$; a hetero ring which may be substituted with a group selected from a group $G_2$; —CO-(hetero ring which may be substituted with a group selected from a group $G_2$); and —CO-N(lower alkyl)(hetero ring).

Examples of the specific compounds included in the present invention include the following compounds:

7-methyl-8-[(4-propoxypiperidin-1-yl)carbonyl]-1-(tetrahydro-2H-pyran-4-yl)-1,5-dihydro-4H-pyrazolo[4,3-c]quinolin-4-one, 8-[(4-{[(2S)-2-fluoropropyl]oxy}piperidin-1-yl)carbonyl]-7-methyl-1-(tetrahydro-2H-pyran-4-yl)-1,5-dihydro-4H-pyrazolo[4,3-c]quinolin-4-one, 7-methyl-1-(tetrahydro-2H-pyran-4-yl)-8-{[4-(3,3,3-trifluoropropyl)piperazin-1-yl]carbonyl}-1,5-dihydro-4H-pyrazolo[4,3-c]quinolin-4-one, 7-methyl-1-(tetrahydro-2H-pyran-4-yl)-8-{[4-(4,4,4-trifluorobutyl)piperazin-1-yl]carbonyl}-1,5-dihydro-4H-pyrazolo[4,3-c]quinolin-4-one, 8-{[4-(2,2-difluoro-3-methoxypropyl)piperazin-1-yl]carbonyl}-7-methyl-1-(tetrahydro-2H-pyran-4-yl)-1,5-dihydro-4H-pyrazolo[4,3-c]quinolin-4-one, 1-cyclobutyl-8-{[(3S)-4-(4-methoxybutyl)-3-methylpiperazin-1-yl]carbonyl}-7-methyl-1,5-dihydro-4H-pyrazolo[4,3-c]quinolin-4-one, and salts thereof.

In another embodiment, examples of the specific compounds included in the present invention include the following compounds:

8-[(4-ethoxypiperidin-1-yl)carbonyl]-7-methyl-1-(tetrahydro-2H-pyran-4-yl)-1,5-dihydro-4H-pyrazolo[4,3-c]quinolin-4-one, 8-{[4-(cyclopropylmethoxy)piperidin-1-yl]carbonyl}-7-methyl-1-(tetrahydro-2H-pyran-4-yl)-1,5-dihydro-4H-pyrazolo[4,3-c]quinolin-4-one, 8-{[4-(ethoxymethyl)piperidin-1-yl]carbonyl}-7-methyl-1-(tetrahydro-2H-pyran-4-yl)-1,5-dihydro-4H-pyrazolo[4,3-c]quinolin-4-one, 8-{[4-(4-ethoxybutyl)piperazin-1-yl]carbonyl}-7-methyl-1-(tetrahydro-2H-pyran-4-yl)-1,5-dihydro-4H-pyrazolo[4,3-c]quinolin-4-one, 8-{[4-(ethoxymethyl)piperidin-1-yl]carbonyl}-7-methyl-1-[(3S)-tetrahydrofuran-3-yl]-1,5-dihydro-4H-pyrazolo[4,3-c]quinolin-4-one, 8-{[4-(cyclobutyloxy)piperidin-1-yl]carbonyl}-7-methyl-1-(tetrahydro-2H-pyran-4-yl)-1,5-dihydro-4H-pyrazolo[4,3-c]quinolin-4-one, 8-[(4-{[(2R)-2-fluoropropyl]oxy}piperidin-1-yl)carbonyl]-7-methyl-1-(tetrahydro-2H-pyran-4-yl)-1,5-dihydro-4H-pyrazolo[4,3-c]quinolin-4-one, 8- [(4-{[(2S)-2-fluoropropyl]oxy}piperidin-1-yl)carbonyl]-7-methyl-1-[(3S)-tetrahydrofuran-3-yl]-1,5 -dihydro-4H-pyrazolo[4,3 -c]quinolin-4-one, 1-cyclobutyl-8-{[(3S)-4-(3-methoxypropyl)-3-methylpiperazin-1-yl]carbonyl}-7-methyl-1,5-dihydro-4H-pyrazolo[4,3 -c]quinolin-4-one, 7-methyl-1-[(3 S)-tetrahydrofuran-3-yl]-8-{[4-(4,4,4-trifluorobutyl)piperazin-1-yl]carbonyl}-1,5-dihydro-4H-pyrazolo[4,3-c]quinolin-4-one, 8-[(4-{[(2R)-2-fluoropropyl]oxy}piperidin-1-yl)carbonyl]-7-methyl-1-[(3S)-tetrahydrofuran-3-yl]-1,5-dihydro-4H-pyrazolo[4,3-c]quinolin-4-one, 8-({4-[(cyclopropyloxy)methyl]piperidin-1-yl}carbonyl)-7-methyl-1-(tetrahydro-2H-pyran-4-yl)-1,5-dihydro-4H-pyrazolo[4,3 -c]quinolin-4-one, 1-cyclopentyl-8-{[(3S)-4-(3-methoxypropyl)-3-methylpiperazin-1-yl]carbonyl}-7-methyl-1,5-dihydro-4H-pyrazolo[4,3-c]quinolin-4-one, and salts thereof.

In a further embodiment, examples of the specific compounds included in the present invention include the following compounds:

8-{[4-(methoxymethyl)piperidin-1-yl]carbonyl}-7-methyl-1-(tetrahydro-2H-pyran-4-yl)-1,5-dihydro-4H-pyrazolo[4,3-c]quinolin-4-one, 8-{[4-(3-ethoxypropyl)piperazin-1-yl]carbonyl}-7-methyl-1-(tetrahydro-2H-pyran-4-yl)-1,5-dihydro-4H-pyrazolo[4,3-c]quinolin-4-one, 8-{[4-(2-methoxyethyl)piperidin-1-yl]carbonyl}-7-methyl-1-(tetrahydro-2H-pyran-4-yl)-1,5-dihydro-4H-pyrazolo[4,3-c]quinolin-4-one, 1-cyclobutyl-8-{[4-(3-ethoxypropyl)piperazin-1-yl]carbonyl}-7-methyl-1,5-dihydro-4H-pyrazolo[4,3-c]quinolin-4-one, 1-cyclobutyl-8-{[4-(4-methoxybutyl)piperazin-1-yl]carbonyl}-7-methyl-1,5-dihydro-4H-pyrazolo[4,3-c]quinolin-4-one, 8-{[4-(4-methoxybutyl)piperazin-1-yl]carbonyl}-7-methyl-1-(tetrahydro-2H-pyran-4-yl)-1,5-dihydro-4H-pyrazolo[4,3-c]quinolin-4-one, 8-{[4-(2,2-difluoroethoxy)piperidin-1-yl]carbonyl}-7-methyl-1-(tetrahydro-2H-pyran-4-yl)-1,5-dihydro-4H-pyrazolo[4,3-c]quinolin-4-one, 1-(cyclopropylmethyl)-8-{[4-(4-methoxybutyl)piperazin-1-yl]carbonyl}-7-methyl-1,5-dihydro-4H-pyrazolo[4,3-c]quinolin-4-one, 1-cyclobutyl-7-methyl-8-{[4-(3,3,3-trifluoropropyl)piperazin-1-yl]carbonyl}-1,5-dihydro-4H-pyrazolo[4,3-c]quinolin-4-one, 8-{[4-(2,2-difluoro-3-methoxypropyl)piperazin-1-yl]carbonyl}-7-methyl-1-[(3S)-tetrahydrofuran-3-yl]-1,5-dihydro-4H-pyrazolo[4,3-c]quinolin-4-one, 8-{[4-(2-ethoxyethyl)piperidin-1-yl]carbonyl}-7-methyl-1-(tetrahydro-2H-pyran-4-yl)-1,5-dihydro-4H-pyrazolo[4,3-c]quinolin-4-one, 7-methyl-1-(tetrahydro-2H-pyran-4-yl)-8-({4-[3-(trifluoromethoxy)propyl]piperazin-1-yl}carbonyl)-1,5-dihydro-4H-pyrazolo[4,3-c]quinolin-4-one, 8-{[4-(2,2-difluoropropoxy)piperidin-1-yl]carbonyl}-7-methyl-1-(tetrahydro-2H-pyran-4-yl)-1,5-dihydro-4H-pyrazolo[4,3 -c]quinolin-4-one, 8-{[(3S)-4-(5-fluoro-6-methylpyridin-2-yl)-3-methylpiperazin-1-yl]carbonyl}-7-methyl-1-[(3S)-1-methylpyrrolidin-3-yl]-1,5-dihydro-4H-pyrazolo[4,3-c]quinolin-4-one, 8-{[(3R)-4-(5-fluoro-6-methylpyridin-2-yl)-3-methylpiperazin-1-yl]carbonyl}-7-methyl-1-[(3S)-1-methylpyrrolidin-3-yl]-1,5-dihydro-4H-pyrazolo[4,3-c]quinolin-4-one, 8-{[(2S,5R)-4-(4-methoxybutyl)-2,5-dimethylpiperazin-1-yl]carbonyl}-7-methyl-1-(tetrahydro-2H-pyran-4-yl)-1,5-dihydro-4H-pyrazolo[4,3-c]quinolin-4-one, 8-{[(2S,5R)-2,5-dimethyl-4-(3,3,3-trifluoropropyl)piperazin-1-yl]carbonyl}-7-methyl-1-(tetrahydro-2H-pyran-4-yl)-1,5-dihydro-4H-pyrazolo[4,3-c]quinolin-4-one, 7-methyl-1-[(3S)-tetrahydrofuran-3-yl]-8-{[4-(3,3,3-trifluoropropyl)piperazin-1-yl]carbonyl}-1,5-dihydro-4H-pyrazolo[4,3-c]quinolin-4-one, 1-cyclopentyl-8-{[(3S)-4-(4-methoxybutyl)-3-methylpiperazin-1-yl]carbonyl}-7-methyl-1,5-dihydro-4H-pyrazolo[4,3-c]quinolin-4-one, 1-(cyclopropylmethyl)-8-{[(2S,5R)-4-(4-methoxybutyl)-2,5-dimethylpiperazin-1-yl]carbonyl}-7-methyl-1,5-dihydro-4H-pyrazolo[4,3-c]quinolin-4-one, 1-(cyclopropylmethyl)-8-{[(2S,5R)-2,5-dimethyl-4-(3,3,3-trifluoropropyl)piperazin-1-yl]carbonyl}-7-methyl-1,5-dihydro-4H-pyrazolo[4,3-c]quinolin-4-one, 1-(cyclobutylmethyl)-8-{[(2S,5R)-4-(4-methoxybutyl)-2,5-dimethylpiperazin-1-yl]carbonyl}-7-methyl-1,5-dihydro-4H-pyrazolo[4,3-c]quinolin-4-one, 1-(cyclobutylmethyl)-8-{[(2S,5R)-2,5-dimethyl-4-(3,3,3-trifluoropropyl)piperazin-1-yl]carbonyl}-7-methyl-1,5-dihydro-4H-pyrazolo[4,3-c]quinolin-4-one, 8-{[4-(2,2-difluoropropoxy)piperidin-1-yl]carbonyl}-7-methyl-1-[(3S)-tetrahydrofuran-3 -yl]-1,5-dihydro-4H-pyrazolo[4,3-c]quinolin-4-one, 1-(4,4-difluorocyclohexyl)-8-{[(3S)-4-(4-methoxybutyl)-3-methylpiperazin-1-yl]carbonyl}-7-methyl-1,5-dihydro-4H-pyrazolo[4,3-c]quinolin-4-one, 1-(cyclopropylmethyl)-8-{[(3 S)-4-(4-methoxybutyl)-3-methylpiperazin-1-yl]carbonyl}-7-methyl-1,5-dihydro-4H-pyrazolo[4,3-c]quinolin-4-one, 7-methyl-1-(tetrahydro-2H-pyran-4-yl)-8-{[4-(trifluoromethyl)piperidin-1-yl]carbonyl}-1,5-dihydro-4H-pyrazolo[4,3-c]quinolin-4-one, 8-{[4-(cyclopropylmethoxy)piperidin-1-yl]carbonyl}-7-methyl-1-[(3S)-tetrahydrofuran-3-yl]-1,5-dihydro-4H-pyrazolo[4,3-c]quinolin-4-one, 7-methyl-8 -[(4-propoxypiperidin-1-yl)carbonyl]-1-[(3S)-tetrahydrofuran-3-yl]-1,5-dihydro-4H-pyrazolo[4,3-c]quinolin-4-one, 8-{[4-(2-ethoxyethyl)piperidin-1-yl]carbonyl}-7-methyl-1-[(3S)-tetrahydrofuran-3-yl]-1,5-dihydro-4H-pyrazolo[4,3-c]quinolin-4-one, 8-{[4-(cyclobutyloxy)piperidin-1-yl]carbonyl}-7-methyl-1-[(3S)-tetrahydrofuran-3-yl]-1,5-dihydro-4H-pyrazolo[4,3-c]quinolin-4-one, 7-methyl-1-[(3S)-tetrahydrofuran-3-yl]-8-{[4-(2,2,2-trifluoroethoxy)piperidin-1-yl]carbonyl}-1,5-dihydro-4H-1-pyrazolo[4,3-c]quinolin-4-one, 1-(4,4-difluorocyclohexyl)-8-{[(3S)-4-(3-methoxypropyl)-3-methylpiperazin-1-yl]carbonyl}-7-methyl-1,5-dihydro-4H-pyrazolo[4,3-c]quinolin-4-one, 1-(cyclopropylmethyl)-8-{[(3S)-4-(3-methoxypropyl)-3-methylpiperazin-1-yl]carbonyl}-7-methyl-1,5-dihydro-4H-pyrazolo[4,3-c]quinolin-4-one, 1-(cyclobutylmethyl)-8-{[(3S)-4-(3-methoxypropyl)-3-methylpiperazin-1-yl]carbonyl}-7-methyl-1,5-dihydro-4H-pyrazolo[4,3-c]quinolin-4-one, 8-{[4-(4-ethoxybutyl)piperazin-1-yl]carbonyl}-7-methyl-1-[(3S)-tetrahydrofuran-3-yl]-1,5-dihydro-4H-pyrazolo[4,3-c]quinolin-4-one, 8-{[4-(2-methoxyethyl)piperidin-1-yl]carbonyl}-7-methyl-1-[(3S)-tetrahydrofuran-3-yl]-1,5-dihydro-4H-pyrazolo[4,3-c]quinolin-4-one, 7-methyl-8-{[(3S)-3-methyl-4-(3,3,3-trifluoropropyl)piperazin-1-yl]carbonyl}-1-(tetrahydro-2H-pyran-4-yl)-1,5-dihydro-4H-pyrazolo[4,3-c]quinolin-4-one,
1-(4,4-difluorocyclohexyl)-7-methyl-8-{[(3S)-3-methyl-4-(3,3,3-trifluoropropyl)piperazin-1-yl]carbonyl}-1,5-dihydro-4H-pyrazolo[4,3-c]quinolin-4-one,
1-(cyclopropylmethyl)-7-methyl-8-{[(3S)-3-methyl-4-(3,3,3-trifluoropropyl)piperazin-1-yl]carbonyl}-1,5-dihydro-4H-pyrazolo[4,3-c]quinolin-4-one,
1-(cyclobutylmethyl)-7-methyl-8-{[(3S)-3-methyl-4-(3,3,3-trifluoropropyl)piperazin-1-yl]carbonyl}-1,5-dihydro-4H-pyrazolo[4,3-c]quinolin-4-one,
1-cyclopentyl-7-methyl-8-{[(3S)-3-methyl-4-(3,3,3-trifluoropropyl)piperazin-1-yl]carbonyl}-1,5-dihydro-4H-pyrazolo[4,3 -c]quinolin-4-one,
7-methyl-1-(1-methylpiperidin-4-yl)-8-({4-[(5-methylpyridin-2-yl)oxy]piperidin-1-yl}carbonyl)-1,5-dihydro-4H-pyrazolo[4,3-c]quinolin-4-one,
8-{[(3S)-4-ethyl-3-phenylpiperazin-1-yl]carbonyl}-7-methyl-1-(1-methylpiperidin-4-yl)-1,5-dihydro-4H-pyrazolo[4,3-c]quinolin-4-one,
8-{[4-(cyclopropyloxy)piperidin-1-yl]carbonyl}-7-methyl-1-[(3S)-tetrahydrofuran-3-yl]-1,5-dihydro-4H-pyrazolo[4,3-c]quinolin-4-one,
7-methyl-1-[(3S)-tetrahydrofuran-3-yl]-8-({4-[3-(trifluoromethoxy)propyl]piperazin-1-yl}carbonyl)-1,5-dihydro-4H-pyrazolo[4,3-c]quinolin-4-one,
1-cyclobutyl-7-methyl-8-{[(3S)-3-methyl-4-(3,3,3-trifluoropropyl)piperazin-1-yl]carbonyl}-1,5-dihydro-4H-pyrazolo[4,3-c]quinolin-4-one,
1-(cyclobutylmethyl)-8-({(3S)-4-[2-(cyclopropylmethoxy)ethyl]-3-methylpiperazin-1-yl}carbonyl)-7-methyl-1,5-dihydro-4H-pyrazolo[4,3-c]quinolin-4-one,
8-({4-[2-(cyclopropylmethoxy)ethyl]piperazin-1-yl}carbonyl)-7-methyl-1-(tetrahydro-2H-pyran-4-yl)-1,5-dihydro-4H-pyrazolo[4,3-c]quinolin-4-one,
8-({4-[2-(cyclopropylmethoxy)ethyl]piperazin-1-yl}carbonyl)-7-methyl-1-[(3S)-tetrahydrofuran-3-yl]-1,5-dihydro-4H-pyrazolo[4,3-c]quinolin-4-one,
8-({(3S)-4-[2-(cyclopropylmethoxy)ethyl]-3-methylpiperazin-1-yl}carbonyl)-1-(cyclopropylmethyl)-7-methyl-1,5-dihydro-4H-pyrazolo[4,3-c]quinolin-4-one,
8-{[4-(cyclopropyloxy)piperidin-1-yl]carbonyl}-7-methyl-1-(tetrahydro-2H-pyran-4-yl)-1,5-dihydro-4H-pyrazolo[4,3-c]quinolin-4-one,
8-({4-[3-(cyclopropyloxy)propyl]piperazin-1-yl}carbonyl)-7-methyl-1-(tetrahydro-2H-pyran-4-yl)-1,5-dihydro-4H-pyrazolo[4,3-c]quinolin-4-one,
8-({4-[3-(cyclopropyloxy)propyl]piperazin-1-yl}carbonyl)-7-methyl-1-[(3S)-tetrahydrofuran-3-yl]-1,5-dihydro-4H-pyrazolo[4,3-c]quinolin-4-one,
8-({4-[(cyclopropyloxy)methyl]piperidin-1-yl}carbonyl)-7-methyl-1-[(3S)-tetrahydrofuran-3-yl]-1,5-dihydro-4H-pyrazolo[4,3-c]quinolin-4-one,
8-{[4-hydroxy-4-(trifluoromethyl)piperidin-1-yl]carbonyl}-7-methyl-1-(tetrahydro-2H-pyran-4-yl)-1,5-dihydro-4H-pyrazolo[4,3-c]quinolin-4-one,
1-[(3,3-difluorocyclobutyl)methyl]-8-{[(3S)-4-(4-methoxybutyl)-3-methylpiperazin-1-yl]carbonyl}-7-methyl-1,5-dihydro-4H-pyrazolo[4,3-c]quinolin-4-one, and salts thereof.

The compound of the formula (I) may exist in the form of tautomers or geometrical isomers depending on the kind of substituents. In the present specification, the compound of the formula (I) shall be described in only one form of isomer, yet the present invention includes other isomers, isolated forms of the isomers, or a mixture thereof.

In addition, the compound of the formula (I) may have asymmetric carbon atoms or axial asymmetry in some cases, and correspondingly, it may exist in the form of optical isomers. The present invention includes both an isolated form of the optical isomers of the compound of the formula (I) or a mixture thereof.

Furthermore, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), Vol. 7, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, arginine, tromethamine, ornithine, and the like, salts with various amino acids or amino acid derivatives such as acetylleucine and the like, ammonium salts, etc.

In addition, the present invention also includes various hydrates or solvates, and polymorphic crystal substances of the compound of the formula (I) and a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituent and by applying various known synthesis methods. During the preparation replacement of the relevant 2 5 functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis ($4^{th}$ edition, 2006)" written by P. G. M. Wuts and T. W. Greene, and one of these should only be selected and used as necessary depending on reaction conditions. In this kind of method, a desired compound can be obtained by introducing the protective group, by carrying out a reaction and by eliminating the protective group as necessary.

In addition, the prodrug of the compound of the formula (I) can be produced by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

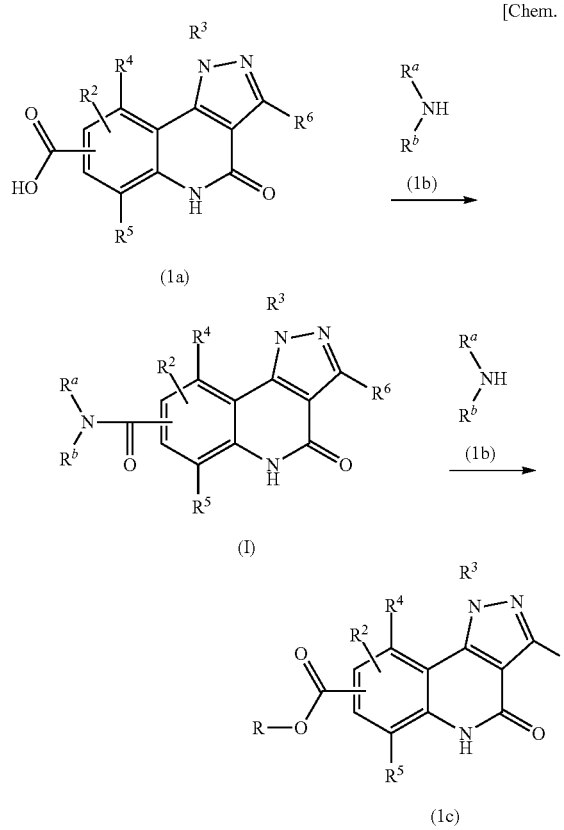

[Chem. 12]

(wherein $R^a$, $R^b$, $R^2$, $R^3$, $R^4$, $R^5$ and $R^6$ represent the same meanings as defined above. R represents lower alkyl. The same shall apply hereinafter.)

The compound (I) of the present invention can be obtained by the reaction of a compound (1a) with a compound (1b).

In this reaction, the compound (1a) and the compound (1b) in equivalent amounts, or with either thereof in an excess amount are used, and a mixture thereof is stirred under any temperature condition from cooling to heating, preferably at −20° C. to 120° C., usually for 0.1 hours to 5 days, in a solvent which is inert to the reaction, in the presence of a fusing agent. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, 1,4-dioxane, dimethoxyethane, and the like, N,N-dimethylformamide (DMF), N-methylpyrrolidone, dimethylsulfoxide, ethyl acetate, acetonitrile or water and a mixture thereof. Examples of the condensation agent include 1-(3-dimethylaminopropyl)-3-ethylcarbodiimide, 1,3-dicyclohexylcarbodiimide, O-(7-azabenzotriazol-1-yl)-N,N,N',N'-tetramethyluronium hexafluorophosphate (HATU), O-(benzotriazol-1-yl)-N,N,N',N'-tetramethyluroniumtetrafluoroborate (TBTU), bromo(tripyrrolidin-1-yl)phosphonium hexafluorophosphate, 1,1'-carbonyldiimidazole (CDI), diphenylphosphoryl azide and phosphoryl chloride, but are not limited to these. Further, a condensation agent-supported polystyrene resin, for example, PS-Carbodiimide (Biotage AB, Sweden) can also be used. It may be preferable for the reaction in some cases to use an additive (for example, 1-hydroxybenzotriazole). It may be advantageous in some cases for the smooth progress of the reaction to carry out the reaction in the presence of an organic base such as triethylamine, N,N-diisopropylethylamine (DIPEA), N-methylmorpholine, and the like, or an inorganic base such as potassium carbonate, sodium carbonate, potassium hydroxide, and the like. Further, use of a microwave reactor (Biotage AB) may allow the smooth progress of the reaction in some cases. Depending on the case, an isocyanate-supported polystyrene resin, for example, PS-Isocyanate (Biotage AB, Sweden) and the like can also be used in order to remove an excess amount of amine after completion of the reaction, and also, a quaternary ammonium salt-supported polystyrene resin, for example, MP-Carbonate (Biotage AB, Sweden) and the like can also be used in order to remove an excess amount of the additives after completion of the reaction.

Moreover, a method in which a carboxylic acid (1a) is converted to its reactive derivative and then reacted with an amine (1b) can also be used. Examples of the reactive derivative of the carboxylic acid include acid halides that can be obtained by the reaction of a halogenating agent such as phosphoryl chloride, thionyl chloride, and the like, mixed acid anhydrides that can be obtained by the reaction of isobutyl chloroformate or the like, active esters obtained by fusion with 1-hydroxybenzotriazole or the like, etc. The reaction of the reactive derivative and the compound (1b) can be carried out under any temperature condition from cooling to heating, preferably at −20° C. to 60° C., in a solvent which is inert to the reaction, such as halogenated hydrocarbons, aromatic hydrocarbons, ethers, and the like.

In addition, a method in which an aluminum amide reagent obtained by reacting an ester (1c) with trimethylaluminum and the amine (1b) is allowed to undergo a reaction can also be used.

For these steps, reference may be made to the methods described in "Organic Functional Group Preparations", written by S. R. Sandler and W. Karo, $2^{nd}$ edition, Vol. 1, Academic Press Inc., 1991, and "Courses in Experimental Chemistry ($5^{th}$ edition)", edited by The Chemical Society of Japan, Vol. 16 (2005) (Maruzen).

In addition, some of the compounds represented by the formula (I) can also be produced from the compound according to the present invention produced as described above by appropriately combining processes usually used by those skilled in the art, such as known alkylation, acylation, substitution, oxidation, reduction, hydrolysis, deprotection, halogenation, and the like (see, for example, "Courses in Experimental Chemistry" ($5^{th}$ edition), edited by The Chemical Society of Japan, (2005) (Maruzen)). Furthermore, a process which can be usually used by those skilled in the art can also be used for intermediates for preparation.

(Starting Material Synthesis 1)

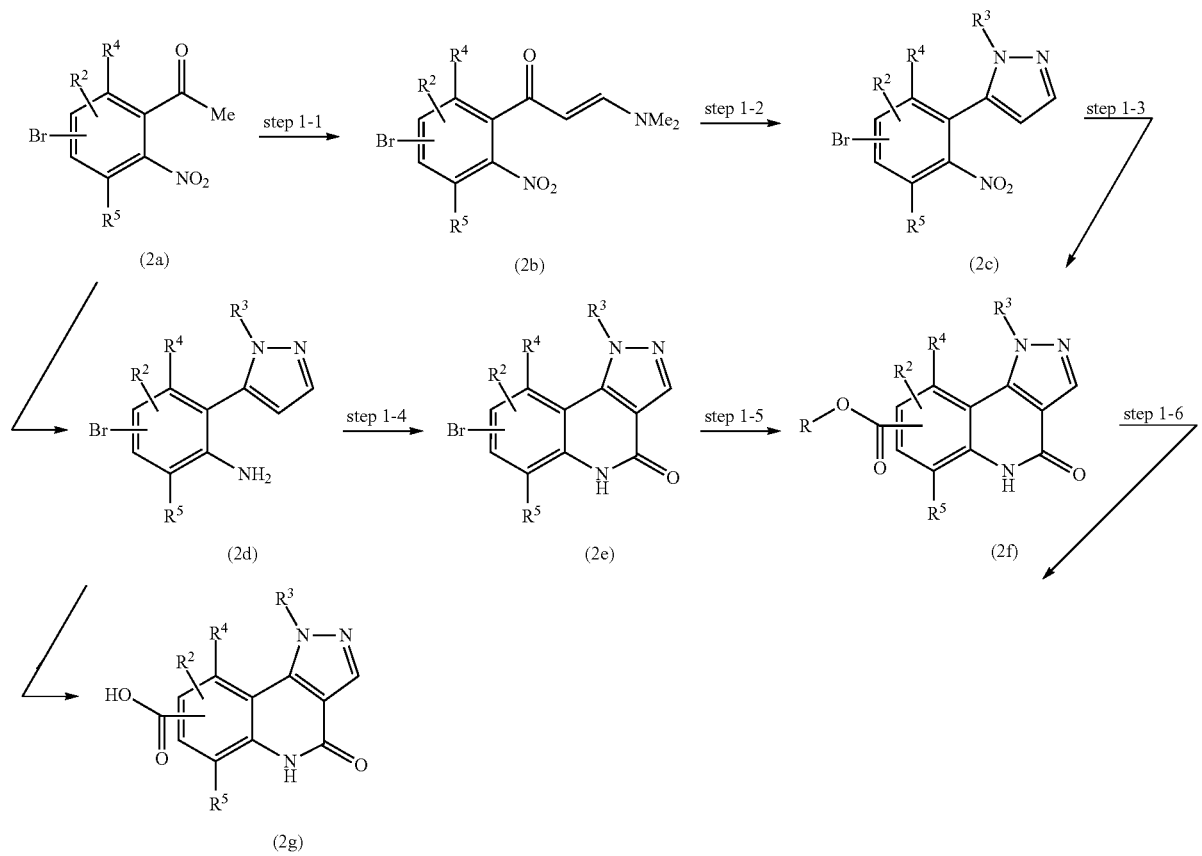

The step represented by Step 1-1 is a reaction for obtaining a compound (2b) by a reaction of a compound (2a) with (dimethoxymethyl)dimethylamine or an equivalent form thereof. In this reaction, the compound (2a) and (dimethoxymethyl)dimethylamine or an equivalent form thereof in equivalent amounts, or with either thereof in an excess amount are used, and a mixture thereof is stirred under any temperature condition from cooling to heating, preferably at 20° C. to 200° C., usually for 0.1 hours to 5 days, in a solvent which is inert to the reaction or without a solvent. As an example of the equivalent form used herein, methoxybis(dimethylamino)methane, (bisethylsulfanylmethyl)dimethylamine, bis(dimethylamino)monomethinium perchlorate, N,N-dimethylformamide diethylacetal, 3-(dimethylamino)-2-azaprop-2-en-1-ylidene dimethylammonium chloride, 2-aza-1,3-bis(dimethylamino)-3-methoxy-1-propene, and the like are known. The solvent as used herein is not particularly limited, but examples thereof include aromatic hydrocarbons such as benzene, toluene, xylene, and the like, ethers such as diethylether, tetrahydrofuran, 1,4-dioxane, dimethoxyethane, and the like, halogenated hydrocarbons such as dichloromethane, 1,2-dichloroethane, chloroform, and the like, N,N-dimethylformamide, N,N-dimethylacetamide, dimethylsulfoxide, ethyl acetate, acetonitrile, N-ethylpyrrolidone and a mixture thereof.

For such a step, reference may be made to the methods described in Bredereck, H. et al., Chemische Berichte, 97, 3397 (1964), Ivanova, I. A. et al., Bulletin of the Academy of Sciences of the USSR, Division of Chemical Science, 1965, 2143, Arnold, Z., Zemlicka, J., Collection of Czechoslovak Chemical Communications, 25, 1302 (1960), Meerwein, H. et al., Justus Liebigs Annalen der Chemie, 641, 1 (1961), Lin, Yang-i, Lang, Stanley, A., Journal of Organic Chemistry, 45(24), 4857 (1980), Cherif, Souheir El, Rene, Loic, Synthesis (1988)2, 138, Gupton, John T., Colon, Cesar et al., Journal of Organic Chemistry, 45(22), 4522 (1980), Kantlehner, Willi, Hauber, Michael, Bulletin des Societes Chimiques Belges, 103(12), 697 (1994), Gorobets, Nikolay Yu. et al., Tetrahedron, 60(39), 8633 (2004), and the like.

Step 1-2 is a step for obtaining a compound (2c) using the compound (2b) and alkylhydrazine or a salt thereof. The mixture thereof is stirred under any temperature condition from cooling to heating, preferably at 20° C. to 120° C., usually for 0.1 hours to 5 days, in a solvent which is inert to the reaction. This reaction may be carried out under any condition of an acidic condition, a neutral condition, and a basic condition. The solvent as used herein is not particularly limited, but examples thereof include aromatic hydrocarbons such as benzene, toluene, xylene, and the like, ethers such as diethylether, tetrahydrofuran, 1,4-dioxane, dimethoxyethane, and the like, halogenated hydrocarbons such as dichloromethane, 1,2-dichloroethane, chloroform, and the like, N,N-dimethylformamide, N,N-dimethylacetamide, dimethylsulfoxide, acetic acid, ethyl acetate, acetonitrile, N-ethylpyrrolidone and a mixture thereof. Although not always clarified, position isomers are generated during the synthesis in the reaction in some cases. However, such a mixture of the position isomers can be isolated by, for example, preparative HPLC, silica gel column chromatography, recrystallization, or the like. For this step, reference may be made to the methods described in Tanaka, Akira et al., Journal of Medicinal Chemistry, 41(13), 2390 (1998), Hernandez, Susana et al., Journal of Organic Chemistry, 75(2), 434 (2010), Adams, Nicholas D. et al., Journal of Medicinal Chemistry, 53(10), 3973 (2010), Speake, Jason D. et al., Bioorganic Medicinal Chemistry Letters, 13(6), 1183 (2006), and the like.

The step represented by Step 1-3 is a step for obtaining a compound (2d) by a reduction reaction of the compound (2c). In this reaction, the compound (2c) is stirred in the presence of a metal catalyst, usually for 1 hour to 5 days, in a solvent which is inert to the reaction. As the metal, iron, zinc, tin, or the like is suitably used. This reaction is carried out under any temperature condition from cooling to heating, preferably at 40° C. to 100° C. This reaction is usually carried out under an acidic condition, but the reduction may also be carried out under a neutral or basic condition in a case of using zinc powder. This reaction can also be carried out using hydrazine monohydrate in an equivalent amount or an excess amount, relative to the compound (2c). In this reaction, stirring is performed in the presence of an iron catalyst such as reduced iron, activated carbon/iron (III) chloride, and the like, usually for 0.5 hours to 5 days, in a solvent inert to the reaction. The solvent as used herein is not particularly limited, but examples thereof include alcohols such as methanol, ethanol, 2-propanol, and the like, ethers such as diethylether, tetrahydrofuran, 1,4-dioxane, dimethoxyethane, and the like, water, acetic acid, ethyl acetate, N,N-dimethylformamide, dimethylsulfoxide and a mixture thereof. For these steps, reference may be made to the methods described in "Courses in Experimental Chemistry" (4$^{th}$ edition), edited by The Chemical Society of Japan, Vol. 20 (1992) (Maruzen), and the like.

Step 1-4 is a step for obtaining a compound (2e) by a cyclization reaction of the compound (2d) with 1,1'-carbonyldiimidazole or triphosgene. The mixture thereof is stirred in the presence of an amine or a base, under any temperature condition from cooling to heating, preferably at 80° C. to 200° C., in a solvent which is inert to the reaction, usually for 0.1 hours to 5 days, more preferably using a microwave reactor.

Further, this reaction may also be carried out in the absence of an amine or a base. Examples of the amine or the base as used herein include triethylamine, diisopropylethylamine, tributylamine, 1,8-diazabicyclo[5.4.0]undecene, 1,5-diazabicyclo[4.3.0]non-5-ene, imidazole, and the like. The solvent as used herein is not particularly limited, but examples thereof include aromatic hydrocarbons such as benzene, toluene, xylene, 1,2-dichlorobenzene, and the like, ethers such as diethylether, tetrahydrofuran, 1,4-dioxane, dimethoxyethane, and the like, halogenated hydrocarbons such as dichloromethane, 1,2-dichloroethane, chloroform, and the like, N,N-dimethylformamide, N,N-dimethylacetamide, N-methylpyrrolidone, N-ethylpyrrolidone, dimethylsulfoxide, sulfolane, acetic acid, ethyl acetate, acetonitrile, and a the mixture thereof. For this step, reference may be made to the method described in J. Med. Chem., 34(9), 2671 (1991).

The step represented by Step 1-5 is a reaction for obtaining a compound (20 by a reaction of the compound (2e) with carbon monoxide and alcohol in the presence of a palladium catalyst. For this step, reference may be made to the method described in Nicolaou, K. C. et al., Angew. Chem. Int. Ed., 44, 4442 (2005), "Topics in Organometallic Chemistry, Vol. 14, Palladium in Organic Synthesis (2005)".

The step represented by Step 1-6 is a reaction for obtaining a compound (2g) by a hydrolysis reaction of the compound (2f). Here, the hydrolysis reaction can be carried out with reference to the method described in "Greene's Protective Groups in Organic Synthesis (4$^{th}$ edition, 2006)".

(Starting Material Synthesis 2)

[Chem. 14]

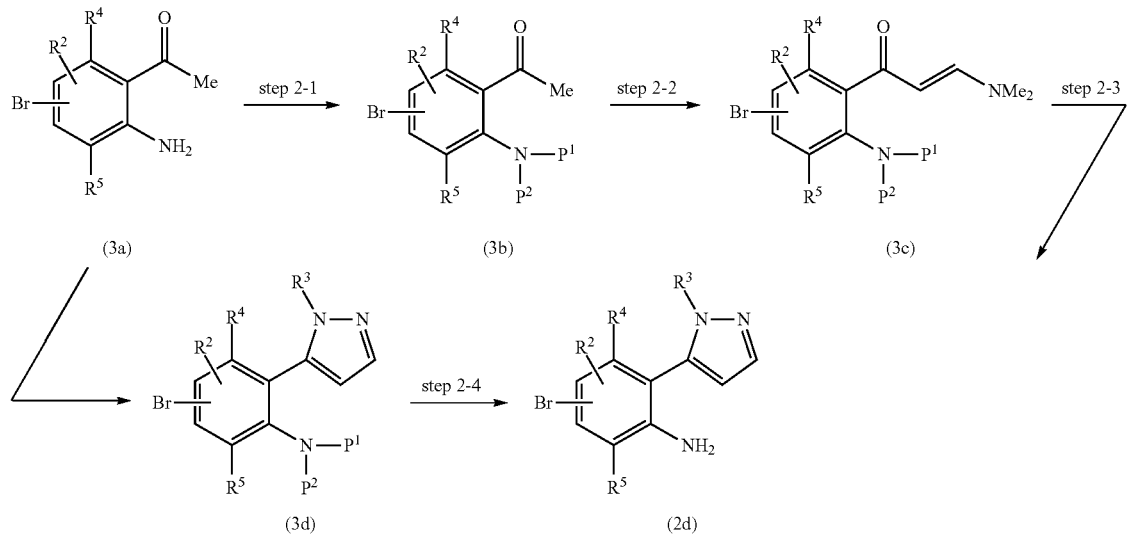

(wherein at least one of $P^1$ and $P^2$ represents a protective group).

The step represented by Step 2-1 is a reaction for obtaining a compound (3b) by introducing a protective group into an amino group of a compound (3a). As the protective group used for protection of the amino group, carbamate, urea, amide, sulfonamide, or the like can be used, and preferably acetyl, methanesulfonyl or p-toluenesulfonyl is used. This reaction can be carried out with reference to the method described in "Greene's Protective Groups in Organic Synthesis (4th edition, 2006)".

The step represented by Step 2-2 is a reaction for obtaining a compound (3c) by a reaction of the compound (3b) with (dimethoxymethyl)dimethylamine or an equivalent form thereof. For this step, the method used in Step 1-1 of (Starting Material Synthesis 1) can be incorporated.

The step represented by Step 2-3 is a reaction for obtaining a compound (3d) by a cyclization reaction using the compound (3c) and alkylhydrazine or a salt thereof. For this step, the method used in Step 1-2 of (Starting Material Synthesis 1) can be incorporated.

The step represented by Step 2-4 is a reaction for obtaining a compound (2d) by a deprotection reaction of the protective group of the compound (3d). This reaction can be carried out with reference to the method described in "Greene's Protective Groups in Organic Synthesis (4th edition, 2006)".

(Starting Material Synthesis 3)

solvent as used herein is not particularly limited, but examples thereof include alcohols such as methanol, ethanol, 2-propanol, and the like, ethers such as diethylether, tetrahydrofuran, 1,4-dioxane, dimethoxyethane, and the like, benzene, toluene, dichloromethane, chloroform, dichloroethane, carbon tetrachloride, and a the mixture thereof. For this step, reference may be made to the methods described in Arnould, J. C. et al., Journal of Medicinal Chemistry, 35(14), 2631 (1992), Sato, Masayuki et al., Chemical Pharmaceutical Bulletin, 31(6) 1896 (1983).

Step 3-2 is a step for obtaining a compound (4c) by the decarboxylation of the compound (4b). In this reaction, the compounds are stirred using an acid in an amount ranging from a catalytic amount to an excess amount, usually for 1 hours to 5 days, in a solvent which is inert to the reaction under a nitrogen atmosphere. This reaction is usually carried out under any temperature condition from cooling to heating. The acid as used herein is not particularly limited, but

[Chem. 15]

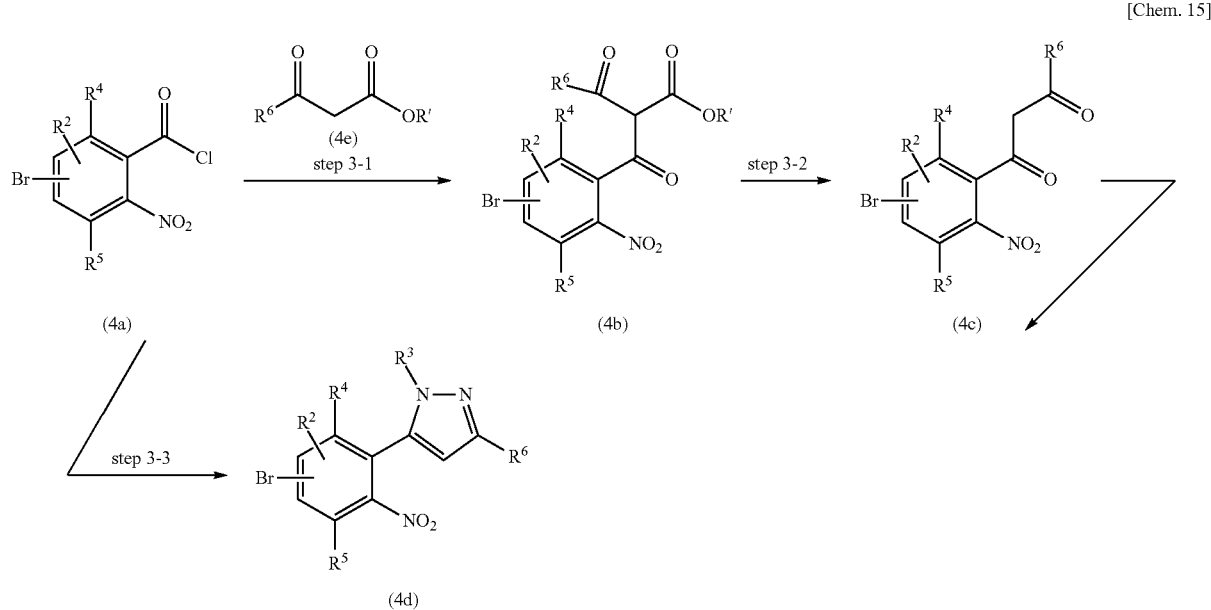

(wherein R' represents lower alkyl).

Step 3-1 is a step for obtaining a compound (4b) by condensation of a compound (4a) with a compound (4e).

In this reaction, the compound (4a) and the compound (4e) are stirred in the presence of a metal or a metal salt, and an equivalent amount or an excess amount of an amine or a base, in a solvent which is inert to the reaction, usually for 1 hour to 5 days, under a nitrogen atmosphere. This reaction is carried out under any temperature condition from cooling to heating, preferably at −20° C. to room temperature. The metal or a metal salt used herein is not particularly limited, but examples thereof include magnesium, magnesium ethoxide, magnesium chloride, samarium chloride, and the like. The amine or the base used herein is not particularly limited, but examples thereof include triethylamine, N-ethyl-N-isopropylpropan-2-amine, tributylamine, 1,8-diazabicyclo[5.4.0]undecene, 1,5-diazabicyclo[4.3.0]non-5-ene, imidazole, pyridine, 2,6-lutidine, quinoline, N,N-dimethylaniline, sodium hydride, sodium hydroxide, potassium hydroxide, sodium methoxide, sodium ethoxide, potassium t-butoxide, sodium carbonate, potassium carbonate, cesium carbonate, and the like. The examples thereof include hydrochloric acid, hydrobromide, sulfuric acid, methanesulfonic acid, 4-toluenesulfonic acid, D-camphorsulfonic acid, trifluoroacetic acid, and the like. The solvent as used herein is not particularly limited, but examples thereof include alcohols such as methanol, ethanol, 2-propanol, and the like, ethers such as diethylether, tetrahydrofuran, 1,4-dioxane, dimethoxyethane, and the like, benzene, toluene, dichloromethane, chloroform, dichloroethane, acetonitrile, water, acetic acid, and a mixture thereof. Further, a method for obtaining the compound (4c) from the compound (4b) using sodium chloride in dimethylsulfoxide can also be obtained. Such step can be carried out with reference to the method described in WO2004/63197 A1, Cegne-Laage, Emmanuelle et al., Chemistry-A European Journal, 10(6), 1445 (2004).

Step 3-3 is a step for obtaining a compound (4d) by a reaction using the compound (4c) with alkylhydrazine or a salt thereof. For this step, the method used in Step 1-2 of (Starting Material Synthesis 1) can be incorporated.

The compounds of the formula (I) can be isolated and purified as their free compounds, salts, hydrates, solvates, or polymorphic crystal substances thereof. The salts of the compound of the formula (I) can also be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting material.

The pharmacological activity of the compound of the formula (I) was confirmed by the tests shown below.

Test Example 1

PDE9-Inhibiting Activity (1) Acquisition of PDE9

The PDE9 used in the present experiment was expressed/purified by the method as in, for example, Guipponi et al., and Fisher et al. (Fisher, D. A., et al., J. Biol. Chem., 273: pp. 15559-15564 (1998), Guipponi, M., et al., Hum. Genet., 103: pp. 386-392 (1998)).

(2) Evaluation of PDE9-Inhibiting Activity

The PDE9-inhibiting activity was measured by the following method. That is, to a buffer solution containing tris(hydroxymethyl)aminomethane-hydrochloric acid (40 mM, pH 8.0), magnesium chloride (5 mM), and 2-mercaptoethanol (4 mM) were added cGMP (1 µM) and $^3$H-cGMP (0.33 µCi/ml) to give a substrate buffer solution.

A test substance solution and an enzyme solution which had been adjusted to an optimal concentration were added thereto to perform a reaction at 30° C. The enzyme reaction was stopped by the addition of Scintillation Proximity Assay (SPA) Beads (Perkin Elmer, USA) containing 5 mM 3-isobutyl-1-methylxanthine (IBMX). For the enzyme activity, the amount of 5'-GMP, which is a reaction degradation product bound to SPA beads, was measured with a TopCount microplate reader (Hewlett Packard, USA).

The inhibitory rate was calculated by taking the radioactivity of the control containing no test substance as (A), taking the radioactivity of the blank containing no enzyme as (B), and taking the radioactivity of the test substance as (C), and using the following equation.

Inhibitory rate=100−{(C)−(B)/(A)−(B)}×100 (%)

In addition, the $IC_{50}$ value was calculated as a compound concentration which inhibits the results obtained by 50% by a Logistic regression method.

(3) Other Evaluation of PDE-Inhibiting Activity

For the PDE1, a recombinant enzyme was purchased (BPS Bioscience Inc., USA). The PDE2 was expressed/purified by a method of Yang et al. (Yang, Q., et al., Biochem. Biophys. Res. Commun., 205: pp. 1850-1858 (1994)), and the PDE4 was expressed/purified by a method of Nemoz et al. (Nemoz, G., et al., FEBS Lett., 384: pp. 97-102 (1996)). The PDE3, PDE5 and PDE6 were isolated from rabbit myocardium, rabbit prostate, and rat retina. That is, desired tissues were selected from each of the animals, and chipped in a buffer solution containing bis(2-hydroxyethyl)iminotris(hydroxymethyl)aminomethane (20 mM), dithiothreitol (5 mM), glycol ether diamine tetraacetic acid (2 mM), and sodium acetate (50 mM). Then, the cells were crushed using a Poritoron homogenizer. Each tissue homogenates were ultracentrifuged (100,000×g, 4° C., 60 minutes), and then, the supernatant was added to a Q Sepharose column. By the concentration gradient of a buffer solution containing 0.05 to 1.2 M sodium acetate, sodium chloride (140 mM), potassium chloride (5 mM), glucose (5 mM), and 2-[4-(2-hydroxyethyl)-1-piperazinyl]ethanesulfonic acid (10 mM), elution was performed by ion exchange to obtain a fraction as a source of enzymes. For each of the eluate fractions, PDE subtypes were identified by enzymatic properties and selective inhibitor susceptibility.

For the PDE enzyme activity, the degradability for cAMP or cGMP was measured by the amount of 5'-AMP or 5'-GMP, which is a reaction degradation product bound to SPA beads, by the method as in PDE9 above.

For the compound of the formula (I), the PDE9-inhibiting activity action was confirmed by the test method above. The PDE9-inhibiting activity actions ($IC_{50}$ values: nM) of some compounds are shown in Table 1, in which Ex denotes Example Nos. as described later (the same shall apply hereinafter).

TABLE 1

| Ex | PDE9 inhibition (nM) |
|---|---|
| 1 | 18 |
| 2 | 12 |
| 6 | 7.6 |
| 12 | 8.6 |
| 13 | 85 |
| 14 | 81 |
| 16 | 9.1 |
| 17 | 2.1 |
| 22 | 2.2 |
| 23 | 0.4 |
| 28 | 9.1 |
| 40 | 8.9 |
| 41 | 5.7 |
| 49 | 3.9 |
| 50 | 7.5 |
| 53 | 3.9 |
| 55 | 15 |
| 56 | 4.4 |
| 63 | 8.4 |
| 66 | 4.3 |
| 70 | 17 |
| 74 | 12 |
| 79 | 23 |
| 84 | 9.3 |
| 86 | 3.3 |
| 87 | 12 |
| 92 | 6.1 |
| 94 | 1.7 |
| 95 | 14 |
| 103 | 13 |
| 107 | 15 |
| 109 | 5.8 |
| 119 | 8.9 |
| 123 | 18 |
| 127 | 5.0 |
| 128 | 5.2 |
| 129 | 1.1 |
| 133 | 8.3 |
| 139 | 3.0 |
| 145 | 8.3 |
| 146 | 5.2 |
| 148 | 5.1 |
| 150 | 8.0 |
| 152 | 53 |
| 154 | 32 |

TABLE 1-continued

| Ex | PDE9 inhibition (nM) |
|---|---|
| 161 | 31 |
| 162 | 7.0 |
| 166 | 10 |
| 168 | 4.3 |
| 169 | 2.5 |
| 173 | 6.3 |
| 176 | 8.4 |
| 177 | 9.7 |
| 178 | 4.4 |
| 179 | 6.8 |
| 181 | 4.4 |
| 182 | 5.5 |
| 183 | 3.5 |
| 184 | 4.7 |
| 185 | 19 |
| 186 | 3.8 |
| 187 | 8.4 |
| 188 | 14 |
| 189 | 6.9 |
| 190 | 7.5 |
| 191 | 9.5 |
| 192 | 11 |
| 193 | 5.7 |
| 195 | 4.4 |
| 198 | 3.2 |
| 199 | 4.7 |
| 200 | 9.0 |
| 201 | 6.6 |
| 202 | 3.7 |
| 203 | 2.8 |
| 204 | 6.2 |
| 207 | 1.7 |
| 208 | 1.7 |
| 210 | 1.3 |
| 211 | 1.2 |
| 212 | 2.4 |
| 213 | 11 |
| 214 | 16 |
| 217 | 4.4 |
| 218 | 17 |
| 219 | 15 |
| 220 | 16 |
| 221 | 24 |
| 283 | 5.9 |
| 427 | 20 |
| 624 | 10 |
| 640 | 3.3 |
| 648 | 2.0 |
| 655 | 4.7 |
| 660 | 28 |
| 668 | 9.8 |

Furthermore, it was confirmed that a majority of the Example compounds included in the compound of the formula (I), in particular, "the compound, wherein $R^2$ is a group of the formula (II), and $R^a$ and $R^b$ are combined with the adjacent nitrogen atom to form a monocyclic nitrogen-containing hetero ring which may be substituted" have a selective PDE9 inhibitory activity. The selective PDE9-inhibiting activity refers to a more potent inhibiting activity than the inhibiting activity particularly on PDE1, PDE3 and PDE6, and it is, for example, a case where the $IC_{50}$ value (nM) is $1/10$ or less, as compared with any of PDE1, PDE3 and PDE6, preferably a case where the $IC_{50}$ value (nM) is $1/50$ or less, as compared with 1, 2, or all of PDE1, PDE3 and PDE6, and more preferably a case where the $IC_{50}$ value (nM) is $1/100$ or less, as compared with 1, 2, or all of PDE1, PDE3, and PDE6.

Test Example 2

Evaluation of PDE9-Inhibiting Activity in Cells

A CRE-luc gene in which a luciferase (luc) gene was linked to the PDE9 gene and the cyclic AMP response element (CRE) gene in the HEK293 cell was transiently introduced to prepare a PDE9 and CRE-luc co-expressing cell. The next day, a 0.5 mM IBMX and a test substance solution were added to the cells and cultured at 37° C. for 6 hours, and then the culture supernatant was removed. 0.2% Triton X-100-containing phosphate buffer solution was added thereto to crush the cells. The PDE9-inhibiting activity in the cell was evaluated by adding a luciferin substrate liquid to the cell solution obtained by crushing the cells and measuring the luciferase activity in a fluorescence/luminescence plate reader.

As a result, it was confirmed that there are some compounds exhibiting the effective activity among the compounds of the formula (I).

Test Example 3

Action in Simultaneous Measurement Model for Rat Bladder Contraction/Urethra Relaxation Responses Simultaneous measurement of the bladder contraction and urethra relaxation responses using a rat was carried out with a partial modification of a method in Wibberley et al. (Wibberley, A., et al., Br. J. Pharmacol., 136: pp. 399-414 (2002)). That is, a female Sprague-Dawley (SD) rat (Charles River Laboratories Japan, Inc.) was anesthetized with urethane, and the bladder was exposed by a midline incision in the lower abdomen. A double lumen cannula (a cannula having a dual structure by PE190 and PE50) from the bladder apex was inserted into the bladder, and the bladder apex and the cannula were fixed by sutures at a point where the tip reached the proximal urethra. While infusing physiological saline into the urethra through the outer cannula, the urethral inner pressure was measured by a pressure transducer through the inner cannula with a saline solution infused into the urethra through the outer cannula. On the other hand, a single cannula (PE50) was inserted into the bladder from the bladder apex and placed therein. The inner pressure of the bladder was measured through this cannula. After a postoperative stabilization period had passed, physiological saline was infused into the bladder through the cannula of the bladder apex to cause a bladder contraction reaction, and thus cause a urethra relaxation response accompanying the bladder contraction reflex. The test substance was administered intravenously or intraduodenally.

As a result, it was confirmed that there are some compounds exhibiting the effective activity among the compounds of the formula (I). For some of the compounds of the formula (I), the ratio with increased urethra relaxation time during voiding at 1 mg/kg (increase relative to the solvent administration group (vs vehicle) (%)) is shown in Table 2.

TABLE 2

| Ex | Ratio with increased urethra relaxation time during voiding (vs vehicle) (%) |
|---|---|
| 22 | 142 |
| 23 | 168 |
| 40 | 138 |
| 41 | 159 |
| 53 | 145 |
| 55 | 166 |

TABLE 2-continued

| Ex | Ratio with increased urethra relaxation time during voiding (vs vehicle) (%) |
|---|---|
| 56 | 158 |
| 79 | 139 |
| 84 | 154 |
| 95 | 166 |
| 109 | 158 |
| 128 | 136 |

Test Example 4

Action in Rat Drug-Induced Voiding Dysfunction Model

A male SD rat (Japan SLC, Inc.) was put under anesthesia with isoflurane to place a cannula in the bladder and the jugular vein and was later aroused in a Ballman cage. After a postoperative stabilization period, physiological saline was infused into the bladder to cause voiding. Infusion of the physiological saline was stopped immediately after voiding, and the amount of the drained urine was measured using a pan balance placed under a Ballman cage. After completion of voiding, the residual urine was collected by gravity through a cannula placed in the bladder, and the weight was measured. Further, the inner pressure of the bladder was measured by a pressure transducer through the bladder cannula. Voiding dysfunction was caused by intravenous administration of one or a combination of an anticholinergic agent, an $\alpha_1$ receptor agonist, and an NO production inhibitor, and the voiding dynamics were observed after the drug administration. The test substance was administered intravenously, orally or gastrically.

As a result, it was confirmed that there are some compounds exhibiting the effective activity among the compounds of the formula (I).

As a result of the test above, it was confirmed that some of the compound of the formula (I) has a PDE9-inhibitory action and it was confirmed that some of the compounds of the formula (I) have a urethra relaxation action during voiding in the animal models as well. Accordingly, the compound of the formula (I) can be used for preventing or treating diseases related to degradation of cGMP by PDE9, for example, diseases such as storage dysfunction, voiding dysfunction, bladder/urethral diseases, in another embodiment, underactive bladder, hypotonic bladder, acontractile bladder, detrusor underactivity, neurogenic bladder, urethra relaxation failure or detrusor-external urethral sphincter dyssynergia, overactive bladder, and lower urinary tract symptoms thereof, and benign prostatic hyperplasia, interstitial cystitis, chronic prostatitis, urethra calculus, and lower urinary tract symptoms accompanying them, and the like, and in a further embodiment, underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis, urethra calculus, and the like.

Furthermore, some compounds, wherein $R^2$ is a group of the formula (II), $R^4$ to $R^6$ are hydrogen, $R^a$ and $R^b$ are combined with the adjacent nitrogen atom to form a monocyclic nitrogen-containing hetero ring which may be substituted, among the compounds of the formula (I), have a selective PDE9 inhibitory activity and as a result, the side effects derived from the action of other PDE subtypes can be avoided, whereby the compounds can be excellent therapeutic agents having higher safety. For example, cardiovascular risk derived from the PDE3 inhibitory action or the risk of blindness derived from the PDE6 inhibitory action can be avoided (A. M. Laties Drug Safety 2009; 32, 1-18/J. B. Shipley et al., Am. J. Med. Sci., 1996; 311, 286-291/T. M. Vinogradova et al., Circ. Res., 2008; 102, 761-769).

A pharmaceutical composition containing one or two or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration injections, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalers, and the like.

The solid composition for use in the oral administration according to the present invention is used in the form of tablets, powders, granules, or the like. In such a solid composition, one or two or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics and antiseptics.

The injections for parenteral administration include sterile aqueous or non-aqueous solution preparations, suspensions and emulsions. The aqueous solvent includes, for example, distilled water for injection and physiological saline. Examples of the non-aqueous solvent include propylene glycol, polyethylene glycol, plant oils such as olive oil, alcohols such as ethanol, Polysorbate 80 (Japanese Pharmacopeia), and the like. Such a composition may further contain a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, patches, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like, or other forms.

In oral administration, the daily dose is generally from about 0.001 to 100 mg/kg, preferably from 0.1 to 30 mg/kg, and more preferably from 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age and the gender, and the like into consideration.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) can be used in combination with various agents for treating or preventing diseases for which the compound of the formula (I) is considered to be effective. The combined preparation may be administered simultaneously, or separately and continuously, or at a desired time interval. The preparations to be co-administered may be a blend, or may be prepared individually.

EXAMPLES

Hereinbelow, the preparation methods for the compound of the formula (I) will be described in more detail with reference to Examples. Further, the present invention is not limited to the compounds described in the Examples as described below. Furthermore, each of the production processes for the starting compounds will be described in Preparation Examples. Further, the preparation methods for the compound of the formula (I) are not limited to the preparation methods of the specific Examples as below, but the compound of the formula (I) can be prepared by any combination of the preparation methods or the methods that are apparent to a person skilled in the art.

In addition, for salt forming reactions that are apparent to a person skilled in the art, there are cases where addition or omission to or of the specific preparation methods of Examples or Preparation Examples. Further, there are cases where the reaction temperatures vary within a range apparent to a person skilled in the art, considering the production of the reaction rate of the compound, the production of by-products, and the like.

The following abbreviations may be used in some cases in the Examples, Preparation Examples and Tables below. tert-: Tertiary, Pr: Preparation Example No., Ex: Example No., No: Compound No., Structure: Structural formula, Syn: Preparation method (the numeral shows that the Example compound was prepared in the same manner as a compound having its number as the Example No.), Data: Physicochemical data, ESI+: m/z values in mass spectroscopy (Ionization ESI, representing (M+H)$^+$ unless otherwise specified), ESI−: m/z values in mass spectroscopy (Ionization ESI, representing (M−H)$^−$ unless otherwise specified), EI+: m/z values in mass spectroscopy (Ionization EI, representing (M)$^+$ unless otherwise specified), FAB+: m/z values in mass spectroscopy (Ionization FAB, representing (M+H)$^+$ unless otherwise specified), FAB−: m/z values in mass spectroscopy (Ionization FAB, representing (M−H)$^−$ unless otherwise specified), APCI+: m/z values in mass spectroscopy (Ionization APCI, representing (M+H)$^+$ unless otherwise specified), APCI/ESI+: m/z values in mass spectroscopy (Ionization APCI and ESI simultaneously performed, representing (M+H)$^+$ unless otherwise specified), APCI/ESI−: m/z values in mass spectroscopy (Ionization APCI and ESI simultaneously performed, representing (M−H)$^−$ unless otherwise specified), mp.: Melting point, dec.: decomposition, NMR: δ (ppm) of peak in $^1$H NMR, s: singlet (spectrum), d: doublet (spectrum), t: triplet (spectrum), q: quartet (spectrum), and br: broad line (spectrum) (example: br s). Further, HCl in the structural formula represents hydrochloride (the numeral prefixed to HCl denotes a molar ratio). In addition, [M] of the concentration represents [mol/L]. A case where there is a description of "Chiral" in the structural formula indicates that the Example compound is an optically active form, but there are some cases where the stereochemistry is not determined. A case where there is no description of "Chiral" in the structural formula indicates that the Example compound is a mixture of geometrical isomers, or a racemate. Accordingly, a case where there is a description of stereochemistry but there is no description of "Chiral" indicates a racemic mixture of diastereomers having relative configurations, and a case where there is neither a description of stereochemistry nor a description of "Chiral" indicates a mixture of geometrical isomers, or a mixture of optical isomers.

Preparation Example 1

To a mixture of 980 mg of 5-(4-bromo-2-nitrophenyl)-1-cyclopentyl-1H-pyrazole, 9.8 mL of tetrahydrofuran, 19.6 mL of ethanol, and 2.9 mL of water was added 102 mg of ammonium chloride, followed by heating at 70° C. 1.03 g of reduced iron was added thereto, followed by heating to reflux for 4 hours, and cooling to room temperature. The insoluble material was filtered through celite, the filtrate was concentrated, and a mixture of chloroform/water was added thereto. The aqueous layer was separated, and then the organic layer was washed with saturated brine and dried over anhydrous magnesium sulfate. The solvent was evaporated under reduced pressure and the residue was purified by silica gel column chromatography (n-hexane/ethyl acetate) to obtain 815 mg of 5-bromo-2-(1-cyclopentyl-1H-pyrazol-5-yl) aniline.

Preparation Example 2

Under a nitrogen atmosphere, to a solution of 1.15 g of (2E)-1-(4-bromo-2-nitrophenyl)-3-(dimethylamino)prop-2-en-1-one in 9.2 mL of acetic acid was added 1.05 g of cyclopentylhydrazine hydrochloride, followed by stirring at room temperature for 60 hours. The reaction mixture was poured into a mixture of water/ethyl acetate, followed by adjusting to pH 10 with a 6 M aqueous sodium hydroxide solution. The aqueous layer was separated, and then the organic layer was washed with water and saturated brine, and dried over anhydrous magnesium sulfate. The solvent was evaporated under reduced pressure, and then the residue was purified by silica gel column chromatography (n-hexane/ethyl acetate) to obtain 940 mg of 5-(4-bromo-2-nitrophenyl)-1-cyclopentyl-1H-pyrazole.

Preparation Example 3

To a solution of 100 mg of 5-bromo-2-(1-cyclopentyl-1H-pyrazol-5-yl)aniline in 2.5 mL of N-methylpyrrolidone was added 105 mg of CDI, followed by stirring at 150° C. for 2 hours using a microwave reactor, and cooling to room temperature. The precipitated solid was collected by filtration, washed with ethyl acetate, and then dried under reduced pressure to obtain 73 mg of 7-bromo-1-cyclopentyl-1,5-dihydro-4H-pyrazolo[4,3-c]quinolin-4-one.

Preparation Example 4

Under a nitrogen atmosphere, a mixture of 3.62 g of 1-(4-bromo-2-nitrophenyl)ethanone and 5.3 g of (dimethoxymethyl)dimethylamine was stirred at 90° C. for 4 hours. The reaction mixture was cooled to room temperature and the precipitated solid was collected by filtration. The obtained solid was washed with diisopropyl ether and dried under reduced pressure to obtain 3.93 g of (2E)-1-(4-bromo-2-nitrophenyl)-3-(dimethylamino)prop-2-en-1-one.

Preparation Example 5

To a solution of 735 mg of 7-bromo-1-cyclopentyl-1,5-dihydro-4H-pyrazolo[4,3-c]quinolin-4-one in 6 mL of dimethylsulfoxide were sequentially added 49 mg of palladium acetate, 91 mg of 1,3-bis(diphenylphosphino)propane, 0.62 mL of triethylamine, and 3 mL of methanol, and the atmosphere in the reaction container was replaced with carbon monoxide. The mixture was stirred at 70° C. for 7 hours, cooled to room temperature, and then poured into a mixture of water and ethyl acetate. The aqueous layer was separated, the organic layer was washed with diluted hydrochloric acid and saturated brine, and then dried over anhydrous magnesium sulfate, and the solvent was evaporated under reduced pressure. The obtained residue was purified by silica gel column chromatography (chloroform/methanol) to obtain 551 mg of methyl 1-cyclopentyl-4-oxo-4,5-dihydro-1H-pyrazolo[4,3-c]quinoline-7-carboxylate.

Preparation Example 6

Under a nitrogen atmosphere, to a solution of 6.95 g of 1-(2-amino-5-bromo-4-methylphenyl)ethanone and 8.5 mL of triethylamine in 104 mL of tetrahydrofuran was slowly added 3.25 mL of acetyl chloride. After stirring at room temperature for 2 hours, the reaction mixture was poured into a mixture of water/ethyl acetate, followed by stirring for 30 minutes and adjusting to pH 3 with 6 M hydrochloric acid, and the aqueous layer was separated. The organic layer was washed with water and saturated brine, and dried over anhydrous magnesium sulfate. The solvent was evaporated under reduced pressure and then the residue was purified by silica gel column chromatography (n-hexane/ethyl acetate) to obtain 6.33 g of N-(2-acetyl-4-bromo-5-methylphenyl)acetamide.

Preparation Example 7

Under a nitrogen atmosphere, 6.33 g of N-(2-acetyl-4-bromo-5-methylphenyl)acetamide was added to a mixture of 3.3 g of (dimethoxymethyl)dimethylamine and 19 mL of toluene, followed by stirring at 120° C. for 16 hours. The mixture was cooled to room temperature, concentrated, and diisopropyl ether was added thereto and triturated. The powder was collected by filtration, washed with diisopropyl ether, and then dried under reduced pressure to obtain 6.92 g of N-{4-bromo-2-[(2E)-3-(dimethylamino)prop-2-enoyl]-5-methylphenyl}acetamide.

Preparation Example 8

To a solution of 3.37 g of tetrahydro-2H-pyran-4-ylhydrazine hydrochloride in 120 mL of ethanol was added 3.82 g of powdery potassium carbonate, followed by stirring at room temperature for 30 minutes. To a mixture was added 6 g of N-{4-bromo-2-[(2E)-3-(dimethylamino)prop-2-enoyl]-5-methylphenyl}acetamide, followed by stirring at 80° C. for 16 hours and cooling to room temperature. The mixture was poured into a mixture of water/ethyl acetate, and the aqueous layer was separated. The organic layer was washed with water and saturated brine, and dried over anhydrous magnesium sulfate. The solvent was evaporated under reduced pressure and the residue was purified by silica gel column chromatography (n-hexane/ethyl acetate) to obtain 3.96 g of N-{4-bromo-5-methyl-2-[1-(tetrahydro-2H-pyran-4-yl)-1H-pyrazol-5-yl]phenyl}acetamide.

Preparation Example 9

A mixture of 3.96 g of N-{4-bromo-5-methyl-2-[1-(tetrahydro-2H-pyran-4-yl)-1H-pyrazol-5-yl]phenyl}acetamide and 18 mL of 12 M hydrochloric acid was stirred at 120° C. for 40 minutes. The reaction mixture was cooled to room temperature, then poured into a mixture of a saturated aqueous sodium hydrogen carbonate solution/ethyl acetate, and adjusted to pH 10 with a 6 M aqueous sodium hydroxide solution. The aqueous layer was separated, and then the organic layer was washed with saturated brine and dried over anhydrous magnesium sulfate. The solvent was evaporated under reduced pressure and then the residue was purified by silica gel column chromatography (n-hexane/ethyl acetate) to obtain 3.36 g of 4-bromo-5-methyl-2-[1-(tetrahydro-2H-pyran-4-yl)-1H-pyrazol-5-yl]aniline.

Preparation Example 10

To a mixture of 2.63 g of methyl 7-methyl-4-oxo-1-(tetrahydro-2H-pyran-4-yl)-4,5-dihydro-1H-pyrazolo[4,3-c]quinoline-8-carboxylate and 52 mL of methanol was added 10.2 mL of a 3 M aqueous sodium hydroxide solution, followed by stirring at 60° C. for 20 hours. The insoluble material was filtered, and the filtrate was adjusted to pH 2 with concentrated hydrochloric acid, and stirred for 1 hour. The precipitated powder was collected by filtration and dried under reduced pressure to obtain 2.49 g of 7-methyl-4-oxo-1-(tetrahydro-2H-pyran-4-yl)-4,5-dihydro-1H-pyrazolo[4,3-c]quinoline-8-carboxylic acid as powder.

Preparation Example 11

Under a nitrogen atmosphere, to a solution of 1.0 g of 1-(4-bromo-2-nitrophenyl)butane-1,3-dione in 10 ml of acetic acid was added 501 mg of cyclopentylhydrazine hydrochloride, followed by stirring at 100° C. for 1 hour and 30 minutes. The reaction mixture was concentrated, and to the obtained residue was added ethyl acetate. The solution was washed with a saturated aqueous sodium hydrogen carbonate solution and saturated brine, and dried over anhydrous magnesium sulfate. The solvent was evaporated under reduced pressure and then the residue was purified by silica gel column chromatography (chloroform/methanol) to obtain 770 mg of 5-(4-bromo-2-nitrophenyl)-1-cyclopentyl-3-methyl-1H-pyrazole.

Preparation Example 12

Under a nitrogen atmosphere, to a solution of 4.95 g of tert-butyl 2-(4-bromo-2-nitrobenzoyl)-3-oxobutanoate in 30 mL of dichloromethane was added 20 mL of trifluoroacetic acid under ice-cooling. The mixture was warmed to room temperature and stirred for 2.5 hours, and then the solvent was evaporated under reduced pressure. To the residue was added ethyl acetate, and the solution was washed with a saturated aqueous sodium hydrogen carbonate solution and saturated brine, and dried over anhydrous magnesium sulfate. The solvent was evaporated under reduced pressure and the residue was purified by silica gel column chromatography (n-hexane/ethyl acetate) to obtain 2.7 g of 1-(4-bromo-2-nitrophenyl) butane-1,3-dione.

Preparation Example 13

Under a nitrogen atmosphere, to a suspension of 2.28 g of magnesium chloride in 50 mL of tetrahydrofuran was added 3.80 g of tert-butyl 3-oxobutanoate at room temperature. The mixture was cooled to −8° C., and 3.9 mL of pyridine was added thereto, followed by stirring at the same temperature for 30 minutes, warming to room temperature, and further stirring for 30 minutes. The mixture was cooled to −8° C., and a solution of 5.3 g of 4-bromo-2-nitrobenzoyl chloride in 20 mL of tetrahydrofuran was added thereto, followed by stirring at the same temperature for 1 hour, warming to room temperature, and further stirring for 1.5 hours. The mixture was poured into a mixture of water and ethyl acetate, and adjusted to pH 3 with concentrated hydrochloric acid. The aqueous layer was separated, and then the organic layer was washed with a saturated aqueous sodium hydrogen carbonate solution and saturated brine, and dried over anhydrous magnesium sulfate. The solvent was evaporated under reduced pressure to obtain 4.95 g of tert-butyl 2-(4-bromo-2-nitrobenzoyl)-3 -oxobutanoate.

Preparation Example 14

To a mixture of 1.60 g of 1-(benzylpyrrolidin-3-yl)-8-bromo-7-methyl-1,5-dihydro-4H-pyrazolo[4,3-c]quinolin-4-one and 80 mL of dimethylsulfoxide were added 1.27 g of tetrakis(triphenylphosphine) palladium (0), 2.04 mL of triethylamine, and 3 mL of methanol. The atmosphere in the reaction container was replaced with carbon monoxide, followed by stirring at 70° C. for 10 hours. The reaction mixture was cooled, and then water was added thereto, followed by extraction with chloroform/methanol. The organic layer was washed with saturated brine and dried over anhydrous sodium sulfate. The solvent was evaporated under reduced pressure. The obtained solid was added to ethyl acetate, and heated, and then stirred at room temperature for 10 minutes. The solid was collected by filtration and dried under reduced pressure to obtain 1.33 g of methyl 1-(1-benzylpyrrolidin-3-yl)-7-methyl-4-oxo-4,5-dihydro-1H-pyrazolo [4,3-c]quinoline-8-carboxylate.

Preparation Example 15

4.3 g of tert-butyl 4-(hydroxymethyl)piperidine-1-carboxylate, 66 mg of 4,7-diphenyl-1,10-phenanthroline, and 45 mg of palladium acetate were added to 50 mL of butylvinyl ether, followed by stirring at room temperature for 15 minutes, and stirring at 75° C. for 2 days. The reaction mixture was filtered through celite, and the filtrate was concentrated under reduced pressure. The residue was purified by silica gel column chromatography (n-hexane/ethyl acetate) to obtain 4.4 g of tert-butyl 4-[(vinyloxy)methyl]piperidine-1-carboxylate.

Preparation Example 16

To a mixture of 3.23 g of 4-bromo-2-[1-(tetrahydro-2H-pyran-4-yl)-1H-pyrazol-5-yl]-5-(trifluoromethyl)aniline and 32 mL of N-methylpyrrolidone were added 2.6 mL of DIPEA and 1.8 g of CDI, followed by stirring at 150° C. for 1.5 hours. After ice-cooling, diisopropyl ether/ethyl acetate (4/1) and ice were added thereto, followed by stirring. The precipitated solid was collected by filtration, and washed with water and diisopropyl ether/ethyl acetate (4/1). The obtained solid was added to diisopropyl ether/ethyl acetate (4/1), and heated, followed by stirring at room temperature for 10 minutes, and the solid was collected by filtration, washed with diethyl ether, and then dried under reduced pressure to obtain 2.95 g of 8-bromo-1-(tetrahydro-2H-pyran-4-yl)-7-(trifluoromethyl)-1,5-dihydro-4H-pyrazolo[4,3-c]quinolin-4-one.

Preparation Example 17

To a mixture of 11.6 g of 1-[2-amino-4-(trifluoromethyl) phenyl]ethanone, 60 mL of acetonitrile, and 230 mL of diethyl ether was added 2.85 g of Amberlyst (registered trademark) 15, and 10.1 g of N-bromosuccinimide was added thereto in three times in an ice bath. After stirring for 30 minutes in an ice bath, the mixture was stirred at room temperature overnight. The insoluble material was filtered and washed with ethyl acetate. To the filtrate were added water and ethyl acetate, and the aqueous layer was separated. The organic layer was washed with a 10% aqueous sodium thiosulfate solution and saturated brine, and dried over anhydrous magnesium sulfate, and then solvent was evaporated. The residue was purified by silica gel column chromatography (n-hexane/ethyl acetate) to obtain 10.36 g of 1[2-amino-5-bromo-4-(trifluoromethyl)phenyl]ethanone.

Preparation Example 18

To a mixture of 6.0 g of tetrahydro-2H-pyran-4-ylhydrazine dihydrochloride and 175 mL of N-methylpyrrolidone was added 11 mL of DIPEA, followed by stirring at room temperature for 20 minutes. To the reaction mixture was added 8.86 g of N-{4-bromo-2-[(2E)-3-(dimethylamino) prop-2-enoyl]-5-(trifluoromethyl)phenyl}-2,2,2-trifluoroacetamide, followed by stirring at 110° C. for 1 hour. To the reaction mixture was added water, followed by extraction with isopropyl acetate, and the organic layer was washed with saturated brine. The solvent was evaporated under reduced pressure and the residue was purified by silica gel column chromatography (chloroform/methanol). The obtained oil was triturated with diethyl ether/n-hexane to obtain 4.19 g of N-{4-bromo-2-[1-(tetrahydro-2H-pyran-4-yl)-1H-pyrazol-5-yl]-5-(trifluoromethyl)phenyl}-2,2,2-trifluoroacetamide.

Preparation Example 19

Under a nitrogen atmosphere, to a solution of 330 mg of tert-butyl (3S)-3-phenylpiperazine-1-carboxylate in 3.5 mL of DMF was added 75.4 mg of sodium hydride (including 40% mineral oil) under ice-cooling, followed by stirring for 30 minutes. To the mixture was added 0.27 mL of 2-bromoethyl methyl ether, followed by stirring at room temperature for 16 hours. To the mixture were added 75.4 mg of sodium hydride (including 40% mineral oil) and 0.6 mL of 2-bromoethyl methyl ether, followed by further stirring for 8 hours. The mixture was poured into a mixture of water and ethyl acetate, and the aqueous layer was separated. The organic layer was washed with saturated brine and dried over anhydrous magnesium sulfate. The solvent was evaporated under reduced pressure and the residue was purified by silica gel column chromatography (chloroform/methanol) to obtain 330 mg of tert-butyl (3S)-4-(2-methoxyethyl)-3-phenylpiperazine-1-carboxylate.

Preparation Example 20

A mixture of 3 g of 4-ethoxybutyl p-toluenesulfonate, 2.65 g of tert-butyl (3R)-3-methylpiperazine-1-carboxylate, 3.07 mL of triethylamine, and 30 mL of acetonitrile was stirred at 90° C. for 3 hours. The reaction mixture was poured into a saturated aqueous sodium hydrogen carbonate solution, followed by extraction with ethyl acetate. The organic layer was washed with saturated brine and dried over anhydrous magnesium sulfate. The solvent was evaporated under reduced pressure and the residue was purified by silica gel column chromatography (chloroform/methanol) to obtain 3.1 g of tert-butyl (3R)-4-(4-ethoxybutyl)-3-methylpiperazine-1-carboxylate.

Preparation Example 21

To a solution of 420 mg of tert-butyl 4-[3-(pyridin-3-yl) propyl]piperazine-1-carboxylate in 6 mL of methanol was added 2 mL of a 4 M hydrogen chloride-dioxane solution, followed by stirring at room temperature for 16 hours. The solvent was evaporated under reduced pressure to obtain 395 mg of 1-[3-(pyridin-3-yl)propyl]piperazine trihydrochloride.

Preparation Example 22

To a solution of 2.0 g of tert-butyl 4-[(cyclopropyloxy) methyl]piperidine-1-carboxylate in 20 mL of dichloromethane was added 3.0 mL of trifluoroacetic acid, followed by stirring at room temperature for 2 hours. The reaction mixture was concentrated under reduced pressure, and to the residue were added a saturated aqueous sodium hydrogen carbonate solution and ethyl acetate, and then the aqueous layer was separated. The organic layer was washed with saturated brine, and dried over anhydrous magnesium sulfate, and the solvent was evaporated under reduced pressure. The residue was purified by basic silica gel column chromatography (chloroform/methanol) to obtain 756 mg of 4-[(cyclopropyloxy)methyl]piperidine.

Preparation Example 23

Under a nitrogen atmosphere, to a mixture of 693 mg of lithium aluminum hydride and 30 mL of tetrahydrofuran was added dropwise a solution of 1.0 g of 1-(piperidin-1-yl)cyclobutanecarbonitrile in 18 mL of tetrahydrofuran under ice-cooling. The reaction mixture was stirred at room temperature for 3 hours. Under ice-cooling, 1.5 mL of water and 1.5 mL of a 15% aqueous sodium hydroxide solution were added dropwise thereto. The mixture was diluted with ethyl acetate and the reaction mixture was filtered. The filtrate was concentrated under reduced pressure. The residue was purified by silica gel column chromatography (chloroform/methanol) to obtain 932 mg of 1-[1-(piperidin-1-yl)cyclobutyl]methanamine.

Preparation Example 24

Under a nitrogen atmosphere, to a solution of 1.5 g of tert-butyl 4-[3-(pyridin-3-yl)propanoyl]piperazine-1-carboxylate in 25 mL of tetrahydrofuran was added 7 mL of a 1 M borane/tetrahydrofuran solution under ice-cooling. The mixture was heated to reflux for 6 hours, and then cooled to room temperature, and 10 mL of methanol was added thereto, followed by further heating to reflux for 16 hours. After cooling to room temperature, the mixture was concentrated under reduced pressure, and a mixture of a saturated aqueous sodium hydrogen carbonate solution and ethyl acetate was added thereto. The aqueous layer was separated, and then the organic layer was washed with saturated brine and dried over anhydrous magnesium sulfate. The solvent was evaporated under reduced pressure and the residue was purified by silica gel column chromatography (chloroform/methanol) to obtain 1.43 g of tert-butyl 4-[3-(pyridin-3-yl)propyl]piperazine-1-carboxylate.

Preparation Example 25

To 3.9 g of (4,4-difluorocyclohexyl)methanol was added 40 mL of toluene. 10.2 g of triphenylphosphine was added thereto at room temperature, followed by stirring for a while. The mixture was ice-cooled, and 7.2 g of di-tert-butyl azodicarboxylate was portionwise added thereto while maintaining the internal temperature at about 10 to 15° C. The reaction mixture was stirred at room temperature for 20 hours. The solvent was evaporated and the residue was purified by silica gel column chromatography (n-hexane/ethyl acetate) to obtain 10.7 g of di-tert-butyl 1-[(4,4-difluorocyclohexyl)methyl]hydrazine-1,2-dicarboxylate.

Preparation Example 26

A solution of 1.5 g of 4-hydroxypyridine, 7.6 g of cyanomethylenetributylphosphorane, and 1.4 g of (2S)-2-fluoro-1-propanol in 20 mL of toluene was stirred at 105° C. overnight. To the reaction mixture were added 1 M hydrochloric acid and ethyl acetate, and the organic layer was separated. The aqueous layer was adjusted to pH 11 by the addition of a 1 M aqueous sodium hydroxide solution, and extracted with ethyl acetate. The organic layer was washed with saturated brine and dried over anhydrous magnesium sulfate, and the solvent was evaporated under reduced pressure. The residue was purified by silica gel column chromatography (chloroform/methanol) to obtain 2.2 g of 4-{[(2S)-2-fluoropropyl]oxy}pyridine.

Preparation Example 27

To a mixture of (3R)-1-methylpyrrolidin-3-ol and 35 mL of tetrahydrofuran was added 18.2 g of triphenylphosphine, and a solution of 13.2 g of di-tert-butyl azodicarboxylate in 10 mL of a tetrahydrofuran was added dropwise thereto under ice-cooling, followed by stirring for 1 hour, and further stirring at room temperature for 1 hour. To the reaction mixture was added 40 mL of a 6 M hydrochloric acid, followed by stirring at room temperature overnight. To the reaction mixture was added 40 mL of water, tetrahydrofuran was evaporated under reduced pressure, and then 20 mL of dichloromethane was added thereto and the organic layer was separated. The obtained aqueous layer was washed with 20 mL of dichloromethane twice, and the aqueous layer was evaporated under reduced pressure, and then coevaporated with isopropanol. After forming a precipitate, the obtained solid was collected by filtration and dried under reduced pressure to obtain 7.92 g of (3S)-3-hydrazino-1-methylpyrrolidine dihydrochloride.

Preparation Example 28

To a solution of 357 mg of methyl 2,2-difluoro-3-methoxypropionate in 7 mL of tetrahydrofuran was added 2.7 mL of a 1 M aqueous sodium hydroxide solution, followed by stirring at room temperature for 3 hours. The reaction mixture was acidified by the addition of 3.0 mL of 1 M hydrochloric acid and then extracted with ethyl acetate, the organic layer was washed with saturated brine and dried over anhydrous magnesium sulfate, and the solvent was concentrated under reduced pressure. To the reside were added 7 mL of 1,2-dichloroethane and 25 µL of DMF, and 219 µL of oxalyl chloride was added thereto under ice-cooling, followed by stirring at room temperature for 1 hour.

The reaction mixture was ice-cooled, and 1.9 mL of triethylamine and 560 mg of tert-butyl piperazine-1-carboxylate were added thereto, followed by stirring at room temperature overnight. To the reaction mixture were added chloroform and water, followed by extraction with chloroform. The organic layer was washed with saturated brine and dried over anhydrous magnesium sulfate, and the solvent was concentrated under reduced pressure. The residue was purified by silica gel column chromatography (n-hexane/ethyl acetate) to obtain 500 mg of tert-butyl 4-(2,2-difluoro-3-methoxypropanoyl)piperazine-1-carboxylate.

Preparation Example 29

Under a nitrogen atmosphere, 63 mL of diethylzinc (1.0 M hexane solution) was added to 92 mL of 1,2-dichloroethane at −40° C., and subsequently a solution of 2.5 g of tert-butyl 4-[(vinyloxy)methyl]piperidine-1-carboxylate in 134 mL of 1,2-dichloroethane was added thereto, followed by stirring at −40° C. for 30 minutes. 7.5 mL of chloroiodomethane was added thereto, followed by stirring for 4 hours while elevating the temperature from −40° C. to −15° C. To the reaction mixture was added portionwise a saturated aqueous ammonium chloride solution, followed by extraction with chloroform. The organic layer was washed with saturated brine, dried over anhydrous magnesium sulfate, and concentrated under reduced pressure. The obtained residue was purified by silica gel column chromatography (n-hexane/ethyl acetate) to obtain 2.0 g of tert-butyl 4-[(cyclopropyloxy)methyl]piperidine-1-carboxylate.

Preparation Example 30

2.2 g of 4-{[(2S)-2-fluoropropyl]oxy}pyridine was added to a solution of 22 mL of acetic acid in 22 mL of methanol, and 500 mg of 10% palladium on carbon (wet type) was added thereto under an argon atmosphere. The mixture was stirred at room temperature overnight under a hydrogen atmosphere of 3 atm. The reaction mixture was filtered through celite and the filtrate was concentrated under reduced pressure. The residue was purified by basic silica gel column chromatography (chloroform/methanol) to obtain 988 mg of 4-{[(2S)-2-fluoropropyl]oxy}piperidine.

Preparation Example 31

To a mixture of 500 mg of 6-bromo-3-fluoro-2-methylpyridine, 580 mg of tert-butyl (3R)-3-methylpiperazine-1-carboxylate, 506 mg of sodium tert-butoxide, and 61 mg of 4,5-bis(diphenylphosphino)-9,9-dimethylxanthene and 7.5 mL of toluene was added 48 mg of tris(dibenzylidenacetone)dipalladium (0), followed by stirring at 110° C. for 3 hours. After cooling to room temperature, the reaction mixture was poured into water and extracted with ethyl acetate. The organic layer was washed with saturated brine and dried over anhydrous magnesium sulfate. The solvent was evaporated under reduced pressure and the residue was purified by silica gel column chromatography (n-hexane/ethyl acetate) to obtain 780 mg of tert-butyl (3R)-4-(5-fluoro-6-methylpyridin-2-yl)-3-methylpiperazine-1-carboxylate.

Preparation Example 32

To a mixture of 500 mg of 3-(cyclopropyloxy)propan-1-ol and 5 mL of dichloromethane were added 1.2 mL of triethylamine and 1.3 g of p-toluenesulfonic acid chloride under ice-cooling, followed by stirring for 4 hours. The reaction mixture was diluted with chloroform, washed with 1 M hydrochloric acid, a saturated aqueous sodium hydrogen carbonate solution, and saturated brine, dried over anhydrous magnesium sulfate, and then concentrated under reduced pressure. The obtained residue was purified by silica gel column chromatography (n-hexane/ethyl acetate) to obtain 522 mg of 3-(cyclopropyloxy)propyl p-toluenesulfonate.

Preparation Example 33

To a solution of 12.8 g of 1-[2-amino-5-bromo-4-(trifluoromethyl)phenyl]ethanone in 190 mL of dichloromethane was added 8.82 mL of triethylamine, and a solution of 7.66 mL of trifluoroacetic anhydride in 5 mL of dichloromethane was added dropwise thereto over 10 minutes under ice-cooling, followed by stirring for 30 minutes. Furthermore, 2.65 mL of triethylamine and 2.3 mL of trifluoroacetic anhydride was added dropwise thereto under ice-cooling, followed by stirring for 30 minutes. To the reaction mixture was added water, followed by extraction with chloroform, and the organic layer was washed with a saturated aqueous sodium hydrogen carbonate solution/ice (1/1) and saturated brine, and dried over anhydrous magnesium sulfate. The insoluble material was separated by filtration, and then the solvent was evaporated under reduced pressure to obtain 18 g of N-[2-acetyl-4-bromo-5-(trifluoromethyl)phenyl]-2,2,2-trifluoroacetamide.

In the same manner as the method of Preparation Example 1, the compounds of Preparation Examples 1-1 to 1-2 were prepared; in the same manner as the method of Preparation Example 2, the compound of Preparation Example 2-1 was prepared; in the same manner as the method of Preparation Example 3, the compounds of Preparation Examples 3-1 to 3-13 were prepared; in the same manner as the method of Preparation Example 5, the compounds of Preparation Examples 5-1 to 5-19 were prepared; in the same manner as the method of Preparation Example 6, the compounds of Preparation Examples 6-1 to 6-2 were prepared; in the same manner as the method of Preparation Example 7, the compounds of Preparation Examples 7-1 to 7-3 were prepared; in the same manner as the method of Preparation Example 8, the compounds of Preparation Examples 8-1 to 8-18 were prepared; in the same manner as the method of Preparation Example 9, the compounds of Preparation Examples 9-1 to 9-17 were prepared; in the same manner as the method of Preparation Example 10, the compounds of Preparation Examples 10-1 to 10-21 were prepared; in the same manner as the method of Preparation Example 14, the compounds of Preparation Examples 14-1 to 14-2 were prepared; in the same manner as the method of Preparation Example 16, the compounds of Preparation Examples 16-1 to 16-8 were prepared; in the same manner as the method of Preparation Example 17, the compounds of Preparation Examples 17-1 to 17-2 were prepared; in the same manner as the method of Preparation Example 19, the compounds of Preparation Examples 19-1 to 19-16 were prepared; in the same manner as the method of Preparation Example 20, the compounds of Preparation Examples 20-1 to 20-3 were prepared; in the same manner as the method of Preparation Example 21, the compounds of Preparation Examples 21-1 to 21-39 were prepared; in the same manner as the method of Preparation Example 24, the compounds of Preparation Examples 24-1 to 24-2 were prepared; in the same manner as the method of Preparation Example 25, the compounds of Preparation Examples 25-1 to 25-4 were prepared; in the same manner as the method of Preparation Example 26, the compounds of Preparation Examples 26-1 to 26-2 were prepared; in the same manner as the method of Preparation Example 28, the compound of Preparation Example 28-1 was prepared; in the same manner as the method of Preparation Example 30, the compounds of Preparation Examples 30-1 to 30-2 were prepared; in the same manner as the method of Preparation Example 31, the compounds of Preparation Examples 31-1 to 31-2 were prepared; in the same manner as the method of Example 7 below, the compounds of Preparation Examples 34-1 to 34-14 were prepared; in the same manner as the method of Example 4 below, the compounds of Preparation Examples 35-1 to 35-6 were prepared; in the same manner as the method of Example 2 below, the compound of Preparation Example 36 was prepared; and in the same manner as the method of Example 5 below, the compounds of Preparation Examples 37-1 to 37-2 were prepared; each using the corresponding starting materials.

The structures of Preparation Example compounds are shown in Tables 3 to 26, and the physicochemical data of Preparation Example compounds are shown in Tables 27 to 34 below.

Example 1

Under a nitrogen atmosphere, to a solution of 148 mg of 5-chloroindoline in 1 mL of toluene was added 0.54 mL of a 1.8 M trimethylaluminum solution in toluene at 0° C., followed by stirring at room temperature for 2 hours (solution A). Under a nitrogen atmosphere, to a mixture of 100 mg of methyl 1-cyclopentyl-4-oxo-4,5-dihydro-1H-pyrazolo[4,3-c]quinoline-7-carboxylate and 3 mL of toluene was added the solution A, followed by stirring at 70° C. for 8 hours. After cooling to room temperature, to the reaction mixture was added diluted hydrochloric acid, and the mixture was poured into a mixture of water and ethyl acetate. The pH was adjusted to 10 with 28% aqueous ammonia. The insoluble material was separated by filtration. The aqueous layer was separated, the organic layer was washed with saturated brine and then dried over anhydrous magnesium sulfate, and the solvent was evaporated under reduced pressure. The obtained residue was purified by silica gel column chromatography (chloroform/methanol=100/0-92/8) to obtain 65 mg of 7-[(5-chloro-2,3-dihydro-1H-indol-1-yl)carbonyl]-1-cyclopentyl-1,5-dihydro-4H-pyrazolo[4,3-c]quinolin-4-one as white powder.

Example 2

To a mixture of 120 mg of 7-methyl-4-oxo-1-(tetrahydro-2H-pyran-4-yl)-4,5-dihydro-1H-pyrazolo[4,3-c]quinoline-8-carboxylic acid and 2.4 mL of DMF were added 130 mg of 1-(pyridin-3-ylmethyl)piperazine, 0.19 mL of DIPEA, and 177 mg of TBTU, followed by stirring at room temperature overnight. The reaction mixture was ice-cooled and poured into a saturated aqueous sodium hydrogen carbonate solution, followed by extraction with ethyl acetate. The organic layer was washed with saturated brine and dried over anhydrous magnesium sulfate. The solvent was evaporated under reduced pressure and the residue was purified by silica gel column chromatography (chloroform/methanol=100/0-92/8) to obtain white powder. The powder was suspended in 1 mL of methanol, and 0.37 mL of a 4 M hydrogen chloride-ethyl acetate solution was added thereto, followed by stirring for 30 minutes. The obtained powder was collected by filtration, washed with methanol, and then dried under reduced pressure to obtain 82 mg of 7-methyl-8-{[4-(pyridin-3-ylmethyl)piperazin-1-yl]carbonyl}-1-(tetrahydro-2H-pyran-4-yl)-1,5-dihydro-4H-pyrazolo[4,3-c]quinolin-4-one dihydrochloride as a white solid.

Example 3

To a mixture of 8.2 mg of 7-methyl-4-oxo-1-(tetrahydro-2H-pyran-4-yl)-4,5-dihydro-1H-pyrazolo[4,3-c]quinoline-8-carboxylic acid, 3.8 mg of 1-(2-aminoethyl)piperidine, 13.1 µL of DIPEA, and 0.4 mL of DMF was added a mixture of 9.8 mg of HATU and 0.1 mL of DMF, followed by stirring at room temperature overnight. The reaction mixture was purified by preparative HPLC (methanol/0.1% aqueous formic acid solution) to obtain 3.6 mg of 7-methyl-4-oxo-N-[2-(piperidin-1-yl)ethyl]-1-(tetrahydro-2H-pyran-4-yl)-4,5-dihydro-1H-pyrazolo[4,3-c]quinoline-8-carboxamide.

Example 4

To a mixture of 224 mg of 1-(1-benzylpyrrolidin-3-yl)-8-{[4-(ethoxymethyl)piperidin-1-yl]carbonyl}-7-methyl-1,5-dihydro-4H-pyrazolo[4,3-c]quinolin-4-one hydrochloride and 9 mL of methanol was added 23 mg of a 10% palladium hydroxide/carbon powder, followed by stirring at room temperature for 20 hours under a hydrogen atmosphere of 3 atm. The insoluble material was removed by filtration, and the solvent was evaporated under reduced pressure. The residue was purified by reverse phase column chromatography (acetonitrile/water=0/100-35/65). The obtained compound was dissolved in 4 mL of methanol, and 1 mL of a 4 M hydrogen chloride-ethyl acetate solution was added thereto, followed by stirring for 1 hour. Then, the solvent was evaporated under reduced pressure and the solid was collected by filtration, washed with diethyl ether, and then dried under reduced pressure to obtain 180 mg of 8-{[4-(ethoxymethyl)piperidin-1-yl]carbonyl}-7-methyl-1-pyrrolidin-3-yl)-1,5-dihydro-4H-pyrazolo[4,3-c]quinolin-4-one hydrochloride as a white solid.

Example 5

To a mixture of 110 mg of 1-cyclopentyl-7-methyl-4-oxo-4,5-dihydro-1H-pyrazolo[4,3-c]quinoline-8-carboxylic acid and 4.4 mL of DMF were added 73 mg of 1-(2-isopropoxyethyl)piperazine, 121 µL of DIPEA, and 202 mg of HATU, followed by stirring at room temperature overnight. To the reaction mixture were added a saturated aqueous sodium hydrogen carbonate solution and water, followed by extraction with ethyl acetate. The organic layer was washed with water and saturated brine, and dried over anhydrous magnesium sulfate, and then solvent was evaporated. The obtained residue was purified by silica gel column chromatography (chloroform/methanol=100/0-95/5). To the obtained oil were added 2 mL of methanol and 265 μL of a 4 M hydrogen chloride-ethyl acetate solution, followed by stirring at room temperature for 30 minutes. The solvent was evaporated under reduced pressure, and 0.5 mL of methanol and 3 mL of diethyl ether were added thereto, followed by stirring at room temperature to give powder, which was collected by filtration and dried under reduced pressure to obtain 140 mg of 1-cyclopentyl-8-{[4-(2-isopropoxyethyl)piperazin-1-yl]carbonyl}-7-methyl-1,5-dihydro-4H-pyrazolo[4,3-c]quinolin-4-one hydrochloride as white powder.

Example 6

To 95 mg of ethyl (3R)-1-{[7-methyl-4-oxo-1-(tetrahydro-2H-pyran-4-yl)-4,5-dihydro-1H-pyrazolo[4,3-c]quinolin-8-yl]carbonyl}piperidine-3-carboxylate were added 5 mL of ethanol and 200 μL of a 3 M aqueous sodium hydroxide solution, followed by stirring at 70° C. for 9 hours. The reaction mixture was cooled, and water and ethyl acetate were added thereto, and then the organic layer was separated. The aqueous layer was adjusted to about pH 4 with 1 mL of 1 M hydrochloric acid, then the solution was coevaporated with toluene. After forming a precipitate, f the precipitared powder was collected by filtration. The obtained powder was dried under reduced pressure to obtain 71 mg of (3R)-1-{[7-methyl-4-oxo-1-(tetrahydro-2H-pyran-4-yl)-4,5-dihydro-1H-pyrazolo[4,3-c]quinolin-8-yl]carbonyl}piperidine-3-carboxylic acid as white powder.

Example 7

To a mixture of 33 mg of 8-{[4-(ethoxymethyl)piperidin-1-yl]carbonyl}-7-methyl-1-pyrrolidin-3-yl)-1,5-dihydro-4H-pyrazolo[4,3-c]quinolin-4-one hydrochloride, 0.66 mL of 1,2-dichloroethane and 0.26 mL of acetic acid were added 210 μL of a 37% aqueous formaldehyde solution and 44 mg of sodium triacetoxyborohydride, followed by stirring at room temperature for 2 hours. The reaction mixture was poured into a 1 M aqueous sodium hydroxide solution, followed by extraction with chloroform. The organic layer was washed with saturated brine and dried over anhydrous magnesium sulfate. The solvent was evaporated under reduced pressure and the residue was purified by silica gel column chromatography (chloroform/methanol=100/0-90/10). The obtained compound was dissolved in 1 mL of dichloromethane, and 20 μL of a 4 M hydrogen chloride-ethyl acetate solution was added thereto, followed by stirring for 15 minutes. Then, the solvent was evaporated under reduced pressure, and the solid was collected by filtration, washed with diethyl ether, and then dried under reduced pressure to obtain 24 mg of 8-{[4-(ethoxymethyl)piperidin-1-yl]carbonyl}-7-methyl-1-(1-methylpyrrolidin-3 -yl)-1,5-dihydro-4H-pyrazolo[4,3-c]quinolin-4-one hydrochloride as a white solid.

Example 8

To a mixture of 8.2 mg of 7-methyl-4-oxo-1-(tetrahydro-2H-pyran-4-yl)-4,5-dihydro-1H-pyrazolo[4,3-c]quinoline-8-carboxylic acid, 7.7 mg of methyl 3-piperidin-4-yl-benzoate monohydrochloride, 3.4 mg of 1-hydroxybenzotriazole, 7.0 μL of triethylamine, and 1.0 mL of DMF was added 100 mg of PS-Carbodiimide (Biotage), followed by stirring at room temperature overnight. To the reaction mixture were added 75 mg of MP-Carbonate (Biotage), 50 mg of PS-Isocyanate (Biotage), and 0.5 mL of DMF at room temperature, followed by stirring for 2 hours. The reaction mixture was filtered and the filtrate was concentrated under reduced pressure. To the obtained residue were added 0.5 mL of methanol, 0.5 mL of tetrahydrofuran, and 0.5 mL of a 1 M aqueous sodium hydroxide solution, followed by stirring at room temperature overnight. To the reaction mixture was added 0.5 mL of 1 M hydrochloric acid and the solvent was evaporated under reduced pressure. The obtained residue was purified by preparative HPLC (methanol/0.1% aqueous formic acid solution) to obtain 5.8 mg of 3-(1-{[7-methyl-4-oxo-1-(tetrahydro-2H-pyran-4-yl)-4,5-dihydro-1H-pyrazolo[4,3-c]quinolin-8-yl]carbonyl}piperidin-4-yl)benzoic acid.

Example 9

To a mixture of 11.9 mg of 7-methyl-8-(piperazin-1-ylcarbonyl)-1-(tetrahydro-2H-pyran-4-yl)-1,5-dihydro-4H-pyrazolo[4,3-c]quinolin-4-one, 15.9 mg of 6-(1-pyrrolidinyl)nicotinaldehyde, 0.3 mL of 1,2-dichloroethane, and 30 μL of acetic acid was added 19.1 mg of sodium triacetoxyborohydride, followed by stirring at room temperature overnight. To the reaction mixture was added a saturated aqueous sodium hydrogen carbonate solution, followed by extraction with chloroform. The organic layer was evaporated under reduced pressure. The obtained residue was purified by preparative HPLC (methanol/0.1% aqueous formic acid solution) to obtain 9.7 mg of 7-methyl-8-[(4-{[6-(pyrrolidin-1-yl)pyridin-3-yl]methyl}piperazin-1-yl)carbonyl]-1-(tetrahydro-2H-pyran-4-yl)-1,5-dihydro-4H-pyrazolo[4,3-c]quinolin-4-one.

Example 10

To a mixture of 6.0 mg of tert-butyl (3S)-3-methylpiperazine-1-carboxylate, 17.3 mg of 6-morpholinopyridine-2-carbaldehyde, 0.3 mL of 1,2-dichloroethane, and 5.2 μL of acetic acid was added 19.1 mg of sodium triacetoxyborohydride, followed by stirring at room temperature overnight. To the reaction mixture was added a saturated aqueous sodium hydrogen carbonate solution, followed by extraction with chloroform. The organic layer was evaporated under reduced pressure. To the obtained residue were added 300 μL of methanol and 100 μL of a 4 M hydrogen chloride-ethyl acetate solution, followed by stirring at room temperature overnight. The solvent was evaporated under reduced pressure, and to the obtained residue were added 8.2 mg of 7-methyl-4-oxo-1-(tetrahydro-2H-pyran-4-yl)-4,5-dihydro-1H-pyrazolo[4,3-c]quinoline-8-carboxylic acid, 26.1 μL of DIPEA, and 0.4 mL of DMF. Then, a mixture of 9.5 mg of HATU and 0.1 mL of DMF was added thereto, followed by stirring at room temperature overnight. The reaction mixture was purified by preparative HPLC (methanol/0. 1% aqueous formic acid solution) to obtain 11 mg of 7-methyl-8-{[(3S)-3-methyl-4-{[6-(morpholin-4-yl)pyridin-2-yl]methyl}piperazin-1-yl]carbonyl}-1-(tetrahydro-2H-pyran-4-yl)-1,5-dihydro-4H-pyrazolo[4,3-c]quinolin-4-one.

In the same manner as in the methods of Examples 1 to 10, the compounds of Examples 11 to 677 shown in Tables below were prepared. The structures of the Example compounds are shown in Tables 35 to 104, and the preparation methods and the physicochemical data of the Example compounds are shown in Tables 105 to 142.

In addition, the structures of other compounds of the compounds of the formula (I) are shown in Tables 143 to 146. These can be easily prepared by any of the preparation methods above, the methods described in Examples, the methods apparent to those skilled in the art, or modified methods thereof.

TABLE 3

| Pr | Structure |
|---|---|
| 1 | (structure) |
| 1-1 | (structure) |
| 1-2 | (structure) |
| 2 | (structure) |
| 2-1 | (structure) |

TABLE 3-continued

| Pr | Structure |
|---|---|
| 3 | (structure) |
| 3-1 | (structure) |
| 3-2 | (structure) |
| 3-3 | (structure) |
| 3-4 | (structure) |

TABLE 4

| Pr | Structure |
|---|---|
| 3-5 | 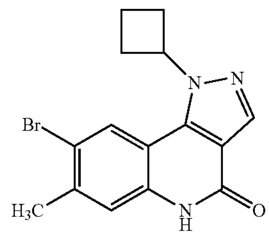 [SMILES: Cc1cc2[nH]c(=O)c3cnn(C4CCC4)c3c2cc1Br] |
| 3-6 | 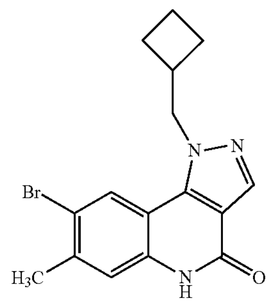 [SMILES: Cc1cc2[nH]c(=O)c3cnn(CC4CCC4)c3c2cc1Br] |
| 3-7 | 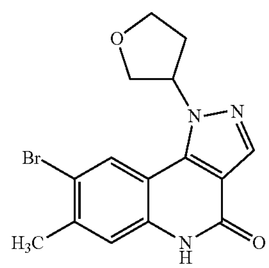 [SMILES: Cc1cc2[nH]c(=O)c3cnn(C4CCOC4)c3c2cc1Br] |
| 3-8 | 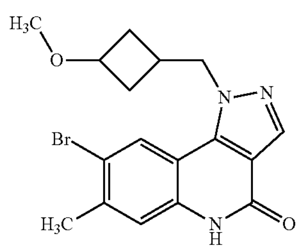 [SMILES: COC1CC(Cn2ncc3c(=O)[nH]c4cc(C)c(Br)cc4c32)C1] |
| 3-9 | 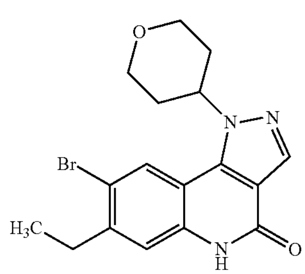 [SMILES: CCc1cc2[nH]c(=O)c3cnn(C4CCOCC4)c3c2cc1Br] |

TABLE 4-continued

| Pr | Structure |
|---|---|
| 3-10 | 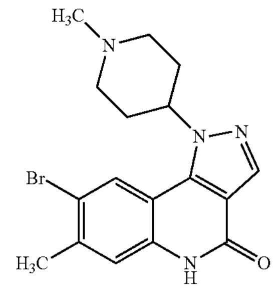 [SMILES: Cc1cc2[nH]c(=O)c3cnn(C4CCN(C)CC4)c3c2cc1Br] |
| 3-11 | Chiral |
| 3-12 | 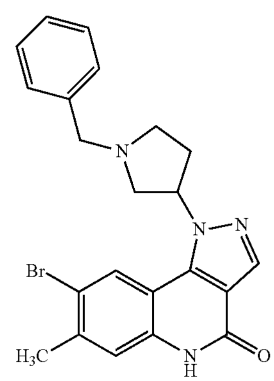 [SMILES: Cc1cc2[nH]c(=O)c3cnn(C4CCN(Cc5ccccc5)C4)c3c2cc1Br] |
| 3-13 | 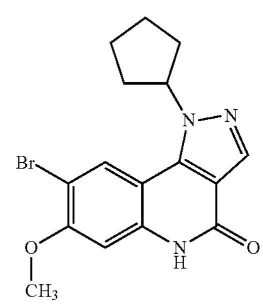 [SMILES: COc1cc2[nH]c(=O)c3cnn(C4CCCC4)c3c2cc1Br] |

TABLE 5
| Pr | Structure |
|---|---|
| 4 | 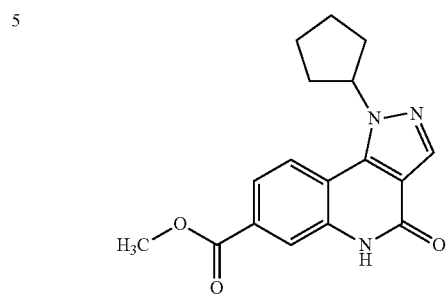 |
| 5 | 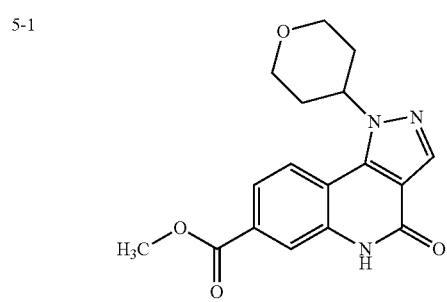 |
| 5-1 | 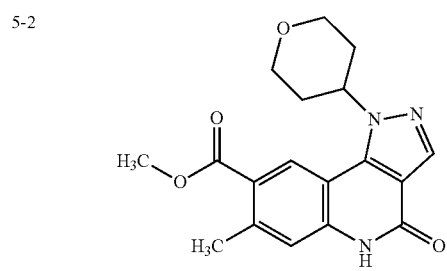 |
| 5-2 | 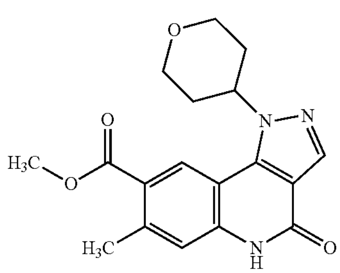 [SMILES: COC(=O)c1cc2c(cc1C)[nH]c(=O)c1cnn(C3CCOCC3)c12] |
| 5-3 | 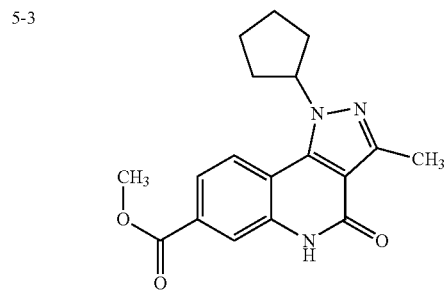 |
TABLE 5-continued
| Pr | Structure |
|---|---|
| 5-4 | 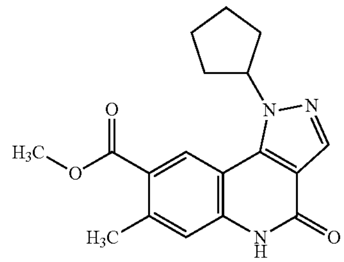 [SMILES: COC(=O)c1cc2c(cc1C)[nH]c(=O)c1cnn(C3CCCC3)c12] |
| 5-5 | 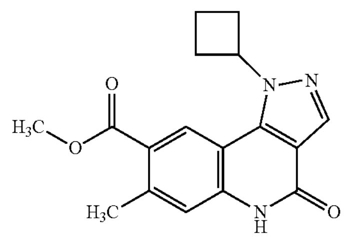 [SMILES: COC(=O)c1cc2c(cc1C)[nH]c(=O)c1cnn(C3CCC3)c12] |
| 5-6 | 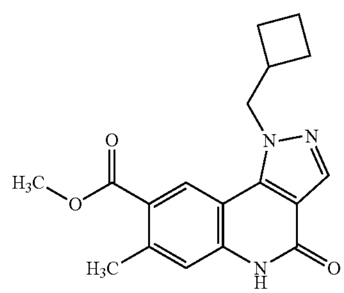 [SMILES: COC(=O)c1cc2c(cc1C)[nH]c(=O)c1cnn(CC3CCC3)c12] |
| 5-7 | 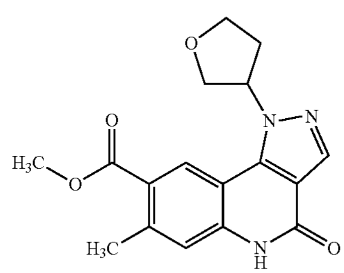 [SMILES: COC(=O)c1cc2c(cc1C)[nH]c(=O)c1cnn(C3CCOC3)c12] |
| 5-8 | 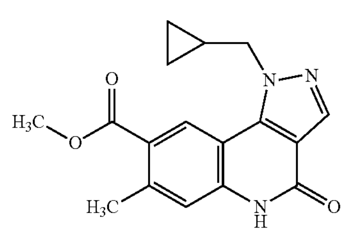 [SMILES: COC(=O)c1cc2c(cc1C)[nH]c(=O)c1cnn(CC3CC3)c12] |

TABLE 6

| Pr | Structure |
|---|---|
| 5-9 | (methyl 1-((3-methoxycyclobutyl)methyl)-7-methyl-4-oxo-4,5-dihydro-1H-pyrazolo[4,3-c]quinoline-8-carboxylate) |
| 5-10 | (methyl 7-ethyl-4-oxo-1-(tetrahydro-2H-pyran-4-yl)-4,5-dihydro-1H-pyrazolo[4,3-c]quinoline-8-carboxylate) |
| 5-11 | (methyl 1-cyclobutyl-7-ethyl-4-oxo-4,5-dihydro-1H-pyrazolo[4,3-c]quinoline-8-carboxylate) |
| 5-12 | Chiral (methyl 7-methyl-4-oxo-1-((S)-tetrahydrofuran-3-yl)-4,5-dihydro-1H-pyrazolo[4,3-c]quinoline-8-carboxylate) |
| 5-13 | (methyl 7-methyl-4-oxo-1-((tetrahydro-2H-pyran-4-yl)methyl)-4,5-dihydro-1H-pyrazolo[4,3-c]quinoline-8-carboxylate) |

TABLE 6-continued

| Pr | Structure |
|---|---|
| 5-14 | Chiral (methyl 7-methyl-4-oxo-1-((R)-tetrahydrofuran-3-yl)-4,5-dihydro-1H-pyrazolo[4,3-c]quinoline-8-carboxylate) |
| 5-15 | (methyl 7-methyl-1-(1-methylpiperidin-4-yl)-4-oxo-4,5-dihydro-1H-pyrazolo[4,3-c]quinoline-8-carboxylate) |
| 5-16 | Chiral (methyl 7-methyl-1-((R)-1-methylpyrrolidin-3-yl)-4-oxo-4,5-dihydro-1H-pyrazolo[4,3-c]quinoline-8-carboxylate) |
| 5-17 | (methyl 1-(4,4-difluorocyclohexyl)-7-methyl-4-oxo-4,5-dihydro-1H-pyrazolo[4,3-c]quinoline-8-carboxylate) |

TABLE 7

| Pr | Structure |
|---|---|
| 5-18 | (structure) |
| 5-19 | (structure) |
| 6 | (structure) |
| 6-1 | (structure) |
| 6-2 | (structure) |
| 7 | (structure) |

TABLE 7-continued

| Pr | Structure |
|---|---|
| 7-1 | (structure) |
| 7-2 | (structure) |
| 7-3 | (structure) |
| 8 | (structure) |

TABLE 8

| Pr | Structure |
|---|---|
| 8-1 | (structure) |

TABLE 8-continued
| Pr | Structure |
|---|---|
| 8-2 | 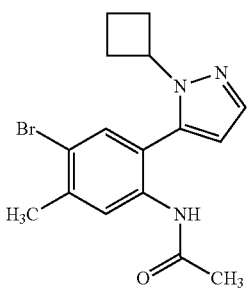 |
| 8-3 | 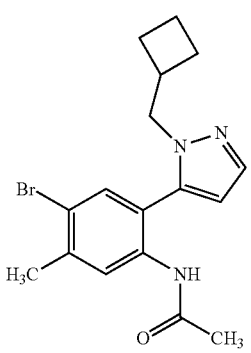 [SMILES: CC(=O)Nc1cc(C)c(Br)cc1-c1ccnn1CC1CCC1] |
| 8-4 | 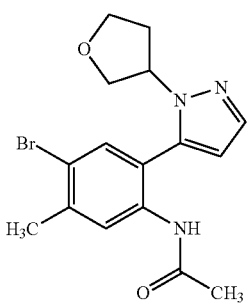 [SMILES: CC(=O)Nc1cc(C)c(Br)cc1-c1ccnn1C1CCOC1] |
| 8-5 | 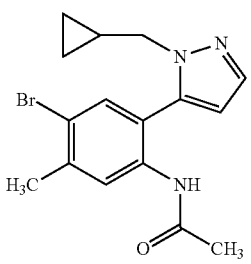 [SMILES: CC(=O)Nc1cc(C)c(Br)cc1-c1ccnn1CC1CC1] |
| 8-6 | 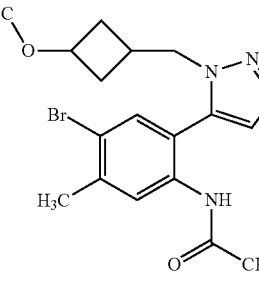 |
| 8-7 | 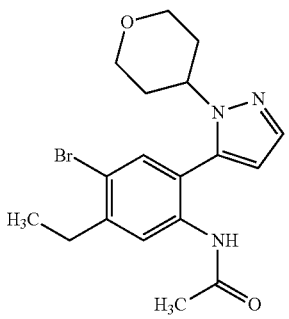 [SMILES: CCc1cc(NC(C)=O)c(-c2ccnn2C2CCOCC2)cc1Br] |
| 8-8 | 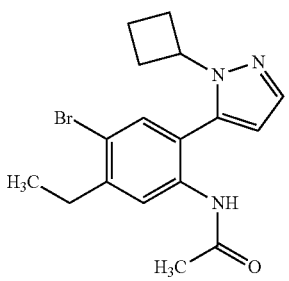 [SMILES: CCc1cc(NC(C)=O)c(-c2ccnn2C2CCC2)cc1Br] |
| 8-9 | Chiral 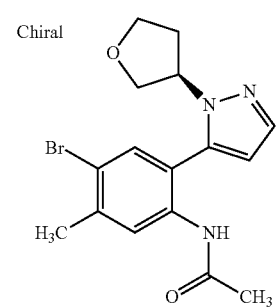 [SMILES: "Chiral" ; CC(=O)Nc1cc(C)c(Br)cc1-c1ccnn1[C@@H]1CCOC1] |
| 8-10 | 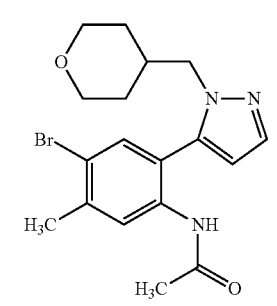 |

TABLE 9
| Pr | Structure |
|---|---|
| 8-11 | 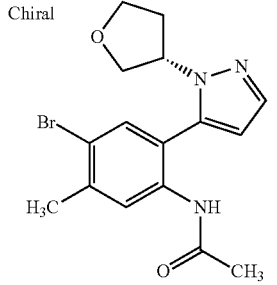 Chiral |
| 8-12 | 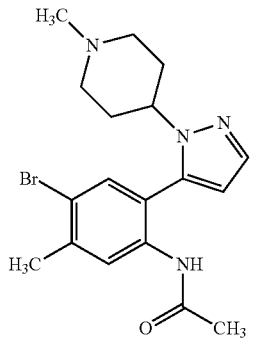 [SMILES: CC(=O)Nc1cc(C)c(Br)cc1-c1ccnn1C1CCN(C)CC1] |
| 8-13 | 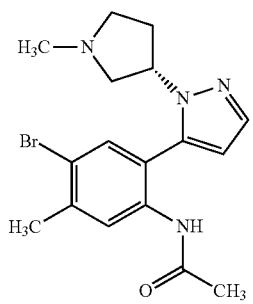 Chiral |
| 8-14 | 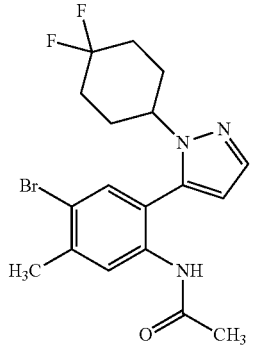 [SMILES: CC(=O)Nc1cc(C)c(Br)cc1-c1ccnn1C1CCC(F)(F)CC1] |
TABLE 9-continued
| Pr | Structure |
|---|---|
| 8-15 | 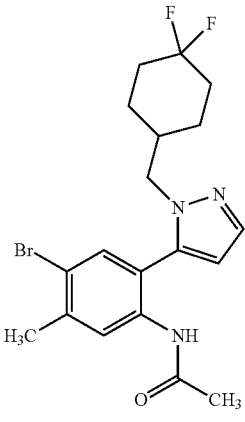 [SMILES: CC(=O)Nc1cc(C)c(Br)cc1-c1ccnn1CC1CCC(F)(F)CC1] |
| 8-16 | 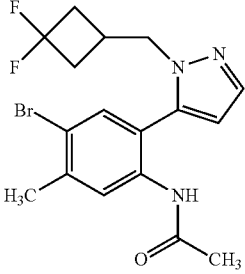 |
| 8-17 | 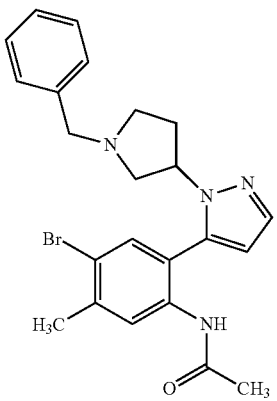 [SMILES: CC(=O)Nc1cc(C)c(Br)cc1-c1ccnn1C1CCN(Cc2ccccc2)C1] |
| 8-18 | 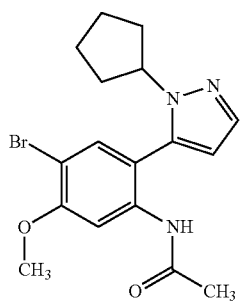 [SMILES: COc1cc(NC(C)=O)c(-c2ccnn2C2CCCC2)cc1Br] |

TABLE 10
| Pr | Structure |
|---|---|
| 9 | 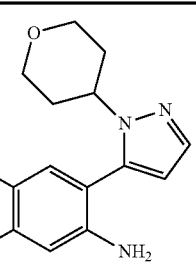 |
| 9-1 | 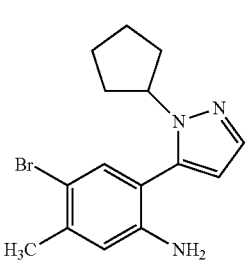 [SMILES: Cc1cc(N)c(-c2ccnn2C2CCCC2)cc1Br] |
| 9-2 | 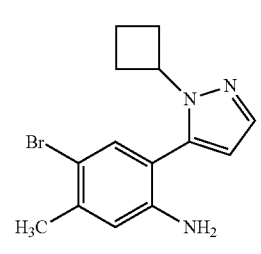 |
| 9-3 | 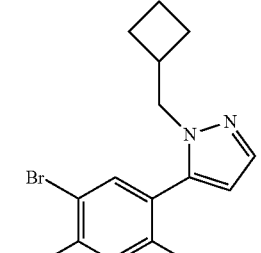 |
| 9-4 | 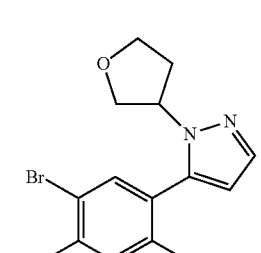 |
| 9-5 | 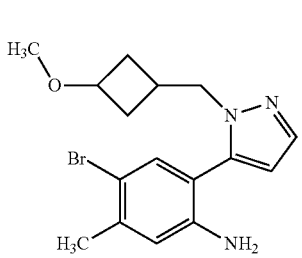 |
TABLE 10-continued
| Pr | Structure |
|---|---|
| 9-6 | 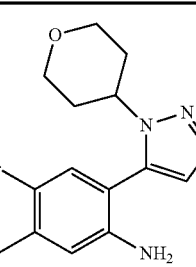 |
| 9-7 | 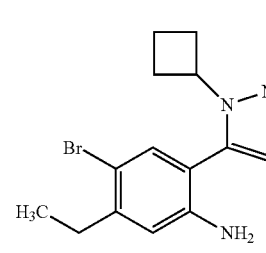 |
| 9-8 | Chiral 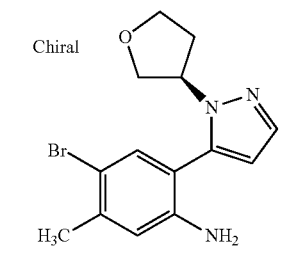 |
| 9-8 | 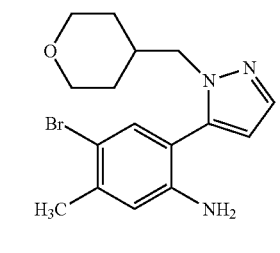 [SMILES: Cc1cc(N)c(-c2ccnn2CC2CCOCC2)cc1Br] |
| 9-10 | Chiral 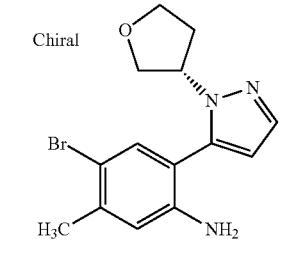 |
| 9-11 | 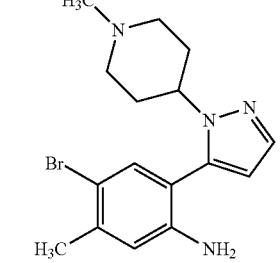 |

TABLE 11

| Pr | Structure |
|---|---|
| 9-12 | Chiral structure with N-methylpyrrolidine-pyrazole, bromo-methyl-aminophenyl |
| 9-13 | 4,4-difluorocyclohexyl-pyrazole, bromo-methyl-aminophenyl |
| 9-14 | (4,4-difluorocyclohexyl)methyl-pyrazole, bromo-methyl-aminophenyl |
| 9-15 | (3,3-difluorocyclobutyl)methyl-pyrazole, bromo-methyl-aminophenyl |
| 9-16 | 1-benzylpyrrolidin-3-yl-pyrazole, bromo-methyl-aminophenyl |

TABLE 11-continued

| Pr | Structure |
|---|---|
| 9-17 | cyclopentyl-pyrazole, bromo-methoxy-aminophenyl |
| 10 | 1-(tetrahydropyran-4-yl)-pyrazolo[4,3-c]quinolin-4-one-8-carboxylic acid, 7-methyl |
| 10-1 | 1-cyclopentyl-pyrazolo[4,3-c]quinolin-4-one-8-carboxylic acid, 7-methyl |
| 10-2 | 1-cyclobutyl-pyrazolo[4,3-c]quinolin-4-one-8-carboxylic acid, 7-methyl |
| 10-3 | 1-(cyclobutylmethyl)-pyrazolo[4,3-c]quinolin-4-one-8-carboxylic acid, 7-methyl |

TABLE 12

| Pr | Structure |
|---|---|
| 10-4 | (tetrahydrofuran-3-yl)-pyrazolo-quinolinone with 7-methyl and 8-carboxylic acid |
| 10-5 | 1-(cyclopropylmethyl)-pyrazole with 5-bromo-4-methyl-2-aminophenyl |
| 10-6 | 1-(cyclopropylmethyl)-pyrazolo-quinolinone with 7-methyl and 8-carboxylic acid |
| 10-7 | 1-((3-methoxycyclobutyl)methyl)-pyrazolo-quinolinone with 7-methyl and 8-carboxylic acid |
| 10-8 | 1-(tetrahydro-2H-pyran-4-yl)-pyrazolo-quinolinone with 7-ethyl and 8-carboxylic acid |
| 10-9 | 1-cyclobutyl-pyrazolo-quinolinone with 7-ethyl and 8-carboxylic acid |

TABLE 12-continued

| Pr | Structure |
|---|---|
| 10-10 | Chiral (S)-tetrahydrofuran-3-yl-pyrazolo-quinolinone with 7-methyl and 8-carboxylic acid |
| 10-11 | 1-((tetrahydro-2H-pyran-4-yl)methyl)-pyrazolo-quinolinone with 7-methyl and 8-carboxylic acid |
| 10-12 | Chiral (R)-tetrahydrofuran-3-yl-pyrazolo-quinolinone with 7-methyl and 8-carboxylic acid |
| 10-13 | 1-(1-methylpiperidin-4-yl)-pyrazolo-quinolinone with 7-methyl and 8-carboxylic acid |
| 10-14 | Chiral (S)-1-methylpyrrolidin-3-yl-pyrazolo-quinolinone with 7-methyl and 8-carboxylic acid |

TABLE 13

| Pr | Structure |
|---|---|
| 10-15 | (structure) |
| 10-16 | (structure) |
| 10-17 | (structure) |
| 10-18 | (structure) |
| 10-19 | (structure) |

TABLE 13-continued

| Pr | Structure |
|---|---|
| 10-20 | (structure) |
| 10-21 | (structure) |
| 11 | (structure) |
| 12 | (structure) |

TABLE 14

| Pr | Structure |
|---|---|
| 13 | (structure) |

TABLE 14-continued
| Pr | Structure |
|---|---|
| 14 | 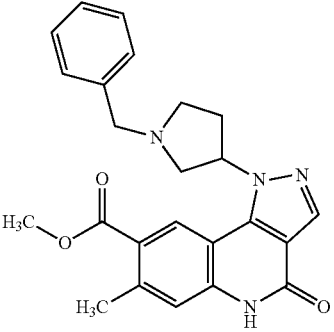 [SMILES: COC(=O)c1cc2c(cc1C)[nH]c(=O)c1cnn(C3CCN(Cc4ccccc4)C3)c12] |
| 14-1 | 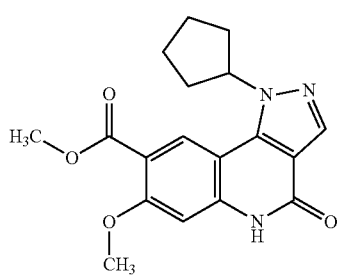 [SMILES: COC(=O)c1cc2c(cc1OC)[nH]c(=O)c1cnn(C3CCCC3)c12] |
| 14-2 | 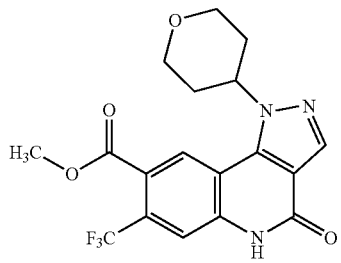 [SMILES: COC(=O)c1cc2c(cc1C(F)(F)F)[nH]c(=O)c1cnn(C3CCOCC3)c12] |
| 15 | 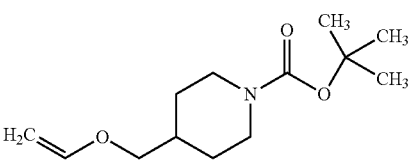 [SMILES: C=COCC1CCN(C(=O)OC(C)(C)C)CC1] |
| 16 | 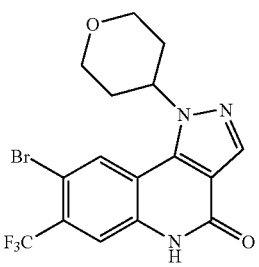 [SMILES: O=c1[nH]c2cc(C(F)(F)F)c(Br)cc2c2c1cnn2C1CCOCC1] |
| 16-1 | 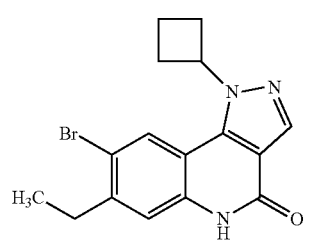 [SMILES: CCc1cc2[nH]c(=O)c3cnn(C4CCC4)c3c2cc1Br] |
| 16-2 | 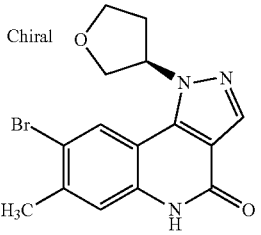 [SMILES: Cc1cc2[nH]c(=O)c3cnn([C@@H]4CCOC4)c3c2cc1Br] |
| 16-3 | 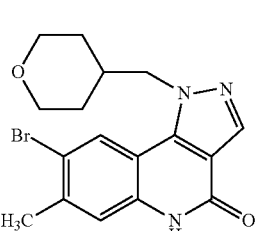 |
TABLE 15
| Pr | Structure |
|---|---|
| 16-4 | 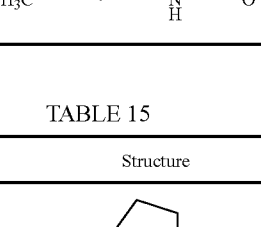 |
| 16-5 | 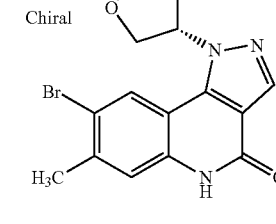 |
| 16-6 | 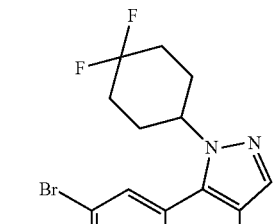 |

TABLE 15-continued
| Pr | Structure |
|---|---|
| 16-7 | 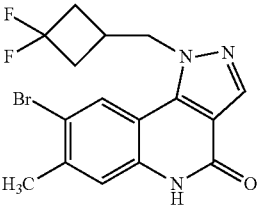 [SMILES: Cc1cc2[nH]c(=O)c3cnn(CC4CC(F)(F)C4)c3c2cc1Br] |
| 16-8 | 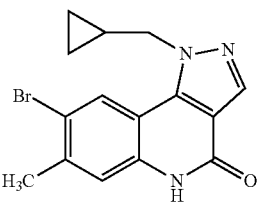 [SMILES: Cc1cc2[nH]c(=O)c3cnn(CC4CC4)c3c2cc1Br] |
| 17 | 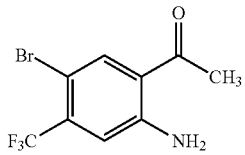 |
| 17-1 | 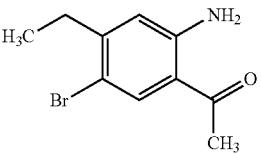 |
| 17-2 | 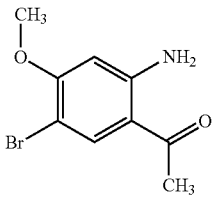 |
| 18 | 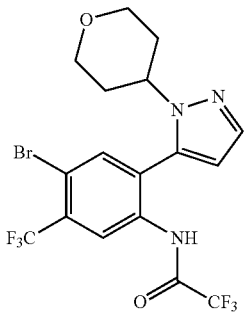 [SMILES: O=C(Nc1cc(C(F)(F)F)c(Br)cc1-c1ccnn1C1CCOCC1)C(F)(F)F] |
TABLE 15-continued
| Pr | Structure |
|---|---|
| 19 | Chiral |
| 19-1 | Chiral |
TABLE 16
| Pr | Structure |
|---|---|
| 19-2 | Chiral |
| 19-3 | 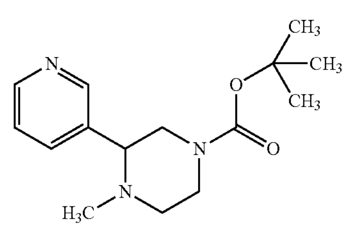 [SMILES: CN1CCN(C(=O)OC(C)(C)C)CC1c1cccnc1] |
| 19-4 | Chiral |

TABLE 16-continued

| Pr | Structure |
|---|---|
| 19-5 | (tert-butyl 4-(3-ethoxypropyl)piperazine-1-carboxylate) |
| 19-6 | (tert-butyl 4-(3-isopropoxypropyl)piperazine-1-carboxylate) |
| 19-7 | (tert-butyl 4-(3-tert-butoxypropyl)piperazine-1-carboxylate) |
| 19-8 | (tert-butyl 4-(3-methoxy-3-methylbutyl)piperazine-1-carboxylate) |
| 19-9 | Chiral (tert-butyl (3S)-4-(4-methoxybutyl)-3-methylpiperazine-1-carboxylate) |
| 19-10 | Chiral (tert-butyl (3R)-4-(4-methoxybutyl)-3-methylpiperazine-1-carboxylate) |

TABLE 17

| Pr | Structure |
|---|---|
| 19-11 | Chiral (tert-butyl (2S)-4-(4-methoxybutyl)-2-methylpiperazine-1-carboxylate) |
| 19-12 | Chiral (tert-butyl (3S)-4-(3-methoxypropyl)-3-methylpiperazine-1-carboxylate) |

TABLE 17-continued
| Pr | Structure |
|---|---|
| 19-13 | 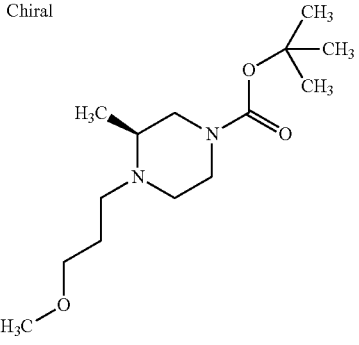 [SMILES: COCCCN1CCN(C(=O)OC(C)(C)C)C[C@@H]1C] |
| 19-14 | 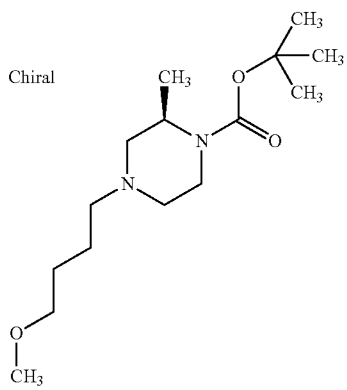 [SMILES: COCCCCN1CCN(C(=O)OC(C)(C)C)[C@H](C)C1] |
| 19-15 | 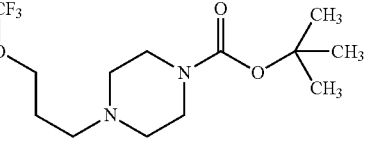 |
| 19-16 | 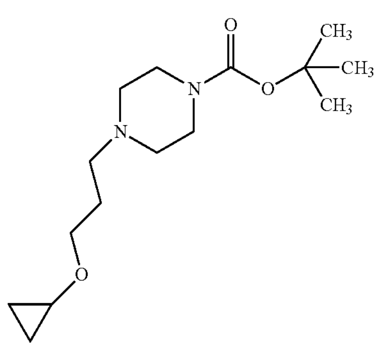 [SMILES: CC(C)(C)OC(=O)N1CCN(CCCOC2CC2)CC1] |
TABLE 17-continued
| Pr | Structure |
|---|---|
| 20 | 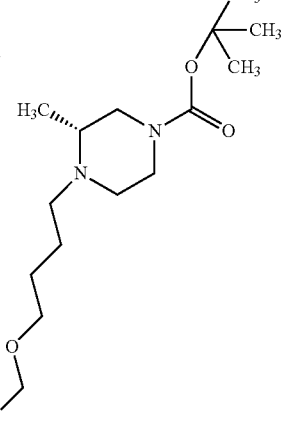 |
| 20-1 | 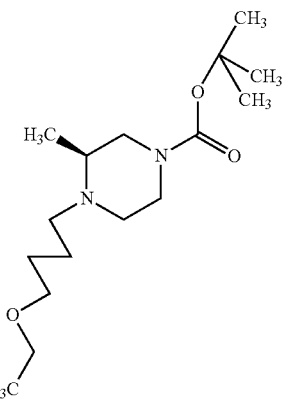 |
TABLE 18
| Pr | Structure |
|---|---|
| 20-2 | 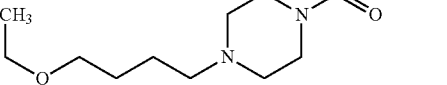 |
| 20-3 | 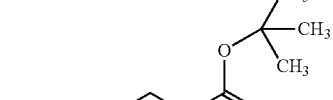 |

TABLE 18-continued

| Pr | Structure |
|---|---|
| 21 | 3HCl; 1-(3-(pyridin-3-yl)propyl)piperazine |
| 21-1 | Chiral, 2HCl; (S)-1-ethyl-2-phenylpiperazine |
| 21-2 | Chiral, 2HCl; (S)-1-(2-methoxyethyl)-2-phenylpiperazine |
| 21-3 | 3HCl; 1-ethyl-2-(pyridin-3-yl)piperazine |
| 21-4 | 3HCl; 1-methyl-2-(pyridin-3-yl)piperazine |
| 21-5 | 2HCl; 1-(4,4-difluoropiperidin-1-yl)piperidine |

TABLE 18-continued

| Pr | Structure |
|---|---|
| 21-6 | 2HCl; 1-(2-methoxycyclohexyl)piperazine |
| 21-7 | Chiral, HCl; 4-((2-fluoropropoxy)methyl)piperidine |
| 21-8 | Chiral, 2HCl; (S)-1-methyl-2-phenylpiperazine |

TABLE 19

| Pr | Structure |
|---|---|
| 21-9 | 2HCl; 1-(3-ethoxypropyl)piperazine |
| 21-10 | 2HCl; 1-(3-isopropoxypropyl)piperazine |

TABLE 19-continued

| Pr | Structure |
|---|---|
| 21-11 | 2HCl, piperazine-N-CH2CH2CH2-O-C(CH3)3 |
| 21-12 | 2HCl, piperazine-N-CH2-C(CH3)2-OCH3 |
| 21-13 | (S)-2-methylpiperazine-N-(CH2)4-OCH3, Chiral, 2HCl |
| 21-14 | Chiral, 2HCl, (S)-2-methylpiperazine-N-(CH2)4-OCH3 |
| 21-15 | Chiral, 2HCl, (2-methylpiperazine)-N-(CH2)4-OCH3 |

TABLE 19-continued

| Pr | Structure |
|---|---|
| 21-16 | Chiral, 2HCl, (S)-2-methylpiperazine-N-CH2CH2CH2-OCH3 |
| 21-17 | Chiral, 2HCl, (2-methylpiperazine)-N-CH2CH2CH2-OCH3 |
| 21-18 | Chiral, 2HCl, (2-methylpiperazine)-N-(CH2)4-O-CH2CH3 |

TABLE 20

| Pr | Structure |
|---|---|
| 21-19 | Chiral, 2HCl, (2-methylpiperazine)-N-(CH2)4-O-CH2CH3 |
| 21-20 | 2HCl, piperazine-N-(CH2)4-O-CH2CH3 |
| 21-21 | HCl, 3-methoxycyclobutyl-CH2-NH-NH2 |
| 21-22 | 2HCl, azetidine-3-N(CH3)-CH2CF3 |

TABLE 20-continued

| Pr | Structure |
|---|---|
| 21-23 | 2HCl, piperazine-CH2-C(F)(F)-CH2-OCH3 |
| 21-24 | 2HCl, piperazine-(CH2)4-O-CH3 |
| 21-25 | Chiral, HCl, (tetrahydrofuran-3-yl)-NH-NH2 |
| 21-26 | 2HCl, Chiral, 2,5-diazabicyclo[2.2.1]heptane-N-(CH2)4-O-CH3 |
| 21-27 | Chiral, 2HCl, 2,5-diazabicyclo[2.2.1]heptane-N-(5-fluoro-6-methylpyridin-2-yl) |
| 21-28 | Chiral, HCl, (tetrahydrofuran-3-yl)-NH-NH2 |

TABLE 20-continued

| Pr | Structure |
|---|---|
| 21-29 | 2HCl, 1-(2-methoxycyclohexyl)piperazine |

TABLE 21

| Pr | Structure |
|---|---|
| 21-30 | Chiral, 2HCl, (3-methylpiperazin-1-yl)-(CH2)4-O-CH3 |
| 21-31 | 2HCl, (4,4-difluorocyclohexyl)methyl-NH-NH2 |
| 21-32 | 2HCl, F3C-O-(CH2)3-piperazine |
| 21-33 | Chiral, 2HCl, (3-methylpiperazin-1-yl)-(5-fluoro-6-methylpyridin-2-yl) |
| 21-34 | Chiral, 2HCl, (3-methylpiperazin-1-yl)-(5-fluoro-6-methylpyridin-2-yl) |

TABLE 21-continued
| Pr | Structure |
|---|---|
| 21-35 | 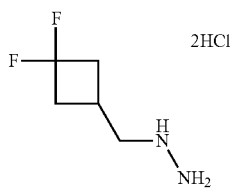 2HCl |
| 21-36 | 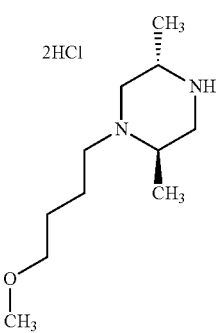 Chiral 2HCl |
| 21-37 | 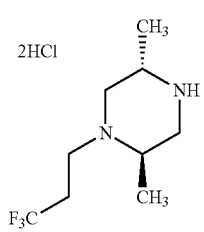 Chiral 2HCl |
| 21-38 | 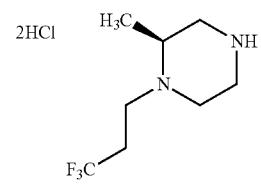 Chiral 2HCl |
| 21-39 | 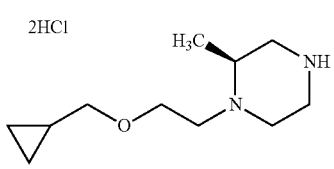 Chiral 2HCl |
TABLE 22
| Pr | Structure |
|---|---|
| 22 | 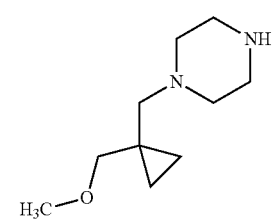 |
| 22-1 | 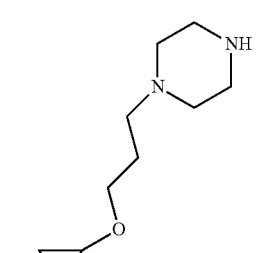 |
| 22-2 | 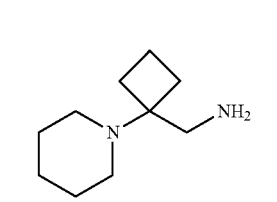 [SMILES: NCC1(N2CCCCC2)CCC1] |
| 23 | 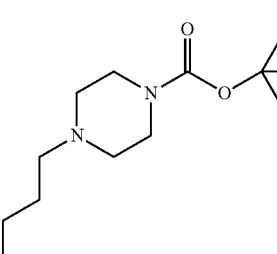 |
| 24 | 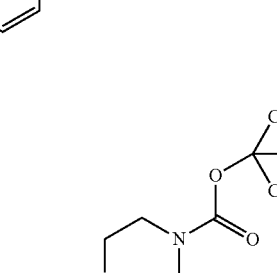 |
| 24-1 | 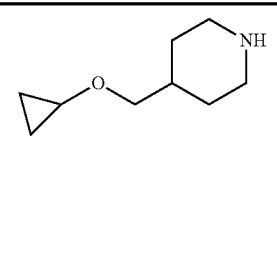 |

| Pr | Structure |
|---|---|
| 24-2 | 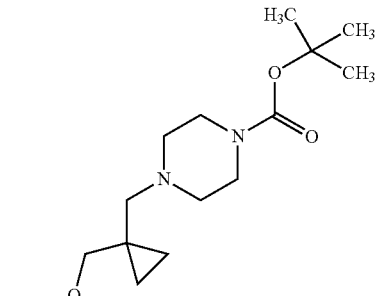 |
| 25 | 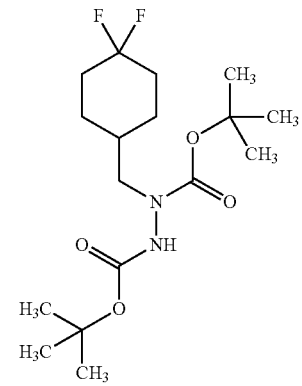 [SMILES: CC(C)(C)OC(=O)NN(CC1CCC(F)(F)CC1)C(=O)OC(C)(C)C] |
| 25-1- | Chiral 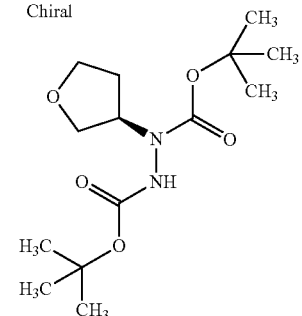 |
| 25-2 | 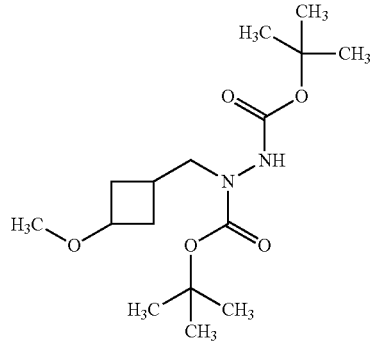 [SMILES: COC1CC(CN(NC(=O)OC(C)(C)C)C(=O)OC(C)(C)C)C1] |
TABLE 23
| Pr | Structure |
|---|---|
| 25-3 | Chiral 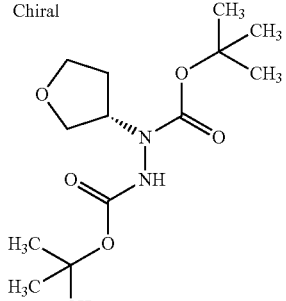 |
| 25-4 | 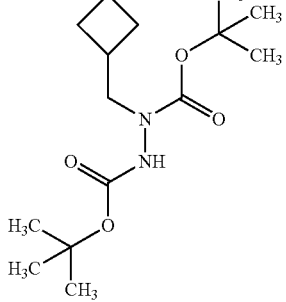 |
| 26 | Chiral 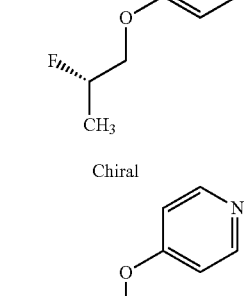 |
| 26-1 | Chiral 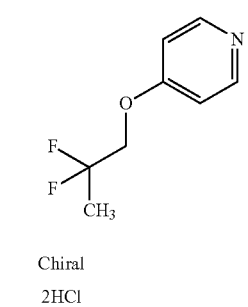 |
| 26-2 | 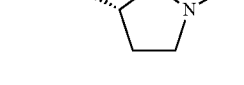 |
| 27 | Chiral 2HCl 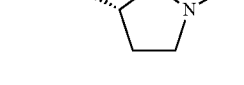 |

TABLE 23-continued

| Pr | Structure |
|---|---|
| 28 | tert-butyl 4-(2,2-difluoro-3-methoxypropanoyl)piperazine-1-carboxylate |
| 28-1 | tert-butyl 4-(1-(methoxymethyl)cyclopropanecarbonyl)piperazine-1-carboxylate |
| 29 | tert-butyl 4-(cyclopropylmethoxy)piperidine-1-carboxylate |
| 30 | Chiral; 4-(((S)-2-fluoropropoxy))piperidine |

TABLE 24

| Pr | Structure |
|---|---|
| 30-1 | Chiral; 4-((2-fluoropropoxy))piperidine |

TABLE 24-continued

| Pr | Structure |
|---|---|
| 30-2 | 4-(2,2-difluoropropoxy)piperidine |
| 31 | Chiral; tert-butyl (S)-4-(5-fluoro-6-methylpyridin-2-yl)-3-methylpiperazine-1-carboxylate |
| 31-1 | Chiral; tert-butyl (R)-4-(5-fluoro-6-methylpyridin-2-yl)-3-methylpiperazine-1-carboxylate |
| 31-2 | Chiral; tert-butyl 5-(5-fluoro-6-methylpyridin-2-yl)-2,5-diazabicyclo[2.2.1]heptane-2-carboxylate |
| 32 | 3-cyclopropoxypropyl 4-methylbenzenesulfonate |
| 33 | N-(2-acetyl-4-bromo-5-(trifluoromethyl)phenyl)-2,2,2-trifluoroacetamide |

TABLE 24-continued
| Pr | Structure |
|---|---|
| 34-1 | 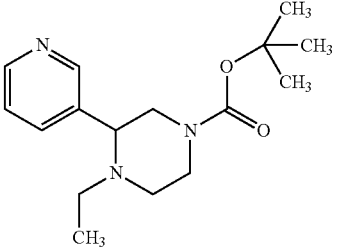 [SMILES: CCN1CCN(C(=O)OC(C)(C)C)CC1c1cccnc1] |
| 34-2 | 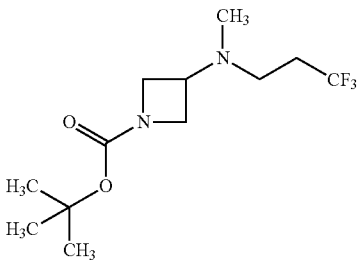 [SMILES: CN(CCC(F)(F)F)C1CN(C(=O)OC(C)(C)C)C1] |
| 34-3 | Chiral 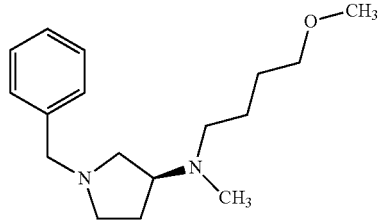 |
TABLE 25
| Pr | Structure |
|---|---|
| 34-4 | Chiral 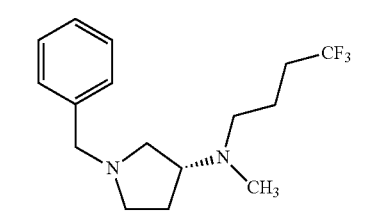 |
| 34-5 | Chiral 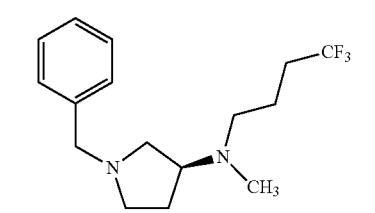 |
TABLE 25-continued
| Pr | Structure |
|---|---|
| 34-6 | Chiral 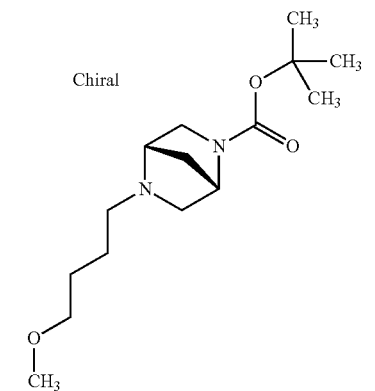 [SMILES: COCCCCN1C[C@@H]2C[C@H]1CN2C(=O)OC(C)(C)C] |
| 34-7 | Chiral |
| 34-8 | Chiral |
| 34-9 | Chiral |
| 34-10 | 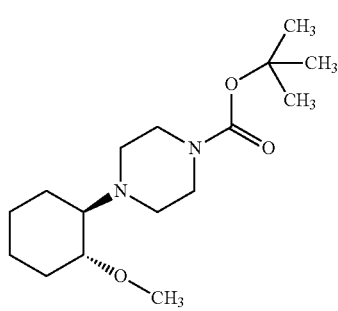 [SMILES: CO[C@@H]1CCCC[C@H]1N1CCN(C(=O)OC(C)(C)C)CC1] |

TABLE 25-continued

| Pr | Structure |
|---|---|
| 34-11 | (tert-butyl 4-(2-methoxycyclohexyl)piperazine-1-carboxylate) |
| 34-12 | Chiral (tert-butyl (2S,5R)-2,5-dimethyl-4-(3,3,3-trifluoropropyl)piperazine-1-carboxylate) |

TABLE 26

| Pr | Structure |
|---|---|
| 34-13 | Chiral (tert-butyl (2S,5R)-4-(4-methoxybutyl)-2,5-dimethylpiperazine-1-carboxylate) |
| 34-14 | Chiral (tert-butyl (3S)-3-methyl-4-(3,3,3-trifluoropropyl)piperazine-1-carboxylate) |
| 35-1 | Chiral (N-methyl-N-[(3S)-pyrrolidin-3-yl]-3,3,3-trifluoropropan-1-amine) |

TABLE 26-continued

| Pr | Structure |
|---|---|
| 35-2 | Chiral |
| 35-3 | Chiral |
| 35-4 | Chiral |
| 35-5 | Chiral |
| 35-6 | Chiral |
| 36 | 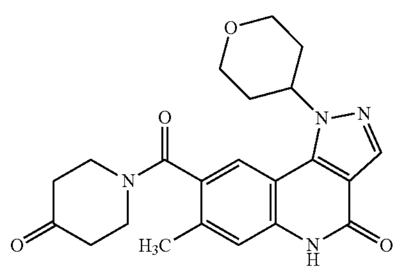 [SMILES: Cc1cc2[nH]c(=O)c3cnn(C4CCOCC4)c3c2cc1C(=O)N1CCC(=O)CC1] |
| 37-1 | Chiral |

TABLE 26-continued

| Pr | Structure |
|---|---|
| 37-2 | 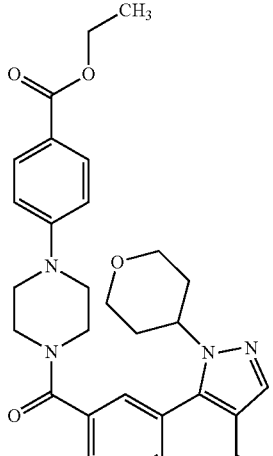 |

TABLE 27

| Pr | Data |
|---|---|
| 1 | ESI+: 306.0, 308.0 |
| 1-1 | ESI+: 322.1, 324.1 |
| 1-2 | ESI+: 320.1, 322.1 |
| 2 | ESI+: 336.0, 338.0 |
| 2-1 | ESI+: 352.0, 354.0 |
| 3 | ESI+: 332.0, 334.0 |
| 3-1 | ESI+: 348.0, 350.0 |
| 3-2 | ESI+: 362.2, 364.2 |
| 3-3 | ESI+: 346.2, 348.2 |
| 3-4 | ESI+: 346.1, 348.1 |
| 3-5 | ESI+: 332.0 |
| 3-6 | ESI+: 346.0, 348.0 |
| 3-7 | ESI−: 346.1, 348.1 |
| 3-8 | ESI+: 376.0, 378.0 |
| 3-9 | ESI+: 376.0, 378.0 |
| 3-10 | ESI+: 375.2, 377.2 |
| 3-11 | ESI+: 361.1, 363.1 |
| 3-12 | ESI+: 437.3, 439.1 |
| 3-13 | ESI+: 362.0, 364.0 |
| 4 | ESI+: 299.0, 301.0 |
| 5 | ESI+: 312.1 |
| 5-1 | ESI+: 328.1 |
| 5-2 | ESI+: 342.3 |
| 5-3 | ESI+: 326.2 |
| 5-4 | ESI+: 326.3 |
| 5-5 | ESI+: 312.0 |
| 5-6 | ESI+: 326.2 |
| 5-7 | ESI+: 328.0 |
| 5-8 | APCI/ESI+: 312.1 |
| 5-9 | ESI+: 356.1 |
| 5-10 | ESI+: 356.1 |
| 5-11 | ESI+: 326.1 |
| 5-12 | ESI+: 328.1 |

TABLE 28

| Pr | Data |
|---|---|
| 5-13 | ESI−: 354.3 |
| 5-14 | ESI+: 328.2 |
| 5-15 | ESI+: 355.2 |
| 5-16 | APCI+: 341.1 |
| 5-17 | ESI+: 376.1 |
| 5-18 | ESI−: 388.3 |
| 5-19 | ESI+: 362.1 |

TABLE 28-continued

| Pr | Data |
|---|---|
| 6 | ESI+: 269.9, 271.9 |
| 6-1 | ESI+: 286.0, 288.0 |
| 6-2 | ESI+: 284.0, 286.0 |
| 7 | ESI+: 324.9, 326.9 |
| 7-1 | ESI+: 339.0, 341.1 |
| 7-2 | ESI+: 341.0, 343.0 |
| 7-3 | ESI+: 433.1, 435.1 |
| 8 | ESI−: 376.1, 378.1 |
| 8-1 | ESI+: 362.2, 364.2 |
| 8-2 | ESI+: 348.0, 350.0 |
| 8-3 | ESI+: 362.2, 364.2 |
| 8-4 | ESI+: 364.0, 366.0 |
| 8-5 | ESI−: 346.2, 348.1 |
| 8-6 | ESI+: 392.0, 394.0 |
| 8-7 | ESI+: 392.0, 394.0 |
| 8-8 | ESI+: 362.0, 364.1 |
| 8-9 | ESI+: 364.1, 366.0 |
| 8-10 | ESI+: 392.0, 394.0 |
| 8-11 | ESI+: 364.1, 366.1 |
| 8-12 | ESI+: 391.1, 393.1 |
| 8-13 | ESI+: 377.3, 379.2 |
| 8-14 | ESI+: 412.0, 414.0 |
| 8-15 | ESI+: 426.0, 428.0 |
| 8-16 | ESI+: 398.0, 400.0 |
| 8-17 | ESI+: 453.2, 455.2 |
| 8-18 | ESI+: 378.2, 380.2 |

TABLE 29

| Pr | Data |
|---|---|
| 9 | ESI+: 336.0, 338.0 |
| 9-1 | ESI+: 320.1, 322.1 |
| 9-2 | ESI+: 306.1, 308.1 |
| 9-3 | ESI+: 320.2, 322.2 |
| 9-4 | ESI+: 322.0, 324.0 |
| 9-5 | ESI+: 350.0, 352.0 |
| 9-6 | ESI+: 350.0, 352.0 |
| 9-7 | ESI+: 320.0, 322.0 |
| 9-8 | ESI+: 322.0, 324.0 |
| 9-9 | ESI+: 350.1, 352.0 |
| 9-10 | ESI+: 322.1, 324.1 |
| 9-11 | ESI+: 349.1, 351.1 |
| 9-12 | ESI+: 335.2, 337.2 |
| 9-13 | ESI+: 370.1, 372.0 |
| 9-14 | ESI+: 384.1, 386.1 |
| 9-15 | ESI+: 356.1, 358.1 |
| 9-16 | ESI+: 411.2, 413.1 |
| 9-17 | ESI+: 336.1, 338.1 |
| 10 | ESI+: 328.2 |
| 10-1 | ESI+: 312.2 |
| 10-2 | ESI+: 298.0 |
| 10-3 | ESI+: 312.2 |
| 10-4 | ESI+: 314.1 |
| 10-5 | ESI+: 306.0, 308.0 |
| 10-6 | ESI−: 296.2 |
| 10-7 | ESI+: 342.1 |
| 10-8 | ESI+: 342.1 |
| 10-9 | ESI−: 310.2 |
| 10-10 | ESI−: 312.3 |
| 10-11 | ESI−: 340.3 |
| 10-12 | ESI−: 312.2 |
| 10-13 | ESI+: 341.2 |
| 10-14 | ESI+: 327.1 |

TABLE 30

| Pr | Data |
|---|---|
| 10-15 | ESI−: 360.2 |
| 10-16 | ESI−: 374.2 |
| 10-17 | ESI+: 403.2 |
| 10-18 | ESI+: 328.1 |

TABLE 30-continued

| Pr | Data |
|---|---|
| 10-19 | ESI−: 346.2 |
| 10-20 | ESI+: 390.1, 392.1 |
| 10-21 | ESI+: 382.2 |
| 11 | APCI/ESI+: 350.1, 352.1 |
| 12 | APCI/ESI+: 287.0 |
| 13 | APCI/ESI−: 384.0, 386.0 |
| 14 | APCI+: 417.2 |
| 14-1 | ESI+: 342.1 |
| 14-2 | ESI+: 396.1 |
| 15 | ESI + (M + Na)$^+$: 264.2 |
| 16 | ESI+: 416.0, 418.0 |
| 16-1 | ESI+: 346.0, 348.0 |
| 16-2 | ESI+: 348.0, 350.0 |
| 16-3 | ESI+: 376.0, 378.0 |
| 16-4 | ESI+: 348.0, 350.0 |
| 16-5 | ESI+: 396.0, 398.0 |
| 16-6 | ESI−: 408.2, 410.2 |
| 16-7 | ESI−: 380.0, 382.0 |
| 16-8 | ESI+: 332.1, 334.2 |
| 17 | ESI+: 281.9, 284.0 |
| 17-1 | ESI+: 242.0, 244.0 |
| 17-2 | ESI+: 244.1, 246.1 |
| 18 | ESI+: 485.9, 487.9 |
| 19 | NMR-CDCl3: 1.34-1.56 (9H, m), 2.10-2.18 (1H, m), 2.25-2.33 (1H, m), 2.66-3.20 (5H, m), 3.24 (3H, s), 3.30-3.46 (2H, m), 3.80-4.16 (2H, m), 7.22-7.43 (5H, m) |
| 19-1 | ESI+: 291.2 |
| 19-2 | ESI+: 277.2 |
| 19-3 | ESI+: 278.3 |
| 19-4 | ESI + (M + Na)$^+$: 298.1 |

TABLE 31

| Pr | Data |
|---|---|
| 19-5 | ESI+: 273.2 |
| 19-6 | ESI+: 287.2 |
| 19-7 | ESI+: 301.3 |
| 19-8 | ESI+: 287.2 |
| 19-9 | ESI+: 287.2 |
| 19-10 | ESI+: 287.3 |
| 19-11 | ESI+: 287.2 |
| 19-12 | ESI+: 273.2 |
| 19-13 | ESI+: 273.2 |
| 19-14 | ESI+: 287.2 |
| 19-15 | ESI+: 313.2 |
| 19-16 | ESI+: 285.2 |
| 20 | ESI+: 301.3 |
| 20-1 | ESI+: 301.1 |
| 20-2 | ESI+: 287.1 |
| 20-3 | ESI+: 299.2 |
| 21 | ESI+: 206.1 |
| 21-1 | ESI+: 191.2 |
| 21-2 | ESI+: 221.3 |
| 21-3 | ESI+: 192.2 |
| 21-4 | ESI+: 178.1 |
| 21-5 | ESI+: 205.2 |
| 21-6 | ESI+: 199.1 |
| 21-7 | ESI+: 176.2 |
| 21-8 | |
| 21-9 | ESI+: 173.1 |
| 21-10 | ESI+: 187.2 |
| 21-11 | ESI+: 201.2 |
| 21-12 | ESI+: 187.2 |
| 21-13 | ESI+: 187.3 |
| 21-14 | ESI+: 187.2 |
| 21-15 | ESI+: 187.2 |
| 21-16 | APCI+: 173.1 |

TABLE 32

| Pr | Data |
|---|---|
| 21-17 | APCI+: 173.0 |
| 21-18 | ESI+: 201.2 |
| 21-19 | ESI+: 201.2 |
| 21-20 | ESI+: 187.2 |
| 21-21 | ESI+: 131.1 |
| 21-22 | ESI+: 183.2 |
| 21-23 | ESI+: 195.1 |
| 21-24 | ESI+: 187.0 |
| 21-25 | ESI+: 103.0 |
| 21-26 | ESI+: 185.1 |
| 21-27 | ESI+: 208.2 |
| 21-28 | ESI+: 103.0 |
| 21-29 | ESI+: 199.1 |
| 21-30 | ESI+: 187.2 |
| 21-31 | ESI+: 165.2 |
| 21-32 | ESI+: 213.1 |
| 21-33 | ESI+: 210.1 |
| 21-34 | ESI+: 210.1 |
| 21-35 | ESI+: 137.2 |
| 21-36 | ESI−: 201.1 |
| 21-37 | ESI+: 211.1 |
| 21-38 | ESI+: 197.1 |
| 21-39 | ESI+: 199.2 |
| 22 | ESI+: 156.2 |
| 22-1 | ESI+: 185.2 |
| 22-2 | ESI+: 185.3 |
| 23 | ESI+: 169.2 |
| 24 | ESI+: 306.1 |
| 24-1 | ESI+: 295.2 |
| 24-2 | ESI+: 285.2 |
| 25 | ESI−: 363.2 |
| 25-1 | ESI + (M + Na)$^+$: 325.1 |
| 25-2 | ESI + (M + Na)$^+$: 353.1 |

TABLE 33

| Pr | Data |
|---|---|
| 25-3 | ESI + (M + Na)$^+$: 325.2 |
| 25-4 | ESI + (M + Na)$^+$: 359.1 |
| 26 | ESI+: 156.1 |
| 26-1 | ESI+: 156.1 |
| 26-2 | ESI+: 174.1 |
| 27 | ESI+: 116.0 |
| 28 | ESI + (M + Na)$^+$: 331.1 |
| 28-1 | ESI + (M + Na)$^+$: 321.1 |
| 29 | ESI + (M + Na)$^+$: 278.2 |
| 30 | ESI+: 162.2 |
| 30-1 | ESI+: 162.2 |
| 30-2 | ESI+: 180.1 |
| 31 | ESI+: 310.2 |
| 31-1 | ESI+: 310.2 |
| 31-2 | ESI+: 308.2 |
| 32 | ESI + (M + Na)$^+$: 293.1 |
| 33 | ESI−: 376.0, 378.0 |
| 34-1 | ESI+: 292.2 |
| 34-2 | ESI+: 283.3 |
| 34-3 | ESI+: 287.2 |
| 34-4 | ESI+: 287.2 |
| 34-5 | ESI+: 277.3 |
| 34-6 | ESI+: 277.3 |
| 34-7 | ESI+: 301.3 |
| 34-8 | ESI+: 301.2 |
| 34-9 | ESI+: 285.2 |
| 34-10 | ESI+: 299.2 |
| 34-11 | ESI+: 299.2 |
| 34-12 | APCI+: 311.2 |
| 34-13 | ESI+: 301.3 |
| 34-14 | ESI+: 297.2 |
| 35-1 | ESI+: 197.1 |
| 35-2 | ESI+: 197.1 |

TABLE 34
| Pr | Data |
|---|---|
| 35-3 | ESI+: 187.2 |
| 35-4 | ESI+: 187.2 |
| 35-5 | ESI+: 211.1 |
| 35-6 | ESI+: 211.1 |
| 36 | ESI+: 409.3 |
| 37-1 | ESI+: 467.1 |
| 37-2 | ESI+: 544.1 |
TABLE 35
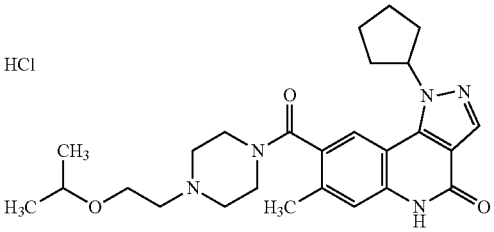 [SMILES: Cc1cc2[nH]c(=O)c3cnn(C4CCCC4)c3c2cc1C(=O)N1CCN(CCOC(C)C)CC1 ; Cl]

TABLE 35-continued
| Ex | Structure |
|---|---|
| 10 | 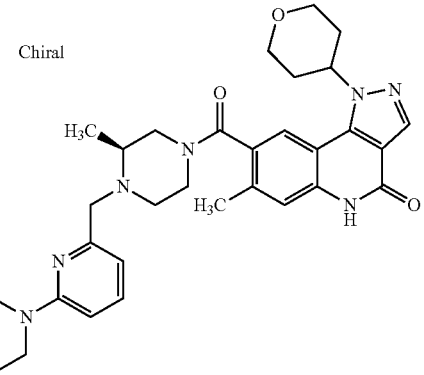 Chiral |
| 11 | 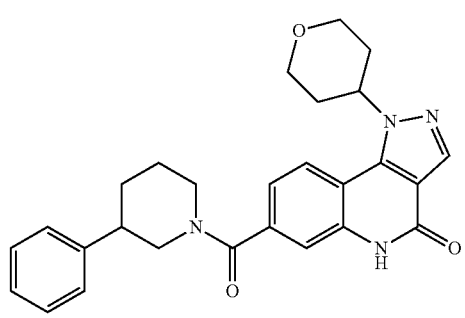 [SMILES: O=C(c1ccc2c(c1)[nH]c(=O)c1cnn(C3CCOCC3)c12)N1CCCC(c2ccccc2)C1] |
TABLE 36
| Ex | Structure |
|---|---|
| 12 | 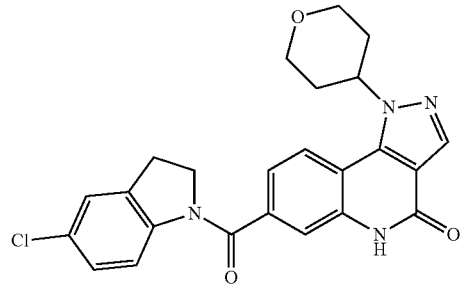 [SMILES: O=C(c1ccc2c(c1)[nH]c(=O)c1cnn(C3CCOCC3)c12)N1CCc2cc(Cl)ccc21] |
| 13 | 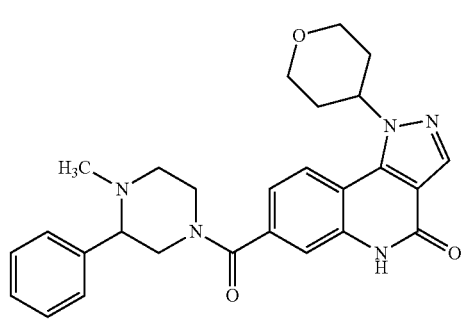 [SMILES: CN1CCN(C(=O)c2ccc3c(c2)[nH]c(=O)c2cnn(C4CCOCC4)c23)CC1c1ccccc1] |
TABLE 36-continued
| Ex | Structure |
|---|---|
| 14 | 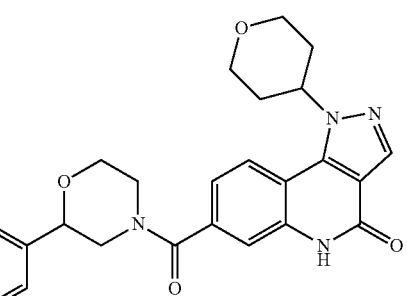 |
| 15 | 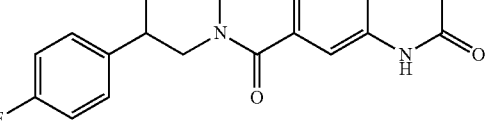 |
| 16 | 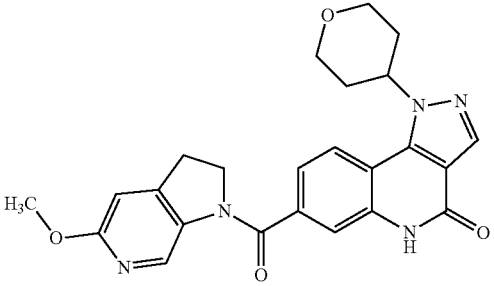 [SMILES: COc1cc2c(cn1)N(C(=O)c1ccc3c(c1)[nH]c(=O)c1cnn(C4CCOCC4)c13)CC2] 2HCl |
| 17 | 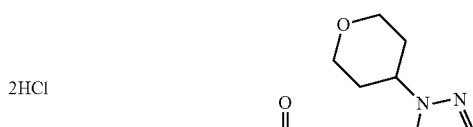 |
| 18 | 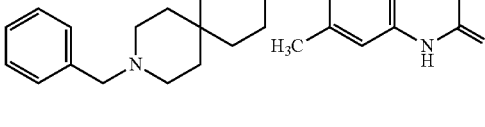 |

TABLE 36-continued

| Ex | Structure |
|---|---|
| 19 | 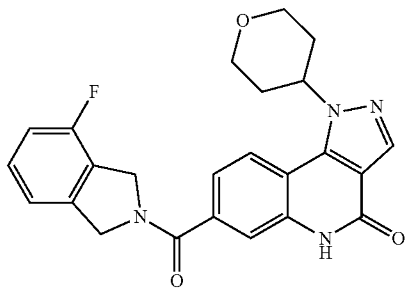 [SMILES: O=C(c1ccc2c(c1)[nH]c(=O)c1cnn(C3CCOCC3)c12)N1Cc2cccc(F)c2C1] |
| 20 | 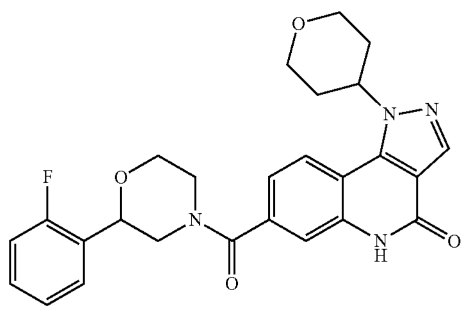 [SMILES: O=C(c1ccc2c(c1)[nH]c(=O)c1cnn(C3CCOCC3)c12)N1CCOC(c2ccccc2F)C1] |
| 21 | 2HCl |
| 22 | 2HCl |
| 23 | HCl |

TABLE 37

| Ex | Structure |
|---|---|
| 24 | 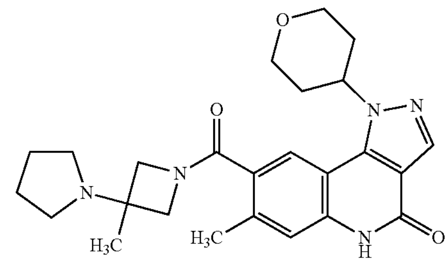 [SMILES: Cc1cc2[nH]c(=O)c3cnn(C4CCOCC4)c3c2cc1C(=O)N1CC(C)(N2CCCC2)C1] |
| 25 | HCl |
| 26 | HCl |
| 27 | 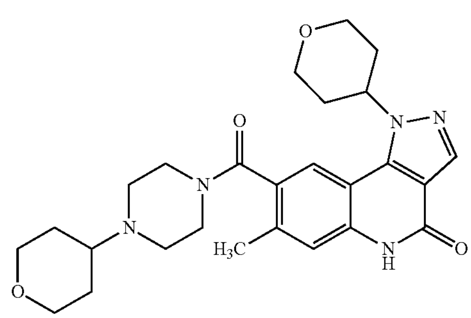 [SMILES: Cc1cc2[nH]c(=O)c3cnn(C4CCOCC4)c3c2cc1C(=O)N1CCN(C2CCOCC2)CC1] |
| 28 | HCl |

TABLE 37-continued
| Ex | Structure |
|---|---|
| 29 | 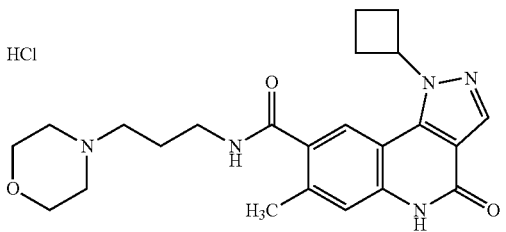 [SMILES: Cc1cc2[nH]c(=O)c3cnn(C4CCC4)c3c2cc1C(=O)NCCCN1CCOCC1 ; Cl] |
| 30 | 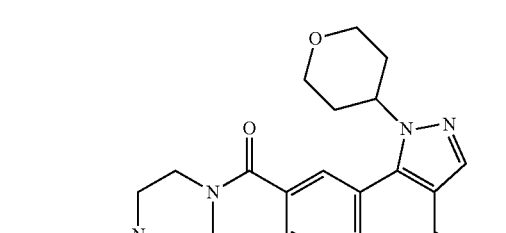 |
| 31 | 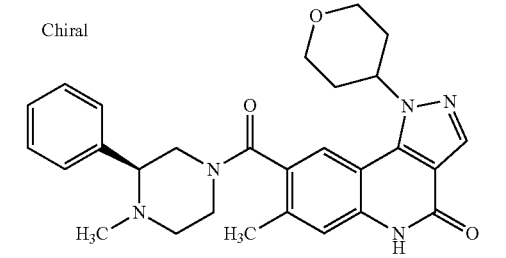 |
| 32 | 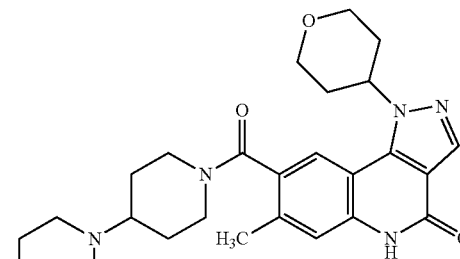 |
| 33 | 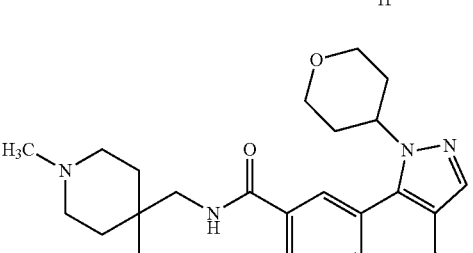 |
TABLE 38
| Ex | Structure |
|---|---|
| 34 | 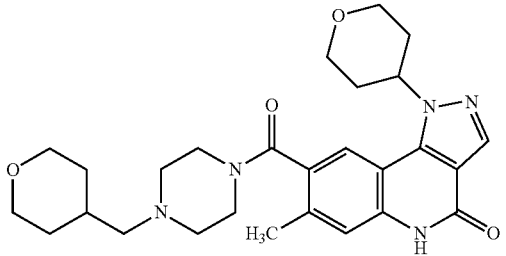 [SMILES: Cc1cc2[nH]c(=O)c3cnn(C4CCOCC4)c3c2cc1C(=O)N1CCN(CC2CCOCC2)CC1] |
| 35 | 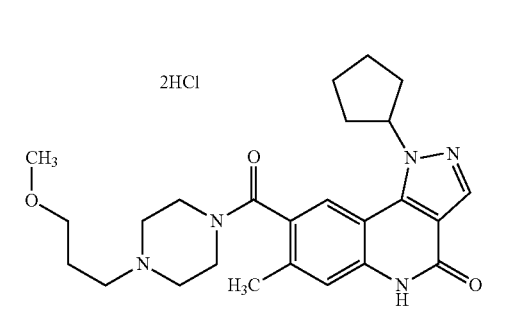 [SMILES: COCCCN1CCN(C(=O)c2cc3c(cc2C)[nH]c(=O)c2cnn(C4CCCC4)c23)CC1 ; "2HCl"] |
| 36 | 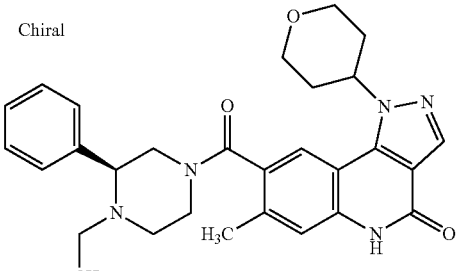 |
| 37 | 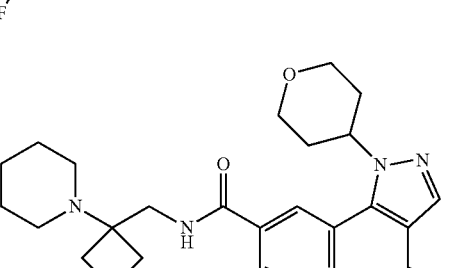 |
| 38 | 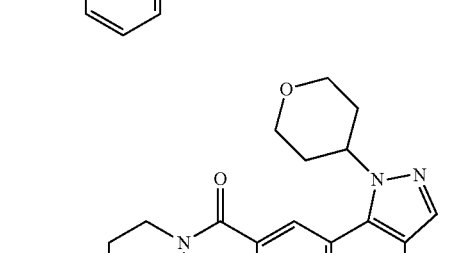 |

TABLE 38-continued

| Ex | Structure |
|---|---|
| 39 | 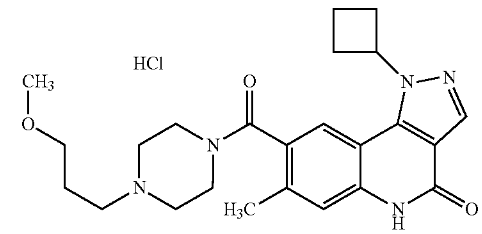 [SMILES: COCCCN1CCN(C(=O)c2cc3c(cc2C)[nH]c(=O)c2cnn(C4CCC4)c23)CC1 ; Cl] |
| 40 | 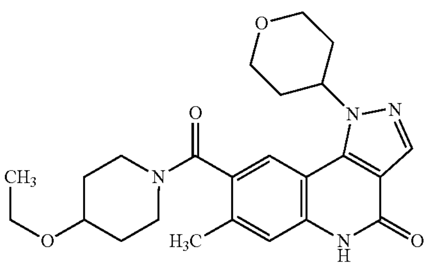 [SMILES: CCOC1CCN(C(=O)c2cc3c(cc2C)[nH]c(=O)c2cnn(C4CCOCC4)c23)CC1] |
| 41 | 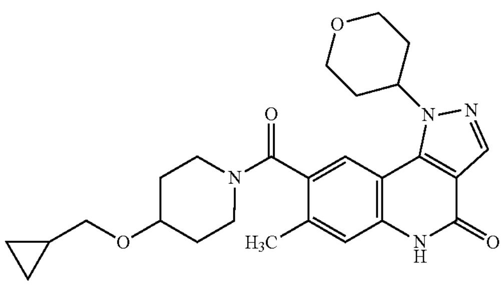 [SMILES: Cc1cc2[nH]c(=O)c3cnn(C4CCOCC4)c3c2cc1C(=O)N1CCC(OCC2CC2)CC1] |
| 42 | 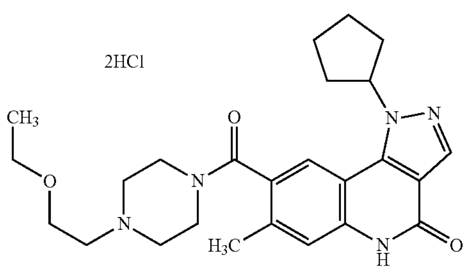 [SMILES: CCOCCN1CCN(C(=O)c2cc3c(cc2C)[nH]c(=O)c2cnn(C4CCCC4)c23)CC1 ; "2HCl"] |
| 43 | 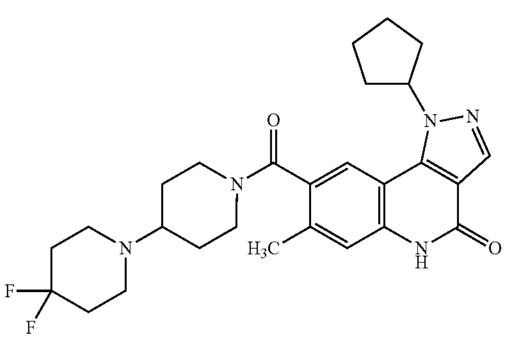 [SMILES: Cc1cc2[nH]c(=O)c3cnn(C4CCCC4)c3c2cc1C(=O)N1CCC(N2CCC(F)(F)CC2)CC1] |

TABLE 39

| Ex | Structure |
|---|---|
| 44 | 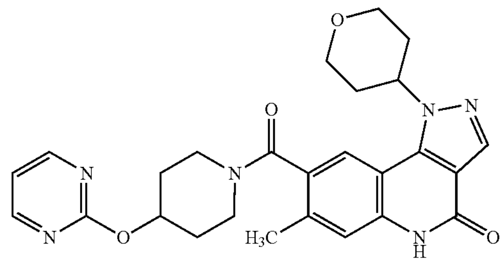 [SMILES: Cc1cc2[nH]c(=O)c3cnn(C4CCOCC4)c3c2cc1C(=O)N1CCC(Oc2ncccn2)CC1] |
| 45 | 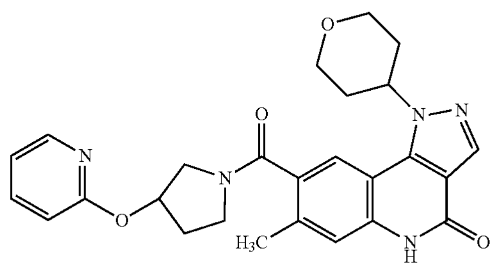 [SMILES: Cc1cc2[nH]c(=O)c3cnn(C4CCOCC4)c3c2cc1C(=O)N1CCC(Oc2ccccn2)C1] |
| 46 | 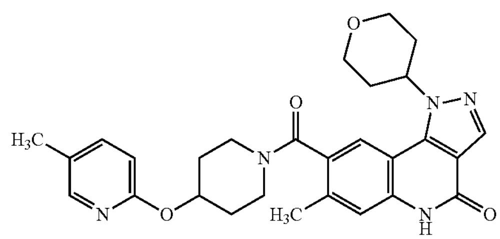 [SMILES: Cc1ccc(OC2CCN(C(=O)c3cc4c(cc3C)[nH]c(=O)c3cnn(C5CCOCC5)c34)CC2)nc1] |
| 47 | Chiral |
| 48 | 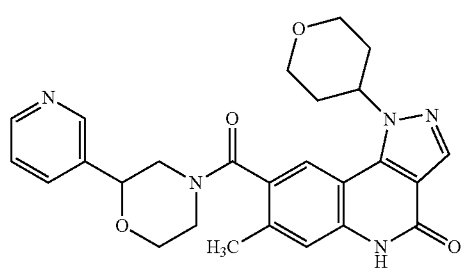 [SMILES: Cc1cc2[nH]c(=O)c3cnn(C4CCOCC4)c3c2cc1C(=O)N1CCOC(c2cccnc2)C1] |

TABLE 39-continued

| Ex | Structure |
|---|---|
| 49 | 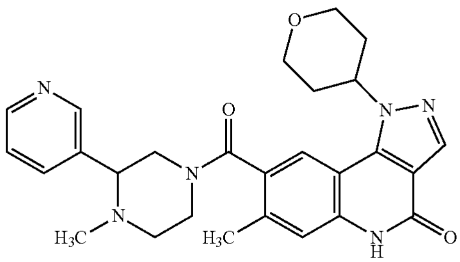 [SMILES: Cc1cc2[nH]c(=O)c3cnn(C4CCOCC4)c3c2cc1C(=O)N1CCN(C)C(c2cccnc2)C1] |
| 50 | 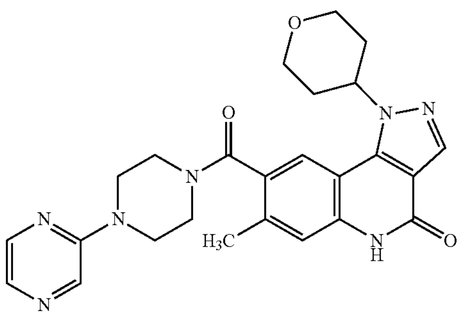 [SMILES: Cc1cc2[nH]c(=O)c3cnn(C4CCOCC4)c3c2cc1C(=O)N1CCN(c2cnccn2)CC1] |
| 51 | 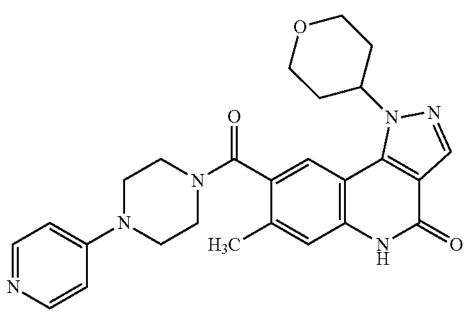 [SMILES: Cc1cc2[nH]c(=O)c3cnn(C4CCOCC4)c3c2cc1C(=O)N1CCN(c2ccncc2)CC1] |
| 52 | 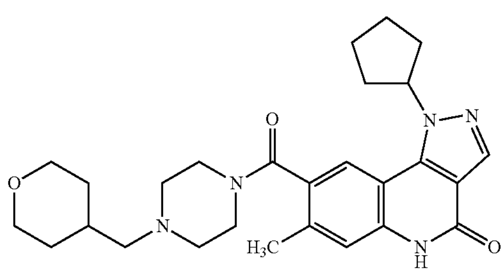 [SMILES: Cc1cc2[nH]c(=O)c3cnn(C4CCCC4)c3c2cc1C(=O)N1CCN(CC2CCOCC2)CC1] |
| 53 | 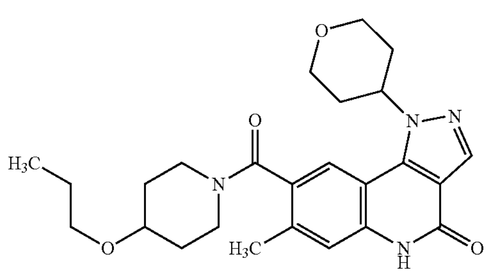 |

TABLE 40

| Ex | Structure |
|---|---|
| 54 | 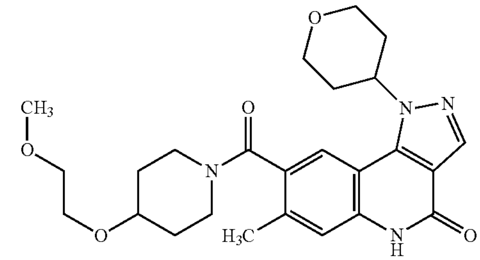 [SMILES: COCCOC1CCN(C(=O)c2cc3c(cc2C)[nH]c(=O)c2cnn(C4CCOCC4)c23)CC1] |
| 55 | 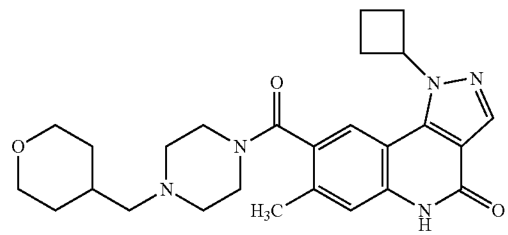 [SMILES: Cc1cc2[nH]c(=O)c3cnn(C4CCC4)c3c2cc1C(=O)N1CCN(CC2CCOCC2)CC1] |
| 56 | 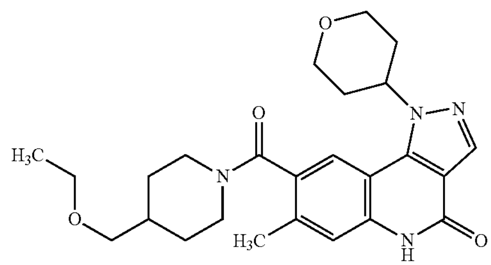 [SMILES: CCOCC1CCN(C(=O)c2cc3c(cc2C)[nH]c(=O)c2cnn(C4CCOCC4)c23)CC1] |
| 57 | 3HCl |
| 58 | 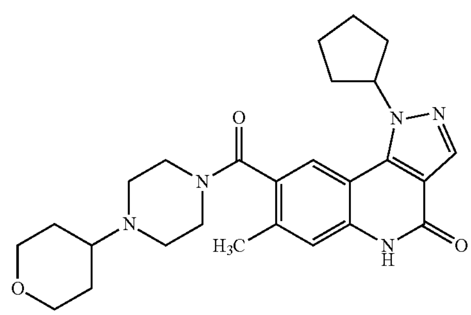 [SMILES: Cc1cc2[nH]c(=O)c3cnn(C4CCCC4)c3c2cc1C(=O)N1CCN(C2CCOCC2)CC1] |
| 59 | 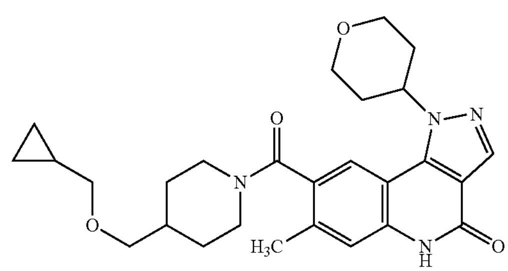 [SMILES: Cc1cc2[nH]c(=O)c3cnn(C4CCOCC4)c3c2cc1C(=O)N1CCC(COCC2CC2)CC1] |

TABLE 40-continued

| Ex | Structure |
|---|---|
| 60 | Chiral |
| 61 | 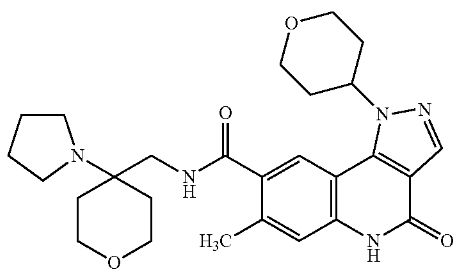 [SMILES: Cc1cc2[nH]c(=O)c3cnn(C4CCOCC4)c3c2cc1C(=O)NCC1(N2CCCC2)CCOCC1] |
| 62 | HCl |
| 63 | 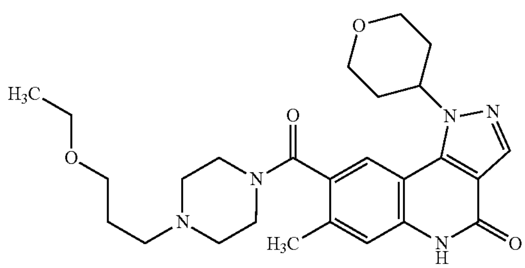 [SMILES: CCOCCCN1CCN(C(=O)c2cc3c(cc2C)[nH]c(=O)c2cnn(C4CCOCC4)c23)CC1] |

TABLE 41

| Ex | Structure |
|---|---|
| 64 | |
| 65 | 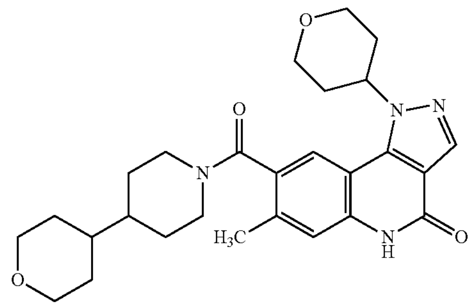 [SMILES: Cc1cc2[nH]c(=O)c3cnn(C4CCOCC4)c3c2cc1C(=O)N1CCC(C2CCOCC2)CC1] |
| 66 | 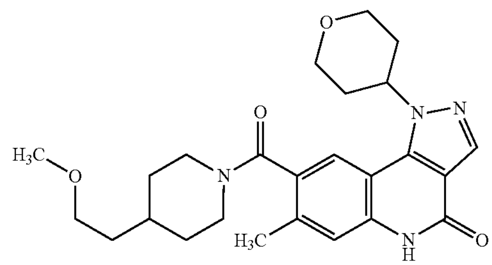 |
| 67 | 2HCl |
| 68 | 2HCl |
| 69 | 2HCl |

TABLE 41-continued

| Ex | Structure |
|---|---|
| 70 | (2HCl salt) structure with ethoxyethyl-piperazine carbonyl linked to 1-cyclobutyl-pyrazolo-quinolinone with methyl |
| 71 | Chiral, HCl; (5-chloropyridin-2-yl)oxy-pyrrolidinyl carbonyl linked to 1-(tetrahydropyran-4-yl)-pyrazolo-quinolinone with methyl |
| 72 | Chiral, HCl; (5-chloropyridin-2-yl)oxy-pyrrolidinyl (opposite stereo) carbonyl linked to 1-(tetrahydropyran-4-yl)-pyrazolo-quinolinone with methyl |
| 73 | 4-(2-methoxyethoxy)piperidinyl carbonyl linked to 1-cyclobutyl-pyrazolo-quinolinone with methyl |
| 74 | 5-benzyl-octahydropyrrolo[3,4-c]pyrrolyl carbonyl linked to 1-(tetrahydropyran-4-yl)-pyrazolo-quinolinone with methyl |

TABLE 41-continued

| Ex | Structure |
|---|---|
| 75 | 4-hydroxy-piperidinyl carbonyl linked to 1-(tetrahydropyran-4-yl)-pyrazolo-quinolinone with methyl |

TABLE 42

| Ex | Structure |
|---|---|
| 76 | 4-((2-fluoroethoxy)methyl)piperidinyl carbonyl linked to 1-(tetrahydropyran-4-yl)-pyrazolo-quinolinone with methyl |
| 77 | 4-(3-(tert-butoxy)propyl)piperazinyl carbonyl linked to 1-(tetrahydropyran-4-yl)-pyrazolo-quinolinone with methyl |
| 78 | 3-(methoxymethyl)azetidinyl carbonyl linked to 1-(tetrahydropyran-4-yl)-pyrazolo-quinolinone with methyl |
| 79 | 2HCl; 4-(4-methoxybutyl)piperazinyl carbonyl linked to 1-cyclobutyl-pyrazolo-quinolinone with methyl |

TABLE 42-continued

| Ex | Structure |
|---|---|
| 80 | Chiral, HCl |
| 81 | 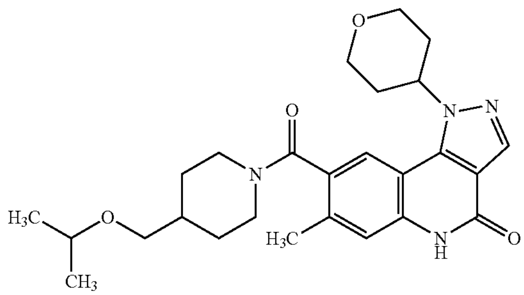 [SMILES: Cc1cc2[nH]c(=O)c3cnn(C4CCOCC4)c3c2cc1C(=O)N1CCC(COC(C)C)CC1] |
| 82 | HCl |
| 83 | HCl |
| 84 | HCl |
| 85 | HCl |
| 86 | 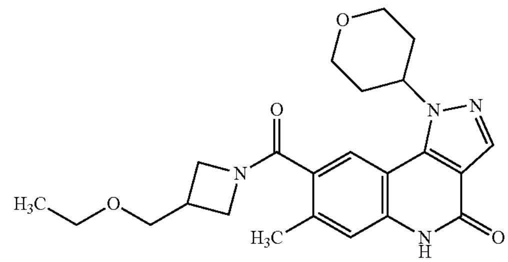 [SMILES: CCOCC1CN(C(=O)c2cc3c(cc2C)[nH]c(=O)c2cnn(C4CCOCC4)c23)C1] |
| 87 | 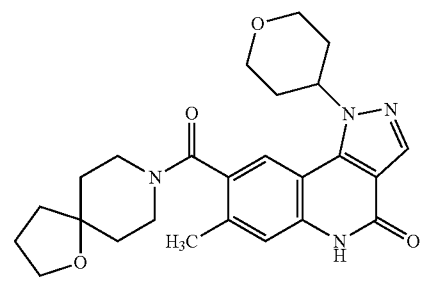 [SMILES: Cc1cc2[nH]c(=O)c3cnn(C4CCOCC4)c3c2cc1C(=O)N1CCC2(CCCO2)CC1] |

TABLE 43

| Ex | Structure |
|---|---|
| 88 | 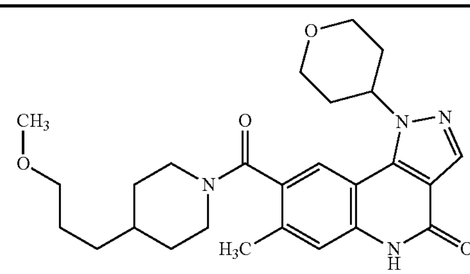 |
| 89 | 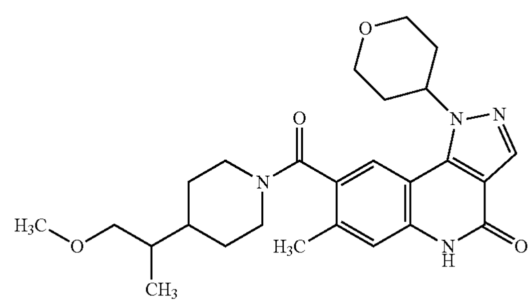 [SMILES: COCC(C)C1CCN(C(=O)c2cc3c(cc2C)[nH]c(=O)c2cnn(C4CCOCC4)c23)CC1] |
| 90 | 2HCl |

TABLE 43-continued

| Ex | Structure |
|---|---|
| 91 | 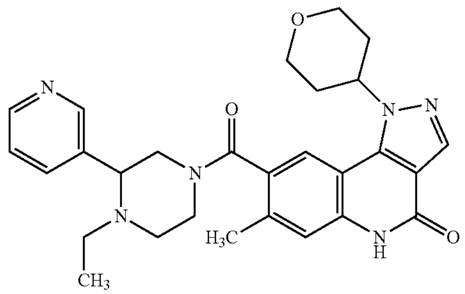 [SMILES: CCN1CCN(C(=O)c2cc3c(cc2C)[nH]c(=O)c2cnn(C4CCOCC4)c23)CC1c1cccnc1] |
| 92 | 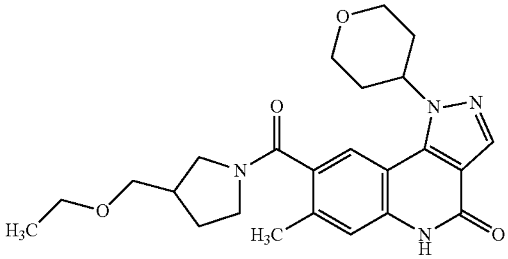 [SMILES: CCOCC1CCN(C(=O)c2cc3c(cc2C)[nH]c(=O)c2cnn(C4CCOCC4)c23)C1] |
| 93 | 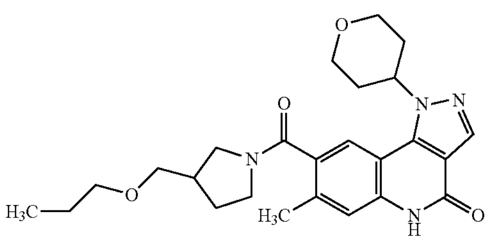 [SMILES: CCCOCC1CCN(C(=O)c2cc3c(cc2C)[nH]c(=O)c2cnn(C4CCOCC4)c23)C1] |
| 94 | 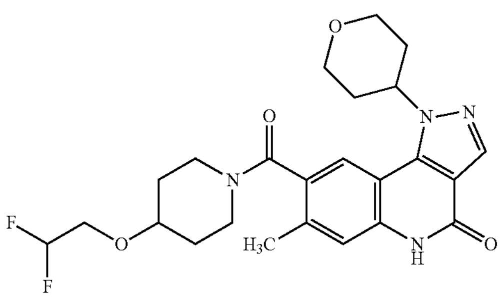 [SMILES: Cc1cc2[nH]c(=O)c3cnn(C4CCOCC4)c3c2cc1C(=O)N1CCC(OCC(F)F)CC1] |
| 95 | Chiral |

TABLE 43-continued

| Ex | Structure |
|---|---|
| 96 | |
| 97 | |
| 98 | HCl |

TABLE 44

| Ex | Structure |
|---|---|
| 99 | HCl |
| 100 | HCl |

TABLE 44-continued

| Ex | Structure |
|---|---|
| 101 | (pyridin-4-yloxy-pyrrolidine carbonyl attached to methyl-pyrazoloquinolinone with tetrahydropyran; HCl) |
| 102 | (methoxymethyl-piperidine carbonyl attached to methyl-pyrazoloquinolinone with cyclopropylmethyl; HCl) |
| 103 | (methoxybutyl-piperazine carbonyl attached to methyl-pyrazoloquinolinone with cyclopropylmethyl; HCl) |
| 104 | (methoxypropyl-piperazine carbonyl attached to methyl-pyrazoloquinolinone with cyclopropylmethyl; HCl) |
| 105 | (tert-butoxypropyl-piperazine carbonyl attached to methyl-pyrazoloquinolinone with tetrahydrofuran) |
| 106 | (methyl-(pyridin-2-yl)piperazine carbonyl attached to methyl-pyrazoloquinolinone with tetrahydropyran; HCl) |

TABLE 44-continued

| Ex | Structure |
|---|---|
| 107 | (ethoxy-piperazine carbonyl attached to methyl-pyrazoloquinolinone with tetrahydropyran; HCl) |
| 108 | Chiral (ethoxy-(S)-methylpiperazine carbonyl attached to methyl-pyrazoloquinolinone with tetrahydropyran; HCl) |
| 109 | Chiral (ethoxy-(R)-methylpiperazine carbonyl attached to methyl-pyrazoloquinolinone with tetrahydropyran; HCl) |

TABLE 45

| Ex | Structure |
|---|---|
| 110 | (isobutyl-piperazine carbonyl attached to methyl-pyrazoloquinolinone with tetrahydropyran; HCl) |
| 111 | Chiral HCl (methoxybutyl-methylpiperazine carbonyl attached to methyl-pyrazoloquinolinone with tetrahydropyran) |

TABLE 45-continued
| Ex | Structure |
|---|---|
| 112 | Chiral, HCl 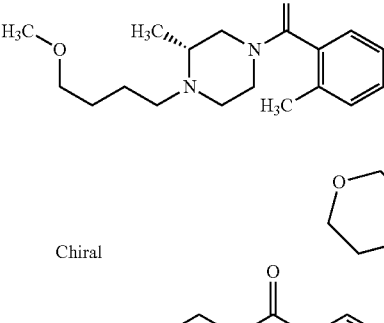 |
| 113 | Chiral 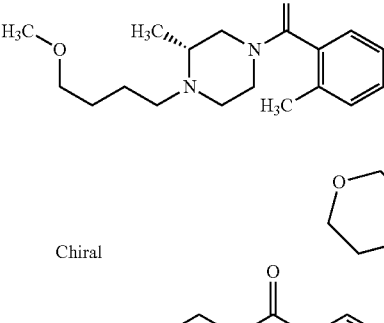 |
| 114 | Chiral, HCl 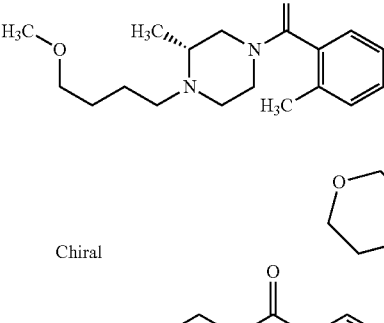 |
| 115 | Chiral, HCl 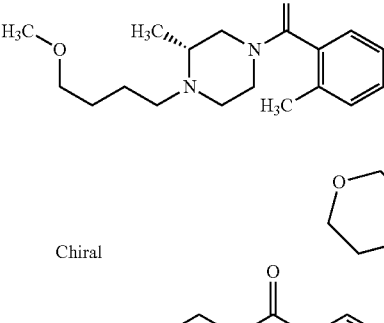 |
| 116 | HCl 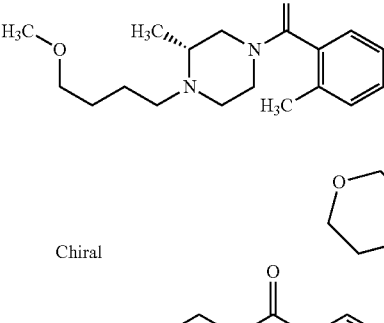 |
| 117 | Chiral, HCl 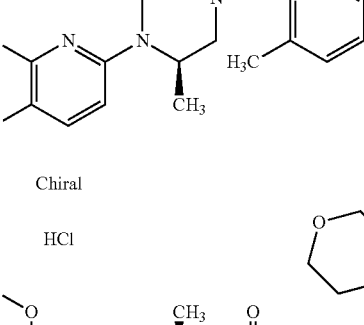 |
| 118 | 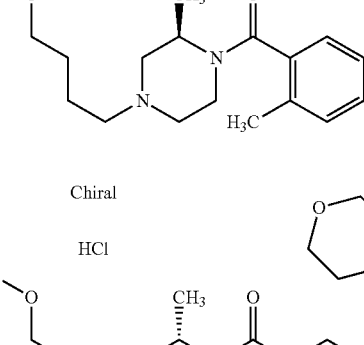 |
| 119 | 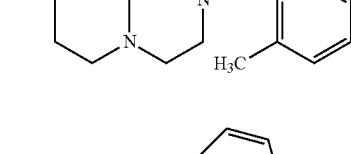 |
TABLE 46
| Ex | Structure |
|---|---|
| 120 | 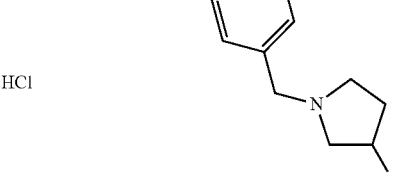 |
| 121 | Chiral, HCl 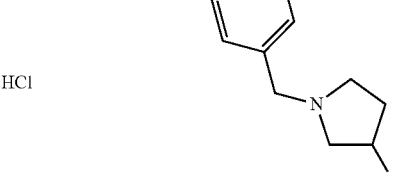 |

TABLE 46-continued
| Ex | Structure |
|---|---|
| 122 | 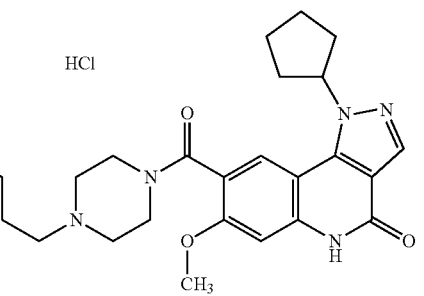 |
| 123 | 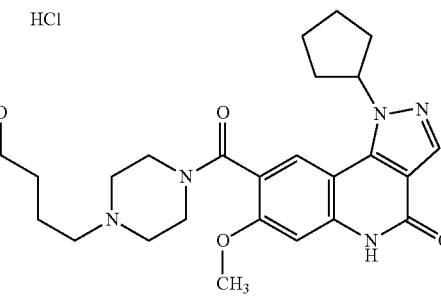 |
| 124 | 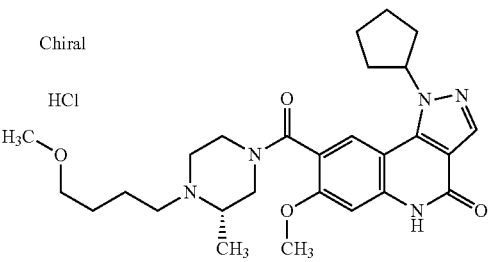 [SMILES: COCCCCN1CCN(C(=O)c2cc3c(cc2OC)[nH]c(=O)c2cnn(C4CCCC4)c23)C[C@@H]1C ; "Chiral" ; Cl] |
| 125 | 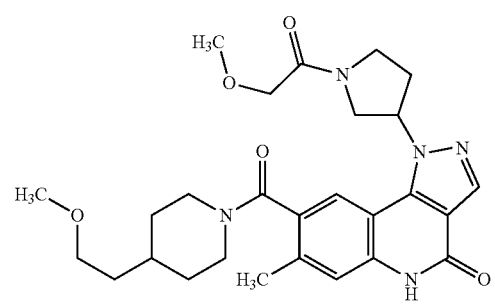 [SMILES: COCCC1CCN(C(=O)c2cc3c(cc2C)[nH]c(=O)c2cnn(C4CCN(C(=O)COC)C4)c23)CC1] |
| 126 | 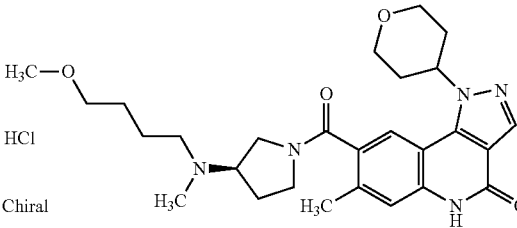 |
| 127 | 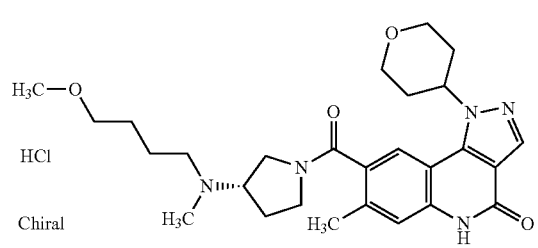 [SMILES: COCCCCN(C)[C@H]1CCN(C(=O)c2cc3c(cc2C)[nH]c(=O)c2cnn(C4CCOCC4)c23)C1 ; Cl ; "Chiral"] |
| 128 | 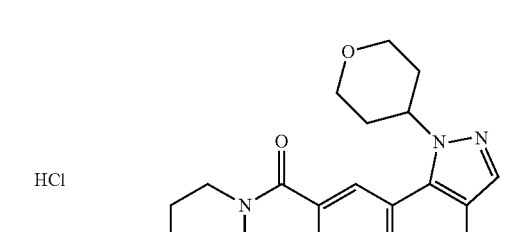 |
| 129 | 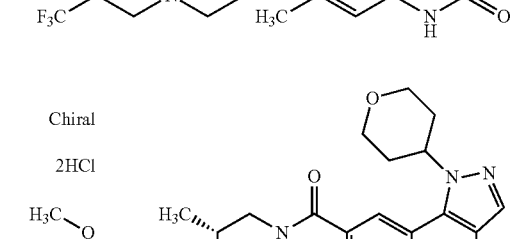 |
TABLE 47
| Ex | Structure |
|---|---|
| 130 | 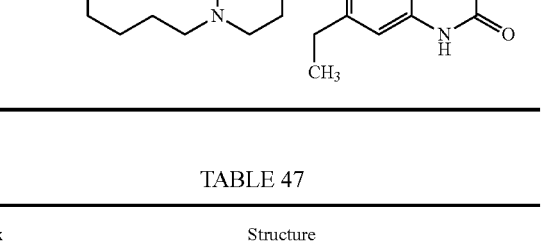 |
| 131 | 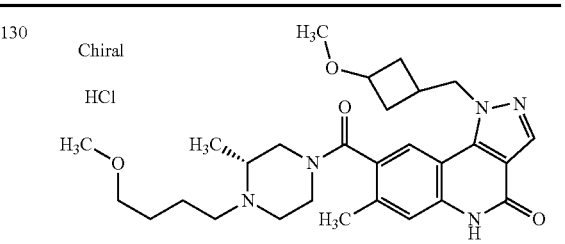 |

TABLE 47-continued

| Ex | Structure |
|---|---|
| 132 | Chiral, HCl |
| 133 | 2HCl |
| 134 | 2HCl |
| 135 | HCl |
| 136 | 2HCl |
| 137 | HCl |
| 138 | HCl |
| 139 | HCl |

TABLE 48

| Ex | Structure |
|---|---|
| 140 | 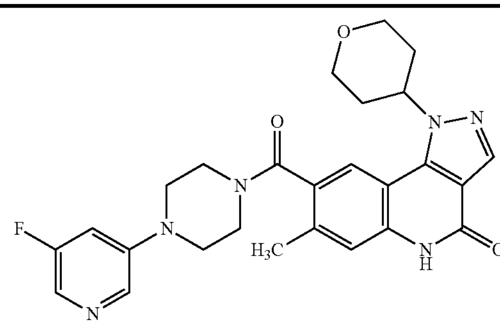 |
| 141 | Chiral |

TABLE 48-continued
| Ex | Structure |
|---|---|
| 142 | Chiral 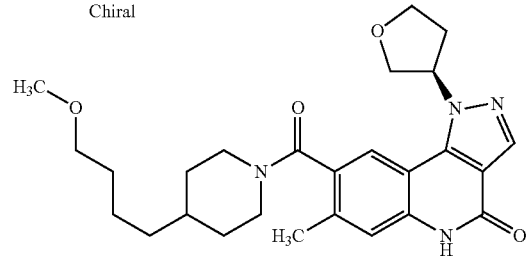 [SMILES: COCCCCC1CCN(C(=O)c2cc3c(cc2C)[nH]c(=O)c2cnn([C@@H]4CCOC4)c23)CC1 ; "Chiral"] |
| 143 | Chiral HCl 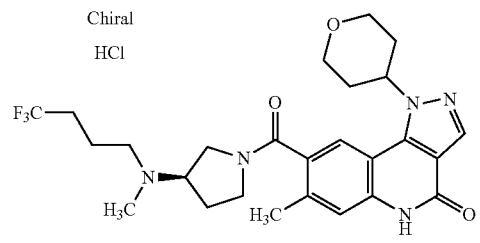 |
| 144 | Chiral HCl 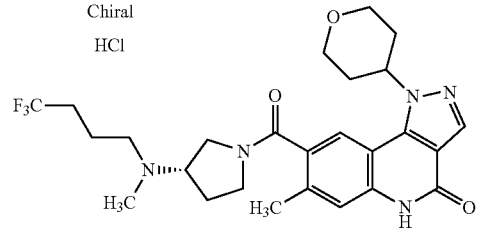 |
| 145 | Chiral HCl 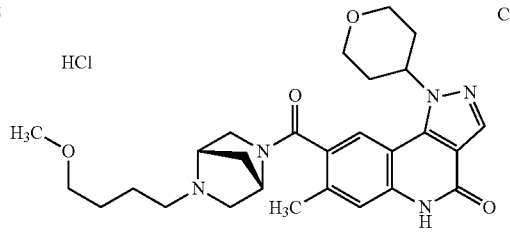 |
| 146 | Chiral HCl 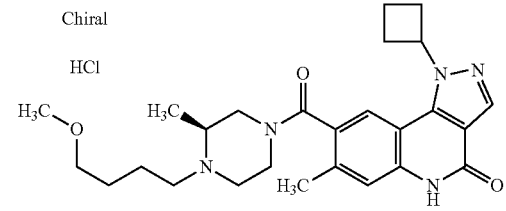 |
| 147 | HCl 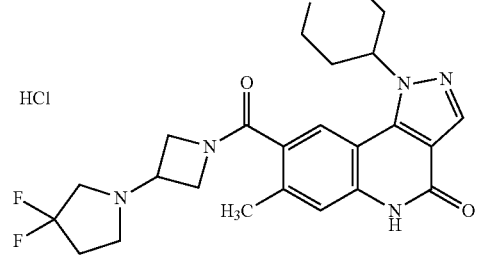 |
TABLE 48-continued
| Ex | Structure |
|---|---|
| 148 | Chiral 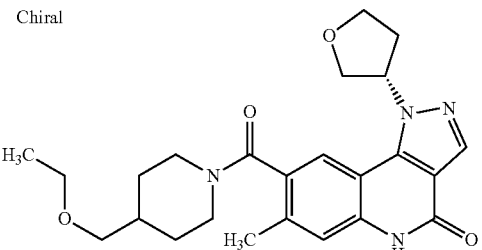 |
| 149 | Chiral 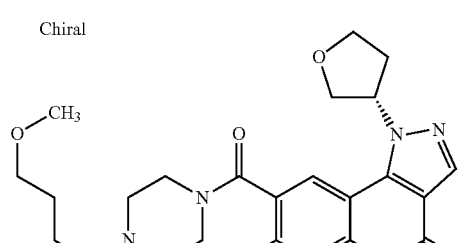 |
| 150 | HCl 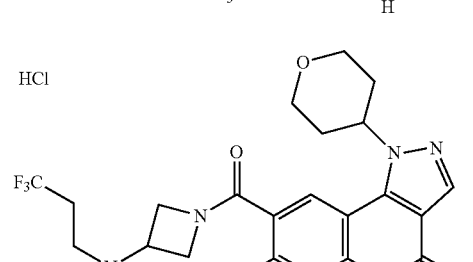 |
TABLE 49
| Ex | Structure |
|---|---|
| 151 | Chiral 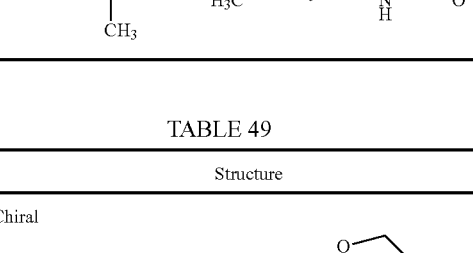 |
| 152 | 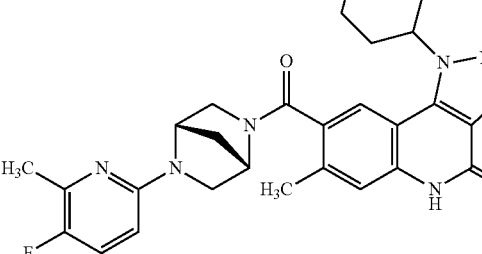 |

TABLE 49-continued
| Ex | Structure |
|---|---|
| 153 | 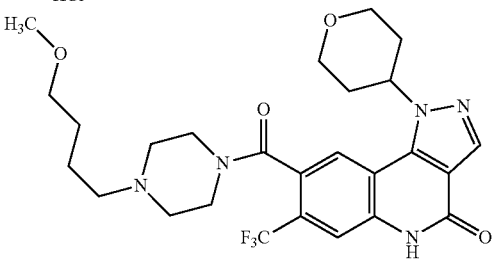 |
| 154 | 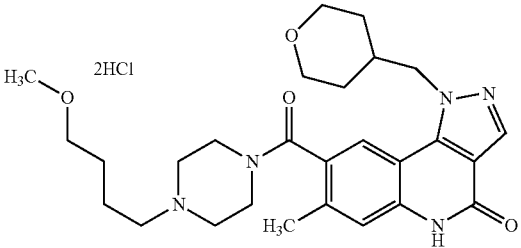 [SMILES: COCCCCN1CCN(C(=O)c2cc3c(cc2C)[nH]c(=O)c2cnn(CC4CCOCC4)c23)CC1] |
| 155 | 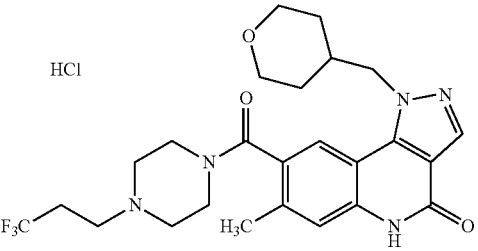 [SMILES: Cc1cc2[nH]c(=O)c3cnn(CC4CCOCC4)c3c2cc1C(=O)N1CCN(CCC(F)(F)F)CC1 ; Cl] |
| 156 | 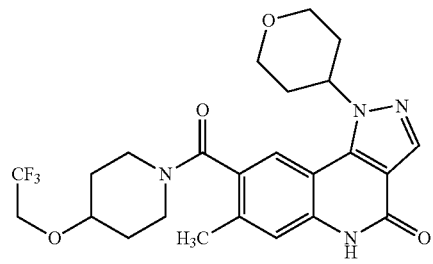 [SMILES: Cc1cc2[nH]c(=O)c3cnn(C4CCOCC4)c3c2cc1C(=O)N1CCC(OCC(F)(F)F)CC1] |
| 157 | 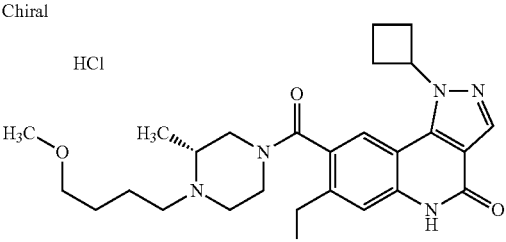 |
| 158 | 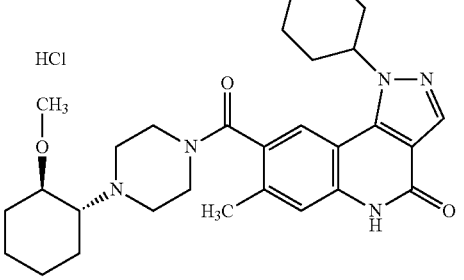 |
| 159 | 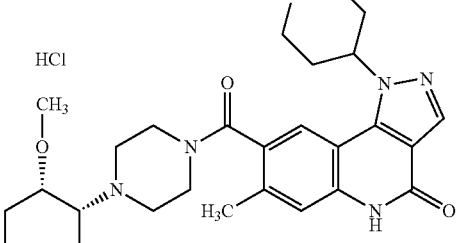 |
| 160 | 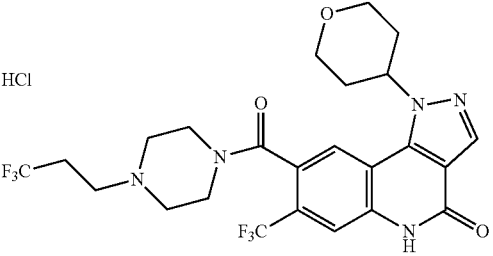 [SMILES: Cl ; O=C(c1cc2c(cc1C(F)(F)F)[nH]c(=O)c1cnn(C3CCOCC3)c12)N1CCN(CCC(F)(F)F)CC1] |
TABLE 50
| Ex | Structure |
|---|---|
| 161 | 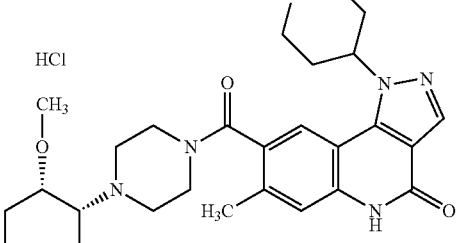 |
| 162 | 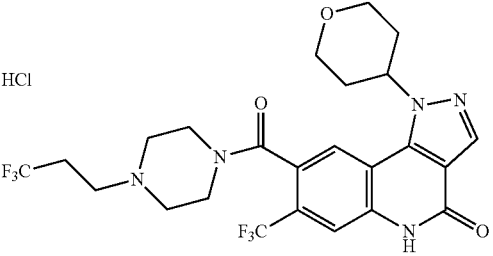 [SMILES: Cl ; O=C(c1cc2c(cc1C(F)(F)F)[nH]c(=O)c1cnn(C3CCOCC3)c12)N1CCN(CCC(F)(F)F)CC1] |

US 8,822,448 B2
TABLE 50-continued
| Ex | Structure |
|---|---|
| 163 | Chiral, HCl |
| 164 | Chiral, HCl |
| 165 | 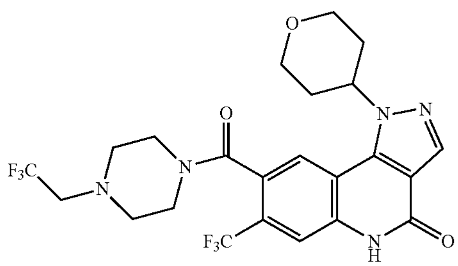 [SMILES: O=C(c1cc2c(cc1C(F)(F)F)[nH]c(=O)c1cnn(C3CCOCC3)c12)N1CCN(CC(F)(F)F)CC1] |
| 166 | Chiral |
| 167 | 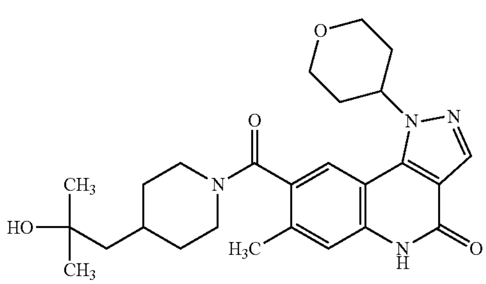 [SMILES: Cc1cc2[nH]c(=O)c3cnn(C4CCOCC4)c3c2cc1C(=O)N1CCC(CC(C)(C)O)CC1] |
TABLE 50-continued
| Ex | Structure |
|---|---|
| 168 | |
| 169 | |
| 170 | Chiral, HCl |
TABLE 51
| Ex | Structure |
|---|---|
| 171 | HCl |
| 172 | 2HCl |
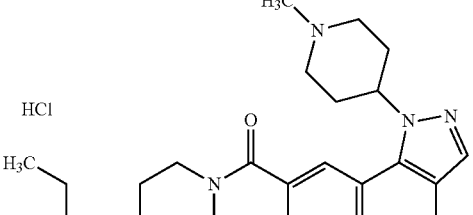

TABLE 51-continued

| Ex | Structure |
|---|---|
| 173 | 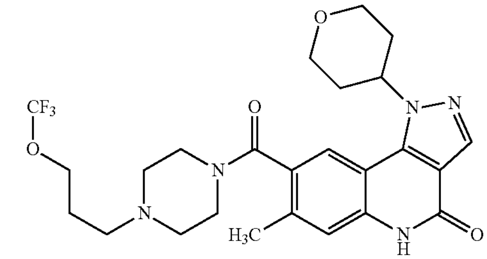 [SMILES: Cc1cc2[nH]c(=O)c3cnn(C4CCOCC4)c3c2cc1C(=O)N1CCN(CCCOC(F)(F)F)CC1] |
| 174 | Chiral, 2HCl |
| 175 | Chiral, 2HCl |
| 176 | 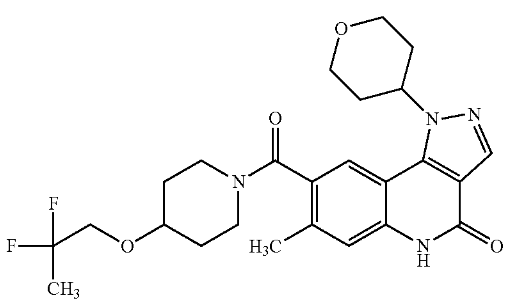 [SMILES: Cc1cc2[nH]c(=O)c3cnn(C4CCOCC4)c3c2cc1C(=O)N1CCC(OCC(C)(F)F)CC1] |
| 177 | Chiral |
| 178 | Chiral |
| 179 | Chiral, HCl |
| 180 | Chiral, HCl |

TABLE 52

| Ex | Structure |
|---|---|
| 181 | Chiral, 2HCl (pyrazoloquinolinone with 1-methylpyrrolidin-3-yl, piperazine linked to 5-fluoro-6-methylpyridin-2-yl, methyl-substituted piperazine) |
| 182 | Chiral, 2HCl (analogous structure, different piperazine methyl stereochemistry) |
| 183 | Chiral, HCl (pyrazoloquinolinone with tetrahydropyran-4-yl on pyrazole; 2,5-dimethylpiperazine bearing 4-methoxybutyl) |
| 184 | Chiral, HCl (pyrazoloquinolinone with tetrahydropyran-4-yl; 2,5-dimethylpiperazine bearing 3,3,3-trifluoropropyl) |
| 185 | Chiral, HCl (pyrazoloquinolinone with (S)-tetrahydrofuran-3-yl; piperazine bearing 3,3,3-trifluoropropyl) |

TABLE 52-continued

| Ex | Structure |
|---|---|
| 186 | Chiral (pyrazoloquinolinone with cyclopentyl on pyrazole; 3-methylpiperazine with 4-methoxybutyl) |
| 187 | HCl, Chiral (pyrazoloquinolinone with cyclopropylmethyl on pyrazole; 2,5-dimethylpiperazine with 4-methoxybutyl) |
| 188 | HCl, Chiral (pyrazoloquinolinone with cyclopropylmethyl; 2,5-dimethylpiperazine with 3,3,3-trifluoropropyl) |
| 189 | HCl, Chiral (pyrazoloquinolinone with cyclobutylmethyl; 2,5-dimethylpiperazine with 4-methoxybutyl) |
| 190 | HCl, Chiral (pyrazoloquinolinone with cyclobutylmethyl; 2,5-dimethylpiperazine with 3,3,3-trifluoropropyl) |

TABLE 53
| Ex | | Structure |
|---|---|---|
| 191 | Chiral | 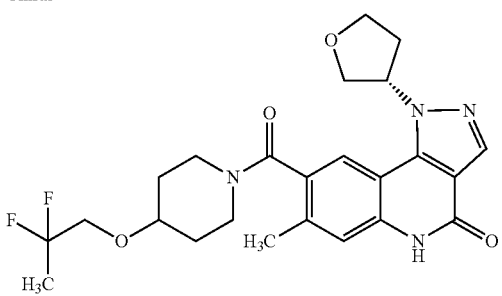 |
| 192 | | 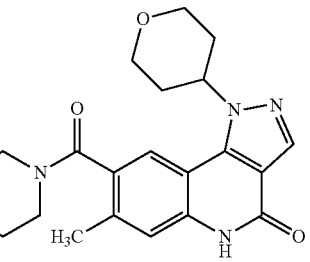 |
| 193 | Chiral | 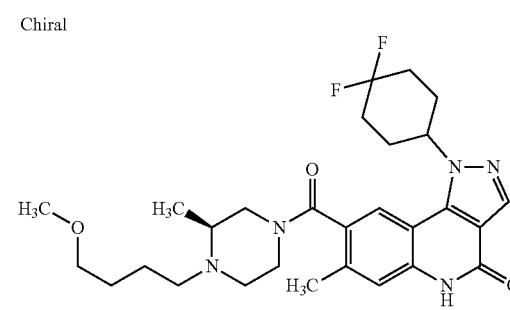 |
| 194 | Chiral | 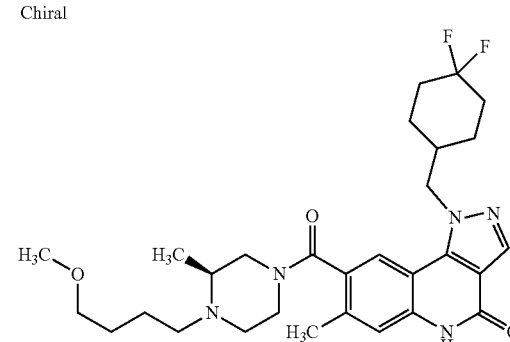 |
| 195 | Chiral | 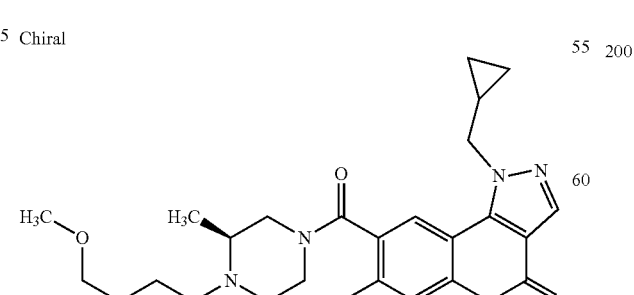 |
| 196 | | 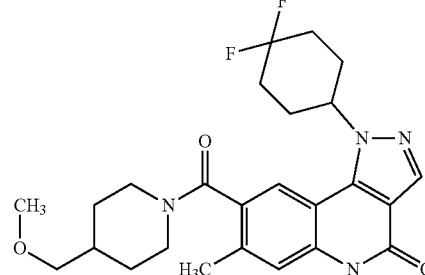 |
| 197 | | 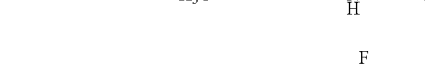 |
| 198 | Chiral |  |
| 199 | Chiral | 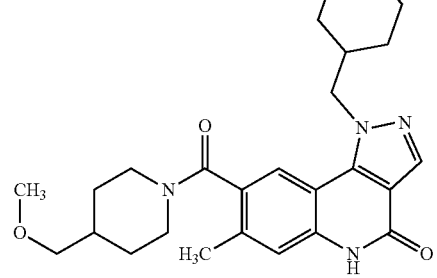 |
| 200 | Chiral |  |

TABLE 54
| Ex | Structure |
|---|---|
| 201 | Chiral 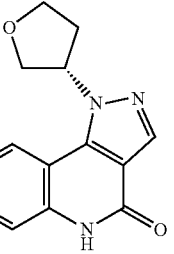 |
| 202 | Chiral 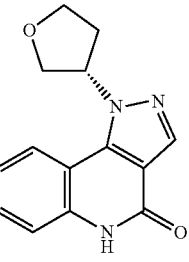 |
| 203 | Chiral 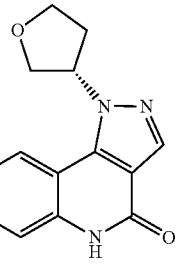 |
| 204 | Chiral 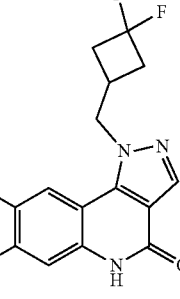 |
| 205 | Chiral 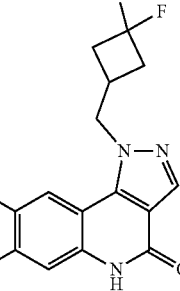 |
TABLE 54-continued
| Ex | Structure |
|---|---|
| 206 | 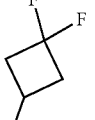 |
| 207 | Chiral HCl 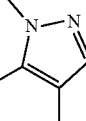 |
| 208 | Chiral HCl 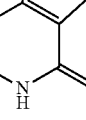 |
| 209 | Chiral HCl  |

TABLE 54-continued

| Ex | Structure |
|---|---|
| 210 | Chiral, HCl |

TABLE 55

| Ex | Structure |
|---|---|
| 211 | Chiral, HCl |
| 212 | Chiral, HCl |
| 213 | 2HCl |

TABLE 55-continued

| Ex | Structure |
|---|---|
| 214 | Chiral, 2HCl |
| 215 | Chiral |
| 216 | Chiral |
| 217 | 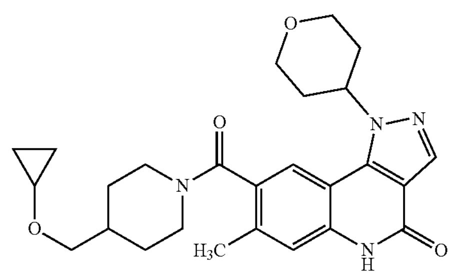 [SMILES: Cc1cc2[nH]c(=O)c3cnn(C4CCOCC4)c3c2cc1C(=O)N1CCC(COC2CC2)CC1] |
| 218 | Chiral |

TABLE 55-continued

| Ex | Structure |
|---|---|
| 219 | Chiral |
| 220 | Chiral |
| 221 | 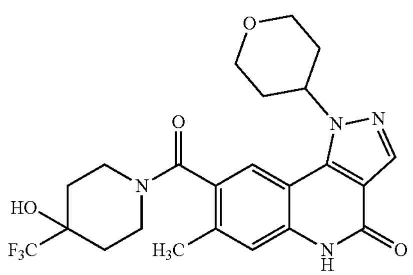 [SMILES: Cc1cc2[nH]c(=O)c3cnn(C4CCOCC4)c3c2cc1C(=O)N1CCC(O)(C(F)(F)F)CC1] |

TABLE 56

| Ex | Structure |
|---|---|
| 222 | Chiral |
| 223 | Chiral |

TABLE 56-continued

| Ex | Structure |
|---|---|
| 224 | Chiral |
| 225 | Chiral |
| 226 | Chiral |
| 227 | 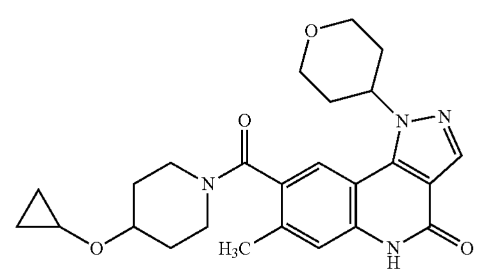 [SMILES: Cc1cc2[nH]c(=O)c3cnn(C4CCOCC4)c3c2cc1C(=O)N1CCC(OC2CC2)CC1] |
| 228 | 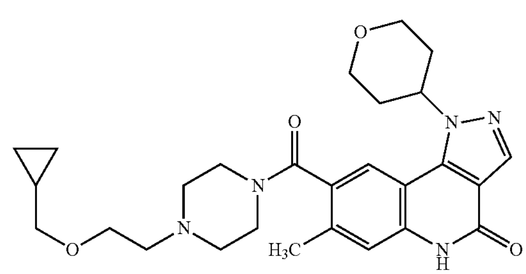 [SMILES: Cc1cc2[nH]c(=O)c3cnn(C4CCOCC4)c3c2cc1C(=O)N1CCN(CCOCC2CC2)CC1] |

US 8,822,448 B2
TABLE 56-continued
| Ex | Structure |
|---|---|
| 229 | 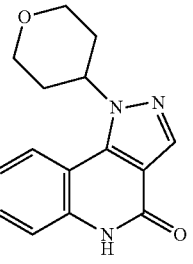 |
| 230 Chiral | 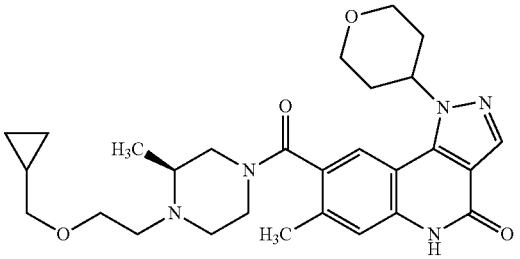 |
| 231 | 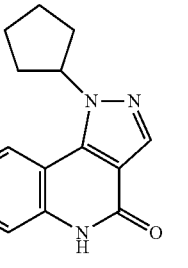 |
TABLE 57
| Ex | Structure |
|---|---|
| 232 Chiral | 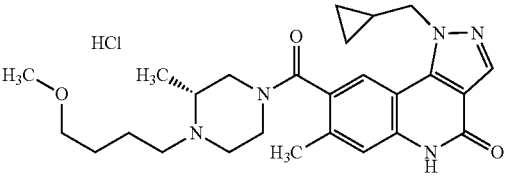 |
| 233 Chiral | 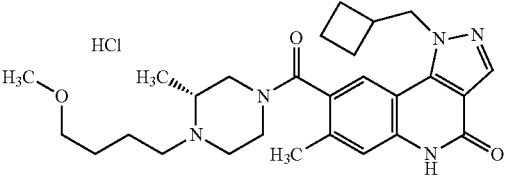 |
| 234 | 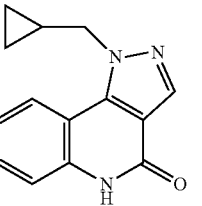 |
TABLE 57-continued
| Ex | Structure |
|---|---|
| 235 Chiral | 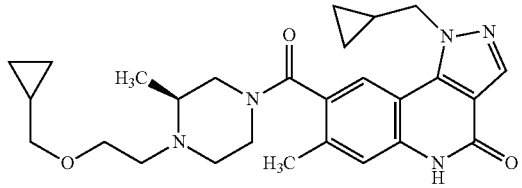 |
| 236 Chiral | 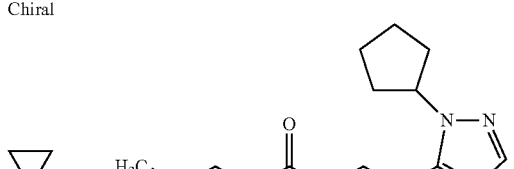 |
| 237 Chiral | 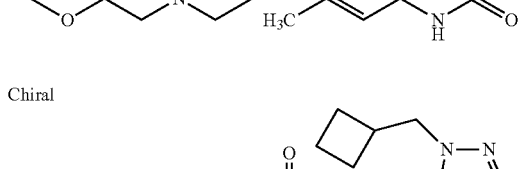 |
| 238 Chiral | 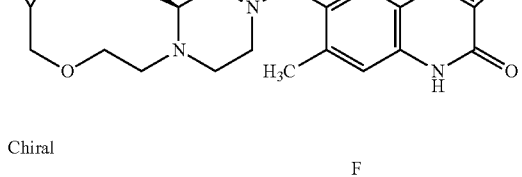 |
| 239 Chiral | 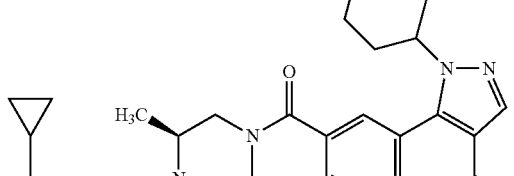 |

TABLE 57-continued

| Ex | Structure |
|---|---|
| 240 | Chiral |

TABLE 58

| Ex | Structure |
|---|---|
| 241 | Chiral |
| 242 | Chiral |
| 243 | Chiral |

TABLE 58-continued

| Ex | Structure |
|---|---|
| 244 | 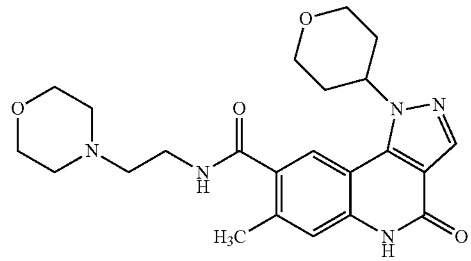 [SMILES: Cc1cc2[nH]c(=O)c3cnn(C4CCOCC4)c3c2cc1C(=O)NCCN1CCOCC1] |
| 245 | 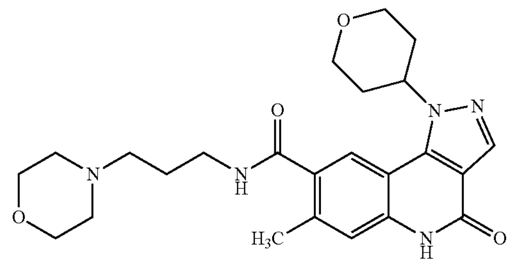 [SMILES: Cc1cc2[nH]c(=O)c3cnn(C4CCOCC4)c3c2cc1C(=O)NCCCN1CCOCC1] |
| 246 | 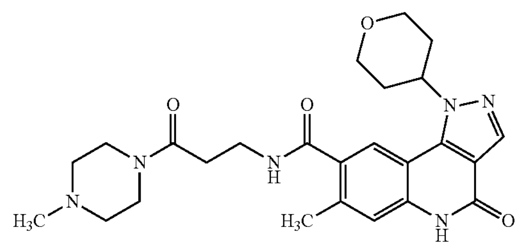 [SMILES: Cc1cc2[nH]c(=O)c3cnn(C4CCOCC4)c3c2cc1C(=O)NCCC(=O)N1CCN(C)CC1] |
| 247 | 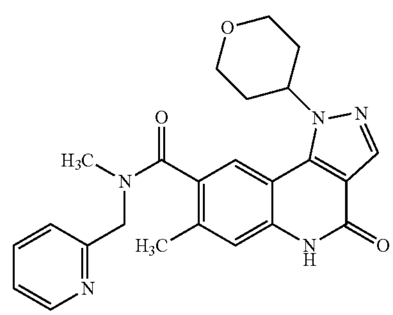 [SMILES: Cc1cc2[nH]c(=O)c3cnn(C4CCOCC4)c3c2cc1C(=O)N(C)Cc1ccccn1] |
| 248 | 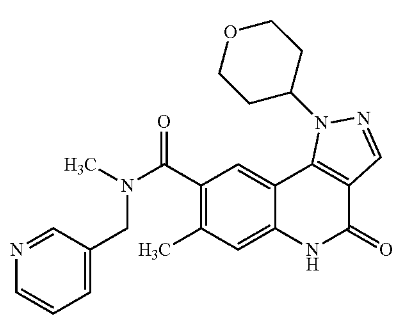 [SMILES: Cc1cc2[nH]c(=O)c3cnn(C4CCOCC4)c3c2cc1C(=O)N(C)Cc1cccnc1] |

161
TABLE 58-continued
| Ex | Structure |
|---|---|
| 249 | 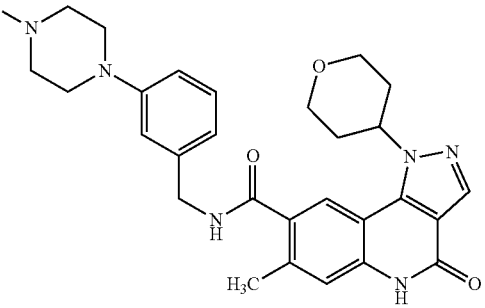 |
| 250 | 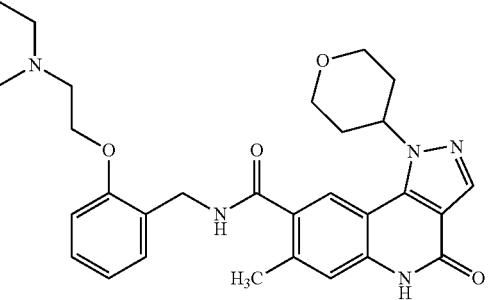 |
TABLE 59
| Ex | Structure |
|---|---|
| 251 | 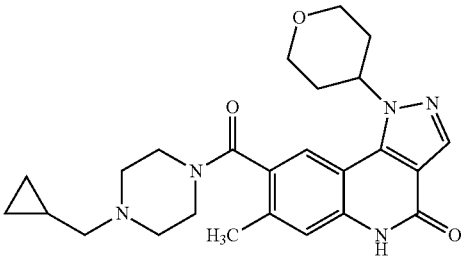 [SMILES: Cc1cc2[nH]c(=O)c3cnn(C4CCOCC4)c3c2cc1C(=O)N1CCN(CC2CC2)CC1] |
| 252 | 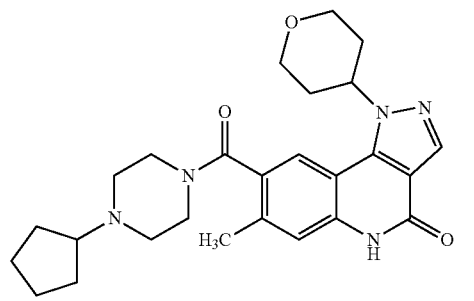 [SMILES: Cc1cc2[nH]c(=O)c3cnn(C4CCOCC4)c3c2cc1C(=O)N1CCN(C2CCCC2)CC1] |
| 253 | 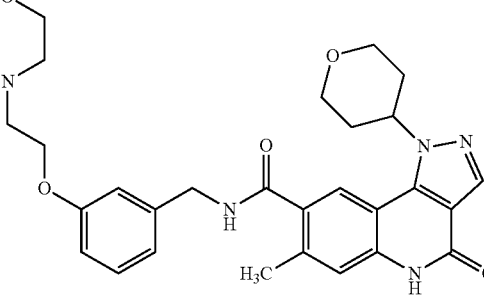 |
162
TABLE 59-continued
| Ex | Structure |
|---|---|
| 254 | 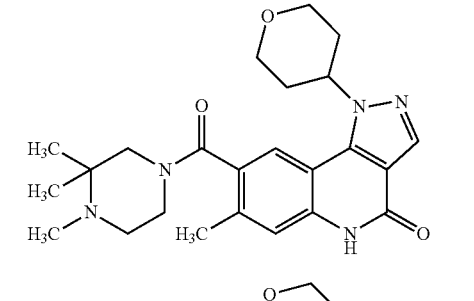 |
| 255 | 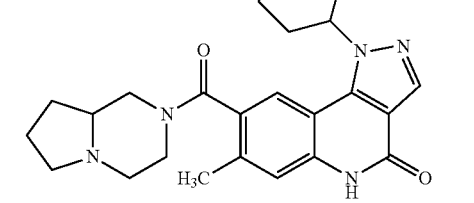 |
| 256 | 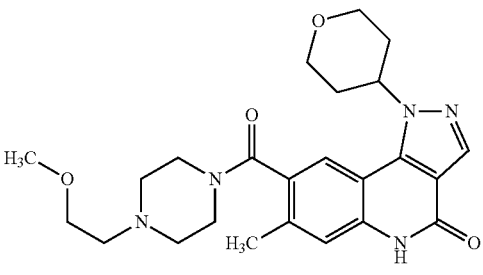 [SMILES: COCCN1CCN(C(=O)c2cc3c(cc2C)[nH]c(=O)c2cnn(C4CCOCC4)c23)CC1] |
| 257 | 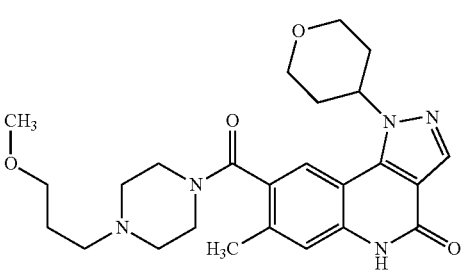 |
| 258 | 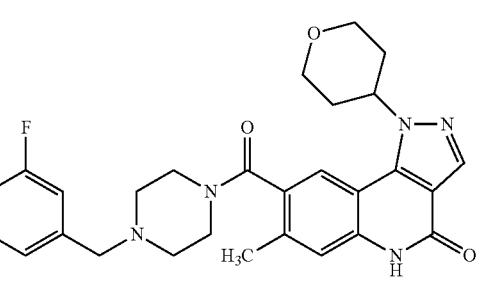 |

TABLE 59-continued

| Ex | Structure |
|---|---|
| 259 | 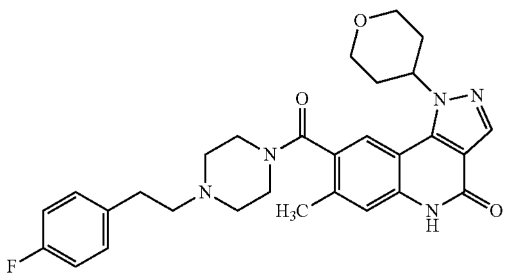 [SMILES: Cc1cc2[nH]c(=O)c3cnn(C4CCOCC4)c3c2cc1C(=O)N1CCN(CCc2ccc(F)cc2)CC1] |
| 260 | 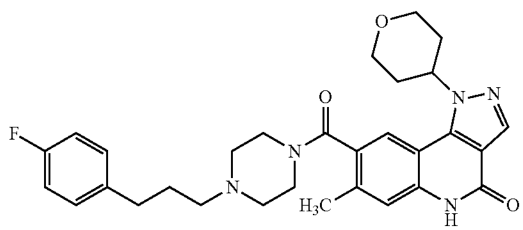 [SMILES: Cc1cc2[nH]c(=O)c3cnn(C4CCOCC4)c3c2cc1C(=O)N1CCN(CCCc2ccc(F)cc2)CC1] |

TABLE 60

| Ex | Structure |
|---|---|
| 261 | 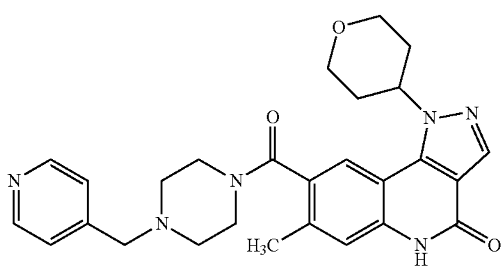 [SMILES: Cc1cc2[nH]c(=O)c3cnn(C4CCOCC4)c3c2cc1C(=O)N1CCN(Cc2ccncc2)CC1] |
| 262 | 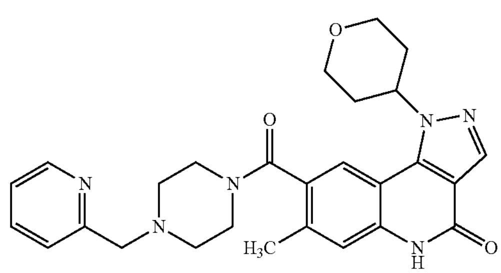 [SMILES: Cc1cc2[nH]c(=O)c3cnn(C4CCOCC4)c3c2cc1C(=O)N1CCN(Cc2ccccn2)CC1] |
| 263 | Chiral |

TABLE 60-continued

| Ex | Structure |
|---|---|
| 264 | 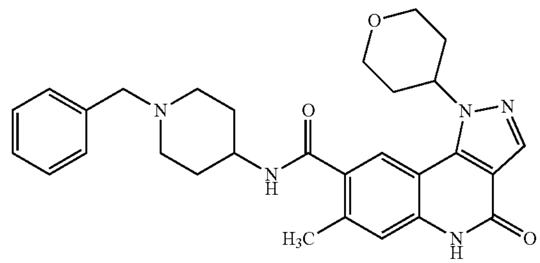 [SMILES: Cc1cc2[nH]c(=O)c3cnn(C4CCOCC4)c3c2cc1C(=O)NC1CCN(Cc2ccccc2)CC1] |
| 265 | 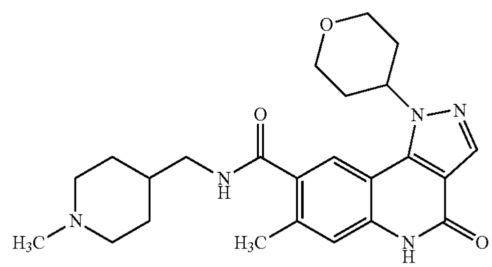 [SMILES: Cc1cc2[nH]c(=O)c3cnn(C4CCOCC4)c3c2cc1C(=O)NCC1CCN(C)CC1] |
| 266 | 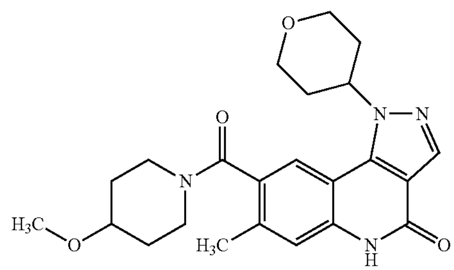 [SMILES: COC1CCN(C(=O)c2cc3c(cc2C)[nH]c(=O)c2cnn(C4CCOCC4)c23)CC1] |
| 267 | 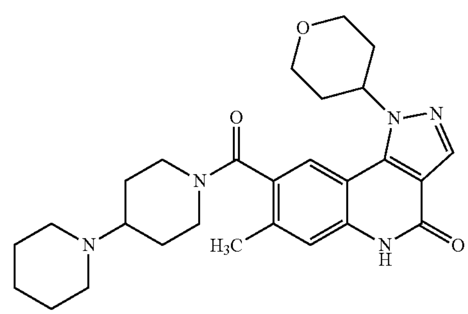 [SMILES: Cc1cc2[nH]c(=O)c3cnn(C4CCOCC4)c3c2cc1C(=O)N1CCC(N2CCCCC2)CC1] |
| 268 | 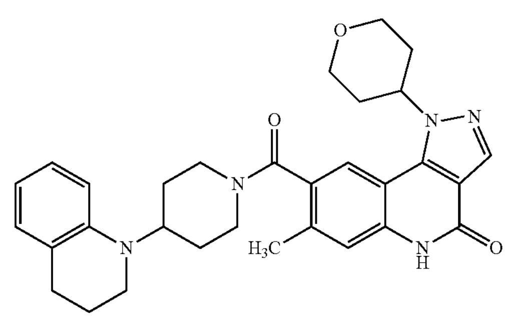 [SMILES: Cc1cc2[nH]c(=O)c3cnn(C4CCOCC4)c3c2cc1C(=O)N1CCC(N2CCCc3ccccc32)CC1] |

TABLE 60-continued

| Ex | Structure |
|---|---|
| 269 | 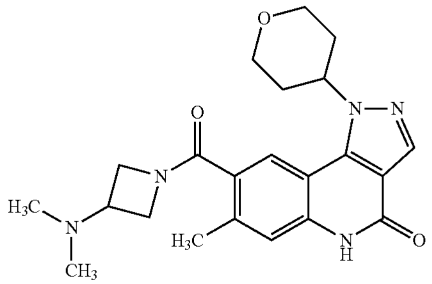 [SMILES: Cc1cc2[nH]c(=O)c3cnn(C4CCOCC4)c3c2cc1C(=O)N1CC(N(C)C)C1] |
| 270 | 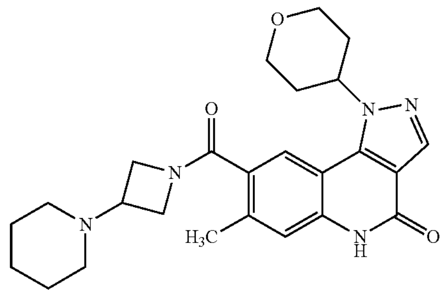 [SMILES: Cc1cc2[nH]c(=O)c3cnn(C4CCOCC4)c3c2cc1C(=O)N1CC(N2CCCCC2)C1] |

TABLE 61

| Ex | Structure |
|---|---|
| 271 | 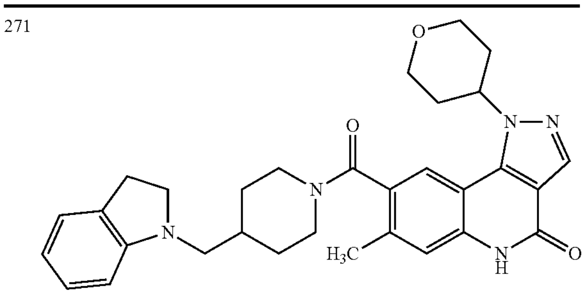 |
| 272 | 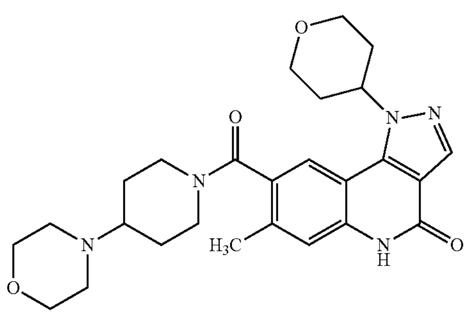 [SMILES: Cc1cc2[nH]c(=O)c3cnn(C4CCOCC4)c3c2cc1C(=O)N1CCC(N2CCOCC2)CC1] |
| 273 | 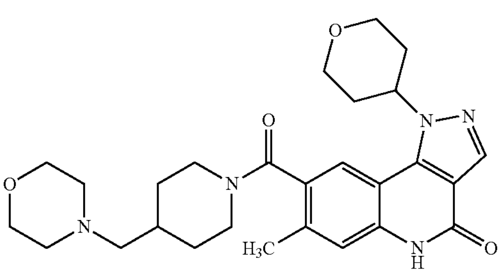 [SMILES: Cc1cc2[nH]c(=O)c3cnn(C4CCOCC4)c3c2cc1C(=O)N1CCC(CN2CCOCC2)CC1] |

TABLE 61-continued

| Ex | Structure |
|---|---|
| 274 | 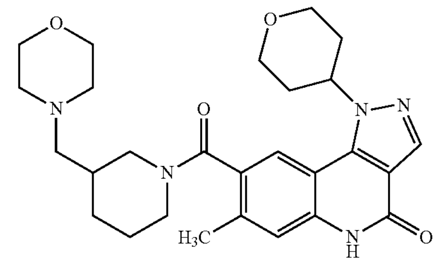 [SMILES: Cc1cc2[nH]c(=O)c3cnn(C4CCOCC4)c3c2cc1C(=O)N1CCCC(CN2CCOCC2)C1] |
| 275 | 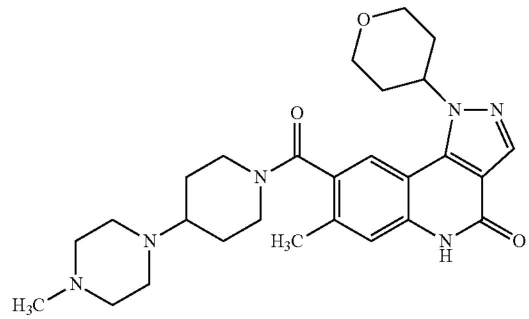 [SMILES: Cc1cc2[nH]c(=O)c3cnn(C4CCOCC4)c3c2cc1C(=O)N1CCC(N2CCN(C)CC2)CC1] |
| 276 | 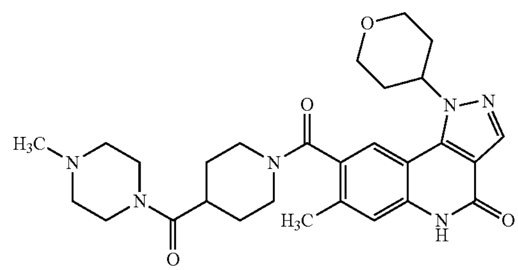 [SMILES: Cc1cc2[nH]c(=O)c3cnn(C4CCOCC4)c3c2cc1C(=O)N1CCC(C(=O)N2CCN(C)CC2)CC1] |
| 277 | 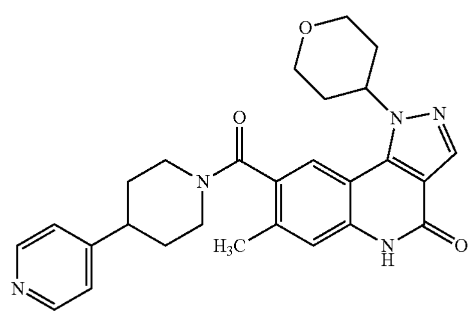 [SMILES: Cc1cc2[nH]c(=O)c3cnn(C4CCOCC4)c3c2cc1C(=O)N1CCC(c2ccncc2)CC1] |
| 278 | 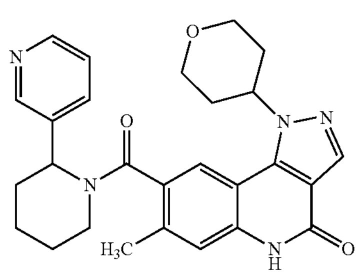 [SMILES: Cc1cc2[nH]c(=O)c3cnn(C4CCOCC4)c3c2cc1C(=O)N1CCCCC1c1cccnc1] |

TABLE 61-continued

| Ex | Structure |
|---|---|
| 279 | 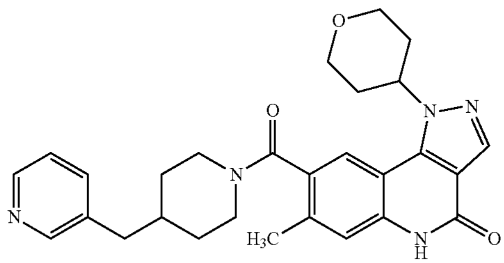 [SMILES: Cc1cc2[nH]c(=O)c3cnn(C4CCOCC4)c3c2cc1C(=O)N1CCC(Cc2cccnc2)CC1] |
| 280 | 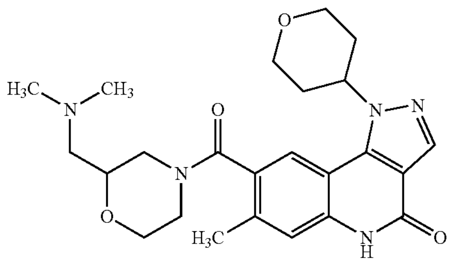 [SMILES: Cc1cc2[nH]c(=O)c3cnn(C4CCOCC4)c3c2cc1C(=O)N1CCOC(CN(C)C)C1] |

TABLE 62

| Ex | Structure |
|---|---|
| 281 | |
| 282 | |
| 283 | |
| 284 | 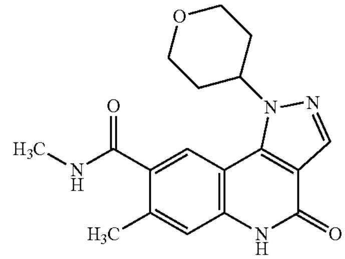 [SMILES: CNC(=O)c1cc2c(cc1C)[nH]c(=O)c1cnn(C3CCOCC3)c12] |
| 285 | 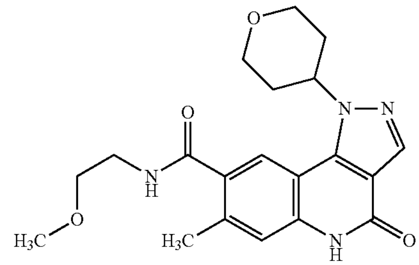 [SMILES: COCCNC(=O)c1cc2c(cc1C)[nH]c(=O)c1cnn(C3CCOCC3)c12] |
| 286 | 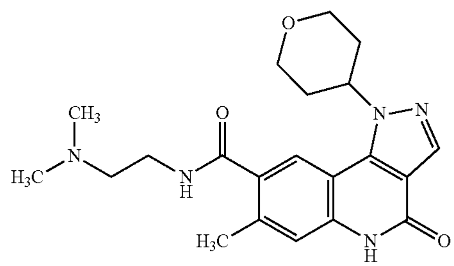 [SMILES: Cc1cc2[nH]c(=O)c3cnn(C4CCOCC4)c3c2cc1C(=O)NCCN(C)C] |
| 287 | 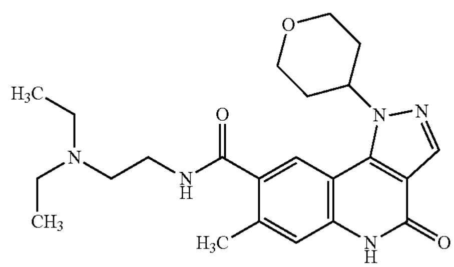 [SMILES: CCN(CC)CCNC(=O)c1cc2c(cc1C)[nH]c(=O)c1cnn(C3CCOCC3)c12] |
| 288 | 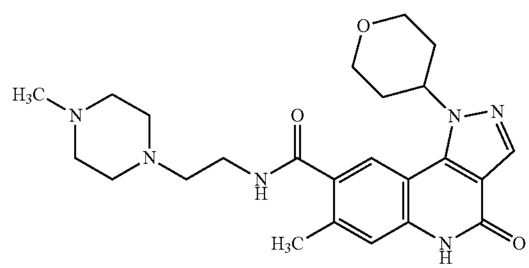 [SMILES: Cc1cc2[nH]c(=O)c3cnn(C4CCOCC4)c3c2cc1C(=O)NCCN1CCN(C)CC1] |
| 289 | 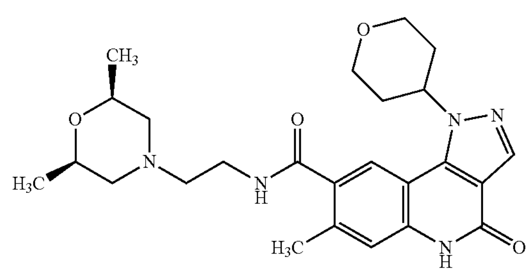 [SMILES: Cc1cc2[nH]c(=O)c3cnn(C4CCOCC4)c3c2cc1C(=O)NCCN1C[C@@H](C)O[C@@H](C)C1] |

TABLE 62-continued

| Ex | Structure |
|---|---|
| 290 | 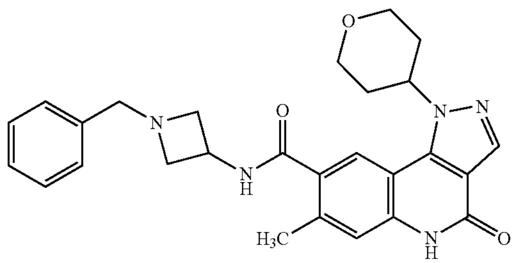 [SMILES: Cc1cc2[nH]c(=O)c3cnn(C4CCOCC4)c3c2cc1C(=O)NC1CN(Cc2ccccc2)C1] |

TABLE 63

| Ex | Structure |
|---|---|
| 291 | 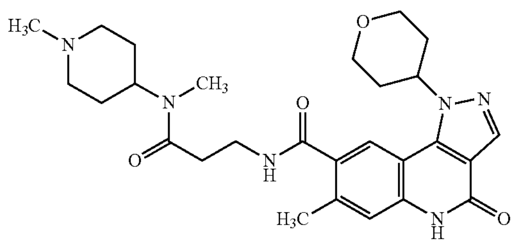 [SMILES: Cc1cc2[nH]c(=O)c3cnn(C4CCOCC4)c3c2cc1C(=O)NCCC(=O)N(C)C1CCN(C)CC1] |
| 292 | 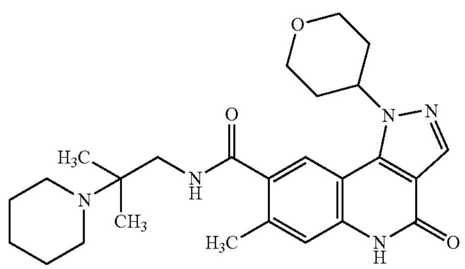 [SMILES: Cc1cc2[nH]c(=O)c3cnn(C4CCOCC4)c3c2cc1C(=O)NCC(C)(C)N1CCCCC1] |
| 293 | 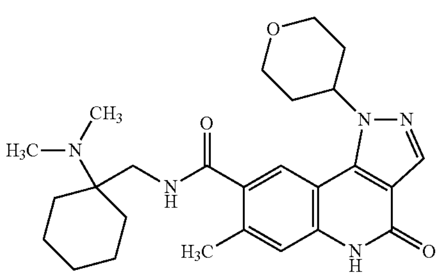 [SMILES: Cc1cc2[nH]c(=O)c3cnn(C4CCOCC4)c3c2cc1C(=O)NCC1(N(C)C)CCCCC1] |
| 294 | 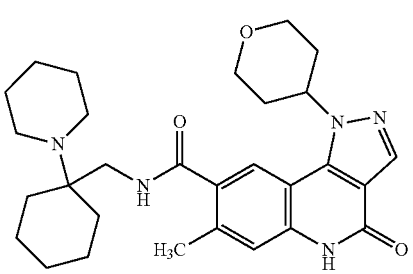 [SMILES: Cc1cc2[nH]c(=O)c3cnn(C4CCOCC4)c3c2cc1C(=O)NCC1(N2CCCCC2)CCCCC1] |

TABLE 63-continued

| Ex | Structure |
|---|---|
| 295 | 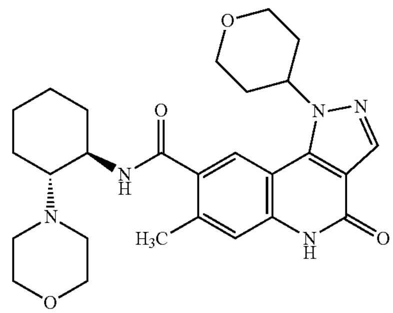 [SMILES: Cc1cc2[nH]c(=O)c3cnn(C4CCOCC4)c3c2cc1C(=O)N[C@@H]1CCCC[C@H]1N1CCOCC1] |
| 296 | 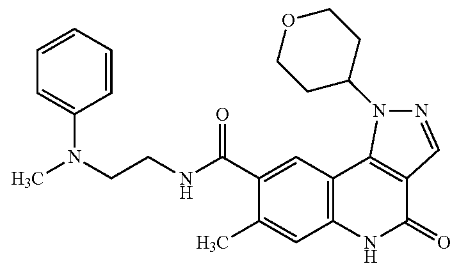 [SMILES: Cc1cc2[nH]c(=O)c3cnn(C4CCOCC4)c3c2cc1C(=O)NCCN(C)c1ccccc1] |
| 297 | 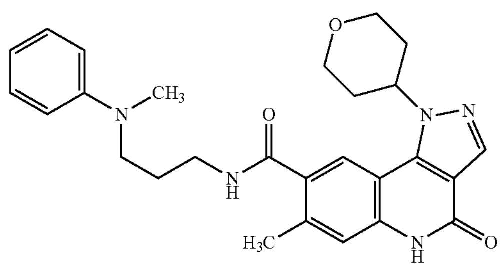 [SMILES: Cc1cc2[nH]c(=O)c3cnn(C4CCOCC4)c3c2cc1C(=O)NCCCN(C)c1ccccc1] |
| 298 | 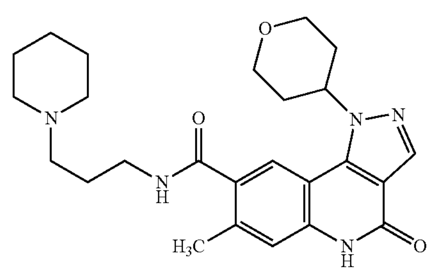 [SMILES: Cc1cc2[nH]c(=O)c3cnn(C4CCOCC4)c3c2cc1C(=O)NCCCN1CCCCC1] |
| 299 | 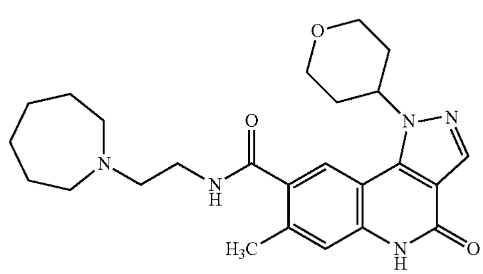 [SMILES: Cc1cc2[nH]c(=O)c3cnn(C4CCOCC4)c3c2cc1C(=O)NCCN1CCCCCC1] |

TABLE 63-continued
| Ex | Structure |
|---|---|
| 300 | 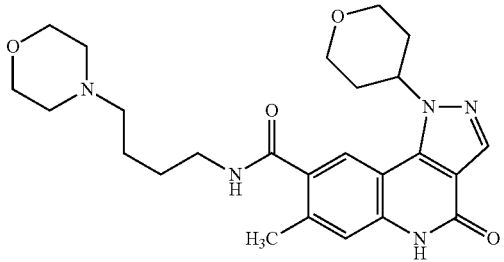 [SMILES: Cc1cc2[nH]c(=O)c3cnn(C4CCOCC4)c3c2cc1C(=O)NCCCCN1CCOCC1] |
TABLE 64
| Ex | Structure |
|---|---|
| 301 | 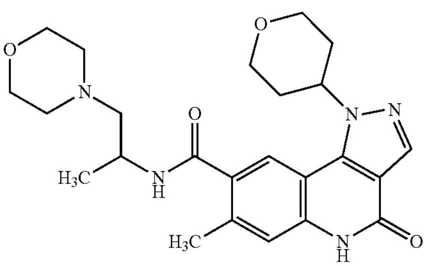 [SMILES: Cc1cc2[nH]c(=O)c3cnn(C4CCOCC4)c3c2cc1C(=O)NC(C)CN1CCOCC1] |
| 302 | 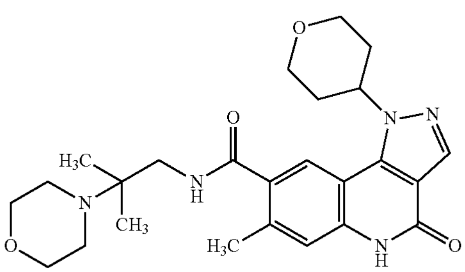 [SMILES: Cc1cc2[nH]c(=O)c3cnn(C4CCOCC4)c3c2cc1C(=O)NCC(C)(C)N1CCOCC1] |
| 303 | 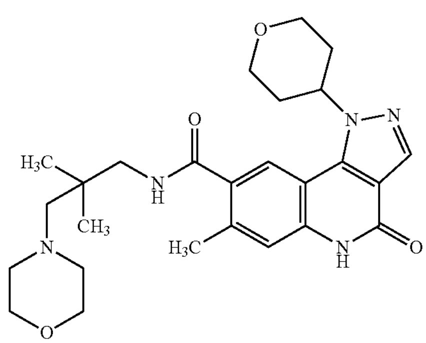 [SMILES: Cc1cc2[nH]c(=O)c3cnn(C4CCOCC4)c3c2cc1C(=O)NCC(C)(C)CN1CCOCC1] |
TABLE 64-continued
| Ex | Structure |
|---|---|
| 304 | 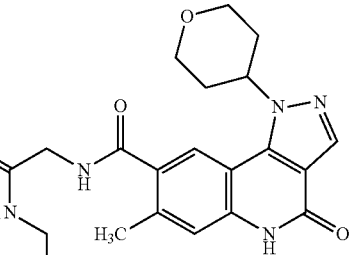 |
| 305 | 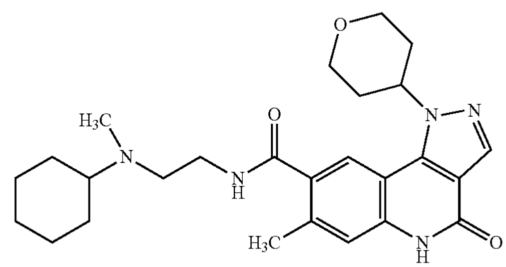 [SMILES: Cc1cc2[nH]c(=O)c3cnn(C4CCOCC4)c3c2cc1C(=O)NCCN(C)C1CCCCC1] |
| 306 | 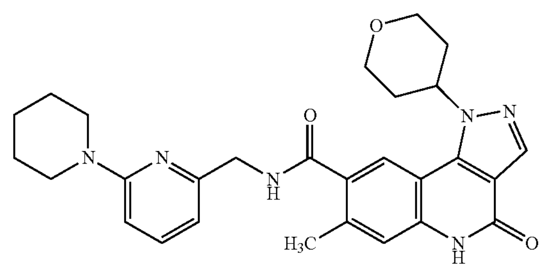 [SMILES: Cc1cc2[nH]c(=O)c3cnn(C4CCOCC4)c3c2cc1C(=O)NCc1cccc(N2CCCCC2)n1] |
| 307 | 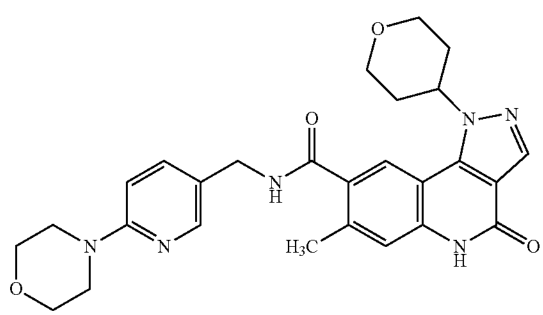 [SMILES: Cc1cc2[nH]c(=O)c3cnn(C4CCOCC4)c3c2cc1C(=O)NCc1ccc(N2CCOCC2)nc1] |
| 308 | 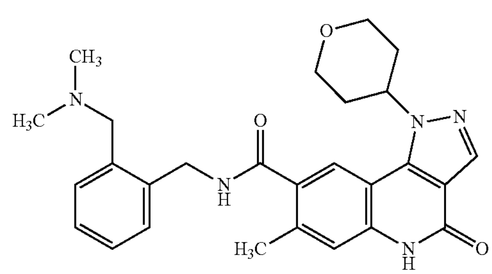 [SMILES: Cc1cc2[nH]c(=O)c3cnn(C4CCOCC4)c3c2cc1C(=O)NCc1ccccc1CN(C)C] |

TABLE 64-continued
| Ex | Structure |
|---|---|
| 309 | 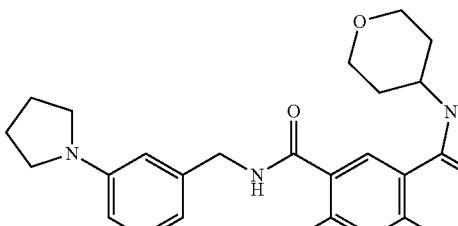 |
| 310 | 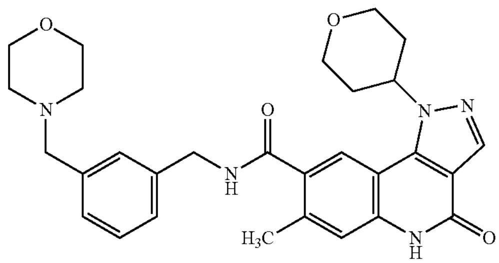 [SMILES: Cc1cc2[nH]c(=O)c3cnn(C4CCOCC4)c3c2cc1C(=O)NCc1cccc(CN2CCOCC2)c1] |
TABLE 65
| Ex | Structure |
|---|---|
| 311 | 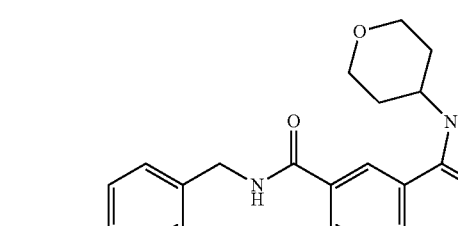 |
| 312 | 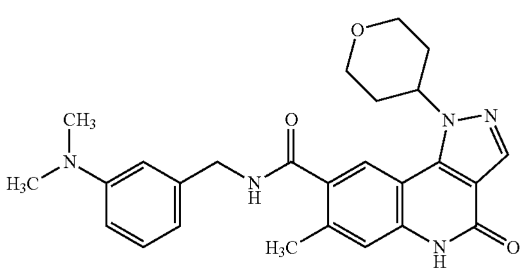 [SMILES: Cc1cc2[nH]c(=O)c3cnn(C4CCOCC4)c3c2cc1C(=O)NCc1cccc(N(C)C)c1] |
| 313 | 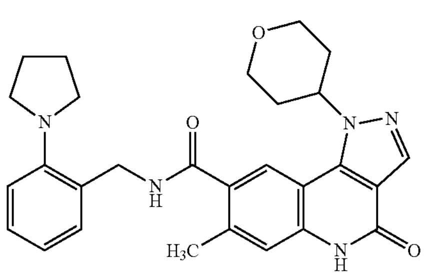 [SMILES: Cc1cc2[nH]c(=O)c3cnn(C4CCOCC4)c3c2cc1C(=O)NCc1ccccc1N1CCCC1] |
TABLE 65-continued
| Ex | Structure |
|---|---|
| 314 | 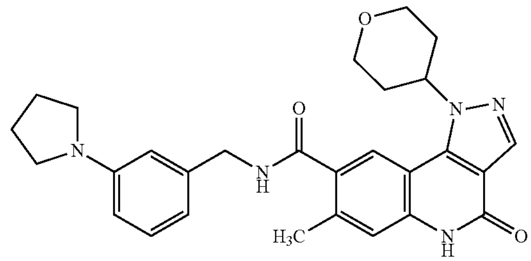 [SMILES: Cc1cc2[nH]c(=O)c3cnn(C4CCOCC4)c3c2cc1C(=O)NCc1cccc(N2CCCC2)c1] |
| 315 | 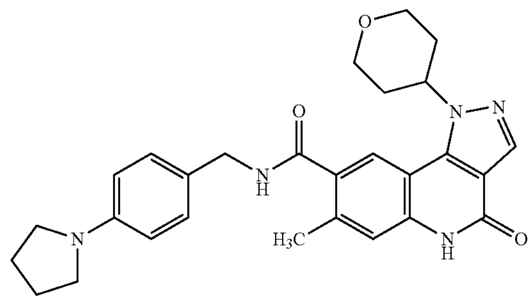 [SMILES: Cc1cc2[nH]c(=O)c3cnn(C4CCOCC4)c3c2cc1C(=O)NCc1ccc(N2CCCC2)cc1] |
| 316 | 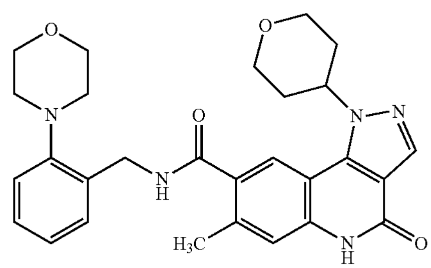 [SMILES: Cc1cc2[nH]c(=O)c3cnn(C4CCOCC4)c3c2cc1C(=O)NCc1ccccc1N1CCOCC1] |
| 317 | 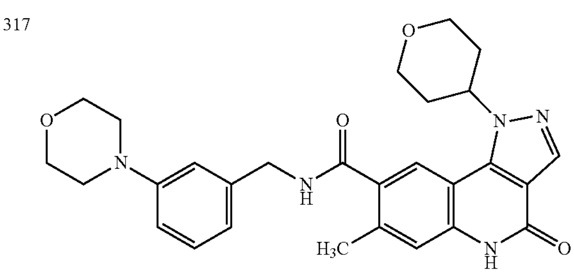 |
| 318 | 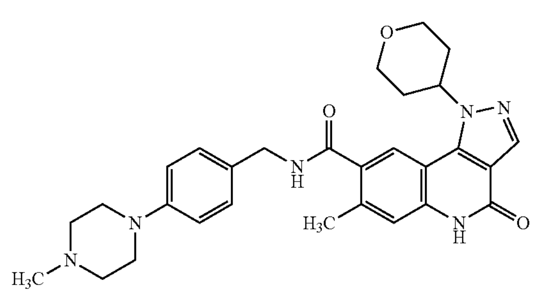 [SMILES: Cc1cc2[nH]c(=O)c3cnn(C4CCOCC4)c3c2cc1C(=O)NCc1ccc(N2CCN(C)CC2)cc1] |

TABLE 65-continued
| Ex | Structure |
|---|---|
| 319 | 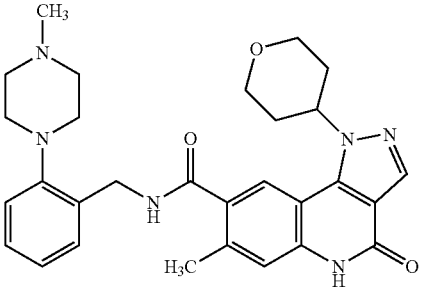 [SMILES: Cc1cc2[nH]c(=O)c3cnn(C4CCOCC4)c3c2cc1C(=O)NCc1ccccc1N1CCN(C)CC1] |
| 320 | 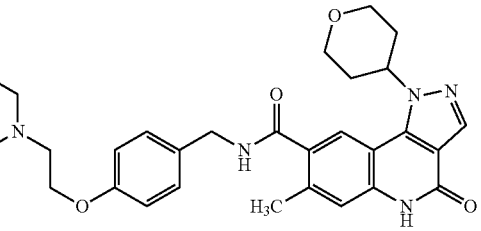 |
TABLE 66
| Ex | Structure |
|---|---|
| 321 | 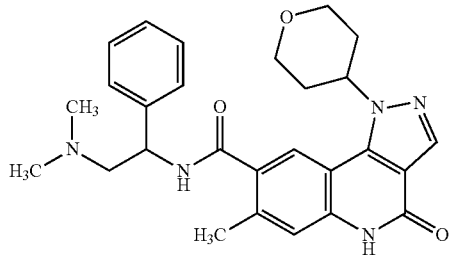 [SMILES: Cc1cc2[nH]c(=O)c3cnn(C4CCOCC4)c3c2cc1C(=O)NC(CN(C)C)c1ccccc1] |
| 322 | 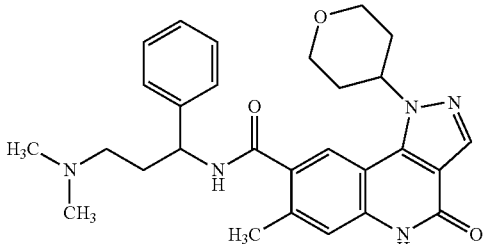 |
| 323 | 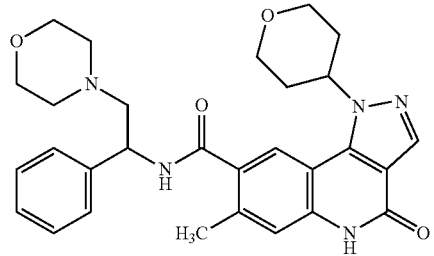 [SMILES: Cc1cc2[nH]c(=O)c3cnn(C4CCOCC4)c3c2cc1C(=O)NC(CN1CCOCC1)c1ccccc1] |
TABLE 66-continued
| Ex | Structure |
|---|---|
| 324 | 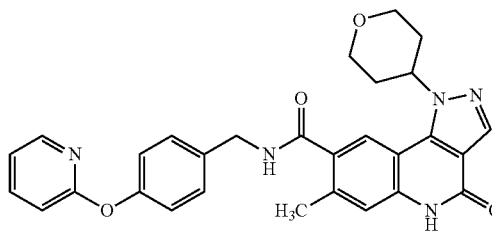 |
| 325 | 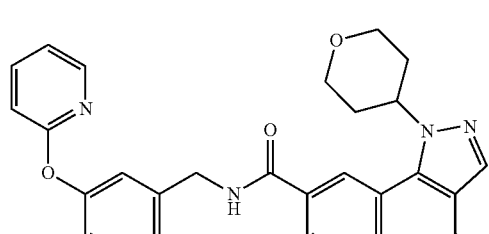 |
| 326 | 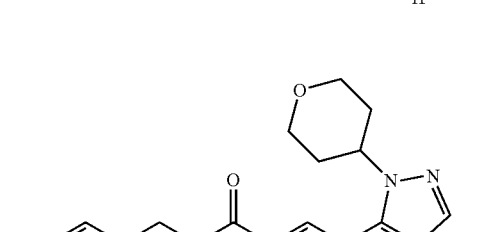 |
| 327 | 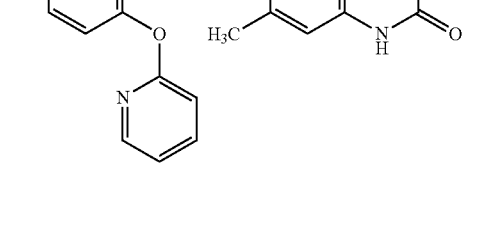 |
| 328 | 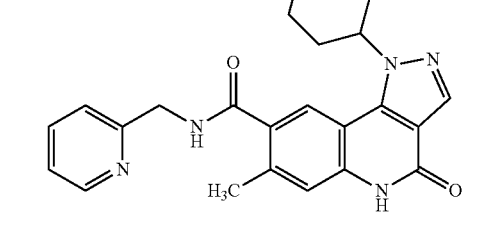 |

TABLE 66-continued

| Ex | Structure |
|---|---|
| 329 | 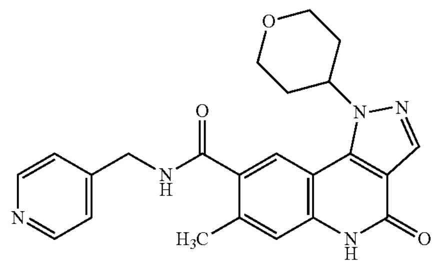 [SMILES: Cc1cc2[nH]c(=O)c3cnn(C4CCOCC4)c3c2cc1C(=O)NCc1ccncc1] |
| 330 | 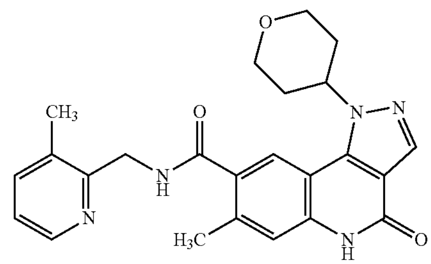 [SMILES: Cc1cc2[nH]c(=O)c3cnn(C4CCOCC4)c3c2cc1C(=O)NCc1ncccc1C] |

TABLE 67

| Ex | Structure |
|---|---|
| 331 | 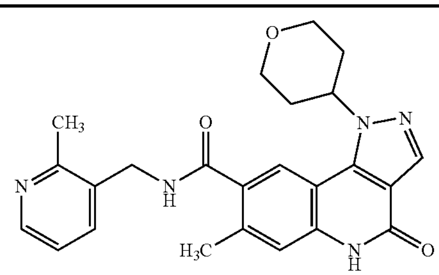 |
| 332 | 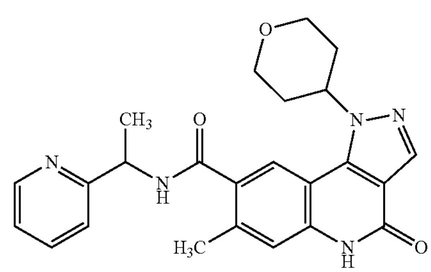 [SMILES: Cc1cc2[nH]c(=O)c3cnn(C4CCOCC4)c3c2cc1C(=O)NC(C)c1ccccn1] |
| 333 | 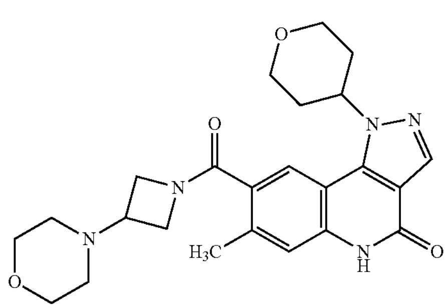 [SMILES: Cc1cc2[nH]c(=O)c3cnn(C4CCOCC4)c3c2cc1C(=O)N1CC(N2CCOCC2)C1] |

TABLE 67-continued

| Ex | Structure |
|---|---|
| 334 | 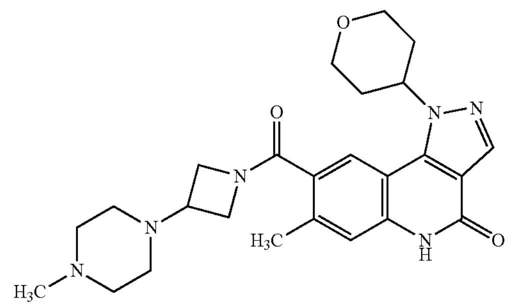 [SMILES: Cc1cc2[nH]c(=O)c3cnn(C4CCOCC4)c3c2cc1C(=O)N1CC(N2CCN(C)CC2)C1] |
| 335 | 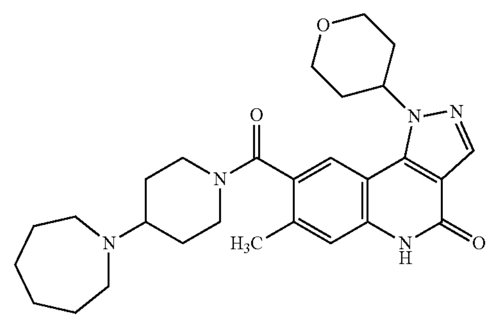 [SMILES: Cc1cc2[nH]c(=O)c3cnn(C4CCOCC4)c3c2cc1C(=O)N1CCC(N2CCCCCC2)CC1] |
| 336 | 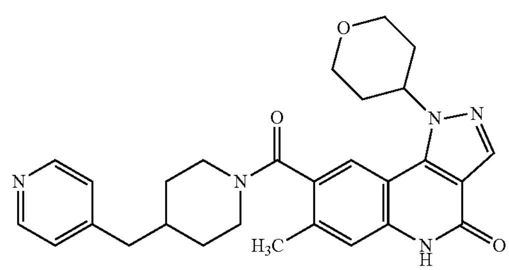 |
| 337 | 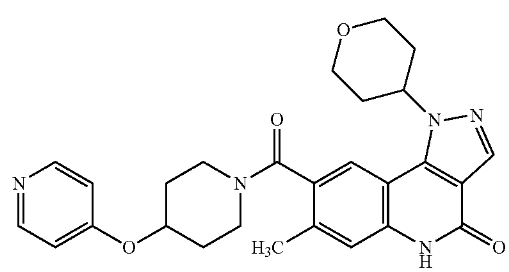 [SMILES: Cc1cc2[nH]c(=O)c3cnn(C4CCOCC4)c3c2cc1C(=O)N1CCC(Oc2ccncc2)CC1] |
| 338 | 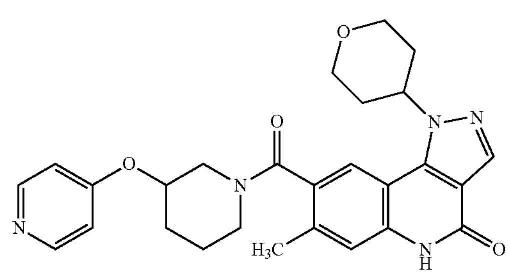 [SMILES: Cc1cc2[nH]c(=O)c3cnn(C4CCOCC4)c3c2cc1C(=O)N1CCCC(Oc2ccncc2)C1] |

TABLE 67-continued

| Ex | Structure |
|---|---|
| 339 | 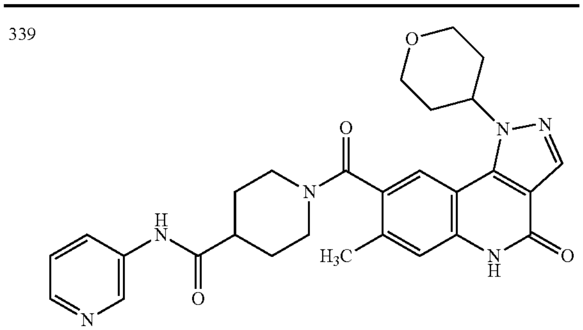 |
| 340 | 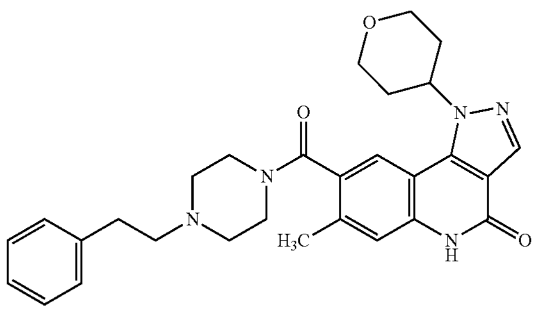 [SMILES: Cc1cc2[nH]c(=O)c3cnn(C4CCOCC4)c3c2cc1C(=O)N1CCN(CCc2ccccc2)CC1] |

TABLE 68

| Ex | Structure |
|---|---|
| 341 | 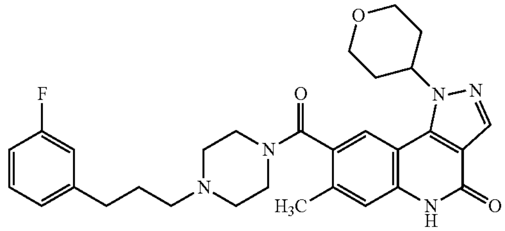 [SMILES: Cc1cc2[nH]c(=O)c3cnn(C4CCOCC4)c3c2cc1C(=O)N1CCN(CCCc2cccc(F)c2)CC1] |
| 342 | 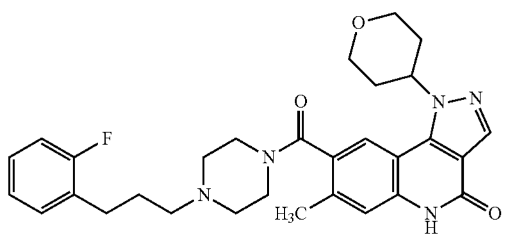 [SMILES: Cc1cc2[nH]c(=O)c3cnn(C4CCOCC4)c3c2cc1C(=O)N1CCN(CCCc2ccccc2F)CC1] |
| 343 | 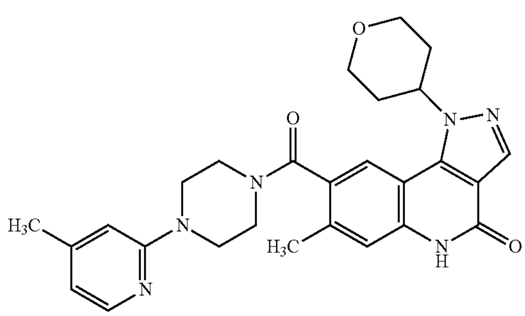 [SMILES: Cc1ccnc(N2CCN(C(=O)c3cc4c(cc3C)[nH]c(=O)c3cnn(C5CCOCC5)c34)CC2)c1] |

TABLE 68-continued

| Ex | Structure |
|---|---|
| 344 | 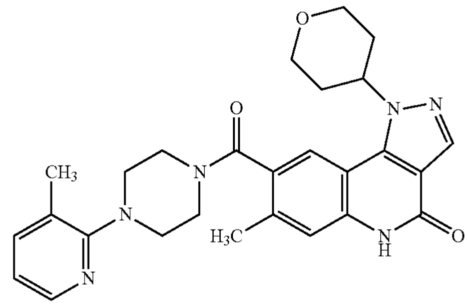 [SMILES: Cc1cc2[nH]c(=O)c3cnn(C4CCOCC4)c3c2cc1C(=O)N1CCN(c2ncccc2C)CC1] |
| 345 | 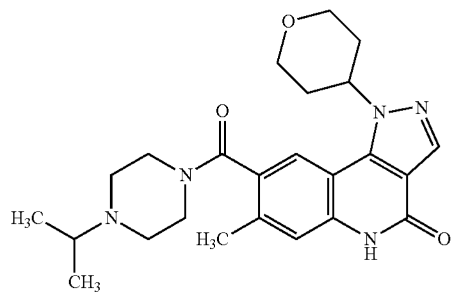 [SMILES: Cc1cc2[nH]c(=O)c3cnn(C4CCOCC4)c3c2cc1C(=O)N1CCN(C(C)C)CC1] |
| 346 | 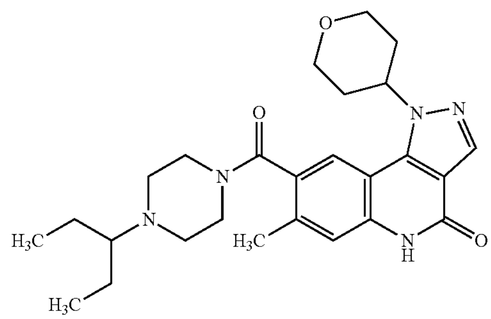 [SMILES: CCC(CC)N1CCN(C(=O)c2cc3c(cc2C)[nH]c(=O)c2cnn(C4CCOCC4)c23)CC1] |
| 347 | 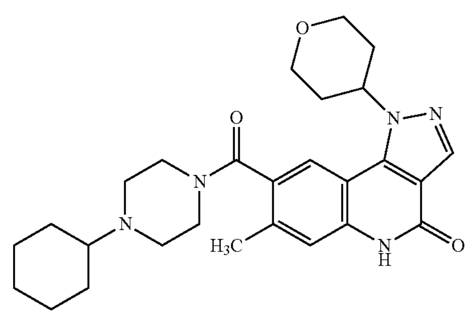 [SMILES: Cc1cc2[nH]c(=O)c3cnn(C4CCOCC4)c3c2cc1C(=O)N1CCN(C2CCCCC2)CC1] |
| 348 | 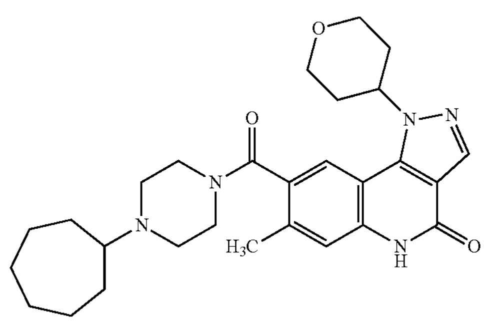 |

TABLE 68-continued

| Ex | Structure |
|---|---|
| 349 | 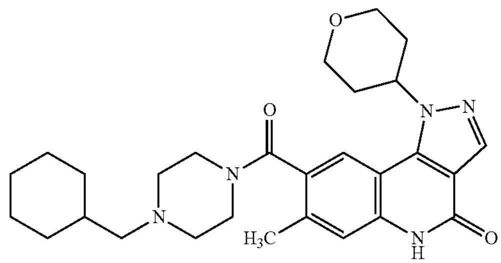 [SMILES: Cc1cc2[nH]c(=O)c3cnn(C4CCOCC4)c3c2cc1C(=O)N1CCN(CC2CCCCC2)CC1] |
| 350 | 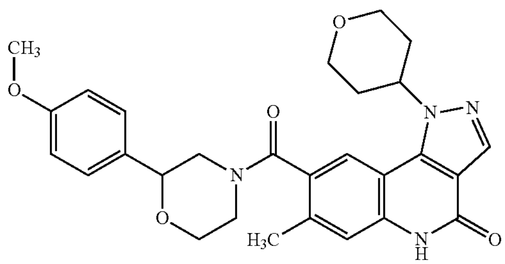 [SMILES: COc1ccc(C2CN(C(=O)c3cc4c(cc3C)[nH]c(=O)c3cnn(C5CCOCC5)c34)CCO2)cc1] |

TABLE 69

| Ex | Structure |
|---|---|
| 351 | |
| 352 | |
| 353 | |
| 354 | 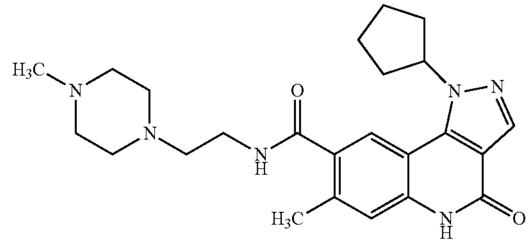 [SMILES: Cc1cc2[nH]c(=O)c3cnn(C4CCCC4)c3c2cc1C(=O)NCCN1CCN(C)CC1] |
| 355 | 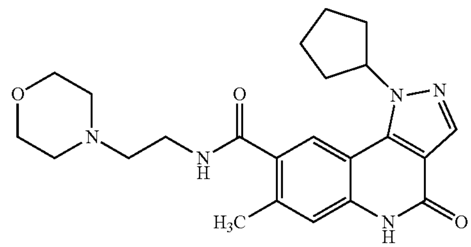 [SMILES: Cc1cc2[nH]c(=O)c3cnn(C4CCCC4)c3c2cc1C(=O)NCCN1CCOCC1] |
| 356 | 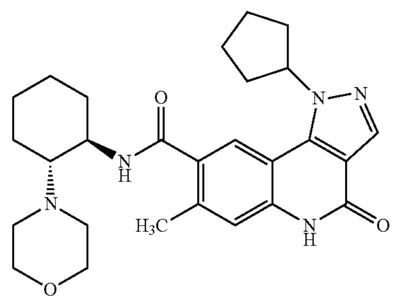 [SMILES: Cc1cc2[nH]c(=O)c3cnn(C4CCCC4)c3c2cc1C(=O)N[C@@H]1CCCC[C@H]1N1CCOCC1] |
| 357 | 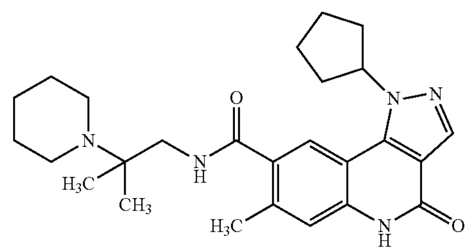 [SMILES: Cc1cc2[nH]c(=O)c3cnn(C4CCCC4)c3c2cc1C(=O)NCC(C)(C)N1CCCCC1] |
| 358 | 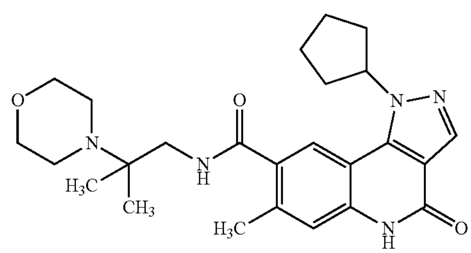 [SMILES: Cc1cc2[nH]c(=O)c3cnn(C4CCCC4)c3c2cc1C(=O)NCC(C)(C)N1CCOCC1] |
| 359 | 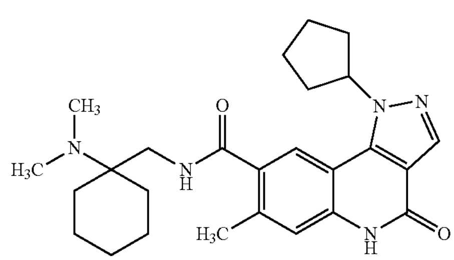 [SMILES: Cc1cc2[nH]c(=O)c3cnn(C4CCCC4)c3c2cc1C(=O)NCC1(N(C)C)CCCCC1] |

TABLE 69-continued

| Ex | Structure |
|---|---|
| 360 | 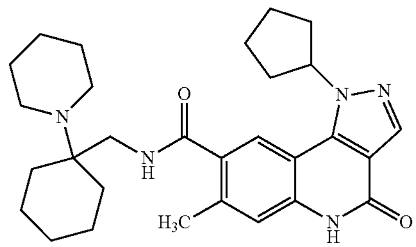 [SMILES: Cc1cc2[nH]c(=O)c3cnn(C4CCCC4)c3c2cc1C(=O)NCC1(N2CCCCC2)CCCCC1] |

TABLE 70

| Ex | Structure |
|---|---|
| 361 | 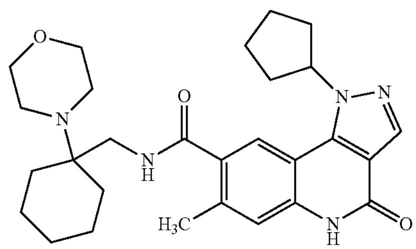 [SMILES: Cc1cc2[nH]c(=O)c3cnn(C4CCCC4)c3c2cc1C(=O)NCC1(N2CCOCC2)CCCCC1] |
| 362 | 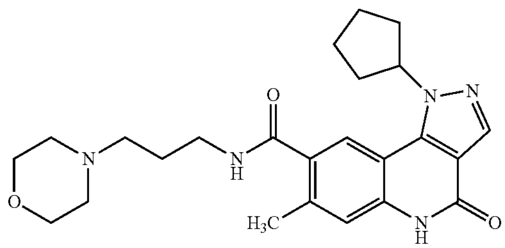 [SMILES: Cc1cc2[nH]c(=O)c3cnn(C4CCCC4)c3c2cc1C(=O)NCCCN1CCOCC1] |
| 363 | 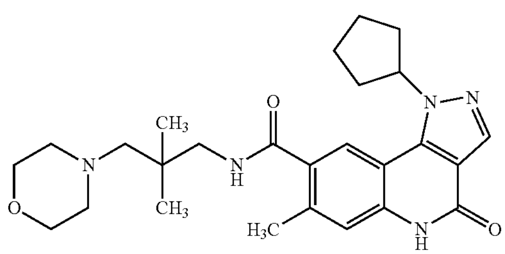 [SMILES: Cc1cc2[nH]c(=O)c3cnn(C4CCCC4)c3c2cc1C(=O)NCC(C)(C)CN1CCOCC1] |
| 364 | 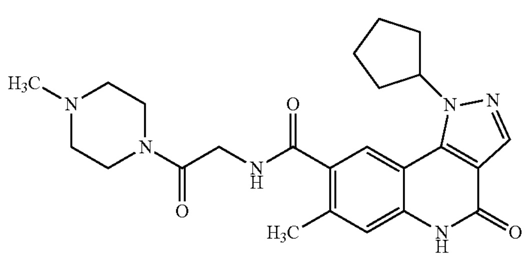 [SMILES: Cc1cc2[nH]c(=O)c3cnn(C4CCCC4)c3c2cc1C(=O)NCC(=O)N1CCN(C)CC1] |

TABLE 70-continued

| Ex | Structure |
|---|---|
| 365 | 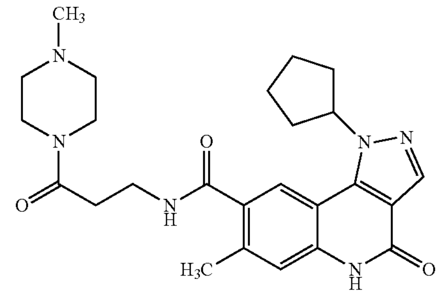 [SMILES: Cc1cc2[nH]c(=O)c3cnn(C4CCCC4)c3c2cc1C(=O)NCCC(=O)N1CCN(C)CC1] |
| 366 | 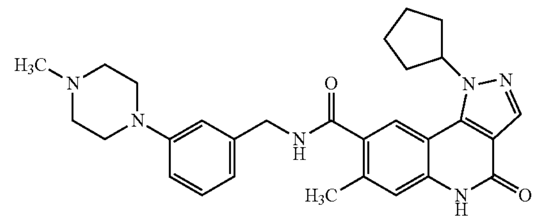 [SMILES: Cc1cc2[nH]c(=O)c3cnn(C4CCCC4)c3c2cc1C(=O)NCc1cccc(N2CCN(C)CC2)c1] |
| 367 | 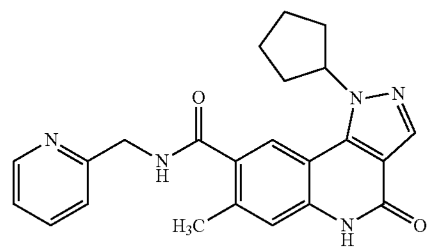 [SMILES: Cc1cc2[nH]c(=O)c3cnn(C4CCCC4)c3c2cc1C(=O)NCc1ccccn1] |
| 368 | 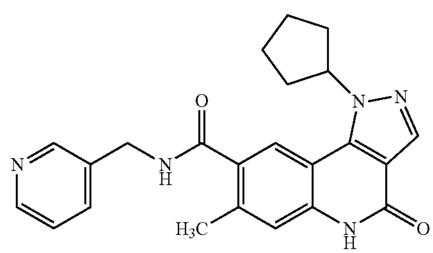 [SMILES: Cc1cc2[nH]c(=O)c3cnn(C4CCCC4)c3c2cc1C(=O)NCc1cccnc1] |
| 369 | 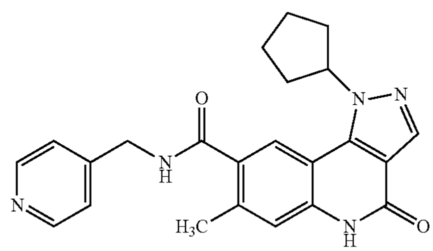 [SMILES: Cc1cc2[nH]c(=O)c3cnn(C4CCCC4)c3c2cc1C(=O)NCc1ccncc1] |
| 370 | 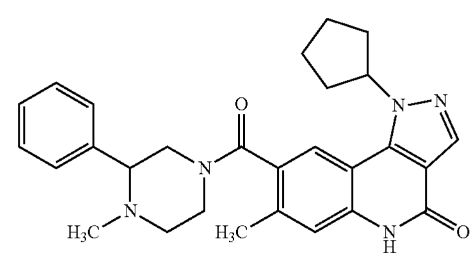 [SMILES: Cc1cc2[nH]c(=O)c3cnn(C4CCCC4)c3c2cc1C(=O)N1CCN(C)C(c2ccccc2)C1] |

TABLE 71

| Ex | Structure |
|---|---|
| 371 | 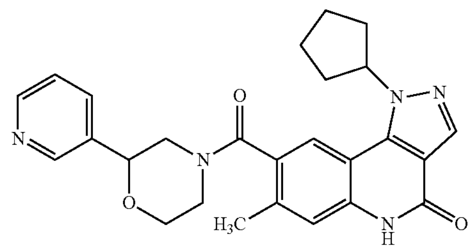 [SMILES: Cc1cc2[nH]c(=O)c3cnn(C4CCCC4)c3c2cc1C(=O)N1CCOC(c2cccnc2)C1] |
| 372 | 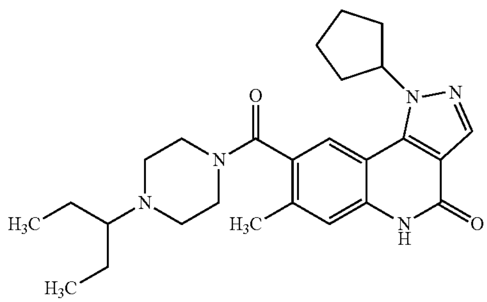 [SMILES: CCC(CC)N1CCN(C(=O)c2cc3c(cc2C)[nH]c(=O)c2cnn(C4CCCC4)c23)CC1] |
| 373 | 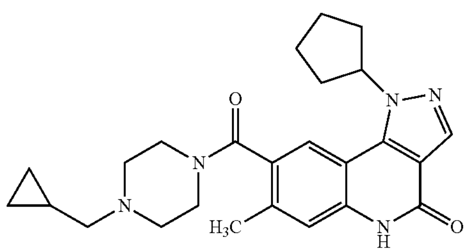 [SMILES: Cc1cc2[nH]c(=O)c3cnn(C4CCCC4)c3c2cc1C(=O)N1CCN(CC2CC2)CC1] |
| 374 | 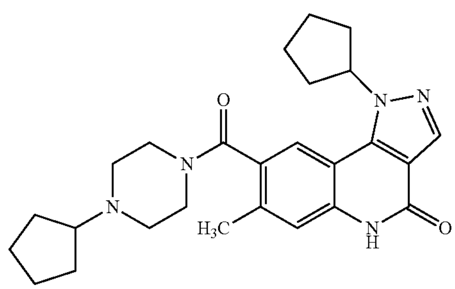 [SMILES: Cc1cc2[nH]c(=O)c3cnn(C4CCCC4)c3c2cc1C(=O)N1CCN(C2CCCC2)CC1] |
| 375 | 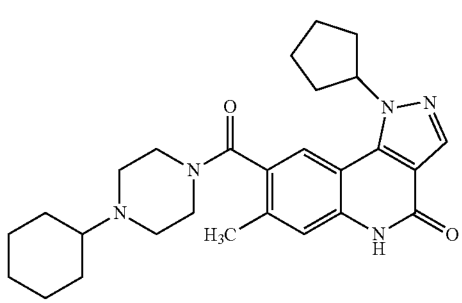 [SMILES: Cc1cc2[nH]c(=O)c3cnn(C4CCCC4)c3c2cc1C(=O)N1CCN(C2CCCCC2)CC1] |

TABLE 71-continued

| Ex | Structure |
|---|---|
| 376 | 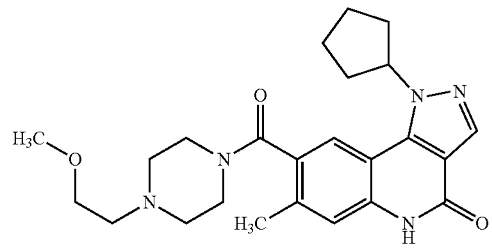 [SMILES: COCCN1CCN(C(=O)c2cc3c(cc2C)[nH]c(=O)c2cnn(C4CCCC4)c23)CC1] |
| 377 | 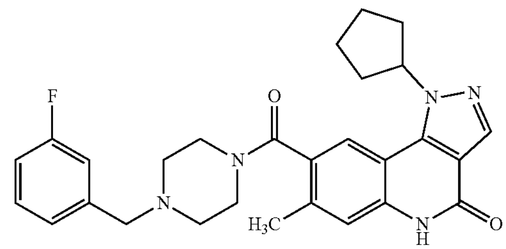 [SMILES: Cc1cc2[nH]c(=O)c3cnn(C4CCCC4)c3c2cc1C(=O)N1CCN(Cc2cccc(F)c2)CC1] |
| 378 | 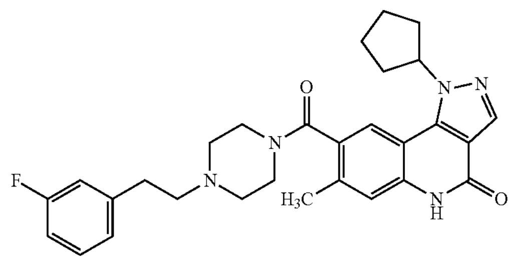 [SMILES: Cc1cc2[nH]c(=O)c3cnn(C4CCCC4)c3c2cc1C(=O)N1CCN(CCc2cccc(F)c2)CC1] |
| 379 | 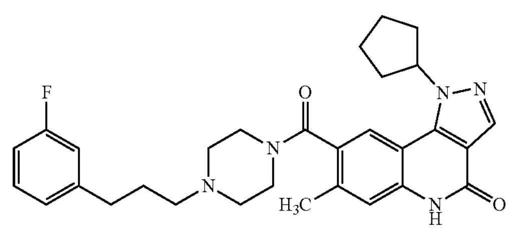 [SMILES: Cc1cc2[nH]c(=O)c3cnn(C4CCCC4)c3c2cc1C(=O)N1CCN(CCCc2cccc(F)c2)CC1] |
| 380 | 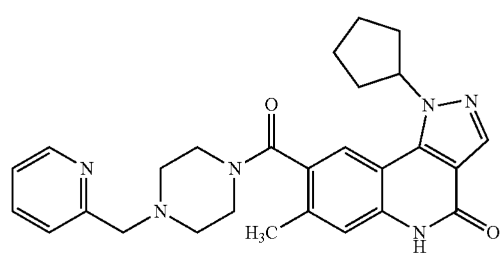 [SMILES: Cc1cc2[nH]c(=O)c3cnn(C4CCCC4)c3c2cc1C(=O)N1CCN(Cc2ccccn2)CC1] |

TABLE 72

| Ex | Structure |
|---|---|
| 381 | (cyclopentyl-pyrazolo-quinolinone with 4-(pyridin-4-ylmethyl)piperazine carbonyl, 7-methyl) |
| 382 | Chiral — (cyclopentyl-pyrazolo-quinolinone with 5-benzyl-2,5-diazabicyclo[2.2.1]heptane carbonyl, 7-methyl) |
| 383 | (cyclopentyl-pyrazolo-quinolinone with N-((1-methylpiperidin-4-yl)methyl)carboxamide, 7-methyl) |
| 384 | (cyclopentyl-pyrazolo-quinolinone with N-((tetrahydro-2H-pyran-4-yl)methyl)carboxamide, 7-methyl) |
| 385 | (cyclopentyl-pyrazolo-quinolinone with 2-benzyl-2,8-diazaspiro[5.5] carbonyl, 7-methyl) |
| 386 | (cyclopentyl-pyrazolo-quinolinone with piperidine-1-carbonyl, 7-methyl) |

TABLE 72-continued

| Ex | Structure |
|---|---|
| 387 | (cyclopentyl-pyrazolo-quinolinone with 4-(hydroxymethyl)piperidine-1-carbonyl, 7-methyl) |
| 388 | (cyclopentyl-pyrazolo-quinolinone with (3,4-dihydroxypyrrolidin-1-yl)carbonyl, 7-methyl) |
| 389 | (cyclopentyl-pyrazolo-quinolinone with N-(2,3-dihydroxypropyl)carboxamide, 7-methyl) |
| 390 | (cyclopentyl-pyrazolo-quinolinone with 4-(methoxymethyl)piperidine-1-carbonyl, 7-methyl) |

TABLE 73

| Ex | Structure |
|---|---|
| 391 | (cyclopentyl-pyrazolo-quinolinone with 3-(dimethylamino)azetidine-1-carbonyl, 7-methyl) |

TABLE 73-continued

| Ex | Structure |
|---|---|
| 392 | 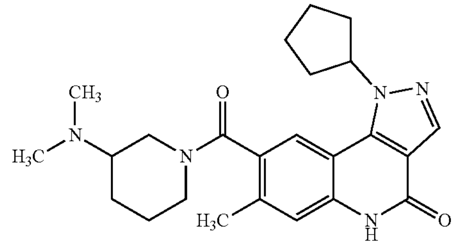 [SMILES: Cc1cc2[nH]c(=O)c3cnn(C4CCCC4)c3c2cc1C(=O)N1CCCC(N(C)C)C1] |
| 393 | 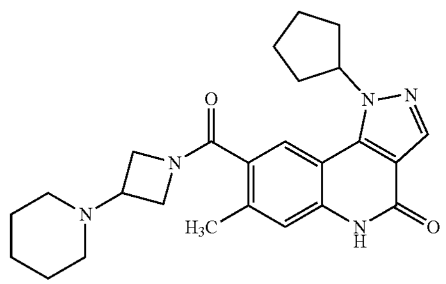 [SMILES: Cc1cc2[nH]c(=O)c3cnn(C4CCCC4)c3c2cc1C(=O)N1CC(N2CCCCC2)C1] |
| 394 | 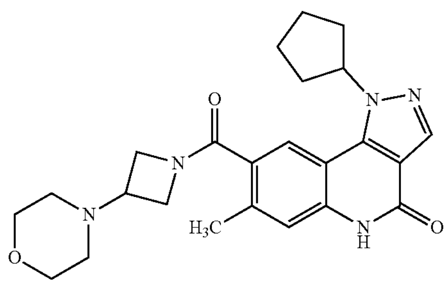 [SMILES: Cc1cc2[nH]c(=O)c3cnn(C4CCCC4)c3c2cc1C(=O)N1CC(N2CCOCC2)C1] |
| 395 | 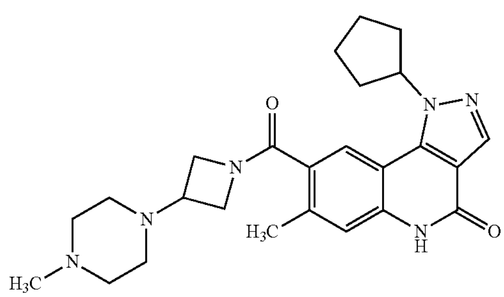 [SMILES: Cc1cc2[nH]c(=O)c3cnn(C4CCCC4)c3c2cc1C(=O)N1CC(N2CCN(C)CC2)C1] |
| 396 | |ель

TABLE 73-continued

| Ex | Structure |
|---|---|
| 397 | |
| 398 | |
| 399 | |
| 400 | |

TABLE 74

| Ex | Structure |
|---|---|
| 401 | 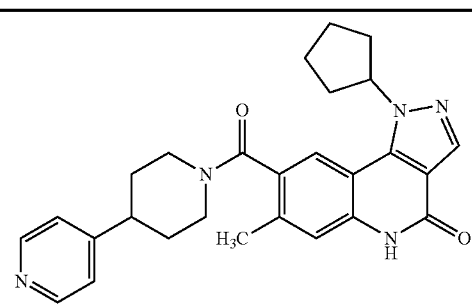 |

TABLE 74-continued

| Ex | Structure |
|----|-----------|
| 402 | 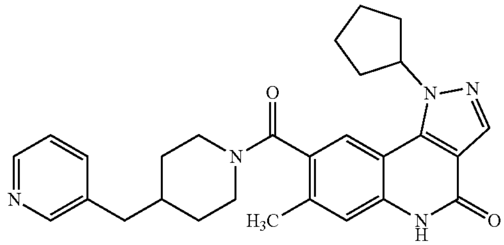 [SMILES: Cc1cc2[nH]c(=O)c3cnn(C4CCCC4)c3c2cc1C(=O)N1CCC(Cc2cccnc2)CC1] |
| 403 | 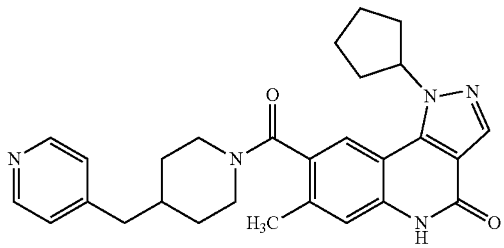 [SMILES: Cc1cc2[nH]c(=O)c3cnn(C4CCCC4)c3c2cc1C(=O)N1CCC(Cc2ccncc2)CC1] |
| 404 | 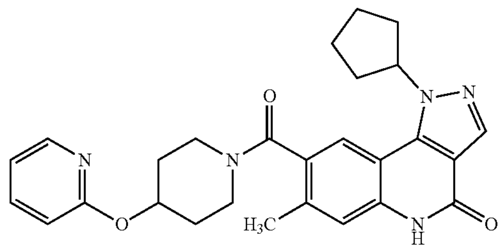 [SMILES: Cc1cc2[nH]c(=O)c3cnn(C4CCCC4)c3c2cc1C(=O)N1CCC(Oc2ccccn2)CC1] |
| 405 | 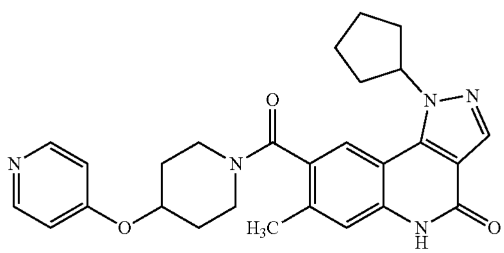 |
| 406 | 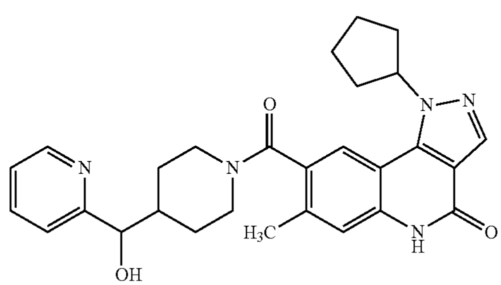 [SMILES: Cc1cc2[nH]c(=O)c3cnn(C4CCCC4)c3c2cc1C(=O)N1CCC(C(O)c2ccccn2)CC1] |
| 407 | 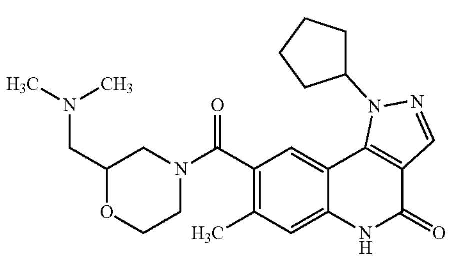 [SMILES: Cc1cc2[nH]c(=O)c3cnn(C4CCCC4)c3c2cc1C(=O)N1CCOC(CN(C)C)C1] |

TABLE 74-continued

| Ex | Structure |
|----|-----------|
| 408 | 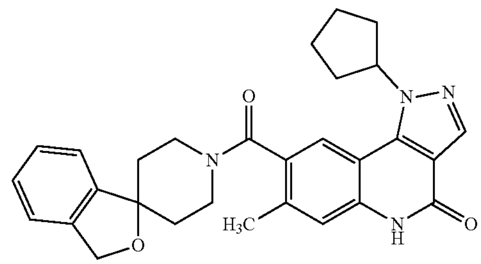 [SMILES: Cc1cc2[nH]c(=O)c3cnn(C4CCCC4)c3c2cc1C(=O)N1CCC2(CC1)OCc1ccccc12] |
| 409 | 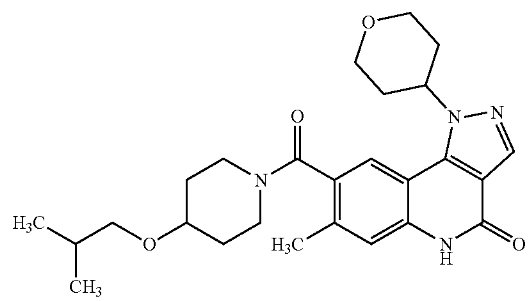 [SMILES: Cc1cc2[nH]c(=O)c3cnn(C4CCOCC4)c3c2cc1C(=O)N1CCC(OCC(C)C)CC1] |
| 410 | 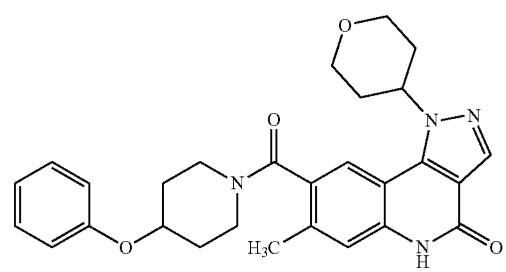 [SMILES: Cc1cc2[nH]c(=O)c3cnn(C4CCOCC4)c3c2cc1C(=O)N1CCC(Oc2ccccc2)CC1] |

TABLE 75

| Ex | Structure |
|----|-----------|
| 411 | 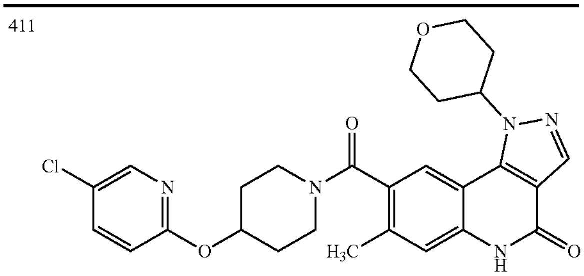 |
| 412 | 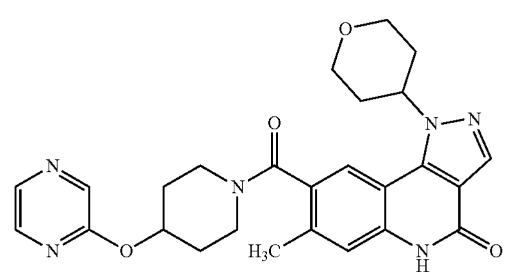 [SMILES: Cc1cc2[nH]c(=O)c3cnn(C4CCOCC4)c3c2cc1C(=O)N1CCC(Oc2cnccn2)CC1] |

TABLE 75-continued

| Ex | Structure |
|---|---|
| 413 | (structure) |
| 414 | (structure) |
| 415 | (structure) |
| 416 | (structure) |
| 417 | (structure) |

TABLE 75-continued

| Ex | Structure |
|---|---|
| 418 | (structure) |
| 419 | (structure) |
| 420 | (structure) |

TABLE 76

| Ex | Structure |
|---|---|
| 421 | (structure) |

TABLE 76-continued

| Ex | Structure |
|---|---|
| 422 | 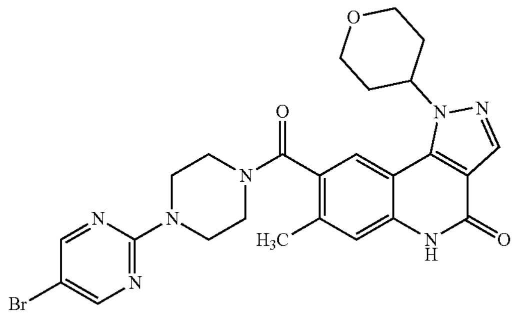 [SMILES: Cc1cc2[nH]c(=O)c3cnn(C4CCOCC4)c3c2cc1C(=O)N1CCN(c2ccc(Cl)cn2)CC1] |
| 423 | 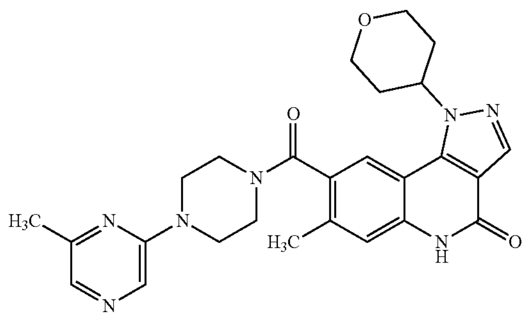 [SMILES: Cc1cncc(N2CCN(C(=O)c3cc4c(cc3C)[nH]c(=O)c3cnn(C5CCOCC5)c34)CC2)n1] |
| 424 | 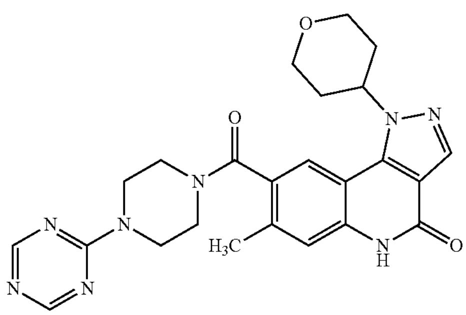 [SMILES: Cc1cc2[nH]c(=O)c3cnn(C4CCOCC4)c3c2cc1C(=O)N1CCN(c2ncncn2)CC1] |
| 425 | 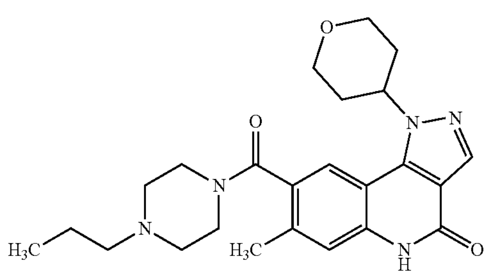 [SMILES: CCCN1CCN(C(=O)c2cc3c(cc2C)[nH]c(=O)c2cnn(C4CCOCC4)c23)CC1] |
| 426 | 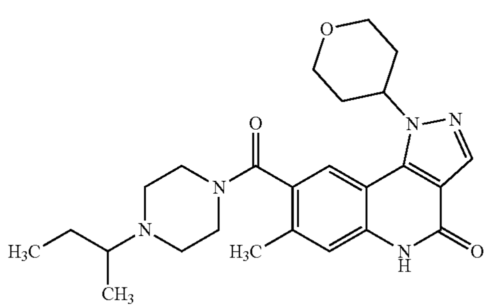 [SMILES: CCC(C)N1CCN(C(=O)c2cc3c(cc2C)[nH]c(=O)c2cnn(C4CCOCC4)c23)CC1] |
| 427 | |
| 428 | |
| 429 | |
| 430 | |

TABLE 77

| Ex | Structure |
|---|---|
| 431 | 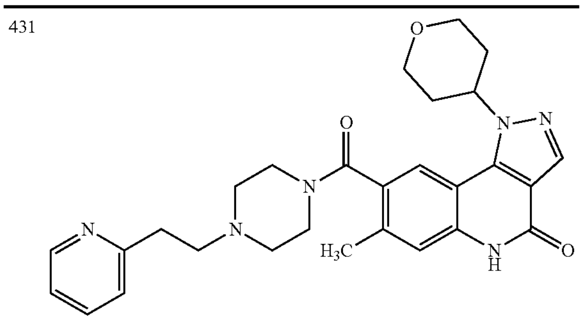 |

TABLE 77-continued

| Ex | Structure |
|---|---|
| 432 | (structure) |
| 433 | (structure) |
| 434 | (structure) |
| 435 | (structure) |
| 436 | (structure) |
| 437 | (structure) |

TABLE 77-continued

| Ex | Structure |
|---|---|
| 438 | (structure) |
| 439 | (structure) |
| 440 | (structure) |

TABLE 78

| Ex | Structure |
|---|---|
| 441 | (structure) |
| 442 | (structure) |

TABLE 78-continued

| Ex | Structure |
|---|---|
| 443 | 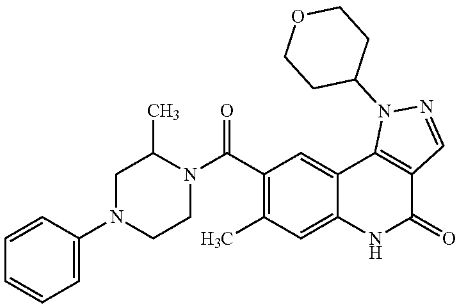 [SMILES: Cc1cc2[nH]c(=O)c3cnn(C4CCOCC4)c3c2cc1C(=O)N1CCN(c2ccccc2)CC1C] |
| 444 | 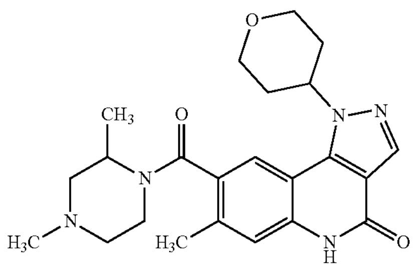 [SMILES: Cc1cc2[nH]c(=O)c3cnn(C4CCOCC4)c3c2cc1C(=O)N1CCN(C)CC1C] |
| 445 | 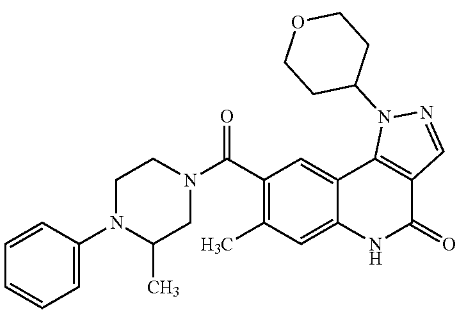 [SMILES: Cc1cc2[nH]c(=O)c3cnn(C4CCOCC4)c3c2cc1C(=O)N1CCN(c2ccccc2)C(C)C1] |
| 446 | 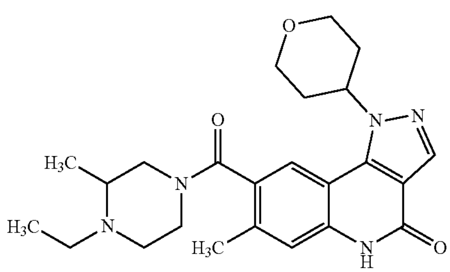 [SMILES: CCN1CCN(C(=O)c2cc3c(cc2C)[nH]c(=O)c2cnn(C4CCOCC4)c23)CC1C] |
| 447 | Chiral |

TABLE 78-continued

| Ex | Structure |
|---|---|
| 448 | Chiral |
| 449 | |
| 450 | |

TABLE 79

| Ex | Structure |
|---|---|
| 451 | 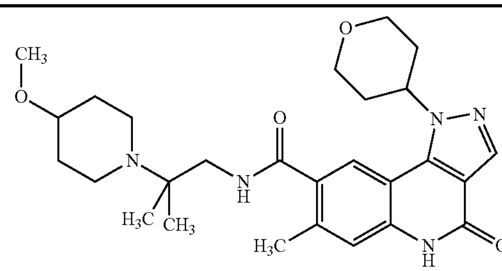 |
| 452 | 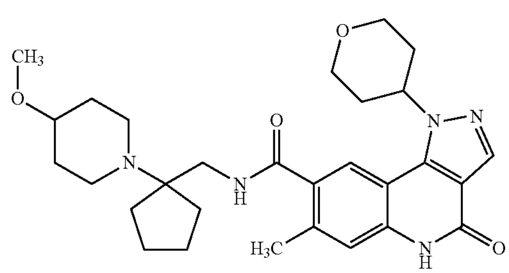 [SMILES: COC1CCN(C2(CNC(=O)c3cc4c(cc3C)[nH]c(=O)c3cnn(C5CCOCC5)c34)CCCC2)CC1] |

TABLE 79-continued
| Ex | Structure |
|---|---|
| 453 | 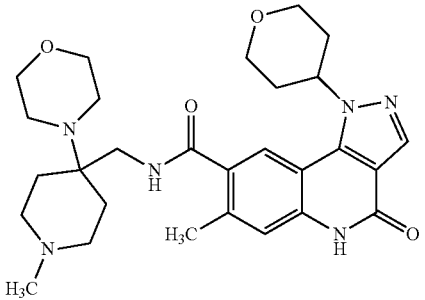 [SMILES: Cc1cc2[nH]c(=O)c3cnn(C4CCOCC4)c3c2cc1C(=O)NCC1(N2CCOCC2)CCN(C)CC1] |
| 454 | 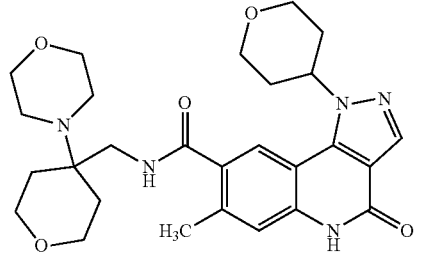 [SMILES: Cc1cc2[nH]c(=O)c3cnn(C4CCOCC4)c3c2cc1C(=O)NCC1(N2CCOCC2)CCOCC1] |
| 455 | 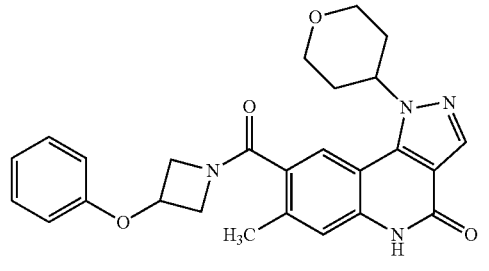 [SMILES: Cc1cc2[nH]c(=O)c3cnn(C4CCOCC4)c3c2cc1C(=O)N1CC(Oc2ccccc2)C1] |
| 456 | 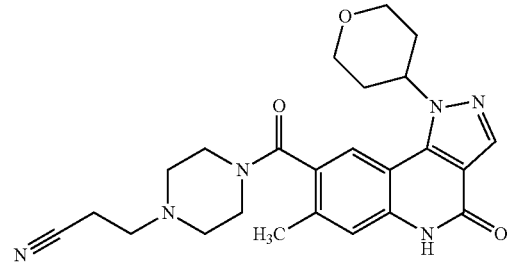 [SMILES: Cc1cc2[nH]c(=O)c3cnn(C4CCOCC4)c3c2cc1C(=O)N1CCN(CCC#N)CC1] |
| 457 | 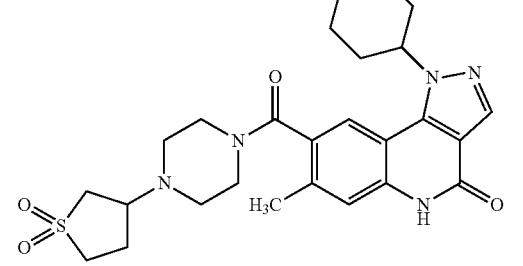 |
TABLE 79-continued
| Ex | Structure |
|---|---|
| 458 | 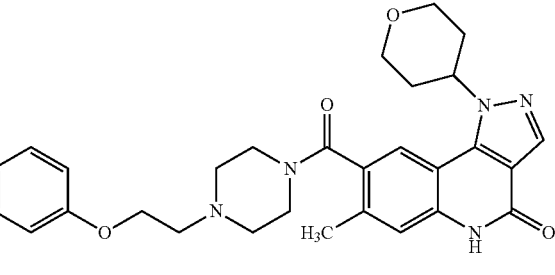 |
| 459 | 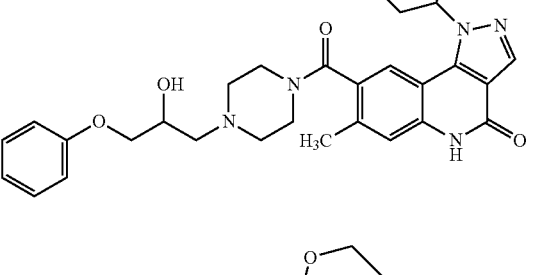 |
| 460 | 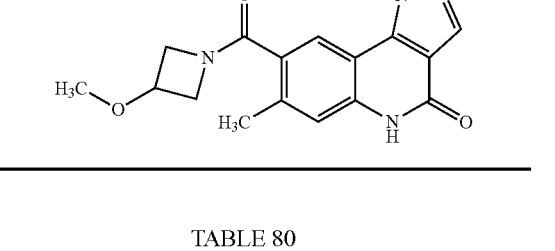 |
TABLE 80
| Ex | Structure |
|---|---|
| 461 | 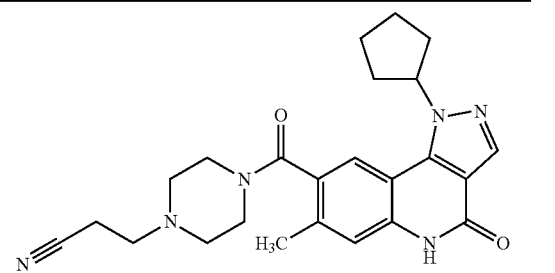 |
| 462 | 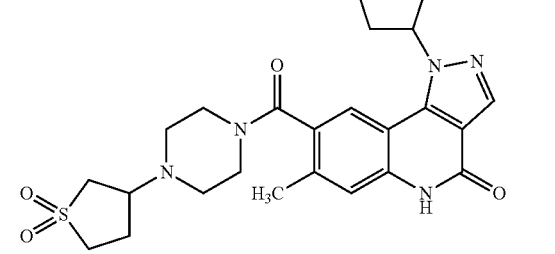 |

TABLE 80-continued
| Ex | Structure |
|---|---|
| 463 | 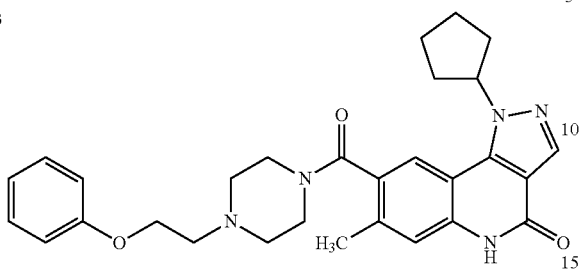 |
| 464 | 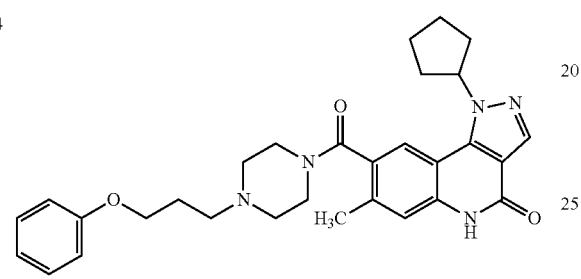 |
| 465 | 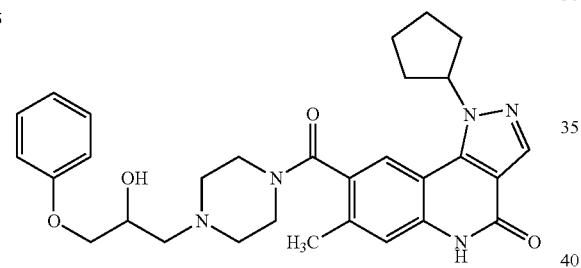 |
| 466 | 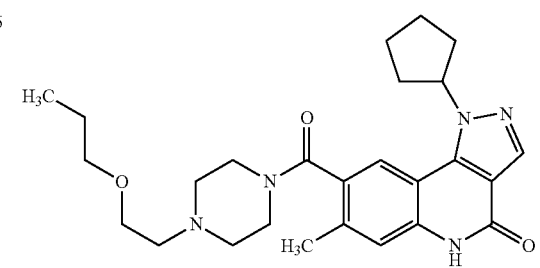 |
| 467 | 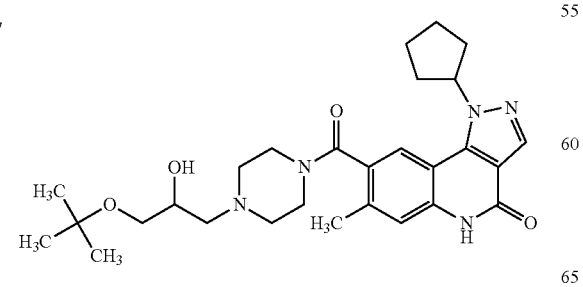 |
TABLE 80-continued
| Ex | Structure |
|---|---|
| 468 | 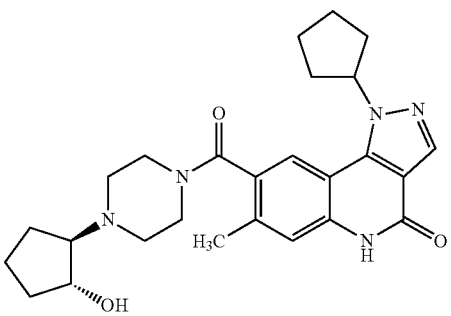 [SMILES: Cc1cc2[nH]c(=O)c3cnn(C4CCCC4)c3c2cc1C(=O)N1CCN([C@@H]2CCC[C@H]2O)CC1] |
| 469 | 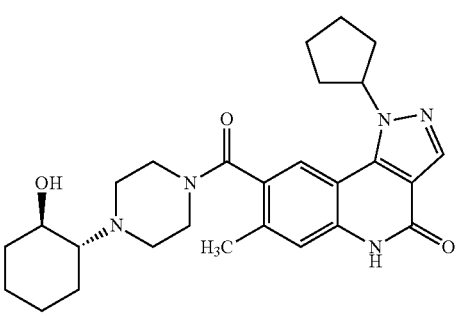 [SMILES: Cc1cc2[nH]c(=O)c3cnn(C4CCCC4)c3c2cc1C(=O)N1CCN([C@@H]2CCCC[C@H]2O)CC1] |
| 470 | 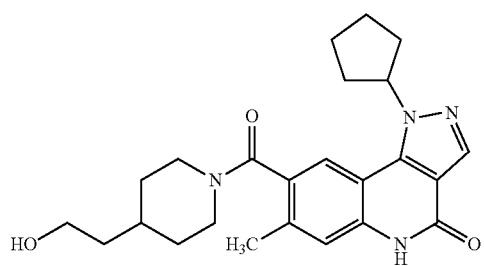 [SMILES: Cc1cc2[nH]c(=O)c3cnn(C4CCCC4)c3c2cc1C(=O)N1CCC(CCO)CC1] |
TABLE 81
| Ex | Structure |
|---|---|
| 471 | 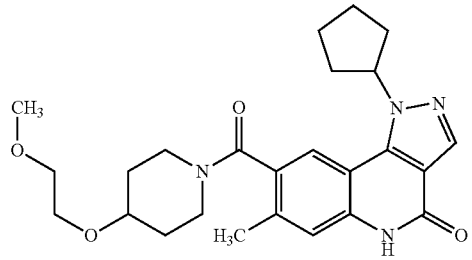 [SMILES: COCCOC1CCN(C(=O)c2cc3c(cc2C)[nH]c(=O)c2cnn(C4CCCC4)c23)CC1] |
| 472 | 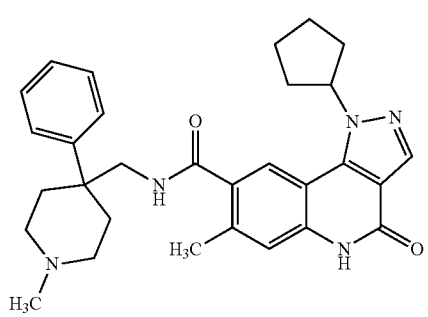 [SMILES: Cc1cc2[nH]c(=O)c3cnn(C4CCCC4)c3c2cc1C(=O)NCC1(c2ccccc2)CCN(C)CC1] |

TABLE 81-continued

| Ex | Structure |
|---|---|
| 473 | (structure) |
| 474 | Chiral (structure) |
| 475 | (structure) |
| 476 | (structure) |
| 477 | (structure) |

TABLE 81-continued

| Ex | Structure |
|---|---|
| 478 | (structure) |
| 479 | (structure) |
| 480 | (structure) |

TABLE 82

| Ex | Structure |
|---|---|
| 481 | (structure) |
| 482 | (structure) |

TABLE 82-continued
| Ex | Structure |
|---|---|
| 483 | 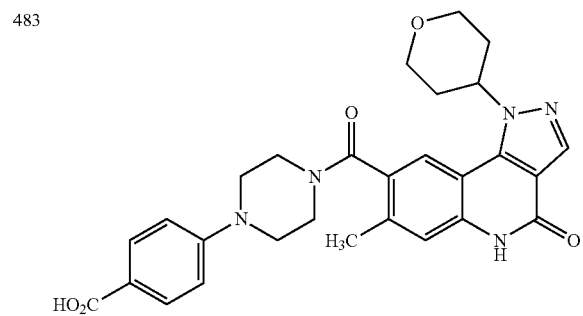 |
| 484 | 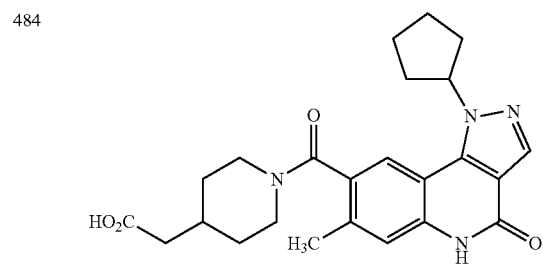 |
| 485 | 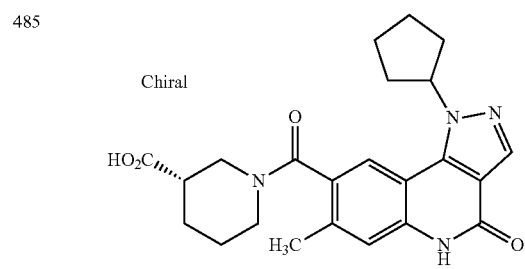 |
| 486 | 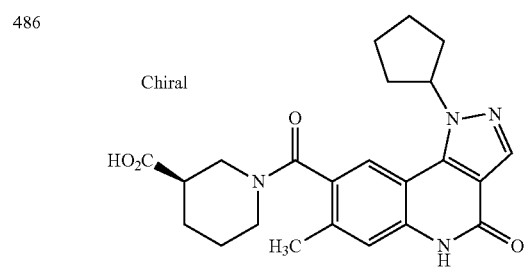 |
| 487 | 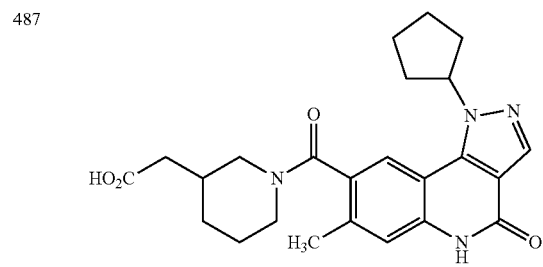 |
TABLE 82-continued
| Ex | Structure |
|---|---|
| 488 | 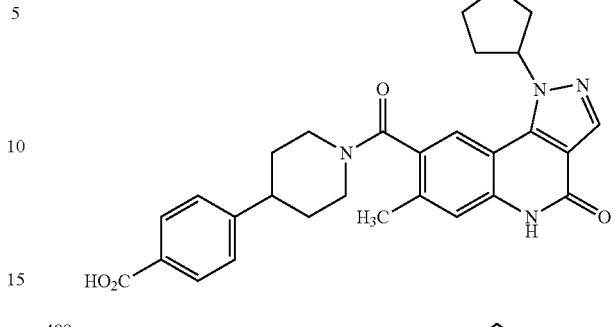 |
| 489 | 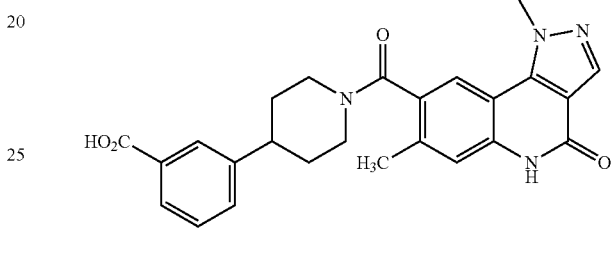 |
| 490 | 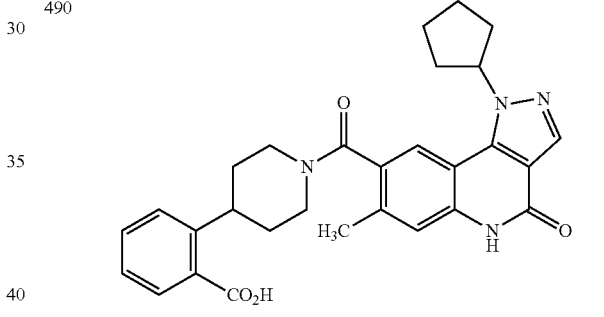 |
TABLE 83
| Ex | Structure |
|---|---|
| 491 | 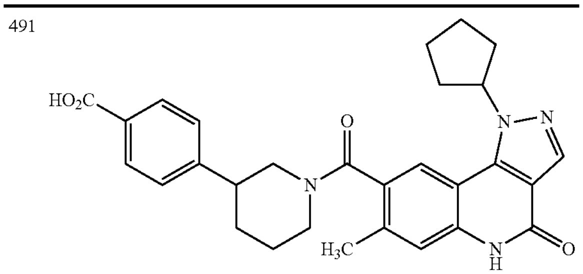 |
| 492 | 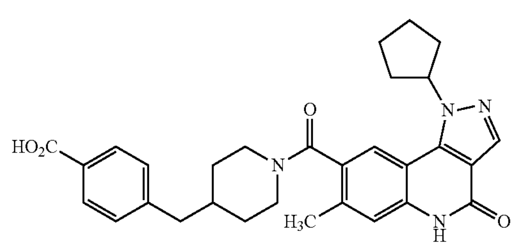 [SMILES: Cc1cc2[nH]c(=O)c3cnn(C4CCCC4)c3c2cc1C(=O)N1CCC(Cc2ccc(C(=O)O)cc2)CC1] |
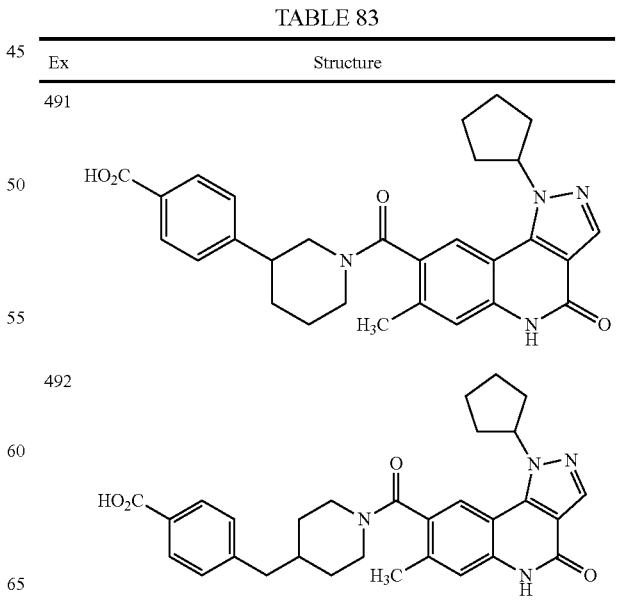

TABLE 83-continued
| Ex | Structure |
|---|---|
| 493 | 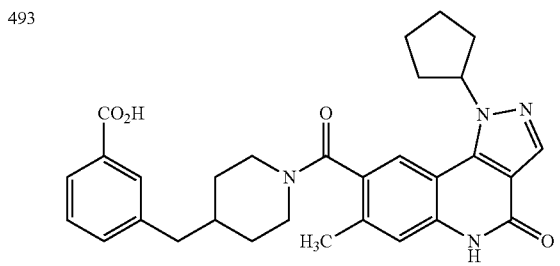 |
| 494 | 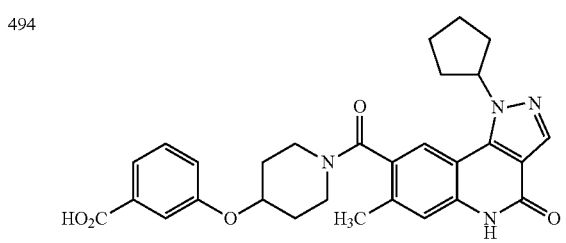 |
| 495 | 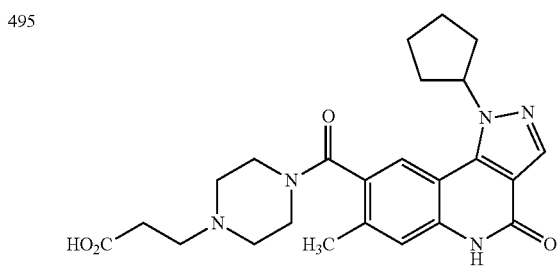 |
| 496 | 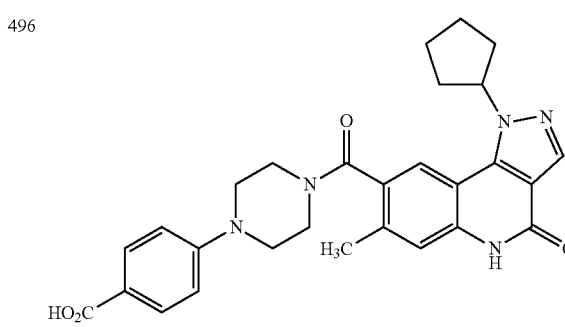 |
| 497 | 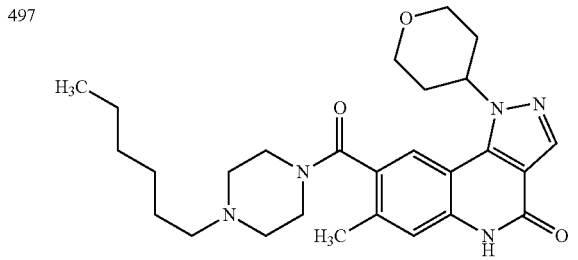 |
TABLE 83-continued
| Ex | Structure |
|---|---|
| 498 | 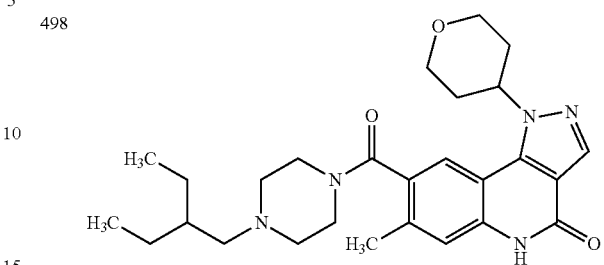 |
| 499 | 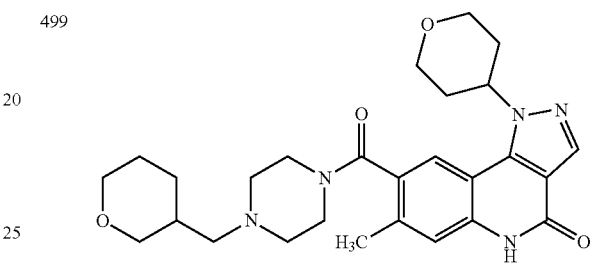 |
| 500 | 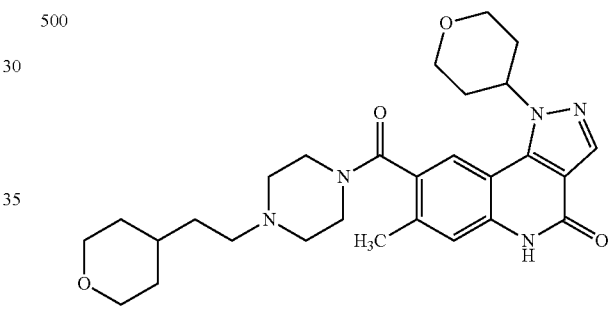 |
TABLE 84
| Ex | Structure |
|---|---|
| 501 | 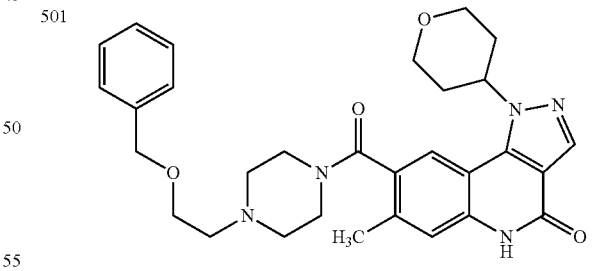 |
| 502 | 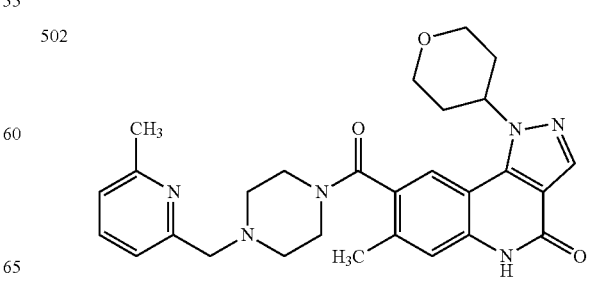 |

TABLE 84-continued
| Ex | Structure |
|---|---|
| 503 | 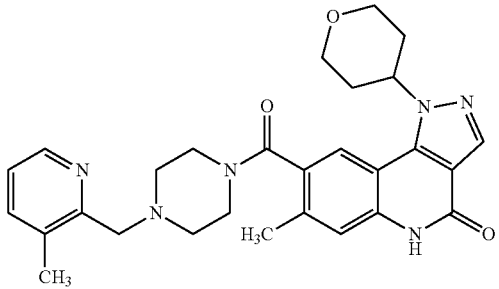 [SMILES: Cc1cc2[nH]c(=O)c3cnn(C4CCOCC4)c3c2cc1C(=O)N1CCN(Cc2ncccc2C)CC1] |
| 504 | 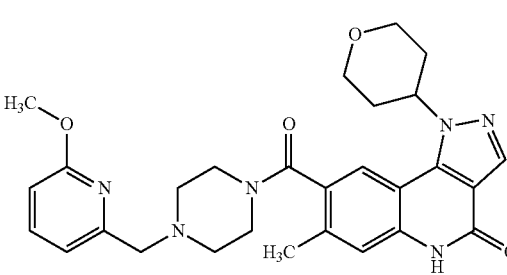 |
| 505 | 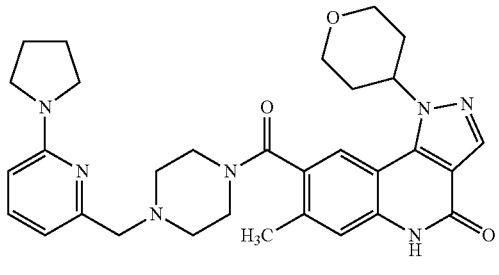 [SMILES: Cc1cc2[nH]c(=O)c3cnn(C4CCOCC4)c3c2cc1C(=O)N1CCN(Cc2cccc(N3CCCC3)n2)CC1] |
| 506 | 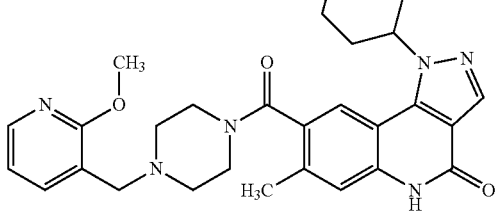 |
| 507 | 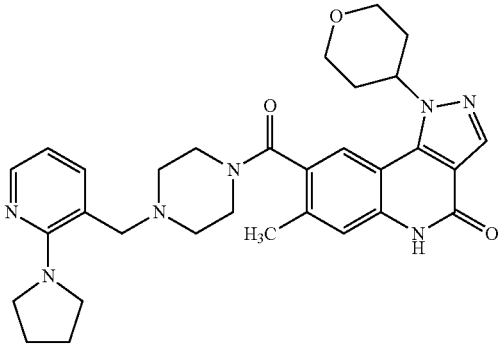 [SMILES: Cc1cc2[nH]c(=O)c3cnn(C4CCOCC4)c3c2cc1C(=O)N1CCN(Cc2cccnc2N2CCCC2)CC1] |
TABLE 84-continued
| Ex | Structure |
|---|---|
| 508 | 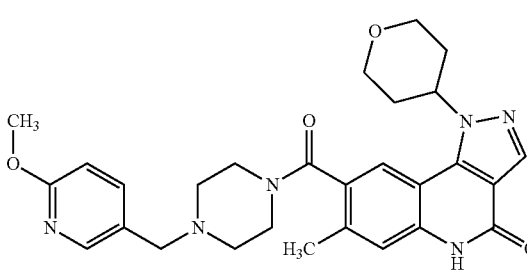 |
| 509 | 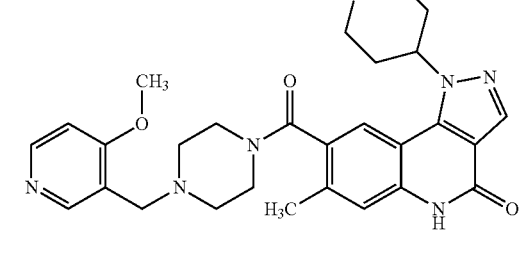 |
| 510 | 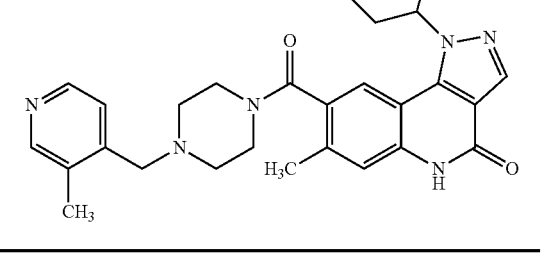 |
TABLE 85
| Ex | Structure |
|---|---|
| 511 | 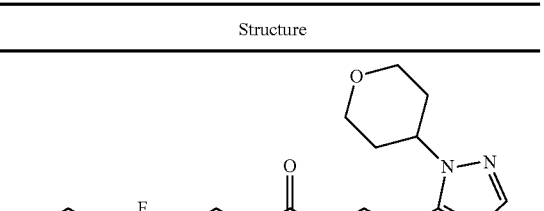 |
| 512 | 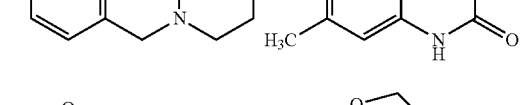 |

TABLE 85-continued

| Ex | Structure |
|---|---|
| 513 | 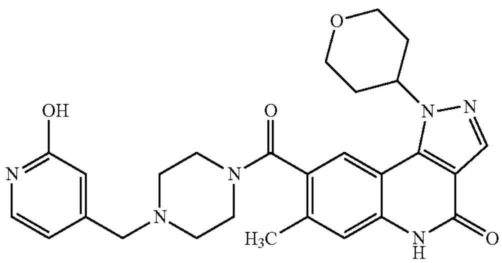 [SMILES: Cc1cc2[nH]c(=O)c3cnn(C4CCOCC4)c3c2cc1C(=O)N1CCN(Cc2ccnc(O)c2)CC1] |
| 514 | 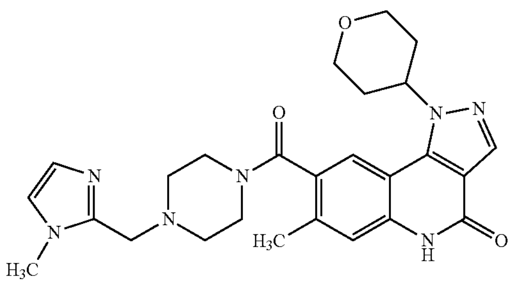 [SMILES: Cc1cc2[nH]c(=O)c3cnn(C4CCOCC4)c3c2cc1C(=O)N1CCN(Cc2nccn2C)CC1] |
| 515 | 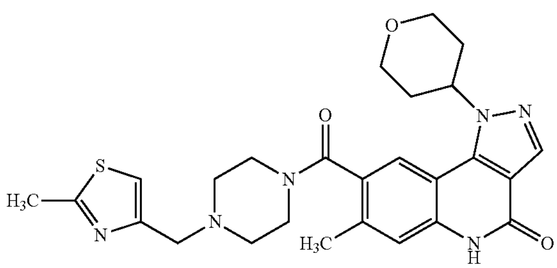 [SMILES: Cc1nc(CN2CCN(C(=O)c3cc4c(cc3C)[nH]c(=O)c3cnn(C5CCOCC5)c34)CC2)cs1] |
| 516 | 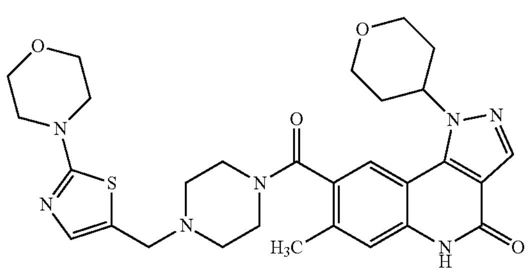 [SMILES: Cc1cc2[nH]c(=O)c3cnn(C4CCOCC4)c3c2cc1C(=O)N1CCN(Cc2cnc(N3CCOCC3)s2)CC1] |
| 517 | 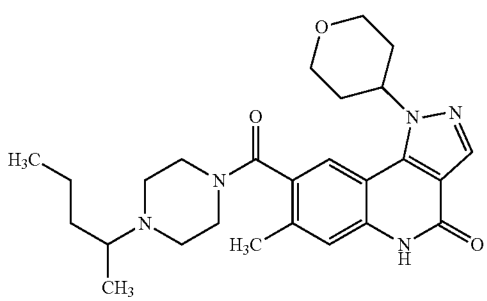 [SMILES: CCCC(C)N1CCN(C(=O)c2cc3c(cc2C)[nH]c(=O)c2cnn(C4CCOCC4)c23)CC1] |

TABLE 85-continued

| Ex | Structure |
|---|---|
| 518 | |
| 519 | |
| 520 | |

TABLE 86

| Ex | Structure |
|---|---|
| 521 | 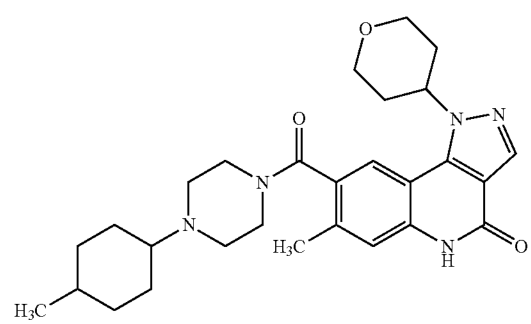 [SMILES: Cc1cc2[nH]c(=O)c3cnn(C4CCOCC4)c3c2cc1C(=O)N1CCN(C2CCC(C)CC2)CC1] |

TABLE 86-continued
| Ex | Structure |
|---|---|
| 522 | 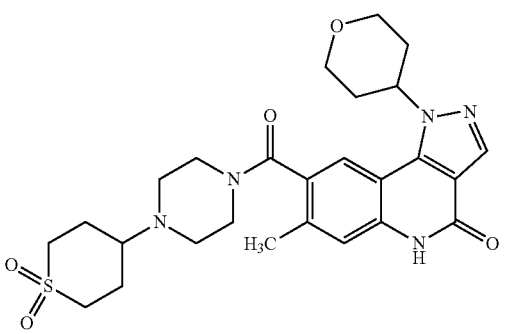 [SMILES: Cc1cc2[nH]c(=O)c3cnn(C4CCOCC4)c3c2cc1C(=O)N1CCN(C2CCS(=O)(=O)CC2)CC1] |
| 523 | 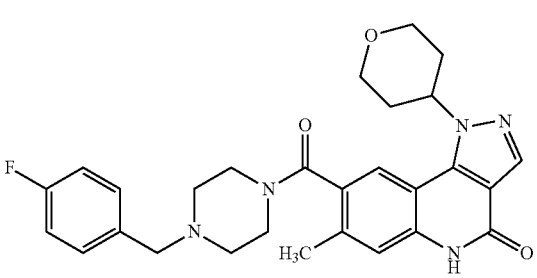 [SMILES: Cc1cc2[nH]c(=O)c3cnn(C4CCOCC4)c3c2cc1C(=O)N1CCN(Cc2ccc(F)cc2)CC1] |
| 524 | 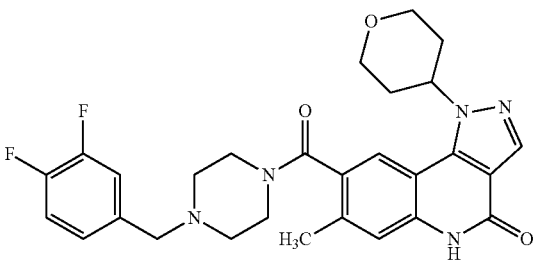 [SMILES: Cc1cc2[nH]c(=O)c3cnn(C4CCOCC4)c3c2cc1C(=O)N1CCN(Cc2ccc(F)c(F)c2)CC1] |
| 525 | 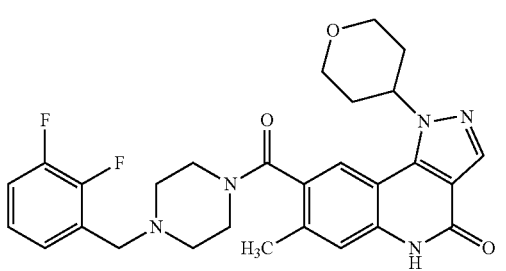 [SMILES: Cc1cc2[nH]c(=O)c3cnn(C4CCOCC4)c3c2cc1C(=O)N1CCN(Cc2cccc(F)c2F)CC1] |
| 526 | 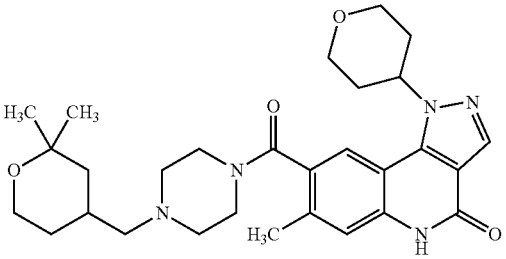 [SMILES: Cc1cc2[nH]c(=O)c3cnn(C4CCOCC4)c3c2cc1C(=O)N1CCN(CC2CCOC(C)(C)C2)CC1] |
| 527 | 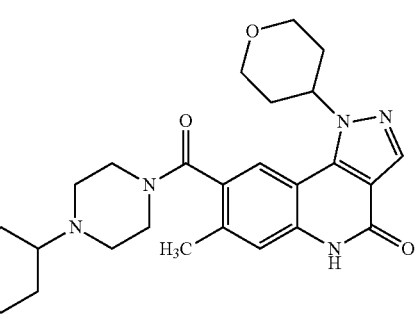 |
| 528 | 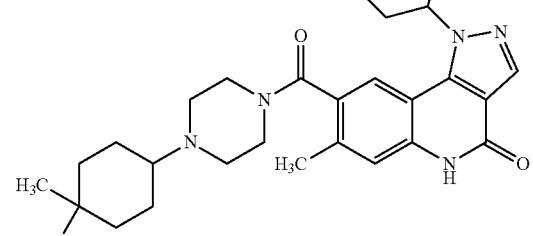 |
| 529 Chiral | 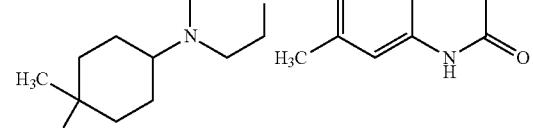 |
| 530 Chiral | 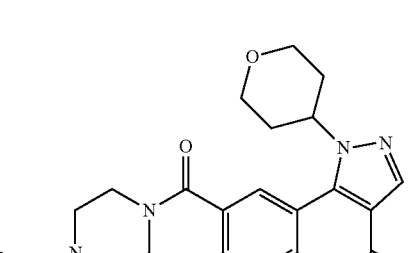 |

TABLE 87
| Ex | Structure |
|---|---|
| 531 | 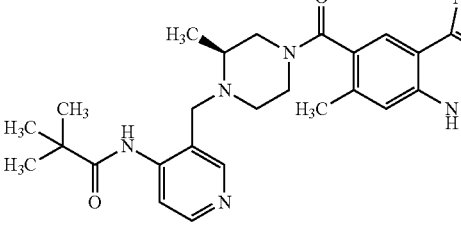 |
| 532 | 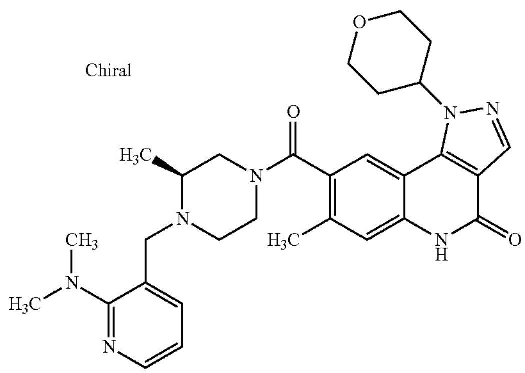 [SMILES: Cc1cc2[nH]c(=O)c3cnn(C4CCOCC4)c3c2cc1C(=O)N1CCN(Cc2cccnc2N(C)C)[C@@H](C)C1] |
| 533 | 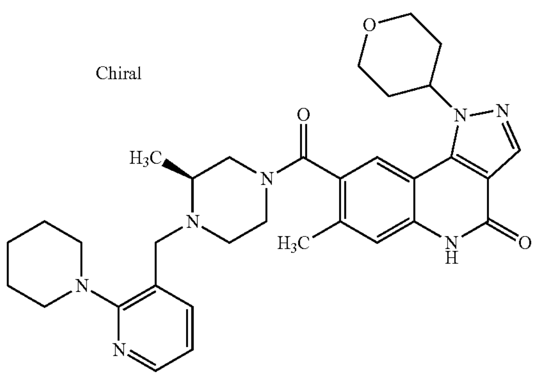 [SMILES: Cc1cc2[nH]c(=O)c3cnn(C4CCOCC4)c3c2cc1C(=O)N1CCN(Cc2cccnc2N2CCCCC2)[C@@H](C)C1] |
| 534 | 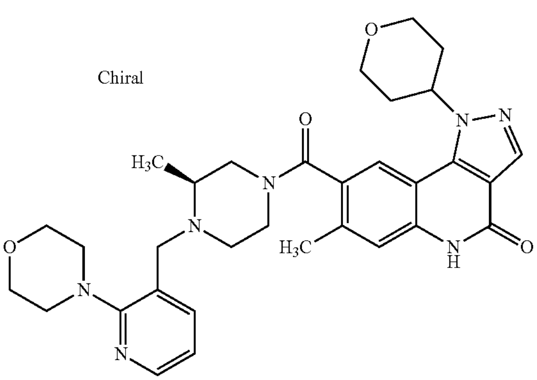 [SMILES: Cc1cc2[nH]c(=O)c3cnn(C4CCOCC4)c3c2cc1C(=O)N1CCN(Cc2cccnc2N2CCOCC2)[C@@H](C)C1] |
TABLE 87-continued
| Ex | Structure |
|---|---|
| 535 | 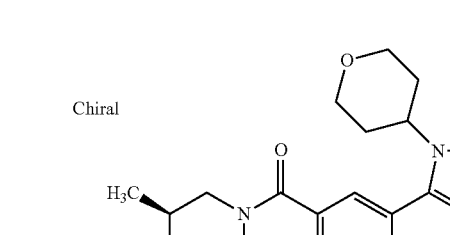 |
| 536 | 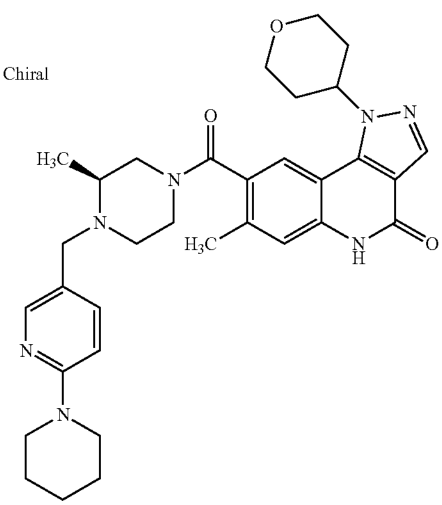 [SMILES: Cc1cc2[nH]c(=O)c3cnn(C4CCOCC4)c3c2cc1C(=O)N1CCN(Cc2ccc(N3CCCCC3)nc2)[C@@H](C)C1] |
| 537 | 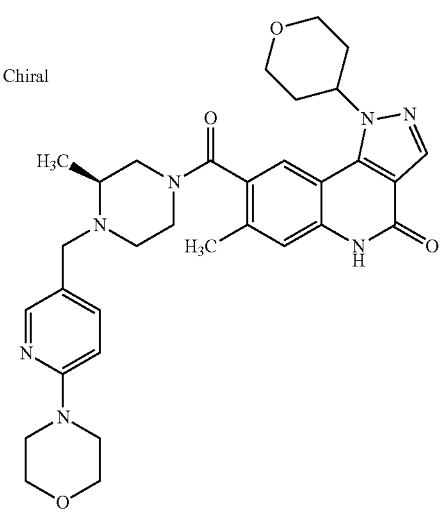 [SMILES: Cc1cc2[nH]c(=O)c3cnn(C4CCOCC4)c3c2cc1C(=O)N1CCN(Cc2ccc(N3CCOCC3)nc2)[C@@H](C)C1] |

TABLE 88
| Ex | Structure |
|---|---|
| 538 | 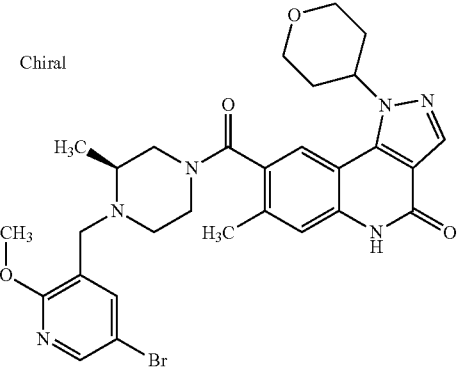 [SMILES: COc1ncc(Br)cc1CN1CCN(C(=O)c2cc3c(cc2C)[nH]c(=O)c2cnn(C4CCOCC4)c23)C[C@@H]1C] |
| 539 | 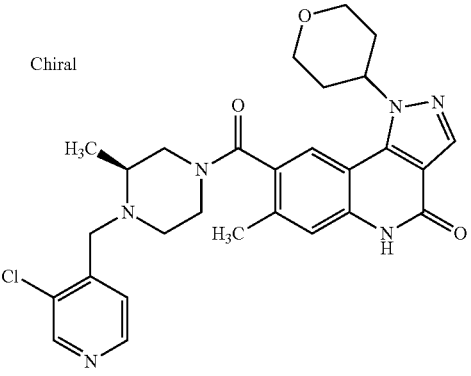 [SMILES: Cc1cc2[nH]c(=O)c3cnn(C4CCOCC4)c3c2cc1C(=O)N1CCN(Cc2ccncc2Cl)[C@@H](C)C1] |
| 540 | 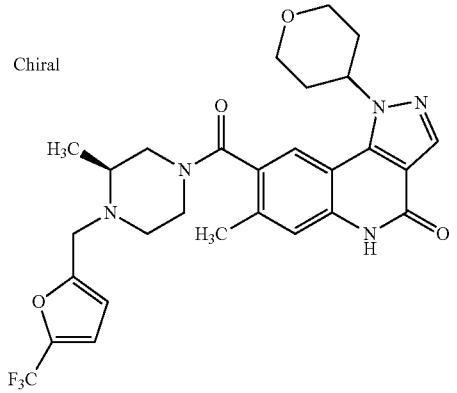 [SMILES: Cc1cc2[nH]c(=O)c3cnn(C4CCOCC4)c3c2cc1C(=O)N1CCN(Cc2ccc(C(F)(F)F)o2)[C@@H](C)C1] |
| 541 | 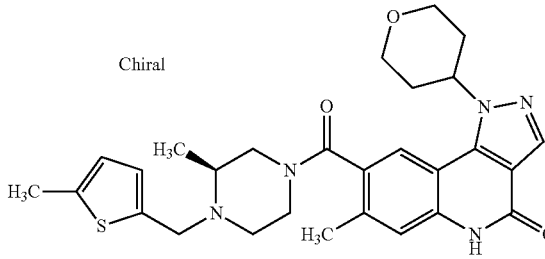 |
TABLE 88-continued
| Ex | Structure |
|---|---|
| 542 | 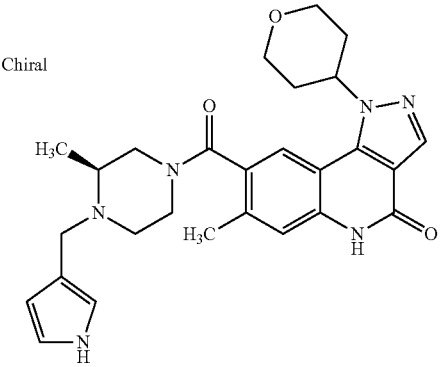 [SMILES: Cc1cc2[nH]c(=O)c3cnn(C4CCOCC4)c3c2cc1C(=O)N1CCN(Cc2cc[nH]c2)[C@@H](C)C1] |
| 543 | 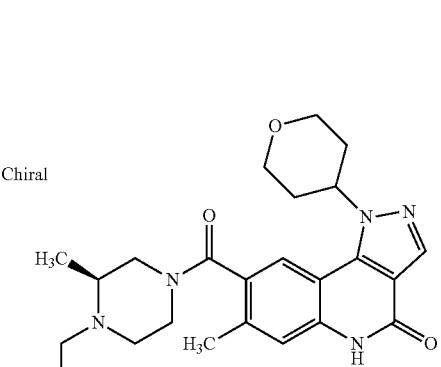 |
| 544 | 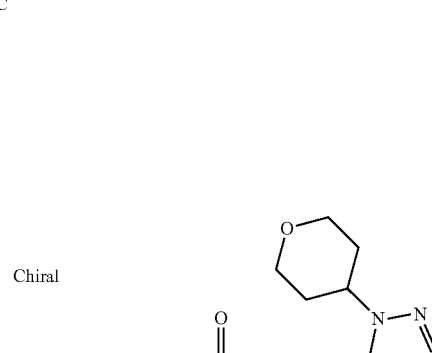 |

TABLE 88-continued
| Ex | Structure |
|---|---|
| 545 | 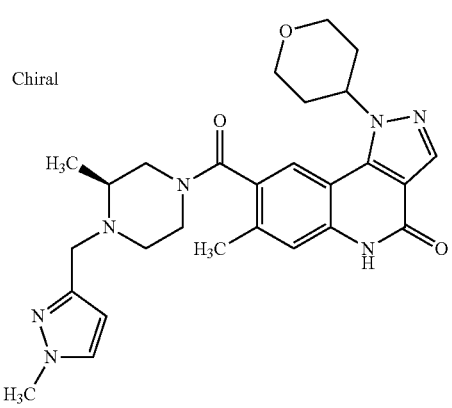 |
TABLE 89
| Ex | Structure |
|---|---|
| 546 | |
| 547 | |
| 548 | 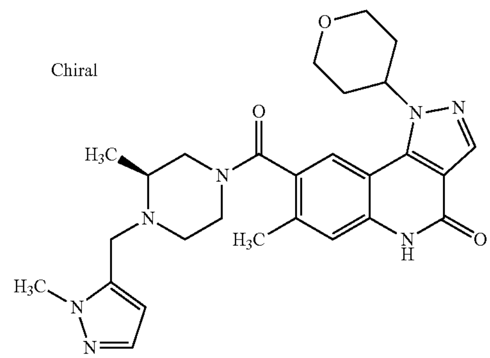 [SMILES: Cc1cc2[nH]c(=O)c3cnn(C4CCOCC4)c3c2cc1C(=O)N1CCN(Cc2ccnn2C)[C@@H](C)C1] |
| 549 | 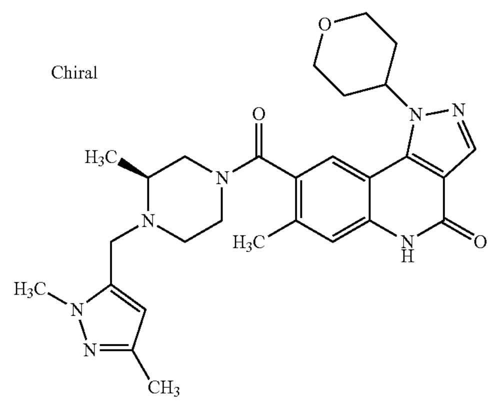 [SMILES: Cc1cc(CN2CCN(C(=O)c3cc4c(cc3C)[nH]c(=O)c3cnn(C5CCOCC5)c34)C[C@@H]2C)n(C)n1] |
| 550 | 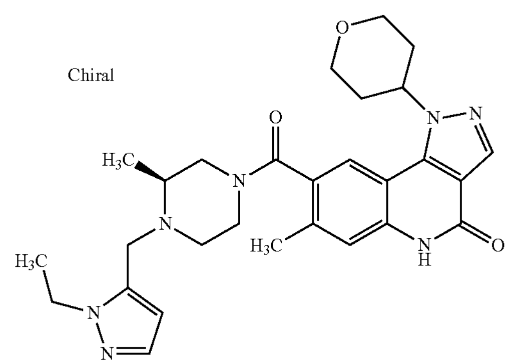 [SMILES: CCn1nccc1CN1CCN(C(=O)c2cc3c(cc2C)[nH]c(=O)c2cnn(C4CCOCC4)c23)C[C@@H]1C] |
| 551 | 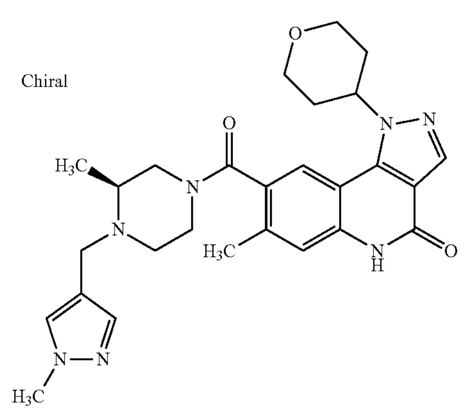 [SMILES: Cc1cc2[nH]c(=O)c3cnn(C4CCOCC4)c3c2cc1C(=O)N1CCN(Cc2cnn(C)c2)[C@@H](C)C1] |

TABLE 89-continued
| Ex | Structure |
|----|-----------|
| 552 | 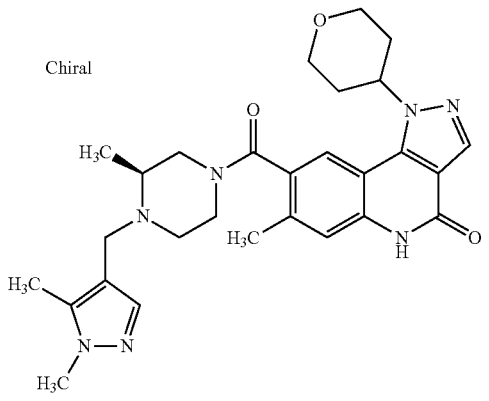 [SMILES: Cc1cc2[nH]c(=O)c3cnn(C4CCOCC4)c3c2cc1C(=O)N1CCN(Cc2cnn(C)c2C)[C@@H](C)C1] Chiral |
| 553 | 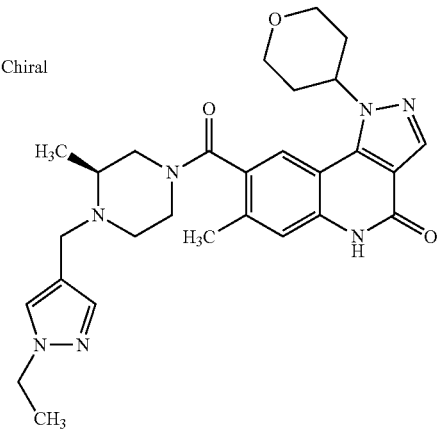 [SMILES: CCn1cc(CN2CCN(C(=O)c3cc4c(cc3C)[nH]c(=O)c3cnn(C5CCOCC5)c34)C[C@@H]2C)cn1] Chiral |
TABLE 90
| Ex | Structure |
|----|-----------|
| 554 | 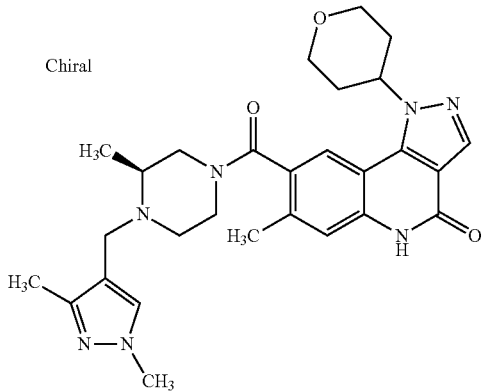 [SMILES: Cc1cc2[nH]c(=O)c3cnn(C4CCOCC4)c3c2cc1C(=O)N1CCN(Cc2cn(C)nc2C)[C@@H](C)C1] Chiral |
| 555 | 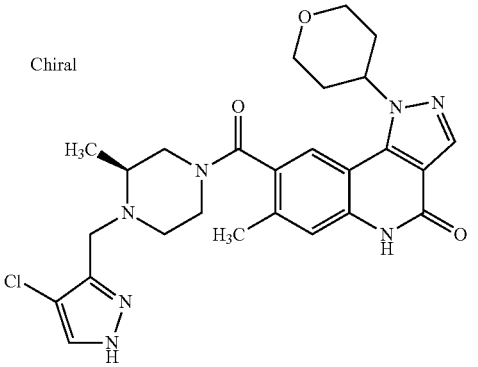 [SMILES: Cc1cc2[nH]c(=O)c3cnn(C4CCOCC4)c3c2cc1C(=O)N1CCN(Cc2n[nH]cc2Cl)[C@@H](C)C1] Chiral |
| 556 | 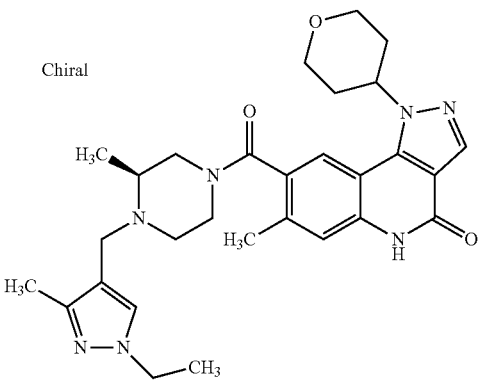 [SMILES: CCn1cc(CN2CCN(C(=O)c3cc4c(cc3C)[nH]c(=O)c3cnn(C5CCOCC5)c34)C[C@@H]2C)c(C)n1] Chiral |
| 557 | 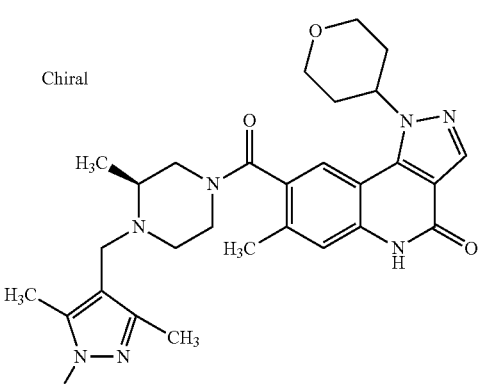 Chiral |
| 558 | 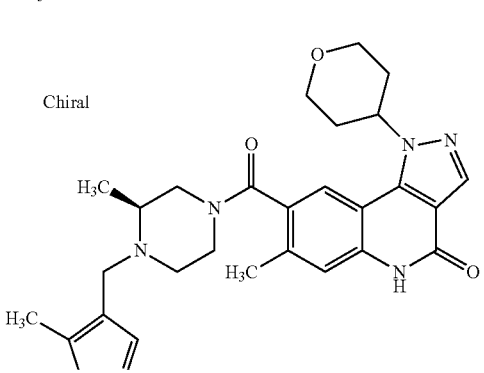 Chiral |

TABLE 90-continued
| Ex | Structure |
|---|---|
| 559 | 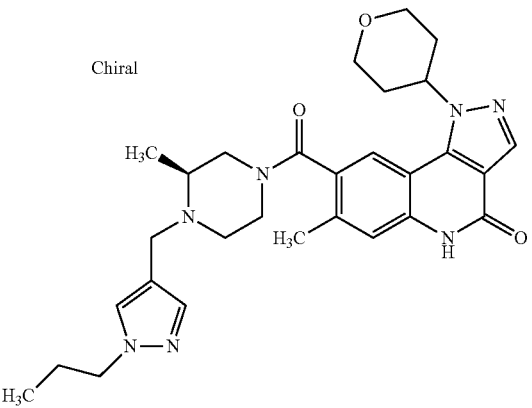 [SMILES: CCCn1cc(CN2CCN(C(=O)c3cc4c(cc3C)[nH]c(=O)c3cnn(C5CCOCC5)c34)C[C@@H]2C)cn1] |
| 560 | 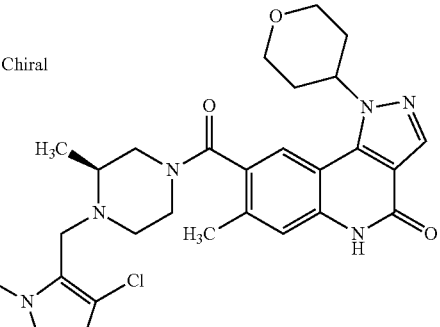 |
| 561 | 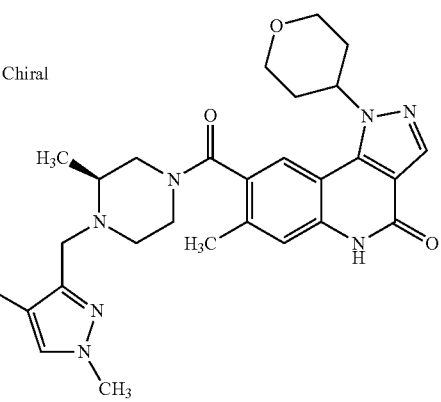 |
TABLE 91
| Ex | Structure |
|---|---|
| 562 | 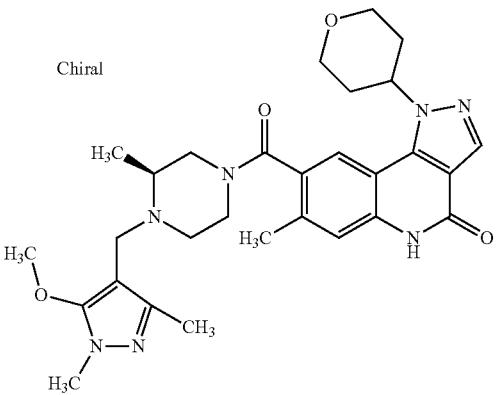 [SMILES: COc1c(CN2CCN(C(=O)c3cc4c(cc3C)[nH]c(=O)c3cnn(C5CCOCC5)c34)C[C@@H]2C)c(C)nn1C] |
| 563 | 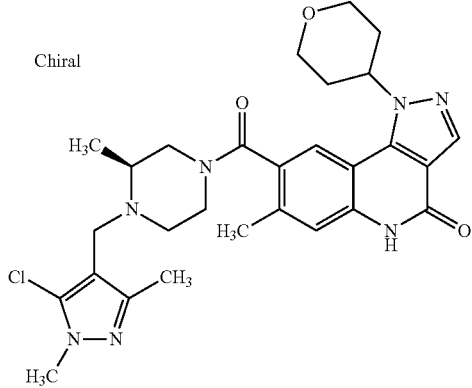 [SMILES: Cc1cc2[nH]c(=O)c3cnn(C4CCOCC4)c3c2cc1C(=O)N1CCN(Cc2c(C)nn(C)c2Cl)[C@@H](C)C1] |
| 564 | 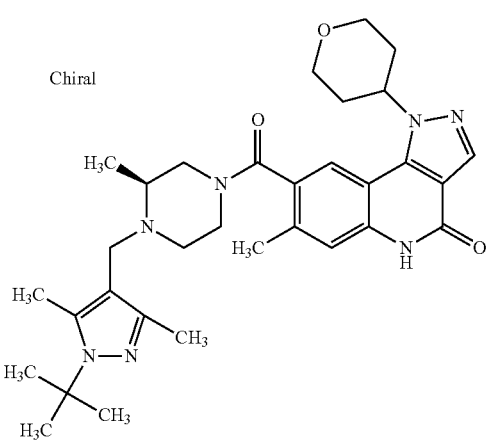 [SMILES: Cc1cc2[nH]c(=O)c3cnn(C4CCOCC4)c3c2cc1C(=O)N1CCN(Cc2c(C)nn(C(C)(C)C)c2C)[C@@H](C)C1] |

TABLE 91-continued
| Ex | Structure |
|---|---|
| 565 | 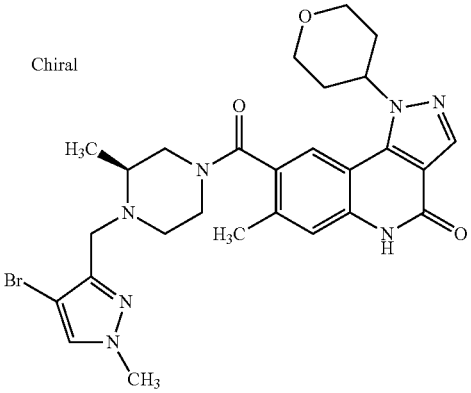 |
| 566 | 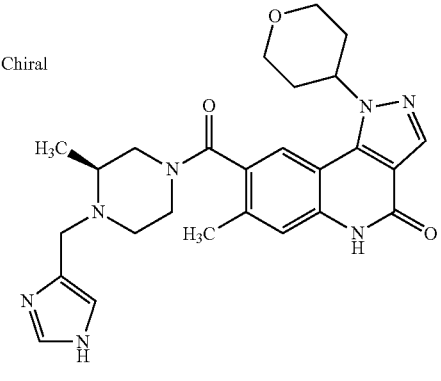 [SMILES: Cc1cc2[nH]c(=O)c3cnn(C4CCOCC4)c3c2cc1C(=O)N1CCN(Cc2c[nH]cn2)[C@@H](C)C1] |
| 567 | 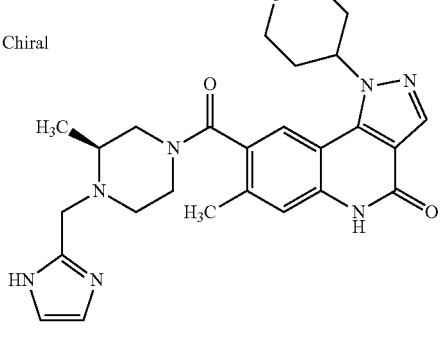 |
| 568 | 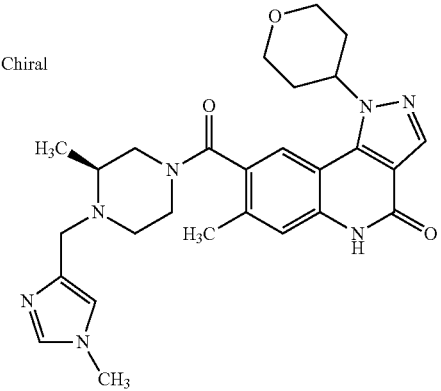 [SMILES: Cc1cc2[nH]c(=O)c3cnn(C4CCOCC4)c3c2cc1C(=O)N1CCN(Cc2cn(C)cn2)[C@@H](C)C1] |
TABLE 91-continued
| Ex | Structure |
|---|---|
| 569 | 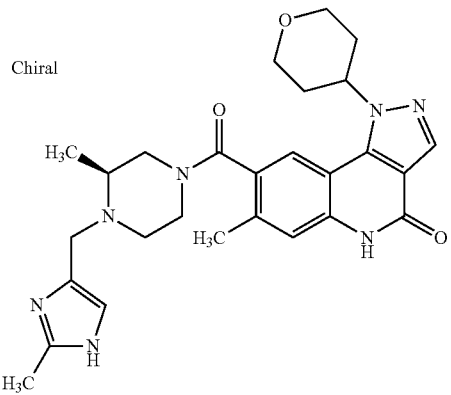 [SMILES: Cc1nc(CN2CCN(C(=O)c3cc4c(cc3C)[nH]c(=O)c3cnn(C5CCOCC5)c34)C[C@@H]2C)c[nH]1] |
TABLE 92
| Ex | Structure |
|---|---|
| 570 | 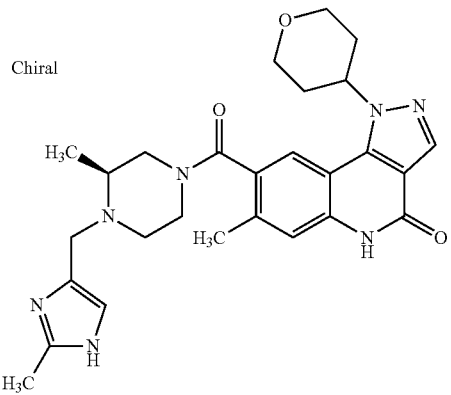 [SMILES: Cc1nc(CN2CCN(C(=O)c3cc4c(cc3C)[nH]c(=O)c3cnn(C5CCOCC5)c34)C[C@@H]2C)c[nH]1] |
| 571 | 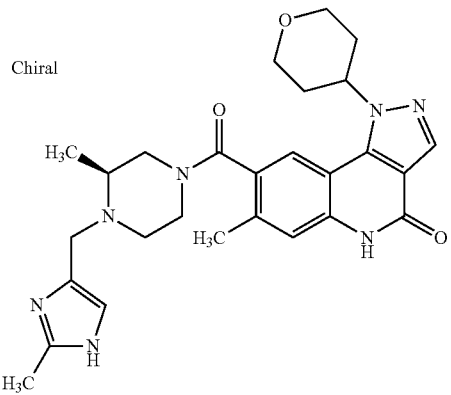 [SMILES: Cc1nc(CN2CCN(C(=O)c3cc4c(cc3C)[nH]c(=O)c3cnn(C5CCOCC5)c34)C[C@@H]2C)c[nH]1] |

TABLE 92-continued
| Ex | Structure |
|---|---|
| 572 | 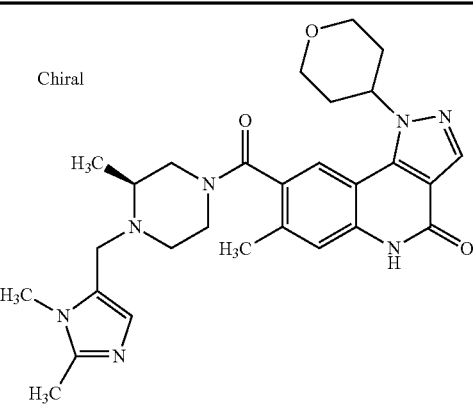 |
| 573 | 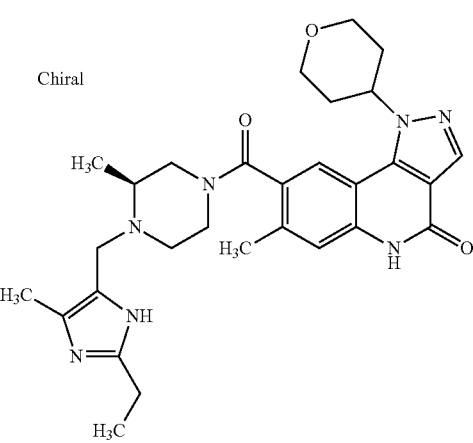 [SMILES: CCc1nc(C)c(CN2CCN(C(=O)c3cc4c(cc3C)[nH]c(=O)c3cnn(C5CCOCC5)c34)C[C@@H]2C)[nH]1] |
| 574 | 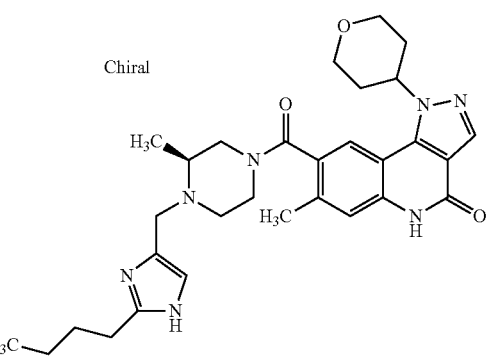 |
| 575 | 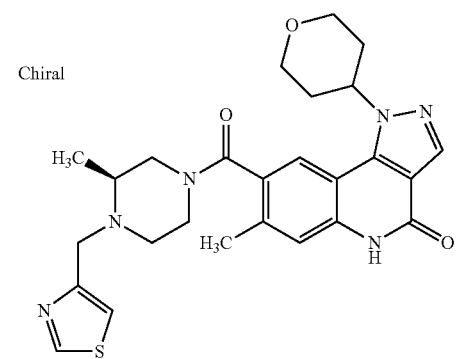 [SMILES: Cc1cc2[nH]c(=O)c3cnn(C4CCOCC4)c3c2cc1C(=O)N1CCN(Cc2cscn2)[C@@H](C)C1] |
TABLE 92-continued
| Ex | Structure |
|---|---|
| 576 | 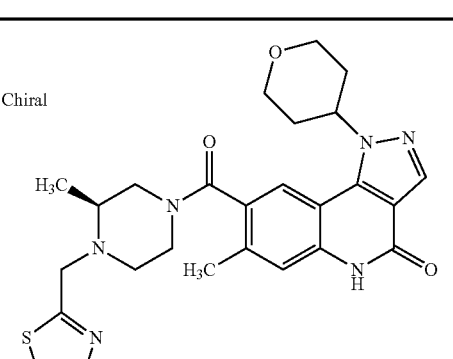 |
| 577 | 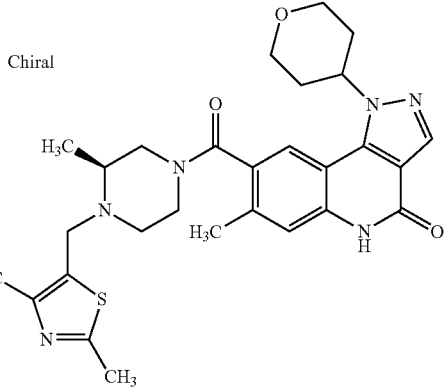 |
TABLE 93
| Ex | Structure |
|---|---|
| 578 | 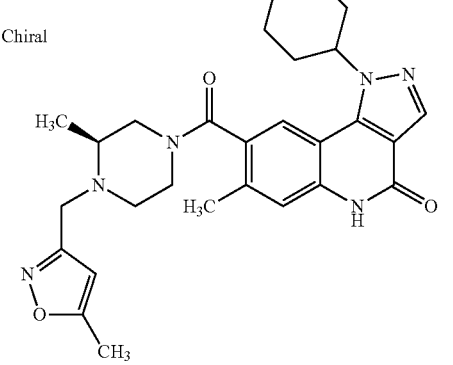 |

TABLE 93-continued
| Ex | Structure |
|---|---|
| 579 | 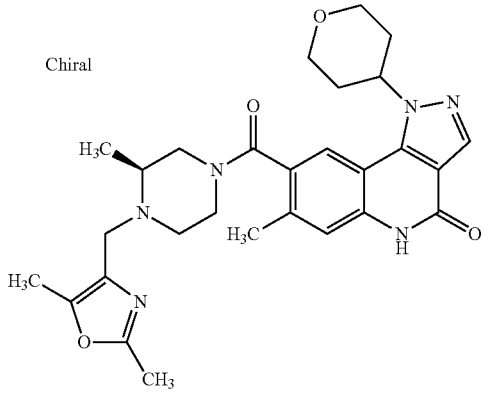 [SMILES: Cc1nc(CN2CCN(C(=O)c3cc4c(cc3C)[nH]c(=O)c3cnn(C5CCOCC5)c34)C[C@@H]2C)c(C)o1] |
| 580 | 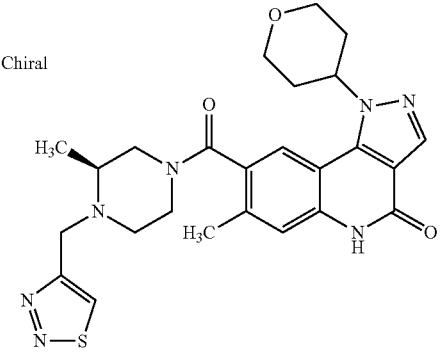 [SMILES: Cc1cc2[nH]c(=O)c3cnn(C4CCOCC4)c3c2cc1C(=O)N1CCN(Cc2csnn2)[C@@H](C)C1] |
| 581 | 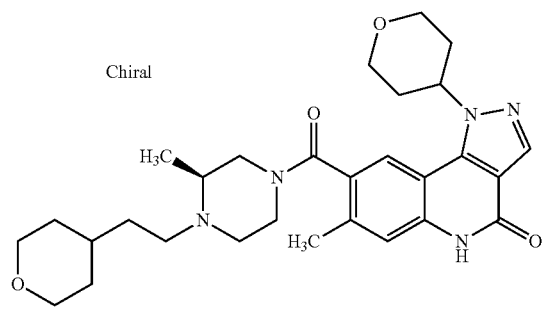 [SMILES: Cc1cc2[nH]c(=O)c3cnn(C4CCOCC4)c3c2cc1C(=O)N1CCN(CCC2CCOCC2)[C@@H](C)C1] |
| 582 | 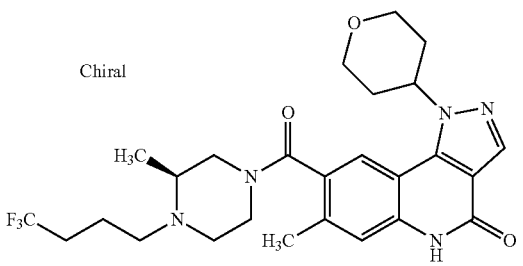 [SMILES: Cc1cc2[nH]c(=O)c3cnn(C4CCOCC4)c3c2cc1C(=O)N1CCN(CCCC(F)(F)F)[C@@H](C)C1] |
| 583 | 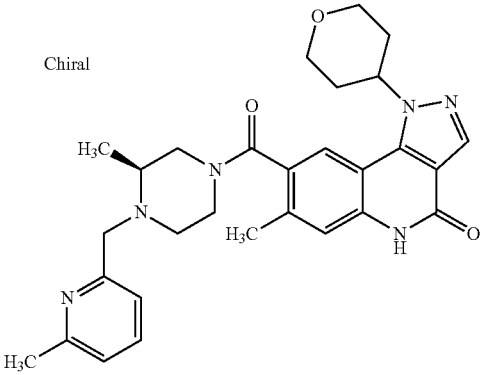 [SMILES: Cc1cccc(CN2CCN(C(=O)c3cc4c(cc3C)[nH]c(=O)c3cnn(C5CCOCC5)c34)C[C@@H]2C)n1] |
| 584 | 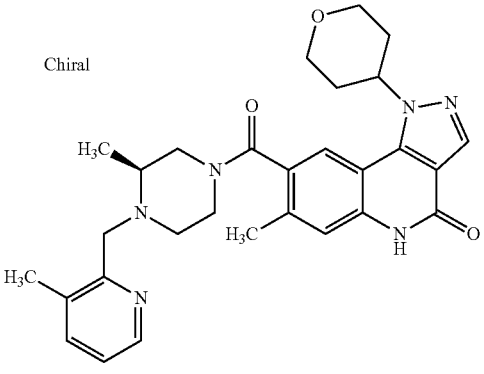 [SMILES: Cc1cc2[nH]c(=O)c3cnn(C4CCOCC4)c3c2cc1C(=O)N1CCN(Cc2ncccc2C)[C@@H](C)C1] |
| 585 | 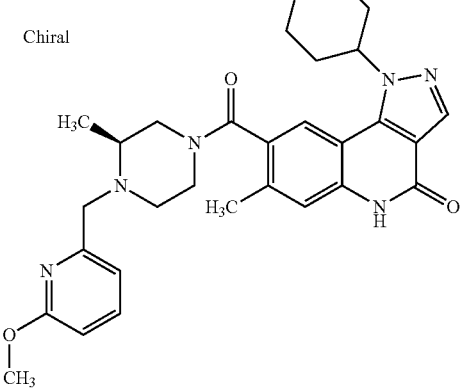 |

TABLE 94
| Ex | Structure |
|---|---|
| 586 | 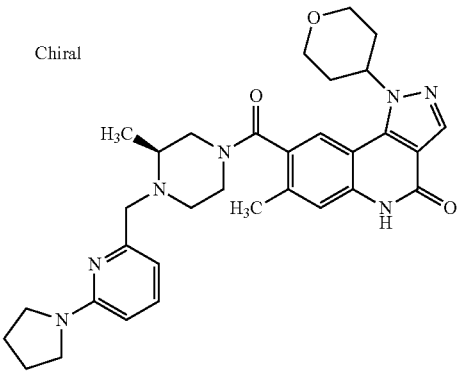 [SMILES: Cc1cc2[nH]c(=O)c3cnn(C4CCOCC4)c3c2cc1C(=O)N1CCN(Cc2cccc(N3CCCC3)n2)[C@@H](C)C1] |
| 587 | 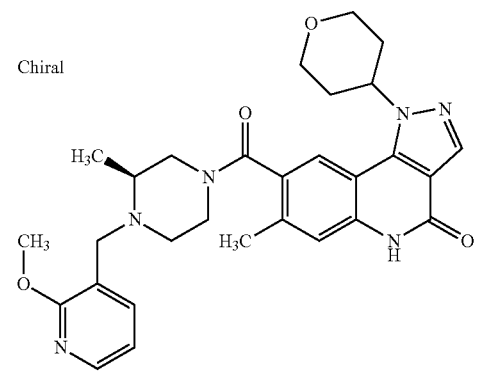 [SMILES: COc1ncccc1CN1CCN(C(=O)c2cc3c(cc2C)[nH]c(=O)c2cnn(C4CCOCC4)c23)C[C@@H]1C] |
| 588 | 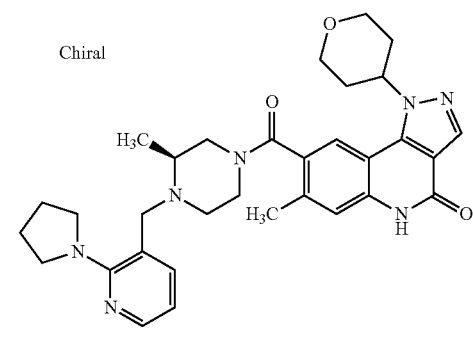 [SMILES: Cc1cc2[nH]c(=O)c3cnn(C4CCOCC4)c3c2cc1C(=O)N1CCN(Cc2cccnc2N2CCCC2)[C@@H](C)C1] |
| 589 | 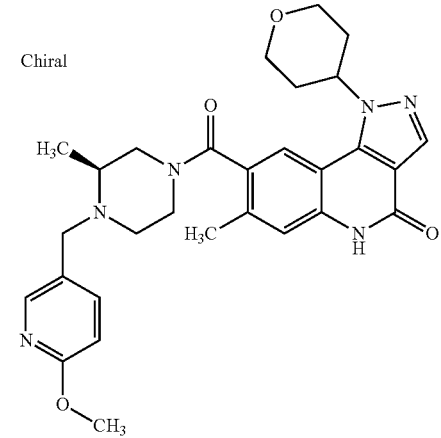 [SMILES: COc1ccc(CN2CCN(C(=O)c3cc4c(cc3C)[nH]c(=O)c3cnn(C5CCOCC5)c34)C[C@@H]2C)cn1] |
TABLE 94-continued
| Ex | Structure |
|---|---|
| 590 | 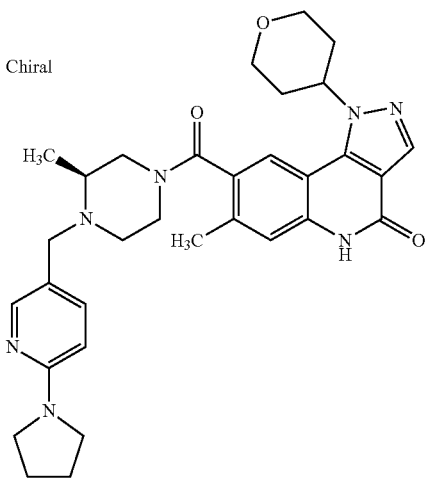 [SMILES: Cc1cc2[nH]c(=O)c3cnn(C4CCOCC4)c3c2cc1C(=O)N1CCN(Cc2ccc(N3CCCC3)nc2)[C@@H](C)C1] |
| 591 | 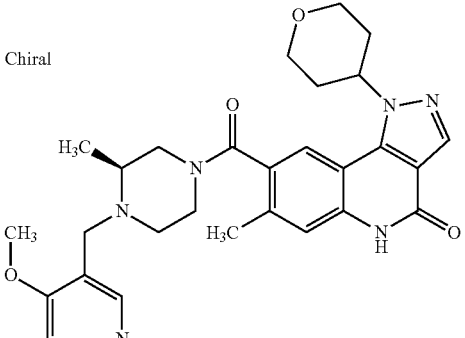 |
| 592 | 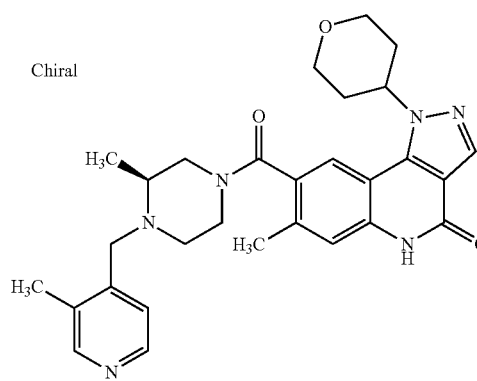 |

TABLE 94-continued
| Ex | Structure |
|---|---|
| 593 | 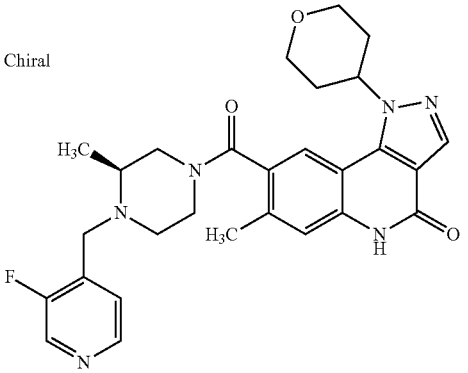 [SMILES: Cc1cc2[nH]c(=O)c3cnn(C4CCOCC4)c3c2cc1C(=O)N1CCN(Cc2ccncc2F)[C@@H](C)C1] |
TABLE 95
| Ex | Structure |
|---|---|
| 594 | 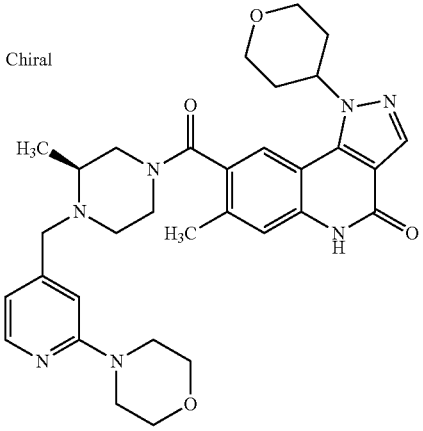 [SMILES: Cc1cc2[nH]c(=O)c3cnn(C4CCOCC4)c3c2cc1C(=O)N1CCN(Cc2ccnc(N3CCOCC3)c2)[C@@H](C)C1] |
| 595 | 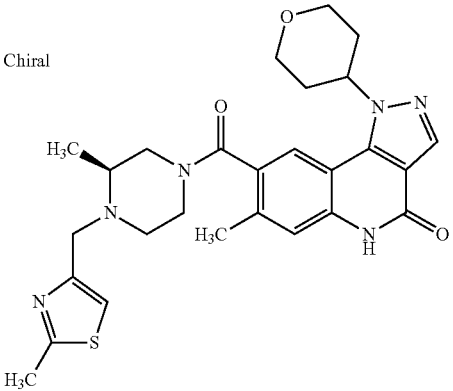 [SMILES: Cc1nc(CN2CCN(C(=O)c3cc4c(cc3C)[nH]c(=O)c3cnn(C5CCOCC5)c34)C[C@@H]2C)cs1] |
TABLE 95-continued
| Ex | Structure |
|---|---|
| 596 | 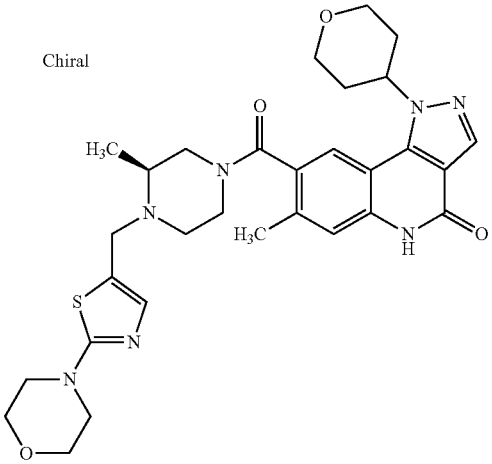 [SMILES: Cc1cc2[nH]c(=O)c3cnn(C4CCOCC4)c3c2cc1C(=O)N1CCN(Cc2cnc(N3CCOCC3)s2)[C@@H](C)C1] |
| 597 | 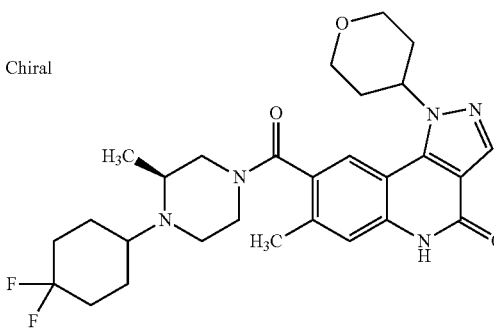 |
| 598 | 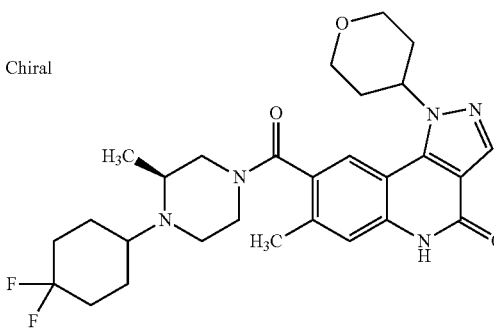 |
| 599 | 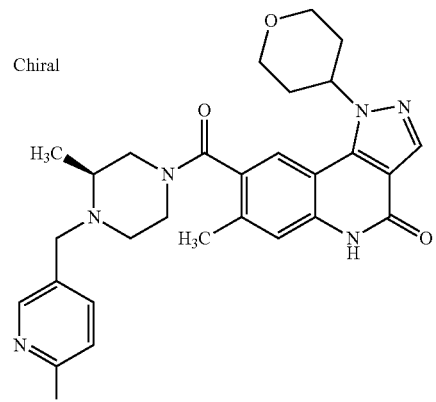 |

TABLE 95-continued
| Ex | Structure |
|---|---|
| 600 | 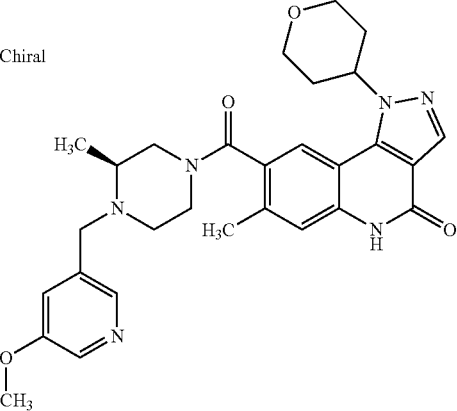 [SMILES: COc1cncc(CN2CCN(C(=O)c3cc4c(cc3C)[nH]c(=O)c3cnn(C5CCOCC5)c34)C[C@@H]2C)c1] |
| 601 | 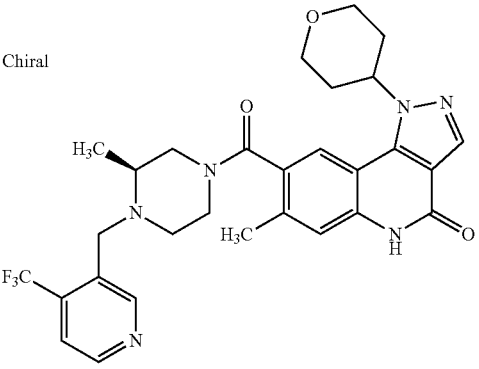 [SMILES: Cc1cc2[nH]c(=O)c3cnn(C4CCOCC4)c3c2cc1C(=O)N1CCN(Cc2cnccc2C(F)(F)F)[C@@H](C)C1] |
TABLE 96
| Ex | Structure |
|---|---|
| 602 | 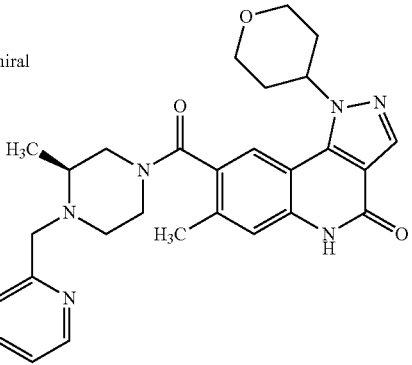 |
TABLE 96-continued
| Ex | Structure |
|---|---|
| 603 | 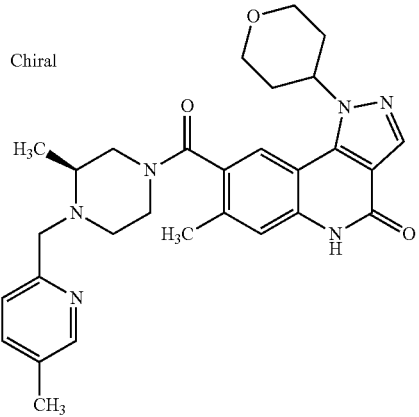 [SMILES: Cc1ccc(CN2CCN(C(=O)c3cc4c(cc3C)[nH]c(=O)c3cnn(C5CCOCC5)c34)C[C@@H]2C)nc1] |
| 604 | 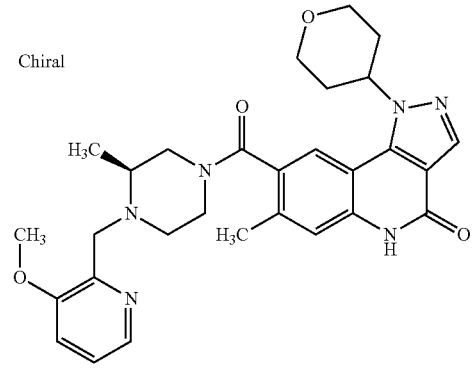 [SMILES: COc1cccnc1CN1CCN(C(=O)c2cc3c(cc2C)[nH]c(=O)c2cnn(C4CCOCC4)c23)C[C@@H]1C] |
| 605 | 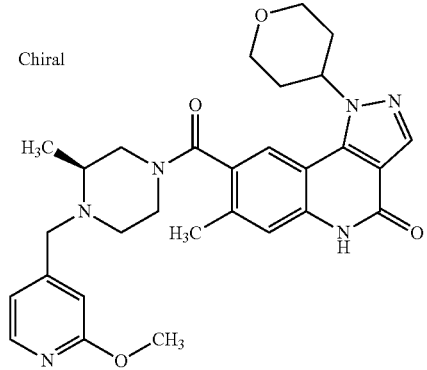 [SMILES: COc1cc(CN2CCN(C(=O)c3cc4c(cc3C)[nH]c(=O)c3cnn(C5CCOCC5)c34)C[C@@H]2C)ccn1] |
| 606 | 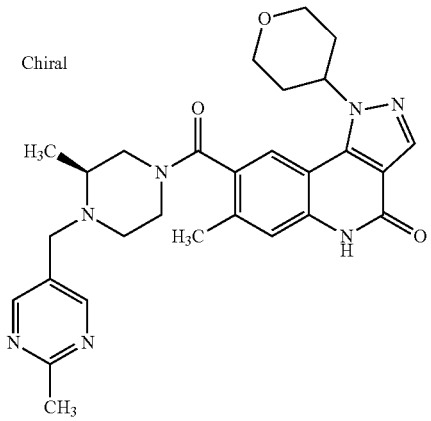 [SMILES: Cc1ncc(CN2CCN(C(=O)c3cc4c(cc3C)[nH]c(=O)c3cnn(C5CCOCC5)c34)C[C@@H]2C)cn1] |

TABLE 96-continued
| Ex | Structure |
|---|---|
| 607 | 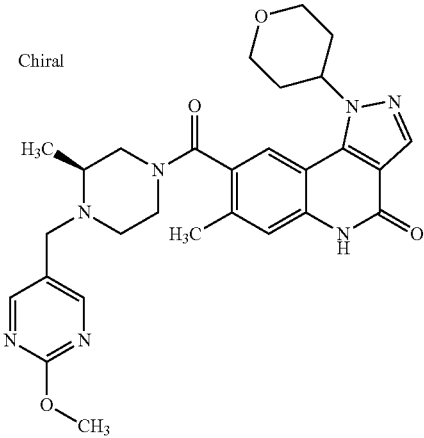 [SMILES: COc1ncc(CN2CCN(C(=O)c3cc4c(cc3C)[nH]c(=O)c3cnn(C5CCOCC5)c34)C[C@@H]2C)cn1] |
| 608 | 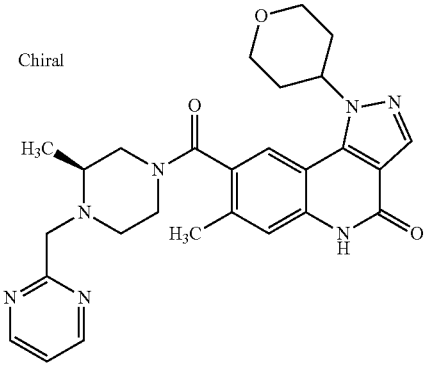 [SMILES: Cc1cc2[nH]c(=O)c3cnn(C4CCOCC4)c3c2cc1C(=O)N1CCN(Cc2ncccn2)[C@@H](C)C1] |
| 609 | 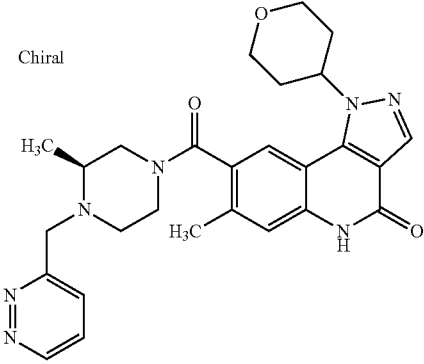 [SMILES: Cc1cc2[nH]c(=O)c3cnn(C4CCOCC4)c3c2cc1C(=O)N1CCN(Cc2cccnn2)[C@@H](C)C1] |
TABLE 97
| Ex | Structure |
|---|---|
| 610 | 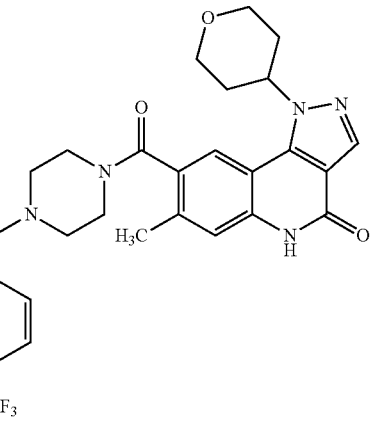 |
| 611 | 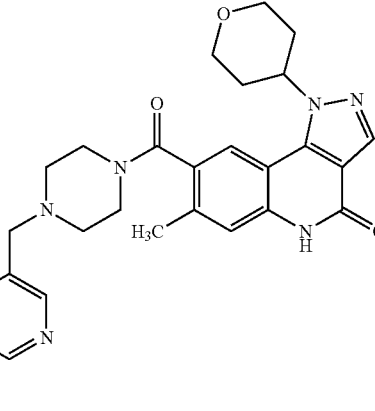 |
| 612 | 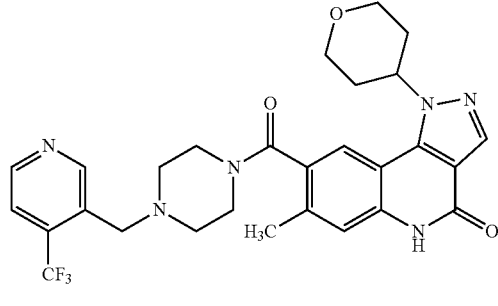 [SMILES: Cc1cc2[nH]c(=O)c3cnn(C4CCOCC4)c3c2cc1C(=O)N1CCN(Cc2cnccc2C(F)(F)F)CC1] |
| 613 | 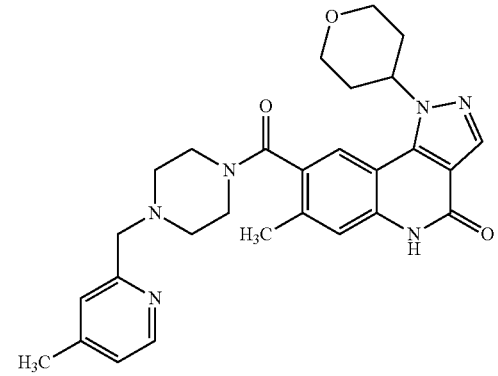 [SMILES: Cc1ccnc(CN2CCN(C(=O)c3cc4c(cc3C)[nH]c(=O)c3cnn(C5CCOCC5)c34)CC2)c1] |

TABLE 97-continued

| Ex | Structure |
|---|---|
| 614 | (structure) |
| 615 | (structure) |
| 616 | (structure) |

TABLE 98

| Ex | Structure |
|---|---|
| 617 | (structure) |
| 618 | (structure) |
| 619 | (structure) |
| 620 | (structure) |

TABLE 98-continued

| Ex | Structure |
|---|---|
| 621 | 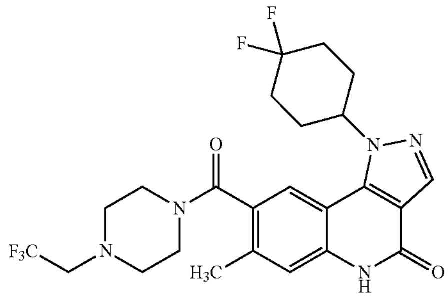 [SMILES: Cc1cc2[nH]c(=O)c3cnn(C4CCC(F)(F)CC4)c3c2cc1C(=O)N1CCN(CC(F)(F)F)CC1] |
| 622 | 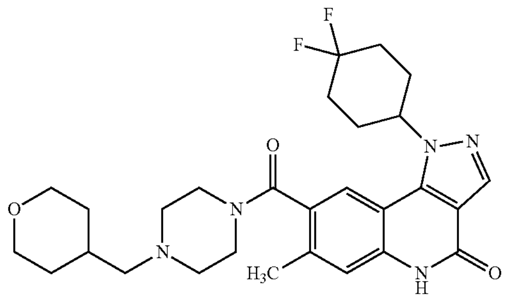 [SMILES: Cc1cc2[nH]c(=O)c3cnn(C4CCC(F)(F)CC4)c3c2cc1C(=O)N1CCN(CC2CCOCC2)CC1] |
| 623 Chiral | |
| 624 Chiral | |

TABLE 99

| Ex | Structure |
|---|---|
| 625 | 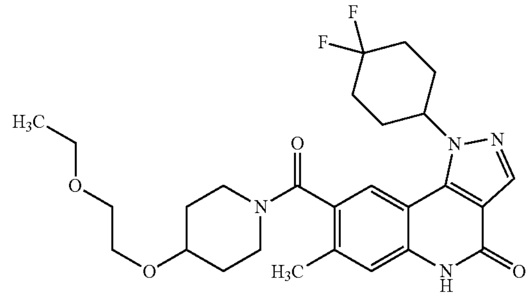 [SMILES: CCOCCOC1CCN(C(=O)c2cc3c(cc2C)[nH]c(=O)c2cnn(C4CCC(F)(F)CC4)c23)CC1] |
| 626 | 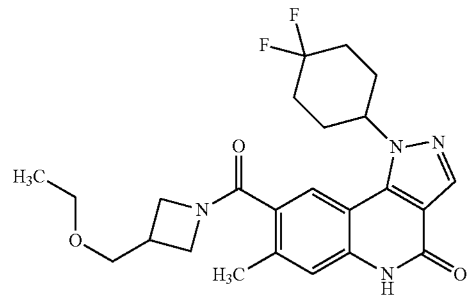 [SMILES: CCOCC1CN(C(=O)c2cc3c(cc2C)[nH]c(=O)c2cnn(C4CCC(F)(F)CC4)c23)C1] |
| 627 | 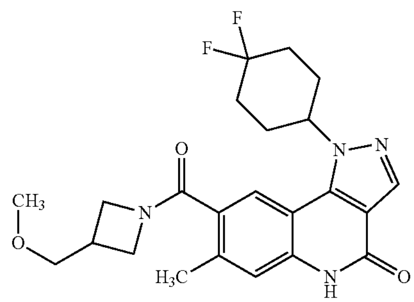 [SMILES: COCC1CN(C(=O)c2cc3c(cc2C)[nH]c(=O)c2cnn(C4CCC(F)(F)CC4)c23)C1] |
| 628 | 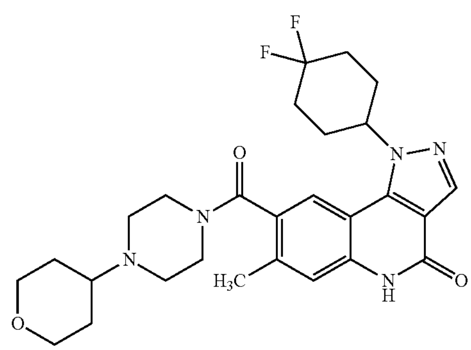 [SMILES: Cc1cc2[nH]c(=O)c3cnn(C4CCC(F)(F)CC4)c3c2cc1C(=O)N1CCN(C2CCOCC2)CC1] |
| 629 | 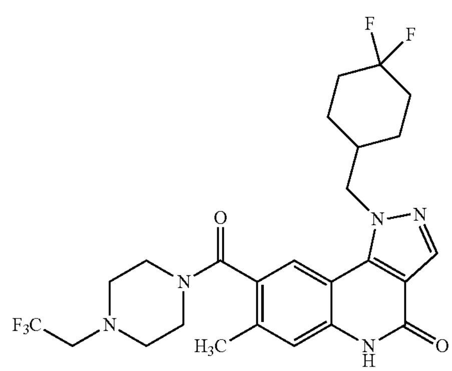 [SMILES: Cc1cc2[nH]c(=O)c3cnn(CC4CCC(F)(F)CC4)c3c2cc1C(=O)N1CCN(CC(F)(F)F)CC1] |

TABLE 99-continued

| Ex | Structure |
|---|---|
| 630 | (structure) |
| 631 Chiral | (structure) |
| 632 Chiral | (structure) |

TABLE 100

| Ex | Structure |
|---|---|
| 633 | (structure) |
| 634 | (structure) |
| 635 | (structure) |
| 636 | (structure) |

TABLE 100-continued

| Ex | Structure |
|---|---|
| 637 | (structure) |
| 638 | (structure) |
| 639 | Chiral (structure) |
| 640 | Chiral (structure) |
| 641 | (structure) |

TABLE 101

| Ex | Structure |
|---|---|
| 642 | (structure) |
| 643 | (structure) |
| 644 | (structure) |
| 645 | (structure) |
| 646 | (structure) |
| 647 | Chiral (structure) |
| 648 | Chiral (structure) |
| 649 | (structure) |

TABLE 101-continued
| Ex | Structure |
|---|---|
| 650 | 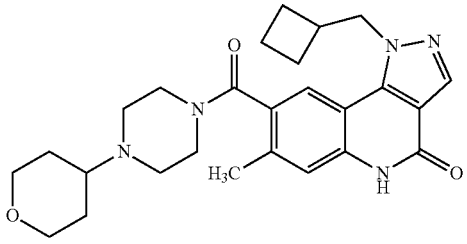 [SMILES: Cc1cc2[nH]c(=O)c3cnn(CC4CCC4)c3c2cc1C(=O)N1CCN(C2CCOCC2)CC1] |
| 651 | 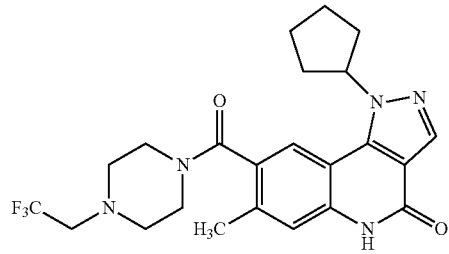 [SMILES: Cc1cc2[nH]c(=O)c3cnn(C4CCCC4)c3c2cc1C(=O)N1CCN(CC(F)(F)F)CC1] |
TABLE 102
| Ex | Structure |
|---|---|
| 652 | 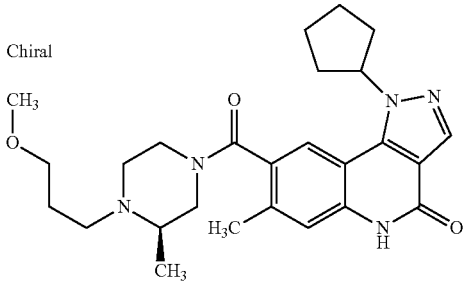 |
| 653 | 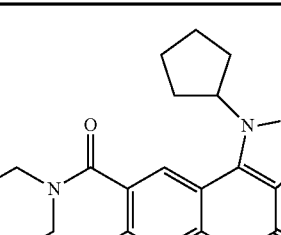 |
| 654 | Chiral 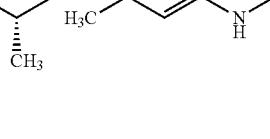 |
| 655 | Chiral 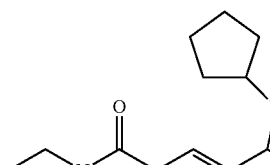 |
| 656 | 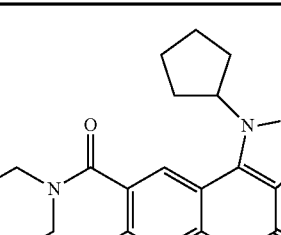 |
| 657 | 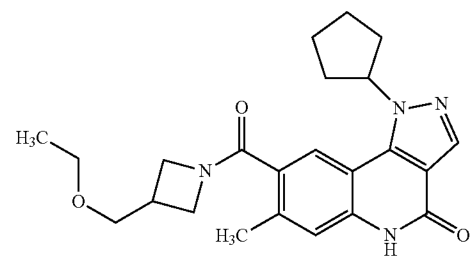 [SMILES: CCOCC1CN(C(=O)c2cc3c(cc2C)[nH]c(=O)c2cnn(C4CCCC4)c23)C1] |
| 658 | Chiral |
| 659 | Chiral |

TABLE 102-continued

| Ex | Structure |
|---|---|
| 660 | Chiral |
| 661 | Chiral |

TABLE 103

| Ex | Structure |
|---|---|
| 662 | Chiral |
| 663 | Chiral |

TABLE 103-continued

| Ex | Structure |
|---|---|
| 664 | Chiral |
| 665 | Chiral |
| 666 | Chiral |
| 667 | Chiral |
| 668 | 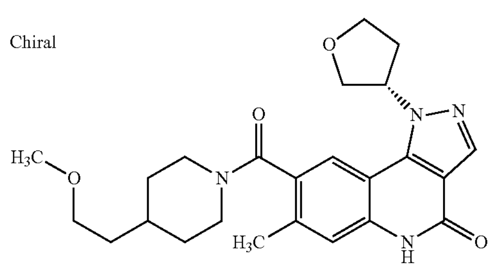 [SMILES: "Chiral" ; COCCC1CCN(C(=O)c2cc3c(cc2C)[nH]c(=O)c2cnn([C@H]4CCOC4)c23)CC1] |

TABLE 103-continued

| Ex | Structure |
|---|---|
| 669 | Chiral |

TABLE 104

| Ex | Structure |
|---|---|
| 670 | Chiral |
| 671 | Chiral |
| 672 | Chiral |
| 673 | Chiral |

TABLE 104-continued

| Ex | Structure |
|---|---|
| 674 | Chiral |
| 675 | Chiral |
| 676 | Chiral |
| 677 | Chiral |

TABLE 105

| Ex | Syn | Data |
|---|---|---|
| 1 | 1 | ESI+: 433.2, 435.2<br>NMR-DMSO-d6: 1.65-1.95 (4H, m), 2.10-2.30 (4H, m), 3.12 (2H, t, J = 8.0 Hz), 4.07 (2H, t, J = 8.0 Hz), 5.5-5.6 (1H, m), 7.36 (1H, s), 7.51 (1H, d, J = 9.0 Hz), 7.64 (1H, s), 8.18 (1H, s), 8.37 (1H, d, J = 9.0 Hz), 11.58 (1H, s)<br>mp: 291-294 |
| 2 | 2 | ESI+: 487.4<br>NMR-DMSO-d6: 1.82-2.43 (4H, m), 2.50 (3H, s), 2.83-3.86 (10H, m), 3.86-4.12 (2H, m), 4.29-4.56 (2H, m), 5.16-5.33 (1H, m), 7.35 (1H, s), 7.64-7.71 (1H, m), 7.98 (1H, s), 8.18 (1H, s), 8.25 (1H, d, J = 6.9 Hz), 8.74 (1H, d, J = 5.2 Hz), 8.85 (1H, s), 11.54 (1H, s)<br>mp: 259-263 |
| 3 | 3 | ESI+: 438.1 |
| 4 | 4 | ESI+: 438.4<br>NMR-DMSO-d6: 0.89-1.92 (8H, m), 2.19-2.36 (3H, m), 2.54-2.58 (2H, m), 2.71-2.90 (1H, m), 2.90-3.09 (1H, m), 3.14-4.24 (9H, m), 4.50-4.64 (1H, m), 5.93-6.01 (1H, m), 7.36 (1H, s), 7.91 (1H, s), 8.24 (1H, s), 9.14-9.32 (1H, br s), 9.50-9.66 (1H, br s), 11.57 (1H, s) |

TABLE 105-continued

| Ex | Syn | Data |
|---|---|---|
| 5 | 5 | ESI+: 466.3<br>NMR-DMSO-d6: 1.11 (6H, d, J = 6.1 Hz), 1.70-1.91 (4H, m), 2.02-2.40 (7H, m), 2.89-3.20 (1H, m), 3.24-3.44 (5H, m), 3.48-3.65 (4H, m), 3.76 (2H, m), 4.63 (1H, br.), 5.52 (1H, m), 7.35 (1H, s), 8.07 (1H, s), 8.13 (1H, s), 10.79-11.08 (1H, br.), 11.51 (1H, s) |
| 6 | 6 | ESI+: 439.3<br>NMR-DMSO-d6: 1.20-2.77 (8H, m), 2.29 (3H, s), 2.90-4.62 (9H, m), 5.13-5.35 (1H, m), 7.33 (1H, s), 7.82-7.99 (1H, br.), 8.17 (1H, s), 11.50 (1H, s), 12.23-12.53 (1H, br.) |
| 7 | 7 | ESI+: 452.3<br>NMR-DMSO-d6: 0.81-1.94 (8H, m), 2.16-4.39 (19H, m), 4.48-4.72 (1H, m), 5.95-6.13 (1H, m), 7.36 (1H, s), 7.91 (1H, s), 8.26 (1H, s), 11.58 (1H, s)<br>mp: 195 |
| 8 | 8 | ESI+: 515.0 |
| 9 | 9 | ESI+: 556.2 |
| 10 | 10 | ESI+: 586.2 |
| 11 | 1 | ESI+: 457.3<br>NMR-DMSO-d6: 1.5-2.3 (8H, m), 3.6-3.8 (2H, m), 3.94-4.06 (2H, m), 4.45-4.65 (1H, m), 5.18-5.34 (1H, m), 7.08-7.40 (6H, m), 7.50 (1H, s), 8.16-8.33 (2H, m), 11.59 (1H, s)<br>mp: 298-301 |

TABLE 106

| Ex | Syn | Data |
|---|---|---|
| 12 | 1 | ESI+: 449.2, 451.2<br>NMR-DMSO-d6: 2.03-2.28 (4H, m), 3.12 (2H, t, J = 7.8 Hz), 3.66-3.76 (2H, m), 3.97-4.13 (4H, m), 5.24-5.36 (1H, m), 7.15-7.6 (4H, m), 7.64 (1H, s), 8.23 (1H, s), 8.31 (1H, d, J = 8.3 Hz), 11.61 (1H, s)<br>mp: 341-343 |
| 13 | 1 | ESI+: 472.2<br>NMR-DMSO-d6: 1.97 (3H, s), 2.0-2.35 (8H, m), 2.9-3.1 (2H, m), 3.6-3.8 (2H, m), 3.95-4.05 (2H, m), 4.3-4.5 (1H, m), 5.15-5.35 (1H, m), 7.16-7.49 (6H, m), 7.52 (1H, s), 8.13-8.33 (2H, m), 11.58 (1H, s)<br>mp: 183-186 |
| 14 | 1 | ESI+: 477.2<br>NMR-DMSO-d6: 1.97-2.29 (4H, m), 3.45-4.63 (11H, m), 5.19-5.36 (1H, m), 7.05-7.65 (6H, m), 8.14-8.40 (2H, m), 11.60 (1H, s)<br>mp: 293-296 |
| 15 | 1 | ESI+: 446.3<br>NMR-DMSO-d6: 2.04-2.27 (4H, m), 3.09-3.16 (2H, m), 3.66-3.75 (2H, m), 3.84 (3H, s), 3.97-4.11 (4H, m), 5.24-5.34 (1H, m), 6.80 (1H, m), 7.54 (1H, d, J = 7.4 Hz), 7.65 (1H, s), 8.23 (1H, s), 8.31 (1H, d, J = 8.3 Hz), 8.79 (1H, s), 11.62 (1H, s)<br>mp: 337-340 |
| 16 | 2 | ESI+: 554.5<br>NMR-DMSO-d6: 1.13-2.15 (10H, m), 2.29 (3H, s), 2.89-4.09 (10H, m), 4.22-4.34 (2H, m), 5.17-5.33 (1H, m), 7.34 (1H, s), 7.40-7.50 (3H, m), 7.53-7.65 (2H, m), 7.87-7.94 (1H, m), 8.17 (1H, s), 11.50 (1H, s)<br>mp: 221-224 |
| 17 | 2 | ESI+: 473.2<br>NMR-DMSO-d6: 1.50-2.60 (4H, m), 2.33 (3H, s), 3.28-4.00 (12H, m), 5.20-5.30 (1H, m), 6.68 (1H, dd, J = 4.8, 7.1 Hz), 6.84 (1H, d, J = 8.7 Hz), 7.35 (1H, s), 7.53-7.59 (1H, m), 7.96 (1H, s), 8.10-8.14 (1H, m), 8.18 (1H, s), 11.52 (1H, s)<br>mp: 272-275 |
| 18 | 1 | ESI+: 431.1<br>NMR-DMSO-d6: 1.68-1.93 (4H, m), 2.10-2.27 (4H, m), 2.53 (3H, s), 3.12 (2H, t, J = 8.2 Hz), 4.07 (2H, t, J = 8.2 Hz), 5.41-5.50 (1H, m), 7.04 (1H, br s), 7.17 (1H, dd, J = 2.7, 8.5 Hz), 7.46 (1H, d, J = 7.8 Hz), 7.59 (1H, s), 8.05 (1H, br), 8.32 (1H, d, J = 8.5 Hz), 11.45 (1H, s)<br>mp: 321-323 |

TABLE 106-continued

| Ex | Syn | Data |
|---|---|---|
| 19 | 1 | ESI+: 433.3<br>NMR-DMSO-d6: 2.04-2.14 (2H, m), 2.14-2.29 (2H, m), 3.66-3.77 (2H, m), 3.99-4.06 (2H, m), 4.89 (2H, d, J = 11.3 Hz), 4.96 (2H, s), 5.25-5.35 (1H, m), 7.09-7.19 (1.5H, m), 7.25-7.30 (0.5H, m), 7.32-7.43 (1H, m), 7.53-7.61 (1H, m), 7.66-7.71 (1H, m), 8.23 (1H, s), 8.29-8.34 (1H, d, J = 8.4 Hz), 11.59 (1H, s)<br>mp 312-318 (dec.) |

TABLE 107

| Ex | Syn | Data |
|---|---|---|
| 20 | 1 | ESI+: 477.4<br>NMR-DMSO-d6: 1.95-2.29 (4H, m), 2.84-4.92 (11H, m), 5.20-5.35 (1H, m), 7.01-7.64 (6H, m), 8.22-8.37 (2H, m), 11.60 (1H, s)<br>mp: 174-176 |
| 21 | 2 | ESI+: 486.4<br>NMR-DMSO-d6: 1.83-2.38 (4H, m), 2.44 (3H, s), 3.00-4.94 (11H, m), 4.16 (3H, s), 5.17-5.43 (1H, m), 7.17-8.26 (8H, m), 11.50, 11.57 (total 1H, both s)<br>mp: 253-256 |
| 22 | 2 | ESI+: 488.3<br>NMR-DMSO-d6: 1.46-2.20 (8H, m), 2.32 (3H, s), 3.15-4.35 (9H, m), 5.21-5.34 (1H, m), 6.77-6.87 (1H, m), 6.98 (1H, t, J = 5.4 Hz), 7.35 (1H, s), 7.73 (1H, dt, J = 2.0, 7.1 Hz), 7.95 (1H, s), 8.13-8.19 (1H, m), 8.17 (1H, s), 11.52 (1H, s)<br>mp: 250-253 |
| 23 | 2 | ESI+: 508.3<br>NMR-DMSO-d6: 1.11-2.34 (14H, m), 2.45 (3H, s), 3.21-3.74 (6H, m), 3.80-4.12 (8H, m), 5.37-5.49 (1H, m), 7.31 (1H, s), 8.17 (1H, m), 9.04-9.13 (1H, m), 10.23-10.40 (1H, m), 11.56 (1H, s)<br>mp: 281-283 |
| 24 | 2 | ESI+: 450.4<br>NMR-DMSO-d6: 1.37 (3H, s), 1.63-1.73 (4H, m), 2.00-2.30 (4H, m), 2.39 (3H, s), 2.50-2.64 (4H, m), 3.51-3.76 (4H, m), 3.93-4.14 (4H, m), 5.21-5.31 (1H, m), 7.33 (1H, s), 8.01 (1H, s), 8.17 (1H, s), 11.51 (1H, s) |
| 25 | 2 | ESI+: 478.4<br>NMR-DMSO-d6: 1.59-2.75 (19H, m), 3.02-4.21 (10H, m), 5.39-5.53 (1H, m), 7.31 (1H, s), 8.19 (1H, s), 8.25 (1H, s), 8.90-9.00 (1H, m), 10.29-10.42 (1H, m), 11.55 (1H, s) |
| 26 | 2 | ESI+: 492,4<br>NMR-DMSO-d6: 1.18-1.33 (2H, m), 1.44-1.76 (6H, m), 1.84-2.04 (6H, m), 2.08-2.29 (4H, m), 2.45 (3H, s), 3.19-3.51 (4H, m), 3.58-3.70 (2H, m), 3.79-3.89 (2H, m), 3.97-4.09 (2H, m), 5.44-5.58 (1H, m), 7.31 (1H, s), 8.19 (1H, s), 8.28 (1H, s), 8.86-8.99 (1H, m), 10.13-10.30 (1H, m), 11.55 (1H, s) |
| 27 | 2 | ESI+: 480.3<br>NMR-DMSO-d6: 1.32-1.46 (2H, m), 1.62-1.73 (2H, m), 1.91-2.12 (2H, m), 2.27-2.64 (6H, m), 2.29 (3H, s), 3.13-3.37 (5H, m), 3.56-4.10 (8H, m), 5.17-5.27 (1H, m), 7.33 (1H, s), 7.86 (1H, s), 8.17 (1H, s), 11.50 (1H, s) |
| 28 | 2 | APCI/ESI+: 439.2<br>NMR-DMSO-d6: 0.89-2.16 (8H, m), 2.27 (3H, s), 2.69-4.24 (10H, m), 3.23 (3H, s), 4.51-4.66 (1H, m), 5.16-5.29 (1H, m), 734 (1H, s), 7.87 (1H, s), 8.17 (1H, s), 11.50 (1H, s)<br>mp: 253-255 |

TABLE 108

| Ex | Syn | Data |
|---|---|---|
| 29 | 2 | ESI+: 424.2<br>NMR-DMSO-d6: 1.77-2.08 (4H, m), 2.42-279 (7H, m), 2.95-3.22 (4H, m), 3,27-3.49 (4H, m), 3.64-4.03 (4H, m), 5.54-5.69 (1H, m), 7.26 (1H, s), 8.06 (1H, s), 8.15 (1H, s), 8.57-8.67 (1H, m), 10.84 (1H, br s), 11.48 (1H, s) |

TABLE 108-continued

| Ex | Syn | Data |
|---|---|---|
| 30 | 2 | ESI+: 494.4<br>NMR-DMSO-d6: 0.97-1.28 (2H, m), 1.51-2.90 (16H, m), 3.09-4.38 (12H, m), 5.07-5.39 (1H, m), 7.33 (1H, s), 7.88 (1H, s), 8.17 (1H, s), 11.5 (1H, s) |
| 31 | 2 | ESI+: 466.4<br>NMR-DMSO-d6: 1.65-1.80 (1H, m), 1.89-4.21 (25H, m), 5.18-5.32 (1H, m), 7.33 (1H, s), 7.89 (1H, s), 8.17 (1H, s), 11.50 (1H, s) |
| 32 | 2 | ESI+: 452.4<br>NMR-DMSO-d6: 1.68-2.44 (13H, m), 2.83-4.13 (14H, m), 4.54-4.74 (1H, m), 5.47-5.60 (1H, m), 7.35 (1H, s), 8.08 (1H, s), 8.13 (1H, s), 10.80-11.30 (1H, m), 11.51 (1H, s)<br>mp: 245 (dec.) |
| 33 | 2 | ESI+: 486.4<br>NMR-DMSO-d6: 1.62-2.55 (4H, m), 2.43 (3H, s), 2.69-4.17 (13H, m), 4.33-4.68 (1H, m), 5.09-5.42 (1H, m), 6.98-7.40 (6H, m), 7.79-8.23 (2H, m), 11.44-11.56 (1H, m) |
| 34 | 2 | ESI+: 500.4<br>NMR-DMSO-d6: 0.73-0.97 (3H, m), 1.88-2.57 (10H, m), 2.42 (3H, s), 2.72-4.73 (7H, m), 5.07-5.41 (1H, m), 6.99-8.25 (8H, m), 11.48, 11.52 (total 1H, both s) |
| 35 | 2 | ESI+: 514.4<br>NMR-DMSO-d6: 1.50-2.45 (12H, m), 2.54-3.06 (6H, m), 2.60 (3H, s), 3.12-3.76 (4H, m), 3.87-4.11 (2H, m), 4.53-4.68 (1H, m), 5.17-5.31 (1H, m), 7.33 (1H, s), 7.84-7.95 (1H, s), 8.17 (1H, s), 11.49 (1H, s) |
| 36 | 5 | ESI+: 478.4<br>NMR-DMSO-d6: 1.24-.278 (19H, m), 2.99-4.17 (10H, m), 5.09-5.42 (1H, m), 7.32 (1H, s), 7.92-8.14 (1H, m), 8.20 (1H, s), 9.09 (0.5H, br s), 9.80 (0.5H, br s), 11.57 (1H, br s) |
| 37 | 5 | ESI+: 514.4<br>NMR-DMSO-d6: 1.85-2.70 (18H, m), 3.14-3.46 (2H, m), 3.58-3.77 (2H, m), 3.94-4.14 (2H, m), 5.08-5.28 (1H, m), 7.16-7.23 (1H, m), 7.26 (1H, s), 7.35 (2H, dd, J = 7.4, 7.4 Hz), 7.40-7.47 (2H, m), 8.00 (1H, s), 8.18 (1H, s), 8.25-8.36 (1H, m), 11.50 (1H, s) |
| 38 | 2 | ESI+: 474.3<br>NMR-DMSO-d6: 2.0-2.1 (4H, m), 2.33 (3H, s), 3.28-3.38 (2H, m), 3.55-4.00 (10H, m), 5.20-5.30 (1H, m), 6.67 (1H, t, J = 4.8 Hz), 7.35 (1H, s), 7.96 (1H, s), 8.18 (1H, s), 8.38 (2H, d, J = 4.8 Hz), 11.52 (1H, s) |

TABLE 109

| Ex | Syn | Data |
|---|---|---|
| 39 | 2 | ESI+: 438.1<br>NMR-DMSO-d6: 1.73-2.05 (4H, m), 2.18-3.94 (20H, m), 4.56-4.77 (1H, m), 5.42-5.63 (1H, m), 7.31 (1H, s), 7.98 (1H, s), 8.18 (1H, s), 9.88-10.40 (1H, m), 11.50 (1H, s) |
| 40 | 2 | ESI+: 439.0<br>NMR-DMSO-d6: 1.08-2.54 (14H, m), 2.89-4.35 (11H, m), 5.12-5.34 (1H, m), 7.33 (1H, s), 7.90 (1H, s), 8.17 (1H, s), 11.49 (1H, br s) |
| 41 | 2 | ESI+: 465.3<br>NMR-DMSO-d6: 0.09-0.21 (2H, m), 0.38-0.48 (2H, m), 0.89-1.04 (1H, m), 1.19-2.59 (11H, m), 2.89-4.35 (11H, m), 5.15-5.31 (1H, m), 7.33 (1H, s), 7.90 (1H, s), 8.17 (1H, s), 11.50 (1H, s)<br>mp: 206-208 |
| 42 | 2 | ESI+: 452.4 |
| 43 | 2 | ESI+: 498.4<br>mp: 274 (dec.) |
| 44 | 2 | ESI+: 489.3<br>NMR-DMSO-d6: 1.36-2.71 (11H, m), 3.00-4.40 (9H, m), 5.16-5.39 (1H, m), 7.12-7.14 (1H, m), 7.35 (1H, s), 7.89-8.04 (1H, m), 8.18 (1H, s), 8.60-8.61 (2H, m), 11.5 (1H, s) |
| 45 | 2 | ESI+: 474.3<br>NMR-DMSO-d6: 1.80-2.52 (9H, m), 3.13-4.17 (8H, m), 5.16-5.35 (1H, m), 5.39-5.47 (0.5H, m), 5.54-5.67 (0.5H, m), 6.75-6.84 (1H, m), 6.90-6.98 (0.5H, m), 6.99-7.07 (0.5H, m), 7.26-7.38 (1H, m), 7.65-7.81 (1H, m), 7.92-8.08 (1.5H, m), 8.11-8.27 (1.5H, m), 11.43-11.56 (1H, m) |

TABLE 109-continued

| Ex | Syn | Data |
|---|---|---|
| 46 | 2 | ESI+: 502.4<br>NMR-DMSO-d6: 1.37-2.53 (14H, m), 3.02-4.40 (8H, m), 5.13-5.38 (2H, m), 6.19-5.76 (1H, m), 7.34 (1H, s), 7.47-7.58 (1H, m), 7.89-8.00 (2H, m), 8.17 (1H, s), 11.50 (1H, s) |
| 47 | 2 | ESI+: 530.3<br>NMR-DMSO-d6: 1.60-2.64 (4H, m), 2.42 (3H, s), 2.76-4.14 (14H, m), 3.11 (3H, s), 4.34-4.66 (1H, m), 5.11-5.39 (1H, m), 7.00-7.52 (6H, m), 7.80-8.02 (1H, m), 8.08-8.23 (1H, m), 11.44-11.56 (1H, m)<br>mp: 218-220 |
| 48 | 2 | ESI+: 474.2<br>NMR-DMSO-d6: 1.68-2.50 (6H, m), 3.00-4.20 (6H, m), 3.16 (3H, s), 4.36-4.84 (2H, m), 5.10-5.35 (2H, m), 7.25-7.50 (2H, m), 7.83-8.11 (1H, m), 8.18 (1H, s), 8.45 (1H, s), 8.57 (1H, s), 8.68 (1H, s), 11.52 (1H, s)<br>mp: 266-268 |

TABLE 110

| Ex | Syn | Data |
|---|---|---|
| 49 | 2 | ESI+: 487.2<br>NMR-DMSO-d6: 1.89-2.53 (7H, m), 1.95 (3H, s), 2.79-4.15 (10H, m), 4.34-4.68 (1H, m), 5.07-5.37 (1H, m), 7.19-7.69 (2H, m), 7.77-8.00 (2H, m), 8.07-8.21 (1H, s), 8.37-8.68 (2H, m), 11.42-11.55 (1H, m)<br>mp: 255-257 |
| 50 | 2 | ESI+: 474.3<br>NMR-DMSO-d6 (measured at 60° C.): 2.01-2.31 (4H, m), 2.34 (3H, s), 3.22-4.10 (12H, m), 5.16-5.25 (1H, m), 7.37 (1H, s), 7.85-7.89 (1H, m), 7.92 (1H, s), 8.07-8.11 (1H, m), 8.15 (1H, s), 8.29-833 (1H, m), 11.34 (1H, s) |
| 51 | 2 | ESI+: 473.3<br>NMR-DMSO-d6: 1.48-2.62 (7H, m), 3.00-4.31 (12H, m), 5.19-5.31 (1H, m), 6.79-6.86 (2H, m), 7.36 (1H, s), 7.97 (1H, s), 8.13-8.23 (3H, m), 11.53 (1H, s) |
| 52 | 2 | ESI+: 478.4<br>NMR-DMSO-d6: 1.01-1.29 (2H, m), 1.48-2.71 (16H, m), 3.07-4.04 (12H, m), 5.43-5.56 (1H, m), 7.32 (1H, s), 7.96 (1H, s), 8.12 (1H, s), 11.46 (1H, s) |
| 53 | 2 | ESI+: 453.4<br>NMR-DMSO-d6: 0.87 (3H, t, J = 7.4 Hz), 0.98-2.60 (13H, m), 2.87-4.39 (11H, m), 5.14-5.33 (1H, m), 7.33 (1H, s), 7.90 (1H, s), 8.17 (1H, s), 11.50 (1H, s)<br>mp: 216-218 |
| 54 | 2 | ESI+: 469.4<br>NMR-DMSO-d6: 1.11-2.55 (11H, m), 2.93-4.24 (16H, m), 5.17-5.31 (1H, m), 7.33 (1H, s), 7.88 (1H, s), 8.17 (1H, s), 11.50 (1H, s) |
| 55 | 2 | ESI+: 464.4<br>NMR-DMSO-d6: 1.01-4.14 (28H, m), 5.47-5.58 (1H, m), 7.31 (1H, s), 7.86 (1H, s), 8.17 (1H, s), 11.5 (1H, s) |
| 56 | 2 | ESI+: 453.4<br>NMR-DMSO-d6: 0.74-1.40 (5H, m), 1.46-2.55 (10H, m), 2.61-3.75 (9H, m), 3.80-4.12 (2H, m), 4.43-4.75 (1H, m), 5.12-5.35 (1H, m), 7.33 (1H, s), 7.87 (1H, s), 8.17 (1H, s), 11.49 (1H, s)<br>mp: 243 |
| 57 | 2 | ESI+: 515.4<br>NMR-DMSO-d6: 1.84-2.43 (6H, m), 2.51 (3H, s), 2.80-4.07 (16H, m), 5.22-5.34 (1H, m), 7.36 (1H, s), 7.95-8.06 (2H, m), 8.18 (1H, s), 8.53 (1H, d, J = 8.3 Hz), 8.82 (1H, d, J = 6.1 Hz), 8.91 (1H, s), 11.55 (1H, s)<br>mp: 254-256 |
| 58 | 2 | ESI+: 464.4<br>NMR-DMSO-d6: 1.27-1.48 (2H, m), 1.58-1.94 (6H, m), 1.94-2.76 (10H, m), 2.30 (3H, s), 3.07-3.38 (3H, m), 3.54-3.95 (4H, m), 5.40-5.57 (1H, m), 7.32 (1H, s), 7.96 (1H, s), 8.11 (1H, s), 11.46 (1H, s)<br>mp: 263-265 |

TABLE 111

| Ex | Syn | Data |
|---|---|---|
| 59 | 2 | ESI+: 479.4<br>NMR-DMSO-d6: 0.05-0.21 (2H, m), 0.31-0.52 (2H, m), 0.78-4.18 (24H, m), 4.45-4.58 (1H, m), 5.11-5.33 (1H, m), 7.33 (1H, s), 7.87 (1H, s), 8.17 (1H, s), 11.50 (1H, s) |
| 60 | 2 | ESI+: 485.4<br>NMR-DMSO-d6: 0.82-1.43 (5H, m), 1.48-3.78 (19H, m), 3.81-4.20 (2H, m), 4.48-4.90 (2H, m), 5.16-5.31 (1H, m), 7.33 (1H, s), 7.88 (1H, s), 8.17 (1H, s), 11.49 (1H, s) |
| 61 | 5 | ESI+: 494.3<br>NMR-DMSO-d6: 1.62-1.74 (8H, m), 2.06-2.27 (4H, m), 2.43 (3H, s), 2.74 (2H, m), 3.37 (2H, m), 3.45 (2H, d, J = 6.2 Hz), 3.55-3.71 (6H, m), 4.04 (2H, m), 5.20 (1H, m), 7.30 (1H, s), 8.02 (1H, s), 8.19 (1H, s), 8.33 (1H, t, J = 6.2 Hz), 11.52 (1H, s) |
| 62 | 5 | ESI+: 464.4<br>NMR-DMSO-d6: 1.53 (1H, m), 1.70-1.93 (6H, m), 1.99-2.41 (10H, m), 2.89-3.23 (2H, m), 3.40-3.67 (7H, m), 4.29 (1H, m), 4.62 (1H, m), 5.53 (1H, m), 7.35 (1H, s), 8.07 (1H, s), 8.13 (1H, s), 10.60-10.86 (1H, br), 11.51 (1H, s) |
| 63 | 2 | ESI+: 482.2<br>NMR-DMSO-d6: 1.08 (3H, t, J = 7.0 Hz), 1.56-1.90 (2H, m), 1.92-2.10 (4H, m), 2.26-2.38 (6H, m), 2.29 (3H, s), 3.00-4.07 (12H, m), 5.18-5.28 (1H, m), 7.33 (1H, s), 7.87 (1H, s), 8.17 (1H, s), 11.50 (1H, s)<br>mp: 217-219 |
| 64 | 2 | ESI+: 496.3<br>NMR-DMSO-d6: 1.05 (6H, d, J = 6.0 Hz), 1.19-1.34 (2H, m), 1.54-1.66 (2H, m), 1.90-2.39 (4H, m), 2.29 (3H, s), 3.02-4.07 (15H, m), 5.16-5.28 (1H, m), 7.33 (1H, s), 7.87 (1H, s), 8.17 (1H, s), 11.50 (1H, s)<br>mp: 122-124 |
| 65 | 2 | ESI+: 479.2<br>NMR-DMSO-d6: 0.77-1.68 (10H, m), 1.71-4.11 (18H, m), 4.54-4.70 (1H, m), 5.15-5.31 (1H, m), 7.33 (1H, s), 7.87 (1H, s), 8.17 (1H, s), 11.49 (1H, s) |
| 66 | 2 | ESI+: 453.2<br>NMR-DMSO-d6: 0.69-3.56 (22H, m), 3.56-3.80 (2H, m), 3.83-4.18 (2H, m), 4.43-4.70 (1H, m), 5.11-5.35 (1H, m), 7.33 (1H, s), 7.88 (1H, s), 8.17 (1H, s), 11.49 (1H, s)<br>mp: 241-242 |
| 67 | 2 | ESI+: 466.2<br>mp: 234-236 |
| 68 | 2 | ESI+: 464.2 |

TABLE 112

| Ex | Syn | Data |
|---|---|---|
| 69 | 2 | ESI+: 466.2<br>NMR-DMSO-d6: 1.10 (3H, t, J = 7.0 Hz), 1.69-2.78 (10H, m), 2.58 (3H, s), 3.07-3.80 (14H, m), 5.49-5.57 (1H, m), 7.35 (1H, s), 8.07 (1H, s), 8.12 (1H, s), 11.50 (1H, s) |
| 70 | 2 | ESI+: 452.4<br>NMR-DMSO-d6: 1.10 (3H, t, J = 6.9 Hz), 1.83-2.06 (4H, m), 2.23-2.62 (7H, m), 3.10-3.68 (14H, m), 5.51-5.61 (1H, m), 7.33 (1H, s), 7.98 (1H, s), 8.18 (1H, s), 11.51 (1H, s) |
| 71 | 2 | ESI+: 508.3<br>NMR-DMSO-d6: 1.80-2.63 (9H, m), 3.12-3.46 (2H, m), 3.50-4.11 (6H, m), 5.14-5.34 (1H, m), 5.36-5.47 (0.5H, m), 5.50-5.68 (0.5H, m), 6.80-6.91 (1H, m), 7.25-7.38 (1H, m), 7.75-9.37 (4H, m), 11.42-11.59 (1H, m) |
| 72 | 2 | ESI+: 508.3<br>NMR-DMSO-d6: 1.85-2.64 (9H, m), 3.20-4.10 (8H, m), 5.18-5.34 (1H, m), 5.36-5.44 (0.5H, m), 5.50-5.61 (0.5H, m), 6.80-6.91 (1H, m), 6.97-7.38 (2H, m), 7.77-8.30 (3H, m), 11.45-11.56 (1H, m) |
| 73 | 2 | ESI+: 439.3 |
| 74 | 2 | ESI+: 512.4<br>NMR-DMSO-d6: 1.96-3.78 (21H, m), 3.89-4.05 (2H, m), 5.17-5.31 (1H, m), 7.17-7.37 (6H, m), 7.95 (1H, s), 8.17 (1H, s), 11.49 (1H, s) |
| 75 | 2 | ESI+: 411.3 |
| 76 | 2 | ESI+: 471.4 |
| 77 | 2 | ESI+: 510.2<br>NMR-DMSO-d6: 1.10 (9H, s), 1.52-1.62 (2H, m), 1.89-2.54 (10H, m), 2.30 (3H, s), 3.10-3.36 (2H, m), 3.51-4.08 (8H, m), 5.18-5.28 (1H, m), 7.33 (1H, s), 7.87 (1H, s), 8.17 (1H, s), 11.50 (1H, s)<br>mp: 238-240 |
| 78 | 2 | ESI+: 411.2<br>NMR-DMSO-d6: 1.97-2.15 (4H, m), 2.39 (3H, s), 2.76-2.87 (1H, m), 3.29 (3H, s), 3.52 (2H, d, J = 6.3 Hz), 3.65-3.83 (4H, m), 3.96-4.17 (4H, m), 5.20-5.30 (1H, m), 7.32 (1H, s), 8.00 (1H, s), 8.17 (1H, s), 11.51 (1H, s) |
| 79 | 2 | ESI+: 452.4<br>NMR-DMSO-d6: 1.37-1.60 (2H, m), 1.61-1.81 (2H, m), 1.81-2.05 (2H, m), 2.06-4.15 (21H, m), 4.47-4.76 (1H, m), 5.49-5.64 (1H, m), 7.33 (1H, s), 7.99 (1H, s), 8.19 (1H, s), 10.71-11.15 (1H, m), 11.51 (1H, s)<br>mp: 161-163 |
| 80 | 2 | ESI+: 474.2 |
| 81 | 2 | ESI+: 467.4 |

TABLE 113

| Ex | Syn | Data |
|---|---|---|
| 82 | 5 | ESI+: 452.3<br>NMR-DMSO-d6: 1.10 (6H, d, J = 6.1 Hz), 1.85-2.05 (2H, m), 2.24-2.39 (4H, m), 2.51-2.62 (4H, m), 2.69-3.21 (2H, m), 3.30-3.65 (7H, m), 3.74 (2H, m), 4.65 (1H, m), 5.56 (1H, m), 7.33 (1H, s), 7.97 (1H, s), 8.19 (1H, s), 10.45-10.75 (1H, br.), 11.52 (1H, s) |
| 83 | 5 | ESI+: 450.2<br>NMR-DMSO-d6: 1.45-1.59 (1H, m), 1.73-2.10 (5H, m), 2.25-2.40 (4H, m), 2.49-2.63 (4H, m), 2.67-3.23 (4H, m), 3.28-3.65 (4H, m), 3.72 (1H, m), 3.82 (1H, m), 4.31 (1H, m), 4.63 (1H, m), 5.57 (1H, m), 7.33 (1H, s), 7.98 (1H, s), 8.19 (1H, s), 10.61-10.92 (1H, br.), 11.52 (1H, s) |
| 84 | 2 | ESI+: 482.2<br>NMR-DMSO-d6: 1.46-2.56 (11H, m), 2.73-4.09 (15H, m), 3.23 (3H, s), 4.56-4.72 (1H, m), 5.21-5.32 (1H, m), 7.36 (1H, s), 8.00 (1H, s), 8.18 (1H, s), 11.55 (1H, s)<br>mp: 240-242 |
| 85 | 7 | ESI+: 494.3<br>NMR-DMSO-d6: 1.88-2.43 (8H, m), 2.50 (3H, s), 2.69-4.22 (15H, m), 3.57 (3H, s), 4.51-4.71 (1H, m), 5.17-5.30 (1H, m), 7.35 (1H, s), 7.89 (1H, s), 8.17 (1H, s), 11.52 (1H, s) |
| 86 | 2 | ESI+: 425.3<br>NMR-DMSO-d6: 1.12 (3H, t, J = 7.2 Hz), 1.97-2.34 (4H, m), 2.39 (3H, s), 2.76-2.87 (1H, m), 3.47 (2H, q, J = 7.2 Hz), 3.55 (2H, d, J = 6.4 Hz), 3.60-3.80 (4H, m), 3.96-4.17 (4H, m), 5.21-5.31 (1H, m), 7.32 (1H, s), 8.00 (1H, s), 8.17 (1H, s), 11.51 (1H, s)<br>mp: 226-228 |

TABLE 113-continued

| Ex | Syn | Data |
|---|---|---|
| 87 | 2 | ESI+: 451.3<br>NMR-DMSO-d6: 1.27-2.19 (11H, m), 2.22-2.58 (4H, m), 3.06-3.48 (3H, m), 3.53-4.28 (7H, m), 5.14-5.38 (1H, m), 7.33 (1H, s), 7.83-8.00 (1H, m), 8.17 (1H, s), 11.49 (1H, s) |
| 88 | 2 | ESI+: 467.4<br>NMR-DMSO-d6: 0.72-1.37 (4H, m), 1.38-1.69 (4H, m), 1.70-1.87 (1H, m), 1.87-2.16 (3H, m), 2.18-2.56 (4H, m), 2.62-3.02 (2H, m), 3.10-3.53 (6H, m), 3.56-3.79 (2H, m), 3.82-4.14 (2H, m), 4.38-4.72 (1H, m), 5.08-5.36 (1H, m), 7.33 (1H, s), 7.88 (1H, s), 8.17 (1H, s), 11.50 (1H, s) |
| 89 | 2 | ESI+: 467.3 |
| 90 | 2 | ESI+: 466.2<br>NMR-DMSO-d6: 1.48-1.59 (2H, m), 1.69-2.02 (8H, m), 2.23-2.40 (2H, m), 2.50 (3H, s), 2.80-3.68 (11H, m), 3.23 (3H, s), 4.68-4.81 (2H, s), 7.34 (1H, s), 7.92 (1H, s), 8.12 (1H, s), 11.52 (1H, s)<br>mp: 178-180 |

TABLE 114

| Ex | Syn | Data |
|---|---|---|
| 91 | 2 | ESI+: 501.2<br>NMR-DMSO-d6: 0.75-1.06 (3H, m), 1.57-2.66 (10H, m), 2.42 (3H, s), 2.78-4.78 (7H, m), 5.05-5.44 (1H, m), 7.18-7.76 (2H, m), 7.76-8.05 (2H, m), 8.05-8.78 (3H, m), 11.45-11.55 (1H, m)<br>mp: 272-274 |
| 92 | 2 | ESI+: 439.2 |
| 93 | 2 | ESI+: 453.2 |
| 94 | 2 | ESI+: 475.0<br>NMR-DMSO-d6: 1.12-1.83 (2H, m), 1.88-2.61 (9H, m), 2.92-4.31 (11H, m), 5.11-5.36 (1H, m), 5.93-6.31 (1H, m), 7.33 (1H, s), 7.91 (1H, s), 8.17 (1H, s), 11.5 (1H, br s) |
| 95 | 2 | ESI+: 471.3<br>NMR-DMSO-d6: 1.10-2.55 (14H, m), 2.84-4.32 (11H, m), 4.64-4.75 (0.5H, m), 4.76-4.88 (0.5H, m), 5.16-5.33 (1H, m), 7.33 (1H, s), 7.90 (1H, s), 8.17 (1H, s), 11.50 (1H, s)<br>mp: 209-210 |
| 96 | 2 | APCI/ESI+: 466.3<br>NMR-DMSO-d6: 1.10 (3H, t, J = 7.2 Hz), 1.76-2.02 (8H, m), 2.25-2.38 (3H, m), 2.50 (3H, s), 2.80-2.95 (1H, m), 3.08-3.65 (4H, m), 3.78-3.92 (6H, m), 4.65-4.85 (3H, s), 7.34 (1H, s), 7.91 (1H, s), 8.12 (1H, s), 11.51 (1H, s) |
| 97 | 2 | ESI+: 452.2<br>NMR-DMSO-d6: 1.60-1.70 (2H, m), 1.76-2.03 (6H, m), 2.25-2.48 (4H, m), 2.29 (3H, s), 2.80-2.92 (1H, m), 3.12-3.39 (6H, m), 3.20 (3H, s), 3.56-3.80 (2H, m), 4.57-4.95 (2H, m), 7.31 (1H, s), 7.77 (1H, s), 8.10 (1H, s), 11.47 (1H, s)<br>mp: 186-188 |
| 98 | 5 | ESI+: 480.2<br>NMR-DMSO-d6: 1.12 (6H, s), 1.70-1.96 (6H, m), 2.01-2.43 (7H, m), 2.84-2.91 (1H, m), 3.04-3.16 (5H, m), 3.35-3.46 (3H, m), 3.48-3.70 (3H, m), 4.59-4.72 (1H, m), 5.53 (1H, m), 7.35 (1H, s), 8.08 (1H, s), 8.13 (1H, s), 11.03-11.34 (1H, br.), 11.51 (1H, s) |
| 99 | 5 | ESI+: 496.2<br>NMR-DMSO-d6: 1.13 (6H, s), 1.81-2.13 (4H, m), 2.24-2.44 (3H, m), 277-2.96 (1H, m), 3.00-3.15 (5H, m), 3.35-3.80 (10H, m), 3.90-4.09 (2H, m), 4.59-4.60 (1H, m), 5.27 (1H, m), 7.36 (1H, s), 8.00 (1H, s), 8.19 (1H, s), 10.89-11.31 (1H, br.), 11.55 (1H, s) |
| 100 | 5 | ESI+: 452.2<br>NMR-DMSO-d6: 0.91 (3H, t, J = 7.3 Hz), 1.30 (2H, m), 1.58-1.74 (2H, m), 1.88-2.17 (3H, m), 2.22-2.45 (4H, m), 2.78-2.94 (1H, m), 2.98-3.14 (3H, m), 3.28-3.80 (7H, m), 3.91-4.08 (2H, m), 4.59-4.72 (1H, m), 5.27 (1H, m), 7.36 (1H, s), 8.00 (1H, s), 8.19 (1H, s), 10.85-11.27 (1H, br.), 11.55 (1H, s) |

TABLE 115

| Ex | Syn | Data |
|---|---|---|
| 101 | 2 | ESI+: 474.2 |
| 102 | 2 | ESI+: 409.3 |
| 103 | 2 | ESI+: 452.4<br>NMR-DMSO-d6: 0..31-0.61 (4H, m), 1.20-1.36 (1H, m), 1.41-1.61 (2H, m), 1.64-1.85 (2H, m), 2.21-2.44 (3H, m), 2.76-3.90 (14H, m), 4.41-4.94 (3H, m), |

TABLE 115-continued

| Ex | Syn | Data |
|---|---|---|
| | | 7.35 (1H, s), 8.02 (1H, s), 8.12 (1H, s), 10.51-1098 (1H, m), 11.52 (1H, s) mp: 207-208 |
| 104 | 2 | ESI+: 438.2<br>NMR-DMSO-d6: 0.32-0.60 (4H, m), 1.22-1.38 (1H, m), 1.86-2.07 (2H, m), 2.20-2.44 (3H, m), 2.76-2.87 (14H, m), 4.41-4.97 (3H, m), 7.35 (1H, s), 8.02 (1H, s), 8.13 (1H, s), 10.72-11.20 (1H, m), 11.53 (1H, s) |
| 105 | 5 | ESI+: 496.2<br>NMR-DMSO-d6: 1.11 (9H, s), 1.56 (2H, m), 2.06-2.23 (1H, br.), 2.30 (3H, s), 2.30-2.42 (5H, m), 2.46-2.71 (4H, m), 3.12-3.25 (2H, m), 3.88-4.29 (4H, m), 5.81 (1H, m), 7.33 (1H, s), 7.87-7.99 (1H, br.), 8.15 (1H, s), 11.50 (1H, s) |
| 106 | 5 | ESI+: 487.2<br>NMR-DMSO-d6: 1.00-1.39 (4H, m), 1.87-4.96 (14H, m), 2.33 (3H, s), 5.25 (1H, m), 6.91 (1H, m), 7.25 (1H, m), 7.37 (1H, s), 7.86-8.03 (2H, m), 8.05 (1H, d, J = 3.2 Hz), 8.19 (1H, s), 11.55 (1H, s) |
| 107 | 2 | ESI+: 496.2<br>NMR-DMSO-d6: 1.11 (3H, t, J = 12.8 Hz), 1.46-2.47 (14H, m), 2.78-3.81 (12H, m), 3.92-4.07 (2H, m), 4.66 (1H, d, J = 12.0 Hz), 5.26-5.31 (1H, m), 7.36 (1H, s), 8.01 (1H, s), 8.19 (1H, s), 11.55 (1H, s) |
| 108 | 2 | ESI+: 510.3<br>NMR-DMSO-d6: 1.10-2.41 (20H, m), 2.96-4.14 (13H, m), 4.62 (1H, d, J = 12.0 Hz), 5.21-5.38 (1H, m), 7.35 (1H, s), 8.00 (1H, s), 8.18 (1H, s), 11.54 (1H, s) |
| 109 | 2 | ESI+: 510.3<br>NMR-DMSO-d6: 1.11-2.40 (20H, m), 2.85-4.70 (14H, m), 5.27 (1H, m), 7.36 (1H, s), 7.98 (1H, m), 8.19 (1H, s), 11.55 (1H, s) |
| 110 | 2 | ESI+: 452.2<br>NMR-DMSO-d6: 0.99 (6H, d, J = 8.0 Hz), 1.74-3.81 (19H, m), 3.84-4.20 (2H, m), 4.45-4.77 (1H, m), 5.16-5.38 (1H, m), 7.36 (1H, s), 8.00 (1H, s), 8.19 (1H, s), 9.91-10.65 (1H, m), 11.55 (1H, s) |
| 111 | 2 | ESI+: 496.3<br>NMR-DMSO-d6: 0.95-2.54 (14H, m), 2.70-4.20 (17H, m), 4.31-4.77 (1H, m), 5.04-5.40 (1H, m), 7.36 (1H, s), 7.88-8.09 (1H, m), 8.19 (1H, s), 10.33-11.10 (1H, m), 11.45-11.67 (1H, m) |

TABLE 116

| Ex | Syn | Data |
|---|---|---|
| 112 | 2 | ESI+: 496.3<br>NMR-DMSO-d6: 0.94-2.59 (14H, m), 2.74-4.15 (17H, m), 4.34-4.79 (1H, m), 5.07-5.39 (1H, m), 7.36 (1H, s), 7.90-8.08 (1H, m), 8.19 (1H, s), 10.36-11.07 (1H, m), 11.50-11.60 (1H, m) |
| 113 | 2 | ESI+: 519.4<br>NMR-DMSO-d6: 0.81-2.60 (13H, m), 2.62-4.14 (9H, m), 4.23-4.72 (2H, m), 5.22 (1H, m), 6.65-6.57 (1H, m), 7.45 (2H, m), 7.85-7.99 (1H, m), 8.18 (1H, s), 11.52 (1H, m)<br>mp: 168 |
| 114 | 2 | ESI+: 496.4<br>NMR-DMSO-d6: 1.08-5.40 (33H, m), 7.36 (1H, s), 7.91-8.10 (1H, m), 8.19 (1H, s), 10.30-10.72 (1H, m), 11.55 (1H, s) |
| 115 | 2 | ESI+: 496.3<br>NMR-DMSO-d6: 1.05-4.32 (31H, m), 4.51-4.78 (0.5H, m), 4.91-5.40 (1.5H, m), 7.36 (1H, s), 7.92-8.11 (1H, m), 8.19 (1H, s), 10.41-10.87 (1H, m), 11.55 (1H, s) |
| 116 | 2 | ESI+: 528.3<br>NMR-DMSO-d6: 1.01-1.98 (8H, m), 2.16-3.07 (7H, m), 3.16-4.12 (2H, m), 4.40-4.08 (7H, m), 4.33-4.69 (3H, m), 5.90-6.08 (1H, m), 7.34 (1H, s), 7.42-7.51 (3H, m), 7.56-7.67 (2H, m), 7.80-7.89 (1H, m), 8.22-8.33 (1H, m), 11.55 (1H, s) |
| 117 | 2 | ESI+: 482.4<br>NMR-DMSO-d6: 0.79-4.18 (29H, m), 4.26-4.70 (1H, m), 5.00-5.44 (1H, m), 7.36 (1H, s), 7.89-8.06 (1H, m), 8.19 (1H, s), 10.53-11.16 (1H, m), 11.50-11.60 (1H, m) |
| 118 | 2 | ESI+: 496.4<br>NMR-DMSO-d6: 1.04 (6H, s), 1.37-1.48 (2H, m), 1.71-1.79 (2H, m), 1.83-1.94 (4H, m), 2.22 (4H, q, J = 6.8 Hz), 2.49-2.51 (2H, m), 2.77-2.84 (2H, m), 3.17-3.21 (1H, m), 3.24 (3H, s), 3.24-3.33 (2H, m), 4.03 (3H, s), 5.33-5.41 (1H, m), 7.19 (1H, s), 8.10 (1H, m), 8.38 (1H, m), 8.86 (1H, s), 11.48 (1H, s) |
| 119 | 2 | ESI+: 468.4<br>NMR-DMSO-d6: 1.04 (6H, s), 1.71-1.82 (2H, m), 1.82-1.95 (2H, m), 2.19-2.27 (4H, q, J = 5.6 Hz), 2.52-2.54 (4H, m), 3.40-3.44 (2H, m), 3.63 (4H, m), 4.05 (3H, s), 5.34-5.42 (1H, m), 7.18 (1H, s), 8.10 (1H, s), 8.38 (1H, m), 8.84 (1H, s), 11.48 (1H, s)<br>mp: 279 |
| 120 | 2 | ESI+: 515.4<br>NMR-DMSO-d6: 1.67-1.80 (2H, m), 1.80-1.92 (2H, m), 2.18-2.24 (4H, m), 2.25 (3H, s), 2.52-2.56 (4H, m), 2.88 (4H, t, J = 4.8 Hz), 3.96 (3H, s), 4.61 (2H, d, J = |

TABLE 116-continued

| Ex | Syn | Data |
|---|---|---|
| | | 6..4 Hz), 5.34-5.43 (1H, m), 7.07 (1H, t, J = 6.4 Hz), 7.13-7.16 (2H, m), 7.24 (1H, t, J = 7.2 Hz), 7.31 (1H, d, J = 8.0 Hz), 8.10 (1H, s), 8.64 (1H, m), 8.70 (1H, s), 11.47 (1H, s)<br>mp: 210 |

TABLE 117

| Ex | Syn | Data |
|---|---|---|
| 121 | 2 | ESI+: 482.4<br>NMR-DMSO-d6: 0.86-4.16 (29H, m), 4.30-4.78 (1H, m), 4.98-5.42 (1H, m), 7.35 (1H, s), 7.89-8.06 (1H, m), 8.18 (1H, s), 10.33-11.11 (1H, m), 11.0-11.57 (1H, m) |
| 122 | 2 | ESI+: 468.3<br>NMR-DMSO-d6: 1.67-2.27 (10H, m), 2.78-3.71 (13H, m), 3.82-3.93 (3H, m), 4.61 (2H, d, J = 13.6 Hz), 5.40-5.47 (1H, m), 7.13 (1H, s), 8.07 (1H, s), 8.10 (1H, s), 10.94 (1H, br s), 11.46 (1H, s) |
| 123 | 2 | ESI+: 482.3<br>NMR-DMSO-d6: 1.49-1.59 (2H, m), 1.65-1.90 (6H, m), 2.06-2.24 (4H, m), 2.41-2.56 (6H, m), 2.79-2.97 (1H, m), 3.02-3.19 (2H, m), 3.27 (3H, s), 3.34 (2H, t, J = 6.4 Hz), 3.83-3.92 (3H, s), 4.55-4.65 (1H, m), 5.40-5.48 (1H, m), 7.13 (1H, s), 8.07 (1H, s), 8.10 (1H, s), 10.85 (1H, br s), 11.46 (1H, s) |
| 124 | 2 | ESI+: 496.4<br>NMR-DMSO-d6: 1.07-2.27 (15H, m), 2.97-3.81 (12H, m), 3.81-3.98 (3H, m), 4.37-4.61 (1H, m), 5.38-5.53 (1H, m), 7.14 (1H, s), 8.05-8.09 (1H, m), 8.11 (1H, s), 10.68-11.02 (1H, m), 11.46 (1H, s) |
| 125 | 2 | ESI+: 510.3<br>NMR-DMSO-d6: 1.09-1.85 (8H, m), 2.06-2.61 (5H, m), 2.65-2.75 (1H, m), 2.75-2.85 (1H, m), 3.00-3.10 (1H, m), 3.23-3.30 (5H, m), 3.39 (2H, q, J = 6.8 Hz), 3.62-3.76 (2H, m), 3.73-4.21 (4H, m), 4.56-4.60 (1H, m), 5.71-5.83 (1H, m), 7.34 (1H, s), 7.84 (1H, s), 8.15 (1H, s), 11.55 (1H, s) |
| 126 | 2 | ESI+: 496.4<br>NMR-DMSO-d6: 1.31-4.10 (32H, m), 5.22-5.35 (1H, m), 7.34 (1H, s), 7.97-8.06 (1H, m), 8.18 (1H, s), 10.90-11.14 (1H, m), 11.53 (1H, s) |
| 127 | 2 | ESI+: 496.4<br>NMR-DMSO-d6: 1.31-4.10 (32H, m), 5.23-5.34 (1H, m), 7.34 (1H, s), 7.96-8.06 (1H, m), 8.18 (1H, s), 10.74-10.96 (1H, m), 11.52 (1H, s) |
| 128 | 2 | ESI+: 492.3<br>NMR-DMSO-d6: 1.80-2.65 (7H, m), 2.80-4.29 (15H, m), 4.52-4.82 (1H, m), 5.21-5.35 (1H, m), 7.36 (1H, s), 7.98 (1H, s), 8.19 (1H, s), 11.33-11.80 (2H, m)<br>mp: 174-176 |
| 129 | 2 | ESI+: 510.4<br>NMR-DMSO-d6: 0.91-4.11 (33H, m), 4.28-4.79 (1H, m), 5.01-5.38 (1H, m), 7.43 (1H, s), 7.90-8.10 (1H, m), 8.14-8.30 (1H, m), 10.92-11.79 (2H, m) |
| 130 | 2 | ESI+: 510.4<br>NMR-DMSO-d6: 0.77-5.15 (35H, m), 7.35 (1H, s), 7.80-8.07 (1H, m), 8.10-8.20 (1H, m), 11.22-11.97 (2H, m) |
| 131 | 2 | ESI+: 506.4<br>NMR-DMSO-d6: 1.90-4.20 (25H, m), 5.23-5.35 (1H, m), 7.34 (1H, s), 7.96-8.08 (1H, m), 8.18 (1H, s), 11.52 (1H, s), 11.55-11.67 (1H, m) |

TABLE 118

| Ex | Syn | Data |
|---|---|---|
| 132 | 2 | ESI+: 506.4<br>NMR-DMSO-d6: 1.91-4.18 (25H, m), 5.24-5.38 (1H, m), 7.34 (1H, s), 7.97-8.08 (1H, m), 8,18 (1H, s), 11.52 (1H, s), 11.71-11.89 (1H, m) |
| 133 | 2 | ESI+: 504.2<br>NMR-DMSO-d6: 1.86-5.70 (27H, m), 7.36 (1H, s), 7.96 (1H, s), 8.19 (1H, s), 11.54 (1H, s)<br>mp: 212-213 |
| 134 | 2 | ESI+: 474.2<br>NMR-DMSO-d6: 1.76-4.51 (24H, m), 5.46-5.63 (1H, m), 7.33 (1H, s), 7.94 (1H, s), 8.18 (1H, s), 11.05 (1H, s) |
| 135 | 2 | ESI+: 496.3<br>NMR-DMSO-d6: 1.10-2.57 (13H, m), 2.4-4.20 (18H, m), 4.46-4.87 (1H, m), 5.11-5.42 (1H, m), 7.36 (1H, s), 8.00 (1H, s), 8.19 (1H, s), 10.36-10.91 (1H, s), 11.54 (1H, s) v |

TABLE 118-continued

| Ex | Syn | Data |
|---|---|---|
| 136 | 2 | ESI+: 494.3<br>NMR-DMSO-d6: 0.50-0.84 (4H, m), 1.93-2.46 (7H, m), 2.80-5.40 (10H, m), 7.36 (1H, s), 7.98 (1H, s), 8.18 (1H, s), 10.35-10.82 (1H, m), 11.55 (1H, s) |
| 137 | 2 | ESI+: 466.3<br>NMR-DMSO-d6: 0.92-2.15 (28H, m), 4.41-4.82 (1H, m), 5.45-5.73 (1H, m), 7.42 (1H, s), 7.99 (1H, s), 8.20 (1H, s), 10.83-11.03 (0.5H, m), 11.10-11.36 (0.5H, m), 11.52 (1H, s) |
| 138 | 2 | ESI+: 514.4<br>NMR-DMSO-d6: 1.02-1.35 (1H, m), 1.59-2.57 (14H, m), 2.80-3.82 (10H, m), 3.88-4.13 (2H, m), 4.50-4.84 (1H, m), 5.14-5.38 (1H, m), 7.36 (1H, s), 8.01 (1H, s), 8.19 (1H, s), 11.54 (1H, s)<br>mp: 210 |
| 139 | 2 | ESI+: 506.4<br>NMR-DMSO-d6: 1.24-1.30 (1H, m), 1.88-2.60 (10H, m), 2.75-3.81 (11H, m), 3.91-4.10 (2H, m), 4.59-4.73 (1H, m), 5.18-5.33 (1H, m), 7.36 (1H, s), 8.00 (1H, s), 8.19 (1H, s), 11.04-11.44 (1H, m), 11.55 (1H, s)<br>mp: 192 |
| 140 | 2 | ESI+: 491.2 |
| 141 | 5 | ESI+: 439.1<br>NMR-DMSO-d6: 0.90-1.20 (2H, m), 1.09 (6H, t, J = 7.0 Hz), 1.50-1.87 (4H, m), 2.23-2.36 (6H, m), 2.56-3.09 (4H, m), 3.20-3.27 (2H, m), 3.40 (2H, q, J = 7.0 Hz), 3.86-4.36 (4H, m), 4.59 (1H, m), 5.82 (1H, m), 7.33 (1H, s), 7.86-8.00 (1H, br.), 8.15 (1H, s), 11.51 (1H, s) |

TABLE 119

| Ex | Syn | Data |
|---|---|---|
| 142 | 5 | ESI+; 468.1<br>NMR-DMSO-d6: 0.70-1.20 (2H, m), 1.47 (4H, m), 2.29 (3H, s), 2.08-2.70 (10H, m), 3.20 (3H, s), 3.30 (2H, m), 3.50-4.26 (4H, m), 5.81 (1H, m), 7.33 (1H, s), 7.87-7.98 (1H, br.), 8.15 (1H, s), 11.52 (1H, s) |
| 143 | 2 | ESI+: 520.4<br>NMR-DMSO-d6: 1.76-4.21 (27H, m), 5.23-5.38 (1H, m), 7.34 (1H, s), 7.97-8.09 (1H, m), 8.18 (1H, s), 11.52 (1H, s) |
| 144 | 2 | ESI+: 520.4<br>NMR-DMSO-d6: 1.78-4.11 (27H, m), 5.23-5.38 (1H, m), 7.34 (1H, s), 7.98-8.07 (1H, m), 8.18 (1H, s), 11.52 (1H, s) |
| 145 | 2 | ESI+: 494.4<br>NMR-DMSO-d6: 1.45-2.54 (15H, m), 2.95-3.41 (9H, m), 3.45-4.08 (4H, m), 4.17-5.00 (2H, m), 5.13-5.63 (1H, m), 7.29-7.39 (1H, m), 7.94-8.01 (1H, m), 8.15-8.24 (1H, m), 11.49-11.57 (1H, m)<br>mp: 203 |
| 146 | 2 | ESI+: 466.4<br>NMR-DMSO-d6: 0.96-2.10 (10H, m), 2.19-3.95 (19H, m), 4.33-4.78 (1H, m), 5.34-5.68 (1H, m), 7.33 (1H, s), 7.89-8.10 (1H, m), 8.19 (1H, s), 10.50-11.00 (1H, br s), 11.51 (1H, s) |
| 147 | 2 | ESI+: 472.2<br>NMR-DMSO-d6: 1.98-2.38 (4H, m), 2.49 (3H, s), 3.10-4.41 (15H, m), 5.27-5.41 (1H, m), 7.32 (1H, s), 8.08 (1H, s), 8.18 (1H, s), 11.51 (1H, s) |
| 148 | 5 | ESI+: 439.4<br>0.90-1.20 (2H, m), 1.09 (3H, t, J = 7.0 Hz), 1.50-1.87 (4H, m), 2.23-2.36 (3H, m), 2.56-3.09 (4H, m), 3.20-3.27 (2H, m), 3.40 (2H, q, J = 7.0 Hz), 3.86-4.36 (4H, m), 4.59 (1H, m), 5.81 (1H, m), 7.33 (1H, s), 7.85-7.98 (1H, br.), 8.15 (1H, s), 11.49 (1H, s) |
| 149 | 5 | ESI+: 468.1<br>0.70-1.20 (2H, m), 1.47 (4H, m), 2.29 (3H, s), 2.08-2.70 (10H, m), 3.20 (3H, s), 3.30 (2H, m), 3.50-4.26 (4H, m), 5.81 (1H, m), 7.33 (1H, s), 7.87-7.98 (1H, br.), 8.15 (1H, s), 11.51 (1H, s) |
| 150 | 2 | ESI+: 492.2<br>NMR-DMSO-d6: 0.79-4.73 (23H, m), 5.11-5.48 (1H, m), 7.33 (1H, s), 7.86-8.10 (1H, m), 8.19 (1H, s), 11.48-11.56 (1H, m) |
| 151 | 2 | ESI+: 517.2<br>NMR-DMSO-d6: 1.74-2.51 (12H, m), 2.95-4.31 (9H, m), 4.72-7.82 (1H, m), 5.04-5.36 (1H, m), 6,27-6.51 (1H, m), 7.22-7.47 (2H, m), 7.85-8.08 (1H, m), 8.13-8.20 (1H, m), 11.47-11.55 (1H, m)<br>mp: 224 |

TABLE 120

| Ex | Syn | Data |
|---|---|---|
| 152 | 2 | ESI+: 507.2<br>NMR-DMSO-d6: 0.80-1.42 (5H, m), 1.48-2.56 (7H, m), 2.60-3.10 (2H, m), 3.14-3.51 (5H, m), 3.60-3.78 (2H, m), 3.86-4.12 (2H, m), 4.49-4.61 (1H, m), 5.30-5.41 (1H, m), 7.88 (1H, s), 8.08-8.17 (1H, m), 8.26-8.30 (1H, m), 11.80 (1H, s) |
| 153 | 2 | ESI+: 536.3 |
| 154 | 2 | ESI+: 496.4<br>NMR-DMSO-d6: 1.07-1.88 (10H, m), 1.97-4.94 (22H, m), 7.35 (1H, s), 7.88-8.08 (1H, m), 8.14 (1H, s), 10.83-11.34 (1H, m), 11.55 (1H, s) |
| 155 | 2 | ESI+: 506.4<br>NMR-DMSO-d6: 1.18-5.00 (26H, m), 7.35 (1H, s), 7.97 (1H, s), 8.13 (1H, s), 11.54 (1H, s) |
| 156 | 2 | ESI+: 493.3,<br>NMR-DMSO-d6: 1.25-2.63 (11H, m), 2.97-4.37 (11H, m), 5.15-5.33 (1H, m), 7.33 (1H, s), 7.91 (1H, s), 8.17 (1H, s), 11.49 (1H, s) |
| 157 | 2 | ESI+: 480.4<br>NMR-DMSO-d6: 0.93-2.13 (12H, m), 2.28-3.97 (19H, m), 4.20-4.80 (1H, m), 5.28-5.77 (1H, m), 7.40 (1H, s), 7.80-8.10 (1H, m), 8.19 (1H, s), 10.45-11.12 (1H, m), 11.49 (1H, s) |
| 158 | 2 | ESI+: 508.4 |
| 159 | 2 | ESI+: 508.4 |
| 160 | 2 | ESI+: 546.4 |
| 161 | 2 | ESI+: 462.4<br>NMR-DMSO-d6: 1.76-2.07 (2H, m), 2.13-3.79 (18H, m), 4.44-4.82 (1H, m), 5.44-5.63 (1H, m), 7.33 (1H, s), 7.97 (1H, s), 8.18 (1H, s), 11.51 (1H, s) |
| 162 | 2 | ESI+: 476.4<br>NMR-DMSO-d6: 1.06-1.26 (3H, m), 1.80-2.06 (2H, m), 2.26-3.82 (17H, m), 4.44-4.82. (1H, m), 5.47-5.62 (1H. m), 7.40 (1H, s), 7.96 (1H, s), 8.19 (1H, s), 11.20-11.71 (2H, m) |
| 163 | 2 | ESI+: 466.4<br>NMR-DMSO-d6: 1.00-2.11 (10H, m), 2.18-4.05 (19H, m), 4.26-4.78 (1H, m), 5.38-5.71 (1H, m), 7.32 (1H, s), 7.87-8.08 (1H, m), 8.19 (1H, s), 11.51 (1H, s) |
| 164 | 2 | ESI+: 480.4 NMR-DMSO-d6: 1.00-2.50 (16H, m), 2.78-4.05 (14H, m), 4.23-5.00 (3H, m), 7.33 (1H, s), 7.78-8.04 (1H, m), 8.12 (1H, s), 11.52 (1H, s) |
| 165 | 2 | ESI+: 532.2 |
| 166 | 5 | ESI+: 490.4<br>NMR-DMSO-d6: 2.30 (3H, s), 2.32-2.63 (6H, m), 2.81 (2H, t, J = 14.2 Hz), 3.35 (3H, s), 3.16-4.26 (8H, m), 3.66 (2H, t, J = 13.5 Hz), 5.81 (1H, m), 7.33 (1H, s), 7.89-7.98 (1H, br.), 8.15 (1H, s), 11.50 (1H, s) |

TABLE 121

| Ex | Syn | Data |
|---|---|---|
| 167 | 2 | ESI+: 467.3<br>NMR-DMSO-d6: 0.76-1.38 (10H, m), 1.49-2.57 (10H, m), 2.59-3.47 (3H, m), 3.55-3.76 (2H, m), 3.84-4.16 (3H, m), 4.37-4.59 (1H, m), 5.15-5.32 (1H, m), 7.33 (1H, s), 7.86 (1H, s), 8.17 (1H, s), 11.49 (1H, s) |
| 168 | 2 | ESI+: 467.3<br>NMR-DMSO-d6: 0.79-1.34 (5H, m), 1.36-2.58 (12H, m), 2.64-3.09 (2H, m), 3.19-3.52 (5H, m), 3.55-3.78 (2H, m), 3.85-4.13 (2H, m), 4.44-4.65 (1H, m), 5.13-5.31 (1H, m), 7.33 (1H, s), 7.89 (1H, br), 8.17 (1H, s), 11.49 (1H, s) |
| 169 | 2 | ESI+: 465.3<br>NMR-DMSO-d6: 1.13-2.62 (17H, m), 2.80-4.30 (10H, m), 5.16-5.31 (1H, m), 7.33 (1H, s), 7.89 (1H, s), 8.17 (1H, s), 11.49 (1H, s) |
| 170 | 2 | ESI+: 452.3<br>NMR-DMSO-d6: 0.76-4.41 (27H, m.), 4.49-4.72 (1H, m), 5.96-6.12 (1H, m), 7.35 (1H, s), 7.89 (1H, s), 8.27 (1H, s), 11.58 (1H, s) |
| 171 | 2 | ESI+: 466.3<br>NMR-DMSO-d6: 0.88-1.95 (8H, m), 2.14-3.07 (11H, m), 3.15-4.26 (10H, m), 4.54-4.69 (1H, m), 5.16-5.57 (1H, m), 7.35 (1H, s), 7.88 (1H, s), 8.20 (1H, s), 10.39-10.74 (1H, m), 11.55 (1H, s) |
| 172 | 2 | ESI+: 505.3<br>NMR-DMSO-d6: 2.14-4.83 (26H, m), 5.22-5.79 (1H, m), 7.37 (1H, s), 7.89-8.25 (2H, m), 11.59 (1H, s)<br>mp: 218 |
| 173 | 2 | ESI+: 522.3<br>NMR-DMSO-d6: 1.62-2.64 (9H, m), 2.73-4.38 (15H, m), 4.44-4.85 (1H, m), 5.08-5.38 (1H, m), 7.29-7.41 (1H, m), 7.87-8.05 (1H, m), 8.13-8.24 (1H, m), 11.47-11.60 (1H, m) |
| 174 | 2 | ESI+: 532.3<br>NMR-DMSO-d6: 0.76-1.31 (3H, m), 2.00-4.80 (23H, m), 5.14-5.60 (2H, m), 6.54-6.70 (1H, m), 7.30-7.51 (2H, m), 7.82-8.07 (1H, m), 8.21 (1H, s), 11.58 (1H, s) |

TABLE 121-continued

| Ex | Syn | Data |
|---|---|---|
| 175 | 2 | ESI+: 532.3<br>NMR-DMSO-d6: 0.82-1.30 (3H, m), 2.02-5.08 (24H, m), 5.16-5,58 (1H, m), 6.53-6.64 (1H, m), 7.28-7.57 (2H, m), 7.83-8.05 (1H, m), 8.21 (1H, s), 11.59 (1H, s)<br>mp: 233 |
| 176 | 2 | ESI+: 489.3<br>NMR-DMSO-d6: 1.17-2.60 (14H, m), 2.89-4.50 (11H, m), 5.11-5.41 (1H, m), 7.33 (1H, s), 7.90 (1H, s), 8.16 (1H, s), 11.49 (1H, s)<br>mp: 210-211 |

TABLE 122

| Ex | Syn | Data |
|---|---|---|
| 177 | 2 | ESI+: 471.3<br>NMR-DMSO-d6: 0.99-2.57 (15H, m), 2.79-4.29 (10H, m), 4.64-4.75 (0.5H, m), 4.77-4.90 (0.5H, m), 5.14-5.32 (1H, m), 7.33 (1H, s), 7.90 (1H, s), 8.17 (1H, s), 11.49 (1H, s)<br>mp: 205-206 |
| 178 | 2 | ESI+: 457.2<br>NMR-DMSO-d6: 1.09-2.73 (13H, m), 3.00-3.69 (5H, m), 3.85-4.30 (5H, m), 4.65-4.89 (1H, m), 5.74-5.91 (1H, m), 7.34 (1H, s), 7.88-8.03 (1H, m), 8.16 (1H, s), 11.50 (1H, s) |
| 179 | 2 | ESI+: 452.3<br>NMR-DMSO-d6: 0.94-1.51 (3H, m), 1.75-2.03 (4H, m), 2.18-2.40 (3H, m), 2.41-3.78 (18H, m), 5.43-5.66 (1H, m), 7.33 (1H, s), 7.93-8.03 (1H, br s), 8.19 (1H, s), 11.51(1H, s)<br>mp: 183 |
| 180 | 2 | ESI+: 452.3<br>NMR-DMSO-d6: 0.96-1.52 (3H, m),1.79-2.09 (4H, m), 2.19-2.41 (3H, m), 2.42-3.95 (18H, m), 5.37-5.63 (1H, m), 7.33 (1H, s), 7.87-8.06 (1H, br s), 8.18 (1H, s), 11.51 (1H, s)<br>mp: 186 |
| 181 | 2 | ESI+: 518.3<br>NMR-DMSO-d6: 0.82-1.28 (3H, m), 2.20-2.68 (8H, m), 2.76-4.70 (14H, m), 5.88-6.14 (1H, m), 6.55-6.68 (1H, m), 7.30-7.51 (2H, m), 7.84-8.08 (1H, m), 8.29 (1H, s), 11.62 (1H, s) |
| 182 | 2 | ESI+: 518.3<br>NMR-DMSO-d6: 0.84-1.31 (3H, m), 2.20-4.77 (22H, m), 5.94-6.11 (1H, m), 6.53-6.69 (1H, m), 7.33-7.50 (2H, m), 7.85-8.11 (1H, m), 8.28 (1H, s), 11.61 (1H, s)<br>mp: 212 |
| 183 | 2 | ESI+: 510.3 NMR-DMSO-d6: 0.98-2.54 (14H, m), 2.83-4.12 (20H, m), 4.95-5.30 (1H, m), 7.23-7.42 (1H, m), 7.67-8.11 (1H, m), 8.20 (1H, s), 11.56 (1H, s)<br>mp: 187 |
| 184 | 2 | ESI+: 520.3<br>NMR-DMSO-d6: 0.85-1.70 (6H, m), 1.84-2.78 (9H, m), 2.85-4.16 (12H, m), 4.93-5.35 (1H, m), 7.28-7.40 (1H, m), 7.45-8.08 (1H, m), 8.19 (1H, s), 11.55 (1H, s)<br>mp: 193 |
| 185 | 2 | ESI+: 478.3<br>NMR-DMSO-d6: 2.06-2.74 (5H, m), 2.77-4.33 (15H, m), 4.41-4.88 (1H, m), 5.71-5.91 (1H, m), 7.36 (1H, s), 8.03 (1H, br s), 8.17 (1H, s), 11.41-11.98 (2H, m) |

TABLE 123

| Ex | Syn | Data |
|---|---|---|
| 186 | 2 | ESI+: 480.3<br>NMR-DMSO-d6: 0.70-1.17 (3H, m), 1.29-1.63 (4H, m), 1.64-3.67 (24H, m), 3.85-4.20 (1H, m), 5.41-5.53 (1H, m), 7.32 (1H, s), 7.95 (1H, s), 8.12 (1H, s), 11.46 (1H, s) |
| 187 | 2 | ESI+: 480.3<br>NMR-DMSO-d6: 0.27-0.70 (4H, m), 1.04-1.90 (12H, m), 2.14-2.62 (4H, m), 2.88-4.00 (11H, m), 4.27-4.81 (2H, m), 7.29-7.44 (1H, m), 7.44-8.06 (1H, m), 8.12 (1H, s), 11.56 (1H, s)<br>mp: 162 |
| 188 | 2 | ESI+: 490.2<br>NMR-DMSO-d6: 0.34-0.64 (4H, m), 1.03-1.69 (7H, m), 2.19-2.44 (3H, m), 2.48-4.00 (10H, m), 4.25-4.83 (2H, m), 7.31-7.39 (1H, m), 7.75-8.05 (1H, m), |

TABLE 123-continued

| Ex | Syn | Data |
|---|---|---|
| | | 8.13 (1H, s), 11.54 (1H, s) |
| 189 | 2 | ESI+: 494.3<br>NMR-DMS0-d6: 0.88-2.08 (17H, m), 2.13-2.43 (3H, m), 2.58-4.01 (13H, m), 4.31-4.88 (2H, m), 7.27-7.39 (1H, m), 7.54-8.01 (1H, m), 8.12 (1H, s), 11.53 (1H, s)<br>mp: 166 |
| 190 | 2 | ESI+: 504.3<br>NMR-DMSO-d6: 1.00-1.61 (6H, m), 1.72-2.12 (7H, m), 2.14-2.42 (3H, m), 2.49-4.00 (10H, m), 4.42-4.88 (2H, m), 7.28-7.41 (1H, m), 7.47-8.02 (1H, m), 8.12 (1H, s), 11.53 (1H, s) |
| 191 | 2 | ESI+: 475.2<br>NMR-DMSO-d6: 1.14-2.10 (7H, m), 2.19-1.73 (5H, m), 2.95-3.80 (6H, m), 3.83-4.42 (5H, m), 5.73-5.98 (1H, m), 7.33 (1H, s), 7.88-8.03 (1H, m), 8.15 (1H, s), 11.49 (1H, s) |
| 192 | 2 | ESI+: 463.2<br>NMR-DMSO-d6: 1.05-3.75 (17H, m), 3.78-4.24 (2H, m), 4.53-4.81 (1H, m), 5.15-5.36 (1H, m), 7.34 (1H, s), 7.85-8.02 (1H, m), 8.17 (1H, s), 11.50 (1H, s) |
| 193 | 5 | ESI+: 530.3<br>NMR-DMSO-d6: 0.75-1.12 (3H, m), 1.33-1.57 (4H, m), 2.29 (3H, s), 1.86-3.51 (21H, m), 3.92-4.18 (1H, m), 5.24 (1H, m), 7.33 (1H, s), 7.90-7.99 (1H, m), 8.16 (1H, s), 11.50 (1H, s) |
| 194 | 5 | ESI+: 544.3 |
| 195 | 5 | ESI+: 466.3<br>NMR-DMSO-d6: 0.36-0.55 (4H, m), 0.74-1.11 (3H, m), 1.29 (1H, m), 1.34-1.58 (4H, m), 2.02-3.42 (10H, m), 2.30 (3H, s), 3.21 (3H, s), 3.93-4.15 (1H, m), 4.41-4.79 (2H, m), 7.32 (1H, s), 7.88 (1H, s), 8.12 (1H, s), 11.50 (1H, s) |
| 196 | 5 | ESI+: 473.3 |
| 197 | 5 | ESI+: 487.3 |

TABLE 124

| Ex | Syn | Data |
|---|---|---|
| 198 | 2 | ESI+: 451.3<br>NMR-DMSO-d6: 0.07-0.22 (2H, m), 0.37-0.51 (2H, m), 0.90-1.04 (1H, m), 1.14-2.05 (4H, m), 2.71-2.74 (5H, m), 2.94-3.63 (6H, m), 3.84-4.28 (5H, m), 5.75-5.88 (1H, m), 7.33 (1H, s), 7.88-8.01 (1H, m), 8.15 (1H, s), 11.49 (1H, s) |
| 199 | 2 | ESI+: 439.3<br>NMR-DMSO-d6: 0.87 (3H, t, J = 7.2 Hz), 1.13-2.06 (6H, m), 2.08-2.71 (5H, m), 2.96-3.59 (6H, m), 3.82-4.29 (5H, m), 5.74-5.88 (1H, m), 7.33 (1H, s), 7.85-8.03 (1H, m), 8.15 (1H, s), 11.49 (1H, s) |
| 200 | 2 | ESI+: 492.3<br>NMR-DMSO-d6: 1.56-1.72 (2H, m), 2.02-2.84 (13H, m), 3.02-3.42 (2H, m), 3.47-4.31 (6H, m), 5.76-5.87 (1H, m), 7.33 (1H, s), 7.85-8.02 (1H, m), 8.15 (1H, s), 11.50 (1H, s) |
| 201 | 2 | ESI+: 453.3<br>NMR-DMSO-d6: 0.80-1.89 (10H, m), 2.08-3.10 (7H, m), 3.19-3.52 (5H, m), 3.81-4.35 (4H, m), 4.42-4.66 (1H, m), 5.73-5.90 (1H, m), 7.33 (1H, s), 7.82-8.01 (1H, m), 8.15 (1H, s), 11.49 (1H, s) |
| 202 | 2 | ESI+: 451.2<br>NMR-DMSO-d6: 1.13-2.02 (8H, m), 2.03-2.73 (7H, m), 2.94-3.62 (4H, m), 3.80-4.32 (6H, m), 5.73-5.89 (1H, m), 7.32 (1H, s), 7.84-8.03 (1H, m), 8.15 (1H, s), 11.49 (1H, s) |
| 203 | 2 | ESI+: 479.2<br>NMR-DMSO-d6: 0.87-2.73 (9H, m), 2.94-3.49 (3H, m), 3.65-3.82 (1H, m), 3.83-4.39 (7H, m), 5.68-5.93 (1H, m), 7.33 (1H, s), 7.80-8.06 (1H, m), 8.15 (1H, s), 11.49 (1H, s) |
| 204 | 5 | ESI+: 516.3<br>NMR-DMSO-d6: 0.76-1.12 (3H, m), 1.32-1.60 (4H, m), 1.99-3.44 (15H, m), 2.29 (3H, s), 3.20 (3H, s), 3.90-4.18 (1H, m), 4.66-5.02 (2H, m), 7.32 (1H, s), 7.85 (1H, s), 8.15 (1H, s), 11.50 (1H, s) |
| 205 | 5 | ESI+: 516.3 |
| 206 | 5 | ESI+: 459.2 |
| 207 | 2 | ESI+: 506.3<br>NMR-DMSO-d6: 1.01-1.57 (3H, m), 1.82-2.65 (7H, m), 2.79-3.84 (13H, m), 3.86-4.18 (2H, m), 5.09-5.35 (1H, m), 7.36 (1H, s), 7.98 (1H, s), 8.19 (1H, s), 11.54 (1H, s)<br>mp: 186 |
| 208 | 2 | ESI+: 540.3<br>NMR-DMSO-d6: 1.00-1.58 (3H, m), 1.83-3.10 (13H, m), 3.17-4.13 (9H, m), 5.12-5.36 (1H, m), 7.37 (1H, s), 8.02 (1H, s), 8.18 (1H, s), 11.55 (1H, s)<br>mp: 190 |

TABLE 125

| Ex | Syn | Data |
| --- | --- | --- |
| 209 | 2 | ESI+: 554.3<br>NMR-DMSO-d6: 1.02-2.55 (17H, m), 2.81-3.99 (9H, m), 4.43-4.80 (2H, m), 7.34 (1H, s), 7.87-8.03 (1H, m), 8.15 (1H, s), 11.55 (1H, s) |
| 210 | 2 | ESI+: 476.2<br>NMR-DMSO-d6: 0.36-0.60 (4H, m), 1.02-1.57 (4H, m), 2.31-4.00 (14H, m), 4.44-4.74 (2H, m), 7.35 (1H, s), 7.91-8.03 (1H, br s), 8.13 (1H, s), 11.52 (1H, s)<br>mp: 187 |
| 211 | 2 | ESI+: 490.2<br>NMR-DMSO-d6: 0.96-1.58 (3H, m), 1.73-2.45 (12H, m), 2.50-3.96 (9H, m), 4.49-4.86 (2H, m), 7.33 (1H, s), 7.81-7.95 (1H, br s), 8.12 (1H, s), 11.52 (1H, s)<br>mp: 171 |
| 212 | 2 | ESI+: 490.3<br>NMR-DMSO-d6: 0.98-1.57 (3H, m), 1.65-4.00 (22H, m), 5.45-5.58 (1H, m), 7.34 (1H, s), 8.02-8.09 (1H, br s), 8.13 (1H, s), 11.51 (1H, s)<br>mp: 176 |
| 213 | 2 | ESI+: 515.3<br>NMR-DMSO-d6: 1.40-2.42 (10H, m), 2.77-2.89 (3H, m), 3.14-3.72 (6H, m), 4.09-4.26 (1H, m), 4.91-5.57 (7H, m), 6.71-6.83 (1H, m), 7.36 (1H, s), 7.50-7.62 (1H, m), 7.88-8.02 (2H, m), 8.20 (1H, s), 11.56 (1H, s) |
| 214 | 2 | ESI+: 513.3<br>NMR-DMSO-d6: 1.01-1.22 (3H, m), 1.96-4.97 (23H, m.), 5.21-5.72 (1H, m), 7.22-8.37 (7H, m), 10.08-10.26 (1H, br s), 11.45-11.67 (1H, m)<br>mp: 221 |
| 215 | 2 | ESI+: 530.3<br>NMR-DMSO-d6: 0.73-1.16 (4H, m), 1.28-1.57 (4H, m), 1.81-3.69 (23H, m), 3.88-4.12 (1H, m), 5.12-5.33 (1H, m), 7.33 (1H, s), 7.85-7.99 (1H, m), 8.16 (1H, s), 11.50 (1H, s) |
| 216 | 2 | ESI+: 544.3<br>NMR-DMSO-d6: 0.72-1.13 (3H, m), 1.25-1.87 (10H, m), 1.92-3.43 (19H, m), 3.91-4.17 (1H, m), 4.34-4.86 (2H, m), 7.32 (1H, s), 7.79-7.89 (1H, m), 8.14 (1H, s), 11.49 (1H, s) |
| 217 | 2 | ESI+: 465.2<br>NMR-DMSO-d6: 0.22-0.49 (4H, m), 0.65-3.77 (20H, m), 3.78-4.15 (2H, m), 4.39-4.76 (1H, m), 4.99-5.40 (1H, m), 7.33 (1H, s), 7.87 (1H, s), 8.17 (1H, s), 11.49 (1H, s)<br>mp: 210-211 |
| 218 | 2 | ESI+: 437.3<br>NMR-DMSO-d6: 0.29-0.53 (4H, m), 0.97-2.69 (9H, m), 2.94-4.31 (10H, m), 5.71-5.91 (1H, m), 7.32 (1H, s), 7.85-8.01 (1H, m), 8.15 (1H, s), 11.49 (1H, s)<br>mp: 197-198 |

TABLE 126

| Ex | Syn | Data |
| --- | --- | --- |
| 219 | 2 | ESI+: 508.3<br>NMR-DMSO-d6: 1.75-1.88 (2H, m), 2.10-2.72 (7H, m), 3.11-4.42 (14H, m), 5.73-5.98 (1H, m), 7.33 (1H, s), 7.84-8.03 (1H, m), 8.15 (1H, s), 11.50 (1H, s) |
| 220 | 2 | ESI+: 457.3<br>NMR-DMSO-d6: 1.59-2.72 (12H, m), 2.89-3.68 (6H, m), 3.71-4.32 (5H, m), 4.64-4.74 (0.5H, m), 4.77-4.90 (0.5H, m), 5.70-5.91 (1H, m), 7.33 (1H, s), 7.83-8.04 (1H, m), 8.15 (1H, s), 11.49 (1H, s)<br>mp: 194 |
| 221 | 2 | ESI+: 479.2<br>NMR-DMSO-d6: 1.31-2.54 (11H, m), 2.89-3.50 (3H, m), 3.53-3.76 (2H, m), 3.78-4.12 (2H, m), 4.46-4.68 (1H, m), 5.13-5.35 (1H, m), 6.15 (1H, s), 7.34 (1H, s), 7.88-8.03 (1H, m), 8.17 (1H, s), 11.50 (1H, s) |
| 222 | 2 | ESI+: 451.2<br>NMR-DMSO-d6: 0.18-0.51 (4H, m), 0.74-1.86 (6H, m), 1.95-3.46 (10H, m), 3.63-4.38 (4H, m), 4.40-4.72 (1H, m), 5.69-5.87 (1H, m), 7.32 (1H, s), 7.79-8.02 (1H, m), 8.15 (1H, s), 11.48 (1H, s) |
| 223 | 2 | ESI+: 480.3<br>NMR-DMSO-d6: 0.07-0.17 (2H, m), 0.37-0.47 (2H, m), 0.87-1.02 (1H, m), 2.02-2.73 (11H, m), 3.00-4.28 (12H, m), 5.74-5.87 (1H, m), 7.33 (1H, s), 7.84-8.02 (1H, m), 8.15 (1H, s), 11.49 (1H, s) |
| 224 | 2 | ESI+: 480.1 |
| 225 | 2 | ESI+: 494.1<br>NMR-DMSO-d6: 0.08-0.29 (2H, m), 0.38-0.55 (2H, m), 0.74-1.36 (4H, m), 2.10-3.63 (17H, m), 3.81-4.48 (5H, m), 5.72-5.91 (1H, m), 7.32 (1H, s), 7.92 (1H, br s), 8.15 (1H, s), 11.50 (1H, s) |
| 226 | 5 | ESI+: 482.3<br>NMR-DMSO-d6: 0.73-1.12 (3H, m), 1.31-1.57 (4H, m), 1.94-3.44 (12H, m), 2.29 (3H, s), 3.20 (3H, s), 3.81-4.41 (5H, m), 5.80 (1H, m), 7.33 (1H, s), 7.93 (1H, s), 8.15 (1H, s), 11.50 (1H, s) |

TABLE 126-continued

| Ex | Syn | Data |
|---|---|---|
| 227 | 2 | ESI+: 451.2<br>NMR-DMSO-d6: 0.35-0.55 (4H, m), 1.02-2.67 (11H, m), 2.87-4.34 (10H, m), 5.14-5.34 (1H, m), 7.33 (1H, s), 7.90 (1H, s), 8.17 (1H, s), 11.49 (1H, s) |
| 228 | 2 | ESI+: 494.3<br>NMR-DMSO-d6: 0.10-0.21 (2H, m), 0.39-0.52 (2H, m), 0.89-1.04 (1H, m), 1.86-2.75 (13H, m), 3.09-4.13 (12H, m), 5.16-5.31 (1H, m), 7.33 (1H, s), 7.87 (1H, s), 8.17 (1H, s), 11.49 (1H, s) |

TABLE 127

| Ex | Syn | Data |
|---|---|---|
| 229 | 2 | ESI+: 494.3<br>NMR-DMSO-d6: 0.36-0.55 (4H, m), 1.72-2.61 (9H, m), 2.69-3.83 (14H, m), 3.84-4.18 (2H, m), 4.50-4.81 (1H, m), 5.12-5.37 (1H, m), 7.35 (1H, s), 7.99 (1H, s), 8.18 (1H, s), 11.54 (1H, m) |
| 230 | 2 | ESI+: 508.1<br>NMR-DMSO-d6: 0.07-0.28 (2H, m), 0.38-0.61 (2H, m), 0.75-1.44 (4H, m), 1.82-3.57 (19H, m), 159-3.85 (2H, m), 3.89-4.44 (3H, m), 5.14-5.42 (1H, m), 7.33(1H, s), 7.78-7.99 (1H, m), 8.17 (1H, s), 11.50 (1H, s) |
| 231 | 2 | ESI+: 451.1<br>NMR-DMSO-d6: 0.84-1.42 (10H, m), 1.53-2.44 (14H, m), 2.70-3.14 (2H, m), 3.24-3.44 (1H, m), 4.08 (1H, s), 4.35-4.61 (1H, m), 5.39-5.57 (1H, m), 7.32 (1H, s), 7.94 (1H, s), 8.11 (1H, s), 11.44 (1H, s) |
| 232 | 2 | ESI+: 466.3<br>NMR-DMSO-d6: 0.24-0.55 (4H, m), 0.93-1.85 (8H, m), 2.00-2.55 (3H, m), 2.67-3.97 (14H, m), 4.10-5.04 (2H, m), 7.34 (1H, s), 7.80-8.08 (1H, m), 8.14 (1H, s), 10.04-10.63 (1H, m), 11.51 (1H, m) |
| 233 | 2 | ESI+: 480.3<br>NMR-DMSO-d6: 1.00-2.43 (17H, m), 2.77-4.12 (13H, m), 4.36-4.98 (3H, m), 7.33 (1H, s), 7.80-8.07 (1H, m), 8.07-8.13 (1H, m), 10.58-11.18 (1H, m), 11.51 (1H, s) |
| 234 | 2 | ESI+: 464.3<br>NMR-DMSO-d6: 0.07-0.21 (2H, m), 0.34-0.57 (6H, m), 0.90-1.02 (1H, m), 1.23-1.36 (1H, m), 2.13-2.72 (9H, m), 3.00-3.41 (4H, m), 3.43-3.56 (2H, m), 3.57-3.84 (2H, m), 4.44-4.81 (2H, m), 7.32 (1H, s), 7.89 (1H, s), 8.11 (1H, s), 11.48 (1H, s) |
| 235 | 2 | ESI+: 478.2<br>NMR-DMSO-d6: 0.07-0.26 (2H, m), 0.35-0.63 (6H, m), 0.73-1.19 (4H, m), 1.22-1.38 (1H, m), 2.18-3.67 (15H, m), 3.92-4.23 (1H, m), 4.35-4.84 (2H, m), 7.32 (1H, s), 7.88 (1H, s), 8.11 (1H, s), 11.48 (1H, s) |
| 236 | 2 | ESI+: 492.3<br>NMR-DMSO-d6: 0.09-0.23 (2H, m), 0.38-0.52 (2H, m), 0.78-1.17 (4H, m), 1.64-3.01 (12H, m), 3.10-3.55 (11H, m), 3.85-4.24 (1H, m), 5.40-5.53 (1H, m), 7.32 (1H, s), 7.95 (1H, s), 8.12 (1H, s), 11.46 (1H, s) |
| 237 | 2 | ESI+: 492.3<br>NMR-DMSO-d6: 0.08-0.23 (2H, m), 0.35-0.51 (2H, m), 0.78-1.15 (4H, m), 1.76-2.06 (6H, m), 2.21-3.66 (16H, m), 3.92-4.20 (1H, m), 4.48-4.96 (2H, m), 7.31 (1H, s), 7.74-7.80 (1H, br s), 8.11 (1H, s), 11.47 (1H, s) |

TABLE 128

| Ex | Syn | Data |
|---|---|---|
| 238 | 2 | ESI+: 542.3<br>NMR-DMSO-d6: 0.05-0.19 (2H, m), 0.35-0.53 (2H, m), 0.73-1.20 (6H, m), 1.82-3.70 (21H, m), 3.90-4.26 (1H, m), 5.17-5.31 (1H, m), 7.34 (1H, s), 7.87-8.00 (1H, m), 8.16 (1H, s), 11.50 (1H, m) |
| 239 | 2 | ESI+: 556.3 |
| 240 | 5 | ESI+: 502.3<br>NMR-DMSO-d6: 0.72-1.10 (3H, m), 1.62 (2H, m), 1.97-3.40 (15H, m), 2.29 (3H, s), 3.20 (3H, s), 3.90-4.16 (1H, m), 4.66-5.01 (2H, m), 7.32 (1H, s), 7.82-7.88 (1H, br.), 8.15 (1H, s), 11.50 (1H, s) |
| 241 | 5 | ESI+: 526.2<br>NMR-DMSO-d6: 0.76-1.12 (3H, m), 2.09-3.35 (15H, m), 2.30 (3H, s), 3.94-4.18 (1H, m), 4.67-4.99 (2H, m), 7.33 (1H, s), 7.87 (1H, s), 8.15 (1H, s), 11.50 (1H, s) |
| 242 | 5 | ESI+: 528.3<br>NMR-DMSO-d6: 0.13 (2H, m), 0.43 (2H, m), 0.75-1.12 (4H, m), 2.07-3.33 (15H, m), 2.29 (3H, s), 3.47 (2H, m), 3.93-4.17 (1H, m), 4.61-5.02 (2H, m), 7.32 (1H, s), 7.82-7.90 (1H, br.), 8.15 (1H, s), 11.50 (1H, s) |
| 243 | 2 | ESI+: 476.1 |
| 244 | 3 | ESI+: 440.1 |
| 245 | 3 | ESI+: 454.1 |
| 246 | 3 | ESI+: 481.1 |
| 247 | 3 | ESI+: 432.1 |
| 248 | 3 | ESI+: 432.1 |
| 249 | 3 | ESI+: 515.2 |
| 250 | 3 | ESI+: 546.1 |
| 251 | 3 | ESI+: 546.1 |
| 252 | 3 | ESI+: 438.1 |
| 253 | 3 | ESI+: 436.1 |
| 254 | 3 | ESI+: 450.1 |
| 255 | 3 | ESI+: 464.4<br>NMR-DMSO-d6: 1.25-1.83 (8H, m), 1.92-2.58 (5H, m), 2.31 (3H, s), 3.10-4.09 (12H, m), 5.18-5.28 (1H, m), 7.33 |

TABLE 128-continued

| Ex | Syn | Data |
|---|---|---|
| | | (1H, s), 7.87 (1H, s), 8.17 (1H, s), 11.50 (1H, s) mp: 228-230 |
| 256 | 3 | ESI+: 454.1 |
| 257 | 3 | ESI+: 468.1 |
| 258 | 3 | ESI+: 504.1 |
| 259 | 3 | ESI+: 518.1 |

TABLE 129

| Ex | Syn | Data |
|---|---|---|
| 260 | 3 | ESI+: 532.1 |
| 261 | 3 | ESI+: 487.1 |
| 262 | 3 | ESI+: 487.1 |
| 263 | 3 | ESI+: 498.1 |
| 264 | 3 | ESI+: 500.1 |
| 265 | 3 | ESI+: 438.1 |
| 266 | 3 | ESI+: 425.1 |
| 267 | 3 | ESI+: 478.1 |
| 268 | 3 | ESI+: 526.2 |
| 269 | 3 | ESI+: 410.1 |
| 270 | 3 | ESI+: 450.1 |
| 271 | 3 | ESI+: 526.2 |
| 272 | 3 | ESI+: 480.1 |
| 273 | 3 | ESI+: 494.2 |
| 274 | 3 | ESI+: 494.1 |
| 275 | 3 | ESI+: 493.1 |
| 276 | 3 | ESI+: 521.2 |
| 277 | 3 | ESI+: 472.1 |
| 278 | 3 | ESI+: 472.1 |
| 279 | 3 | ESI+: 486.1 |
| 280 | 3 | ESI+: 454.1 |
| 281 | 3 | ESI+: 473.1 |
| 282 | 3 | ESI+: 499.1 |
| 283 | 3 | ESI+: 499.1 |
| 284 | 3 | ESI+: 341.0 |
| 285 | 3 | ESI+: 385.0 |
| 286 | 3 | ESI+: 398.1 |
| 287 | 3 | ESI+: 426.1 |
| 288 | 3 | ESI+: 453.1 |
| 289 | 3 | ESI+: 468.1 |
| 290 | 3 | ESI+: 472.1 |

TABLE 130

| Ex | Syn | Data |
|---|---|---|
| 291 | 3 | ESI+: 509.1 |
| 292 | 3 | ESI+: 466.1 |
| 293 | 3 | ESI+: 466.1 |
| 294 | 3 | ESI+: 506.1 |
| 295 | 3 | ESI+: 494.1 |
| 296 | 3 | ESI+: 460.1 |
| 297 | 3 | ESI+: 474.1 |
| 298 | 3 | ESI+: 452.1 |
| 299 | 3 | ESI+: 452.1 |
| 300 | 3 | ESI+: 468.1 |
| 301 | 3 | ESI+: 454.1 |
| 302 | 3 | ESI+: 468.1 |
| 303 | 3 | ESI+: 482.1 |
| 304 | 3 | ESI+: 467.1 |
| 305 | 3 | ESI+: 466.1 |
| 306 | 3 | ESI+: 501.1 |
| 307 | 3 | ESI+: 503.1 |
| 308 | 3 | ESI+: 474.1 |
| 309 | 3 | ESI+: 516.1 |
| 310 | 3 | ESI+: 516.1 |
| 311 | 3 | ESI+: 516.1 |
| 312 | 3 | ESI+: 460.1 |
| 313 | 3 | ESI+: 486.0 |
| 314 | 3 | ESI+: 486.1 |
| 315 | 3 | ESI+: 486.1 |
| 316 | 3 | ESI+: 502.1 |

TABLE 130-continued

| Ex | Syn | Data |
|---|---|---|
| 317 | 3 | ESI+: 502.1 |
| 318 | 3 | ESI+: 515.1 |
| 319 | 3 | ESI+: 515.1 |
| 320 | 3 | ESI+: 546.1 |
| 321 | 3 | ESI+: 474.1 |

TABLE 131

| Ex | Syn | Data |
|---|---|---|
| 322 | 3 | ESI+: 488.1 |
| 323 | 3 | ESI+: 516.1 |
| 324 | 3 | ESI+: 510.0 |
| 325 | 3 | ESI+: 510.0 |
| 326 | 3 | ESI+: 510.0 |
| 327 | 3 | ESI+: 418.0 |
| 328 | 3 | ESI+: 418.0 |
| 329 | 3 | ESI+: 418.0 |
| 330 | 3 | ESI+: 432.1 |
| 331 | 3 | ESI+: 432.1 |
| 332 | 3 | ESI+: 432.1 |
| 333 | 3 | ESI+: 452.1 |
| 334 | 3 | ESI+: 465.1 |
| 335 | 3 | ESI+: 492.1 |
| 336 | 3 | ESI+: 486.0 |
| 337 | 3 | ESI+: 488.1 |
| 338 | 3 | ESI+: 488.1 |
| 339 | 3 | ESI+: 515.1 |
| 340 | 3 | ESI+: 500.1 |
| 341 | 3 | ESI+: 532.1 |
| 342 | 3 | ESI+: 532.0 |
| 343 | 3 | ESI+: 487.1 |
| 344 | 3 | ESI+: 487.1 |
| 345 | 3 | ESI+: 438.1 |
| 346 | 3 | ESI+: 466.1 |
| 347 | 3 | ESI+: 478.1 |
| 348 | 3 | ESI+: 492.1 |
| 349 | 3 | ESI+: 492.1 |
| 350 | 3 | ESI+: 503.1 |
| 351 | 3 | ESI+: 325.1 |
| 352 | 3 | ESI+: 450.1 |

TABLE 132

| Ex | Syn | Data |
|---|---|---|
| 353 | 3 | ESI+: 422.1 |
| 354 | 3 | ESI+: 437.1 |
| 355 | 3 | ESI+: 424.1 |
| 356 | 3 | ESI+: 478.1 |
| 357 | 3 | ESI+: 450.1 |
| 358 | 3 | ESI+: 452.1 |
| 359 | 3 | ESI+: 450.1 |
| 360 | 3 | ESI+: 490.1 |
| 361 | 3 | ESI+: 492.1 |
| 362 | 3 | ESI+: 438.1 |
| 363 | 3 | ESI+: 466.1 |
| 364 | 3 | ESI+: 451.1 |
| 365 | 3 | ESI+: 465.1 |
| 366 | 3 | ESI+: 499.1 |
| 367 | 3 | ESI+: 402.0 |
| 368 | 3 | ESI+: 402.0 |
| 369 | 3 | ESI+: 402.0 |
| 370 | 3 | ESI+: 470.1 |
| 371 | 3 | ESI+: 458.0 |
| 372 | 3 | ESI+: 450.1 |
| 373 | 3 | ESI+: 434.1 |
| 374 | 3 | ESI+: 448.1 |
| 375 | 3 | ESI+: 462.1 |
| 376 | 3 | ESI+: 438.1 |
| 377 | 3 | ESI+: 488.1 |
| 378 | 3 | ESI+: 502.1 |
| 379 | 3 | ESI+: 516.1 |

TABLE 132-continued

| Ex | Syn | Data |
|---|---|---|
| 380 | 3 | ESI+: 471.1 |
| 381 | 3 | ESI+: 471.1 |
| 382 | 3 | ESI+: 482.1 |
| 383 | 3 | ESI+: 422.1 |

TABLE 133

| Ex | Syn | Data |
|---|---|---|
| 384 | 3 | ESI+: 409.1 |
| 385 | 3 | ESI+: 538.2 |
| 386 | 3 | ESI+: 379.1 |
| 387 | 3 | ESI+: 409.1 |
| 388 | 3 | ESI+: 397.0 |
| 389 | 3 | ESI+: 385.1 |
| 390 | 3 | ESI+: 423.1 |
| 391 | 3 | ESI+: 394.1 |
| 392 | 3 | ESI+: 422.1 |
| 393 | 3 | ESI+: 434.1 |
| 394 | 3 | ESI+: 436.1 |
| 395 | 3 | ESI+: 449.1 |
| 396 | 3 | ESI+: 462.1 |
| 397 | 3 | ESI+: 464.1 |
| 398 | 3 | ESI+: 477.1 |
| 399 | 3 | ESI+: 478.1 |
| 400 | 3 | ESI+: 505.1 |
| 401 | 3 | ESI+: 456.1 |
| 402 | 3 | ESI+: 470.1 |
| 403 | 3 | ESI+: 470.1 |
| 404 | 3 | ESI+: 472.1 |
| 405 | 3 | ESI+: 472.1 |
| 406 | 3 | ESI+: 486.1 |
| 407 | 3 | ESI+: 438.1 |
| 408 | 3 | ESI+: 483.1 |
| 409 | 3 | ESI+: 467.1 |
| 410 | 3 | ESI+: 487.0 |
| 411 | 3 | ESI+: 522.0, 524.0 |
| 412 | 3 | ESI+: 489.0 |
| 413 | 3 | ESI+: 502.0 |
| 414 | 3 | ESI+: 487.0 |

TABLE 134

| Ex | Syn | Data |
|---|---|---|
| 415 | 3 | ESI+: 503.0 |
| 416 | 3 | ESI+: 507.0, 509.0 |
| 417 | 3 | ESI+: 498.0 |
| 418 | 3 | ESI+: 498.0 |
| 419 | 3 | ESI+: 541.0 |
| 420 | 3 | ESI+: 502.0 |
| 421 | 3 | ESI+: 542.0 |
| 422 | 3 | ESI+: 551.9, 553.9 |
| 423 | 3 | ESI+: 488.1 |
| 424 | 3 | ESI+: 475.0 |
| 425 | 3 | ESI+: 438.1 |
| 426 | 3 | ESI+: 452.1 |
| 427 | 2 | ESI+: 478.3<br>NMR-DMSO-d6: 1.86-2.88 (11H, m), 3.12-4.18 (10H, m), 5.16-5.31 (1H, m), 7.33 (1H, s), 7.88 (1H, s), 8.17 (1H, s), 11.50 (1H, s) |
| 428 | 3 | ESI+: 507.1 |
| 429 | 3 | ESI+: 509.1 |
| 430 | 3 | ESI+: 548.0 |
| 431 | 3 | ESI+: 501.1 |
| 432 | 3 | ESI+: 516.1 |
| 433 | 3 | ESI+: 544.1 |
| 434 | 3 | ESI+: 544.1 |
| 435 | 3 | ESI+: 544.1 |
| 436 | 3 | ESI+: 411.1 |
| 437 | 3 | ESI+: 473.0 |
| 438 | 3 | ESI+: 488.1 |
| 439 | 3 | ESI+: 474.0 |

TABLE 134-continued

| Ex | Syn | Data |
|---|---|---|
| 440 | 3 | ESI+: 487.0 |
| 441 | 3 | ESI+: 425.0 |
| 442 | 3 | ESI+: 486.0 |
| 443 | 3 | ESI+: 486.0 |
| 444 | 3 | ESI+: 424.1 |

TABLE 135

| Ex | Syn | Data |
|---|---|---|
| 445 | 3 | ESI+: 486.0 |
| 446 | 3 | ESI+: 438.1 |
| 447 | 3 | ESI+: 492.1 |
| 448 | 3 | ESI+: 492.1 |
| 449 | 3 | ESI+: 424.1 |
| 450 | 3 | ESI+: 504.0 |
| 451 | 3 | ESI+: 496.1 |
| 452 | 3 | ESI+: 522.1 |
| 453 | 3 | ESI+: 523.1 |
| 454 | 3 | ESI+: 510.1 |
| 455 | 3 | ESI+: 459.0 |
| 456 | 3 | ESI+: 449.0 |
| 457 | 3 | ESI+: 514.0 |
| 458 | 3 | ESI+: 516.1 |
| 459 | 3 | ESI+: 546.0 |
| 460 | 3 | ESI+: 397.0 |
| 461 | 3 | ESI+: 433.1 |
| 462 | 3 | ESI+: 498.1 |
| 463 | 3 | ESI+: 500.1 |
| 464 | 3 | ESI+: 514.1 |
| 465 | 3 | ESI+: 530.1 |
| 466 | 3 | ESI+: 466.1 |
| 467 | 3 | ESI+: 510.1 |
| 468 | 3 | ESI+: 464.1 |
| 469 | 3 | ESI+: 478.1 |
| 470 | 3 | ESI+: 423.1 |
| 471 | 3 | ESI+: 453.0 |
| 472 | 3 | ESI+: 498.1 |
| 473 | 8 | ESI+: 453.0 |
| 474 | 8 | ESI+: 439.0 |
| 475 | 8 | ESI+: 453.0 |

TABLE 136

| Ex | Syn | Data |
|---|---|---|
| 476 | 8 | ESI+: 515.0 |
| 477 | 8 | ESI+: 515.0 |
| 478 | 8 | ESI+: 515.0 |
| 479 | 8 | ESI+: 529.0 |
| 480 | 8 | ESI+: 529.0 |
| 481 | 8 | ESI+: 531.0 |
| 482 | 8 | ESI+: 468.0 |
| 483 | 6 | ESI+: 516.0 |
| 484 | 8 | ESI+: 437.0 |
| 485 | 8 | ESI+: 423.0 |
| 486 | 8 | ESI+: 423.0 |
| 487 | 8 | ESI+: 437.0 |
| 488 | 8 | ESI+: 499.0 |
| 489 | 8 | ESI+: 499.0 |
| 490 | 8 | ESI+: 499.0 |
| 491 | 8 | ESI+: 499.0 |
| 492 | 8 | ESI+: 513.1 |
| 493 | 8 | ESI+: 513.1 |
| 494 | 8 | ESI+: 515.1 |
| 495 | 8 | ESI+: 452.1 |
| 496 | 8 | ESI+: 500.1 |
| 497 | 9 | ESI+: 480.1 |
| 498 | 9 | ESI+: 480.1 |
| 499 | 9 | ESI+: 494.1 |
| 500 | 9 | ESI+: 508.1 |
| 501 | 9 | ESI+: 530.1 |
| 502 | 9 | ESI+: 501.1 |

TABLE 136-continued

| Ex | Syn | Data |
| --- | --- | --- |
| 503 | 9 | ESI+: 501.1 |
| 504 | 9 | ESI+: 517.1 |
| 505 | 9 | ESI+: 556.2 |
| 506 | 9 | ESI+: 517.1 |

TABLE 137

| Ex | Syn | Data |
| --- | --- | --- |
| 507 | 9 | ESI+: 556.2 |
| 508 | 9 | ESI+: 517.1 |
| 509 | 9 | ESI+: 517.1 |
| 510 | 9 | ESI+: 501.1 |
| 511 | 9 | ESI+: 505.1 |
| 512 | 9 | ESI+: 572.1 |
| 513 | 9 | ESI+: 503.1 |
| 514 | 9 | ESI+: 490.1 |
| 515 | 9 | ESI+: 507.0 |
| 516 | 9 | ESI+: 578.1 |
| 517 | 9 | ESI+: 466.1 |
| 518 | 9 | ESI+: 464.1 |
| 519 | 9 | ESI+: 468.1 |
| 520 | 9 | ESI+: 496.1 |
| 521 | 9 | ESI+: 492.1 |
| 522 | 9 | ESI+: 528.1 |
| 523 | 9 | ESI+: 504.1 |
| 524 | 9 | ESI+: 522.0 |
| 525 | 9 | ESI+: 522.1 |
| 526 | 9 | ESI+: 522.2 |
| 527 | 9 | ESI+: 506.1 |
| 528 | 9 | ESI+: 508.1 |
| 529 | 10 | ESI+: 517.1 |
| 530 | 10 | ESI+: 600.2 |
| 531 | 10 | ESI+: 600.2 |
| 532 | 10 | ESI+: 544.1 |
| 533 | 10 | ESI+: 584.2 |
| 534 | 10 | ESI+: 586.2 |
| 535 | 10 | ESI+: 572.2 |
| 536 | 10 | ESI+: 584.2 |
| 537 | 10 | ESI+: 586.2 |

TABLE 138

| Ex | Syn | Data |
| --- | --- | --- |
| 538 | 10 | ESI+: 609.0, 611.0 |
| 539 | 10 | ESI+: 535.1, 537.1 |
| 540 | 10 | ESI+: 558.1 |
| 541 | 10 | ESI+: 520.1 |
| 542 | 10 | ESI+: 489.1 |
| 543 | 10 | ESI+: 503.1 |
| 544 | 10 | ESI+: 602.2 |
| 545 | 10 | ESI+: 504.1 |
| 546 | 10 | ESI+: 518.1 |
| 547 | 10 | ESI+: 518.1 |
| 548 | 10 | ESI+: 504.1 |
| 549 | 10 | ESI+: 518.1 |
| 550 | 10 | ESI+: 518.1 |
| 551 | 10 | ESI+: 504.1 |
| 552 | 10 | ESI+: 518.1 |
| 553 | 10 | ESI+: 518.1 |
| 554 | 10 | ESI+: 518.1 |
| 555 | 10 | ESI+: 524.1, 526.1 |
| 556 | 10 | ESI+: 532.2 |
| 557 | 10 | ESI+: 532.2 |
| 558 | 10 | ESI+: 532.2 |
| 559 | 10 | ESI+: 532.2 |
| 560 | 10 | ESI+: 538.1, 540.1 |
| 561 | 10 | ESI+: 538.1, 540.1 |
| 562 | 10 | ESI+: 548.2 |
| 563 | 10 | ESI+: 552.1, 554.1 |
| 564 | 10 | ESI+: 574.2 |
| 565 | 10 | ESI+: 582.0, 584.0 |

TABLE 138-continued

| Ex | Syn | Data |
| --- | --- | --- |
| 566 | 10 | ESI+: 490.1 |
| 567 | 10 | ESI+: 490.1 |
| 568 | 10 | ESI+: 504.1 |

TABLE 139

| Ex | Syn | Data |
| --- | --- | --- |
| 569 | 10 | ESI+: 504.1 |
| 570 | 10 | ESI+: 504.1 |
| 571 | 10 | ESI+: 504.1 |
| 572 | 10 | ESI+: 518.1 |
| 573 | 10 | ESI+: 532.2 |
| 574 | 10 | ESI+: 546.2 |
| 575 | 10 | ESI+: 507.1 |
| 576 | 10 | ESI+: 507.1 |
| 577 | 10 | ESI+: 535.1 |
| 578 | 10 | ESI+: 505.1 |
| 579 | 10 | ESI+: 519.1 |
| 580 | 10 | ESI+: 508.1 |
| 581 | 10 | ESI+: 522.2 |
| 582 | 10 | ESI+: 520.1 |
| 583 | 10 | ESI+: 515.2 |
| 584 | 10 | ESI+: 515.2 |
| 585 | 10 | ESI+: 531.1 |
| 586 | 10 | ESI+: 570.2 |
| 587 | 10 | ESI+: 531.1 |
| 588 | 10 | ESI+: 570.2 |
| 589 | 10 | ESI+: 531.1 |
| 590 | 10 | ESI+: 570.2 |
| 591 | 10 | ESI+: 531.1 |
| 592 | 10 | ESI+: 515.2 |
| 593 | 10 | ESI+: 519.1 |
| 594 | 10 | ESI+: 586.2 |
| 595 | 10 | ESI+: 521.1 |
| 596 | 10 | ESI+: 592.1 |
| 597 | 10 | ESI+: 528.2 |
| 598 | 10 | ESI+: 522.2 |
| 599 | 10 | ESI+: 569.1 |

TABLE 140

| Ex | Syn | Data |
| --- | --- | --- |
| 600 | 10 | ESI+: 531.1 |
| 601 | 10 | ESI+: 569.2 |
| 602 | 10 | ESI+: 515.2 |
| 603 | 10 | ESI+: 515.2 |
| 604 | 10 | ESI+: 531.1 |
| 605 | 10 | ESI+: 531.1 |
| 606 | 10 | ESI+: 516.2 |
| 607 | 10 | ESI+: 532.1 |
| 608 | 10 | ESI+: 502.1 |
| 609 | 10 | ESI+: 502.1 |
| 610 | 10 | ESI+: 555.1 |
| 611 | 10 | ESI+: 517.1 |
| 612 | 10 | ESI+: 555.1 |
| 613 | 10 | ESI+: 501.1 |
| 614 | 10 | ESI+: 501.1 |
| 615 | 10 | ESI+: 517.1 |
| 616 | 10 | ESI+: 517.1 |
| 617 | 10 | ESI+: 502.2 |
| 618 | 10 | ESI+: 518.1 |
| 619 | 10 | ESI+: 488.1 |
| 620 | 10 | ESI+: 488.1 |
| 621 | 3 | ESI+: 512.1 |
| 622 | 3 | ESI+: 528.2 |
| 623 | 3 | ESI+: 516.2 |
| 624 | 3 | ESI+: 516.2 |
| 625 | 3 | ESI+: 517.2 |
| 626 | 3 | ESI+: 459.1 |
| 627 | 3 | ESI+: 445.1 |
| 628 | 3 | ESI+: 514.2 |

TABLE 140-continued

| Ex | Syn | Data |
|---|---|---|
| 629 | 3 | ESI+: 526.1 |
| 630 | 3 | ESI+: 542.2 |

TABLE 141

| Ex | Syn | Data |
|---|---|---|
| 631 | 3 | ESI+: 530.2 |
| 632 | 3 | ESI+: 530.2 |
| 633 | 3 | ESI+: 531.2 |
| 634 | 3 | ESI+: 473.1 |
| 635 | 3 | ESI+: 459.1 |
| 636 | 3 | ESI+: 528.2 |
| 637 | 3 | ESI+: 448.1 |
| 638 | 3 | ESI+: 464.2 |
| 639 | 3 | ESI+: 452.2 |
| 640 | 3 | ESI+: 452.2 |
| 641 | 3 | ESI+: 453.2 |
| 642 | 3 | ESI+: 395.1 |
| 643 | 3 | ESI+: 381.1 |
| 644 | 3 | ESI+: 450.2 |
| 645 | 3 | ESI+: 462.1 |
| 646 | 3 | ESI+: 478.2 |
| 647 | 3 | ESI+: 466.2 |
| 648 | 3 | ESI+: 466.2 |
| 649 | 3 | ESI+: 467.2 |
| 650 | 3 | ESI+: 409.2 |
| 651 | 3 | ESI+: 395.1 |
| 652 | 3 | ESI+: 464.1 |
| 653 | 3 | ESI+: 462.1 |
| 654 | 3 | ESI+: 466.2 |
| 655 | 3 | ESI+: 466.2 |
| 656 | 3 | ESI+: 467.2 |
| 657 | 3 | ESI+: 409.2 |
| 658 | 3 | ESI+: 464.1 |
| 659 | 3 | ESI+: 397.1 |
| 660 | 3 | ESI+: 482.2 |
| 661 | 3 | ESI+: 496.2 |

TABLE 142

| Ex | Syn | Data |
|---|---|---|
| 662 | 3 | ESI+: 496.2 |
| 663 | 3 | ESI+: 482.2 |
| 664 | 3 | ESI+: 459.1 |
| 665 | 3 | ESI+: 505.1 |
| 666 | 3 | ESI+: 505.1 |
| 667 | 3 | ESI+: 480.1 |
| 668 | 3 | ESI+: 439.1 |
| 669 | 3 | ESI+: 453.2 |
| 670 | 3 | ESI+: 465.2 |
| 671 | 3 | ESI+: 425.2 |
| 672 | 3 | ESI+: 473.1 |
| 673 | 3 | ESI+: 473.1 |
| 674 | 3 | ESI+: 493.1 |
| 675 | 3 | ESI+: 493.1 |
| 676 | 3 | ESI+: 507.1 |
| 677 | 3 | ESI+: 507.1 |

TABLE 143

| No | Structure |
|---|---|
| 1 | (structure) |
| 2 | (structure) |
| 3 | (structure) |
| 4 | (structure) |
| 5 | (structure) |

TABLE 143-continued

| No | Structure |
|---|---|
| 6 | 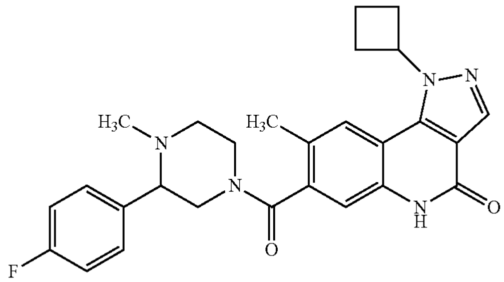 [SMILES: Cc1cc2c(cc1C(=O)N1CCN(C)C(c3ccc(F)cc3)C1)[nH]c(=O)c1cnn(C3CCC3)c12] |
| 7 | 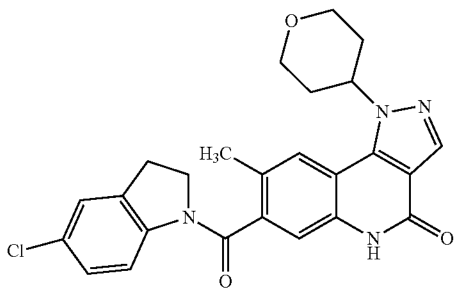 [SMILES: Cc1cc2c(cc1C(=O)N1CCc3cc(Cl)ccc31)[nH]c(=O)c1cnn(C3CCOCC3)c12] |
| 8 | 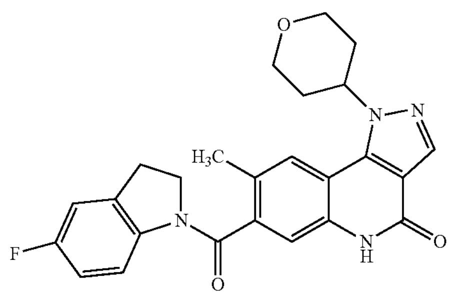 [SMILES: Cc1cc2c(cc1C(=O)N1CCc3cc(F)ccc31)[nH]c(=O)c1cnn(C3CCOCC3)c12] |
| 9 | 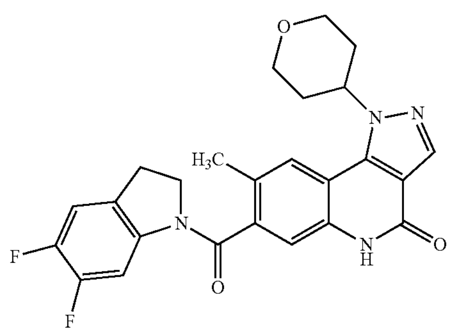 [SMILES: Cc1cc2c(cc1C(=O)N1CCc3cc(F)c(F)cc31)[nH]c(=O)c1cnn(C3CCOCC3)c12] |
| 10 | 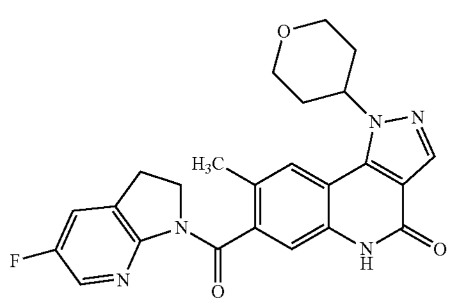 [SMILES: Cc1cc2c(cc1C(=O)N1CCc3cc(F)cnc31)[nH]c(=O)c1cnn(C3CCOCC3)c12] |

TABLE 144

| No | Structure |
|---|---|
| 11 | 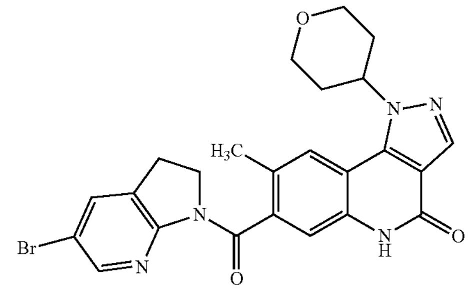 |
| 12 | 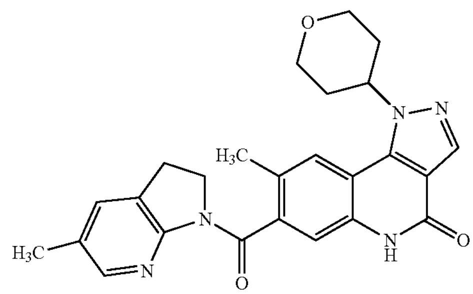 [SMILES: Cc1cnc2c(c1)CCN2C(=O)c1cc2[nH]c(=O)c3cnn(C4CCOCC4)c3c2cc1C] |
| 13 | 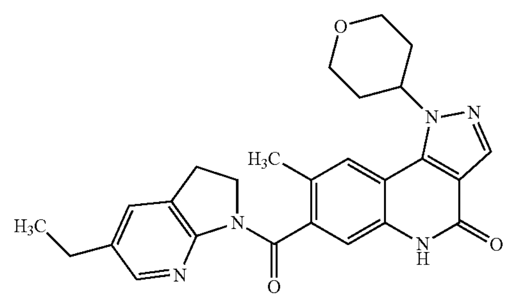 [SMILES: CCc1cnc2c(c1)CCN2C(=O)c1cc2[nH]c(=O)c3cnn(C4CCOCC4)c3c2cc1C] |
| 14 | 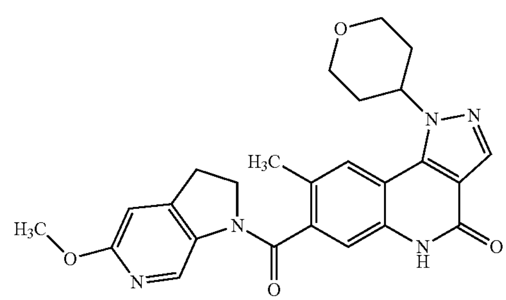 [SMILES: COc1cc2c(cn1)N(C(=O)c1cc3[nH]c(=O)c4cnn(C5CCOCC5)c4c3cc1C)CC2] |
| 15 | 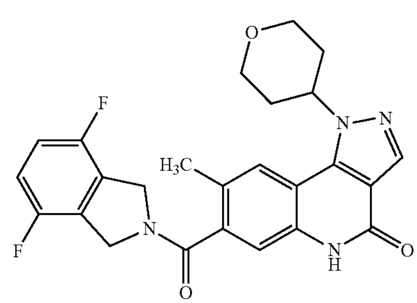 [SMILES: Cc1cc2c(cc1C(=O)N1Cc3c(F)ccc(F)c3C1)[nH]c(=O)c1cnn(C3CCOCC3)c12] |

TABLE 144-continued

| No | Structure |
|---|---|
| 16 | 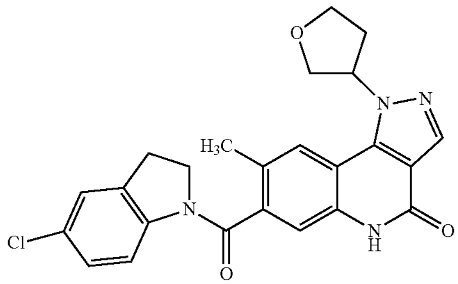 |
| 17 | 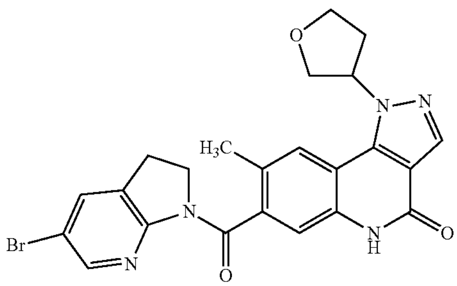 [SMILES: Cc1cc2c(cc1C(=O)N1CCc3cc(Cl)ccc31)[nH]c(=O)c1cnn(C3CCOC3)c12] |
| 18 | 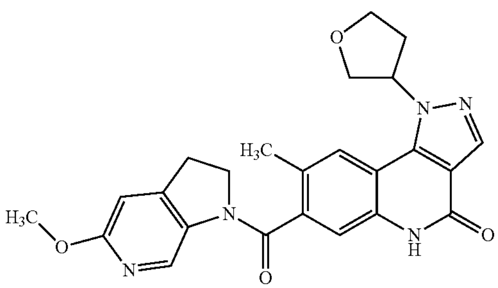 [SMILES: COc1cc2c(cn1)N(C(=O)c1cc3[nH]c(=O)c4cnn(C5CCOC5)c4c3cc1C)CC2] |
| 19 | 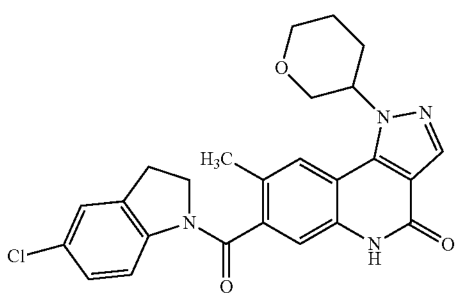 [SMILES: Cc1cc2c(cc1C(=O)N1CCc3cc(Cl)ccc31)[nH]c(=O)c1cnn(C3CCCOC3)c12] |
| 20 | 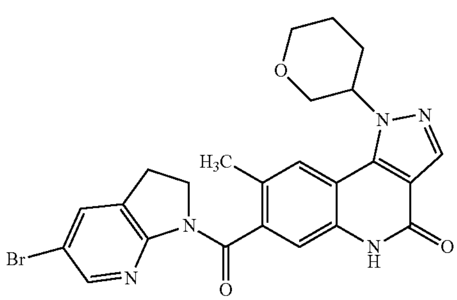 |

TABLE 145

| No | Structure |
|---|---|
| 21 | 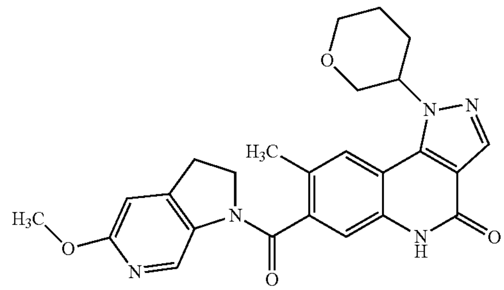 [SMILES: COc1cc2c(cn1)N(C(=O)c1cc3[nH]c(=O)c4cnn(C5CCCOC5)c4c3cc1C)CC2] |
| 22 | 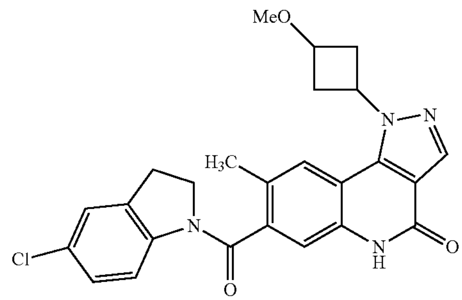 |
| 23 | 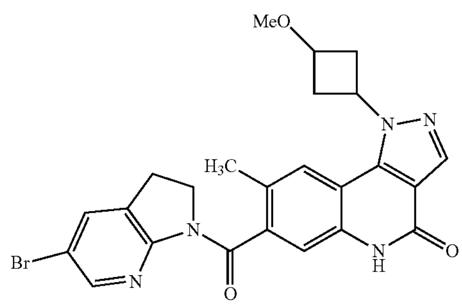 [SMILES: COC1CC(n2ncc3c(=O)[nH]c4cc(C(=O)N5CCc6cc(Cl)ccc65)c(C)cc4c32)C1] |
| 24 | 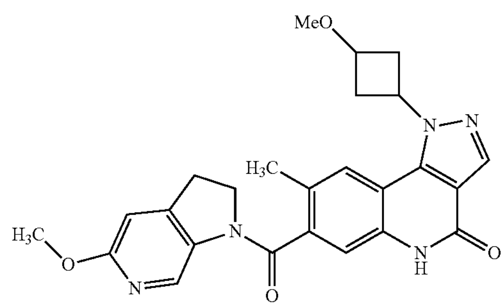 [SMILES: COc1cc2c(cn1)N(C(=O)c1cc3[nH]c(=O)c4cnn(C5CC(OC)C5)c4c3cc1C)CC2] |
| 25 | 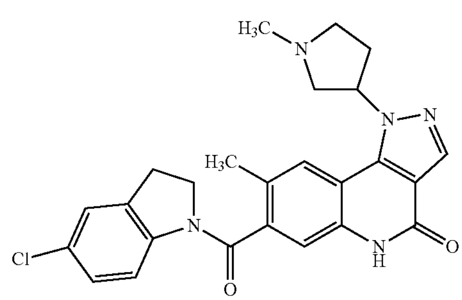 |

TABLE 145-continued

| No | Structure |
|---|---|
| 26 | 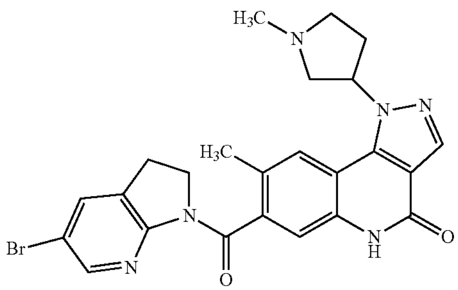 [SMILES: Cc1cc2c(cc1C(=O)N1CCc3cc(Cl)ccc31)[nH]c(=O)c1cnn(C3CCN(C)C3)c12] |
| 27 | 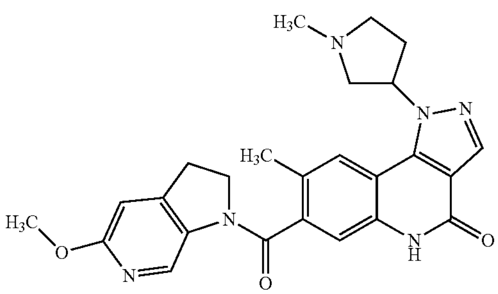 [SMILES: COc1cc2c(cn1)N(C(=O)c1cc3[nH]c(=O)c4cnn(C5CCN(C)C5)c4c3cc1C)CC2] |
| 28 | 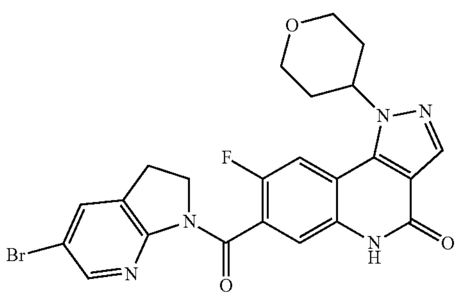 [SMILES: O=C(c1cc2[nH]c(=O)c3cnn(C4CCOCC4)c3c2cc1F)N1CCc2cc(Br)cnc21] |
| 29 | 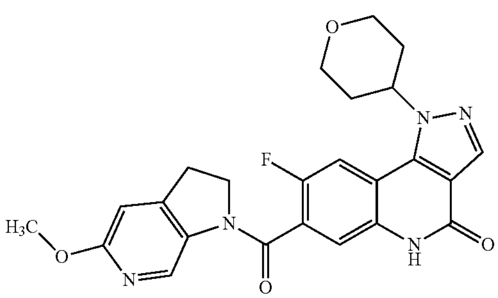 [SMILES: COc1cc2c(cn1)N(C(=O)c1cc3[nH]c(=O)c4cnn(C5CCOCC5)c4c3cc1F)CC2] |
| 30 | 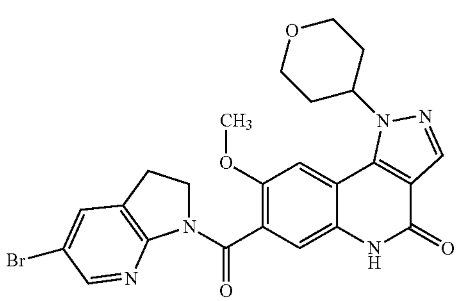 [SMILES: COc1cc2c(cc1C(=O)N1CCc3cc(Br)cnc31)[nH]c(=O)c1cnn(C3CCOCC3)c12] |

TABLE 146

| No | Structure |
|---|---|
| 31 | 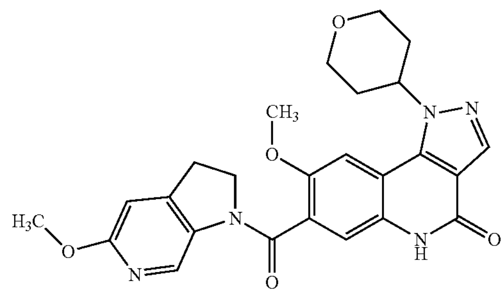 [SMILES: COc1cc2c(cn1)N(C(=O)c1cc3[nH]c(=O)c4cnn(C5CCOCC5)c4c3cc1OC)CC2] |
| 32 | 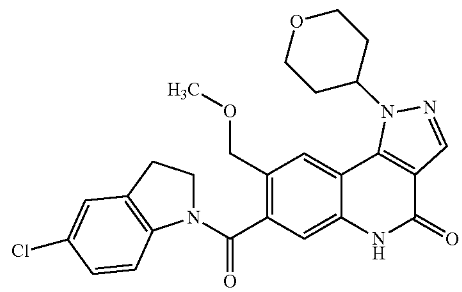 [SMILES: COCc1cc2c(cc1C(=O)N1CCc3cc(Cl)ccc31)[nH]c(=O)c1cnn(C3CCOCC3)c12] |
| 33 | 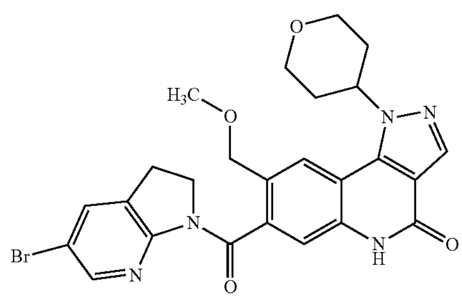 |
| 34 | 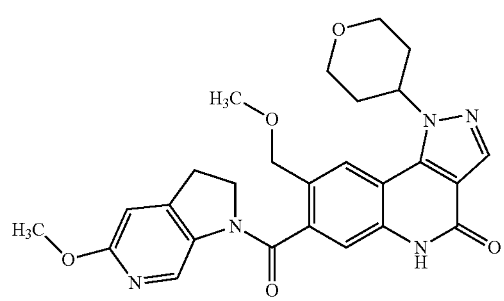 [SMILES: COCc1cc2c(cc1C(=O)N1CCc3cc(OC)ncc31)[nH]c(=O)c1cnn(C3CCOCC3)c12] |
| 35 | 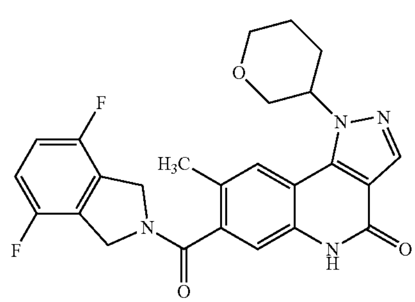 [SMILES: Cc1cc2c(cc1C(=O)N1Cc3c(F)ccc(F)c3C1)[nH]c(=O)c1cnn(C3CCCOC3)c12] |

TABLE 146-continued

| No | Structure |
|----|-----------|
| 35 | 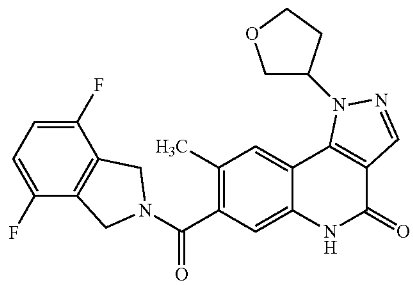 [SMILES: Cc1cc2c(cc1C(=O)N1Cc3c(F)ccc(F)c3C1)[nH]c(=O)c1cnn(C3CCOC3)c12] |
| 37 | 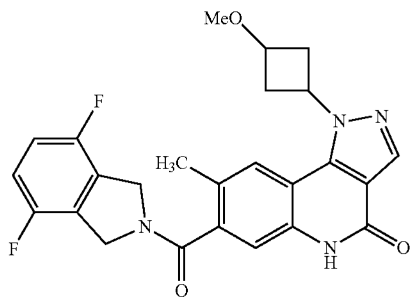 [SMILES: COC1CC(n2ncc3c(=O)[nH]c4cc(C(=O)N5Cc6c(F)ccc(F)c6C5)c(C)cc4c32)C1] |
| 38 | 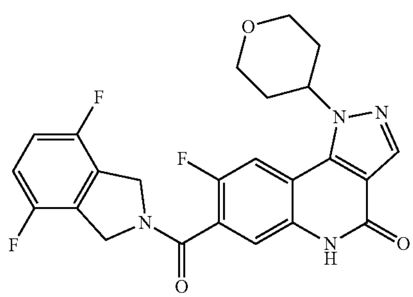 [SMILES: O=C(c1cc2[nH]c(=O)c3cnn(C4CCOCC4)c3c2cc1F)N1Cc2c(F)ccc(F)c2C1] |
| 39 | 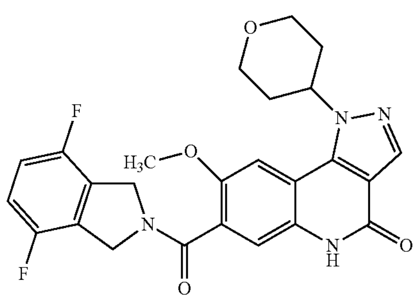 [SMILES: COc1cc2c(cc1C(=O)N1Cc3c(F)ccc(F)c3C1)[nH]c(=O)c1cnn(C3CCOCC3)c12] |
| 40 | 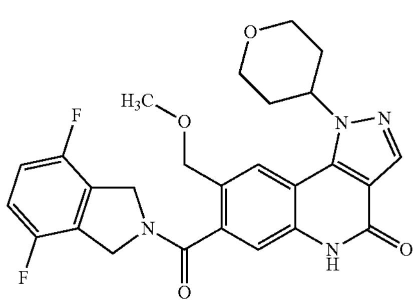 [SMILES: COCc1cc2c(cc1C(=O)N1Cc3c(F)ccc(F)c3C1)[nH]c(=O)c1cnn(C3CCOCC3)c12] |

INDUSTRIAL APPLICABILITY

The compound of the formula (I) or a salt thereof has a PDE9 inhibitory action, and can be used as an agent for preventing and/or treating diseases related to degradation of cGMP by PDE9, for example, underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis, or urethra calculus.

The invention claimed is:

1. A compound of formula (I) or a pharmaceutically acceptable salt thereof:

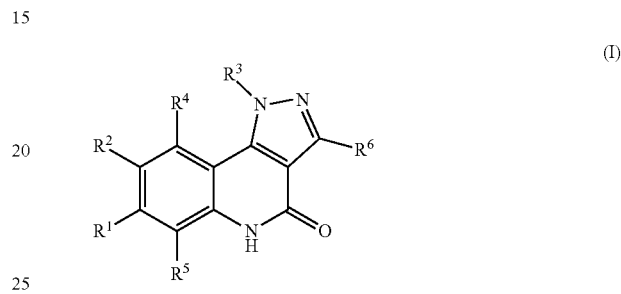

wherein
one of $R^1$ and $R^2$ is hydrogen, halogen, halogeno-lower alkyl, or lower alkyl, —O-lower alkyl or cycloalkyl, each of which may be substituted, and the other is a group of formula (II):

$R^3$ is lower alkyl, cycloalkyl or a saturated hetero ring, each of which may be substituted, $R^4$, $R^5$ and $R^6$ are the same as or different from each other, and each is hydrogen or lower alkyl, and $R^a$ and $R^b$ are the same as or different from each other, and each is hydrogen, or lower alkyl, cycloalkyl, aryl or a hetero ring, each of which may be substituted, or $R^a$ and $R^b$ are combined with the adjacent nitrogen atom to form a monocyclic nitrogen-containing hetero ring or a polycyclic nitrogen-containing hetero ring, each of which may be substituted.

2. A compound of formula (I-1) or a pharmaceutically acceptable salt thereof:

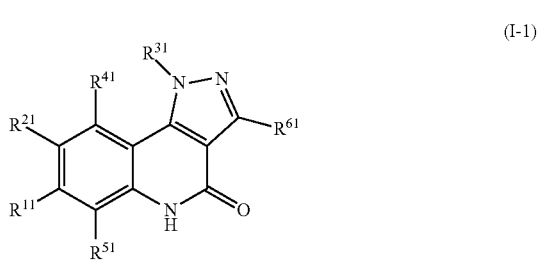

wherein
one of $R^{11}$ and $R^{21}$ is hydrogen, halogen, or lower alkyl, —O-lower alkyl or cycloalkyl, each of which may be substituted, and the other is a group of formula (II-1):

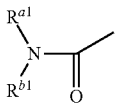

(II-1)

$R^{31}$ is lower alkyl, cycloalkyl or a saturated hetero ring, each of which may be substituted, $R^{41}$, $R^{51}$ and $R^{61}$ are the same as or different from each other, and each is hydrogen or lower alkyl, and $R^{a1}$ and $R^{b1}$ are the same as or different from each other, and each is hydrogen, or lower alkyl, cycloalkyl, aryl or a hetero ring, each of which may be substituted, or $R^{a1}$ and $R^{b1}$ are combined with the adjacent nitrogen atom to form a monocyclic nitrogen-containing hetero ring or a polycyclic nitrogen-containing hetero ring, each of which may be substituted.

3. The compound or a pharmaceutically acceptable salt thereof as set forth in claim 1, wherein
one of $R^1$ and $R^2$ is hydrogen, halogen, halogeno-lower alkyl, lower alkyl, —O-lower alkyl, or lower alkylene-O-lower alkyl,
and the other is a group of the formula (II),
$R^3$ is lower alkylene-(cycloalkyl which may be substituted with halogen or —O-lower alkyl); lower alkylene-oxygen-containing saturated hetero ring; cycloalkyl which may be substituted with halogen or —O-lower alkyl; an oxygen-containing saturated hetero ring; or a monocyclic nitrogen-containing saturated hetero ring which may be substituted with lower alkyl, lower alkylene-aryl, or —CO-lower alkylene-O-lower alkyl,
$R^4$ and $R^5$ are hydrogen,
$R^6$ is hydrogen or lower alkyl,
one of $R^a$ and $R^b$ is hydrogen, and the other is lower alkyl which may be substituted; cycloalkyl which may be substituted with a hetero ring which may be substituted with a group selected from a group $G_2$; or a hetero ring which may be substituted with lower alkylene-(aryl which may be substituted with a group selected from a group $G_1$), or
$R^a$ and $R^b$ are combined with the adjacent nitrogen atom to form a monocyclic nitrogen-containing hetero ring which may be substituted, or a polycyclic nitrogen-containing hetero ring which may be substituted with a group selected from the group consisting of halogen; —O-lower alkyl; a hetero ring which may be substituted with a group selected from a group $G_2$; lower alkylene-(aryl which may be substituted with a group selected from a group $G_1$); lower alkyl; and lower alkylene-O-lower alkyl.

4. The compound or a pharmaceutically acceptable salt thereof as set forth in claim 1, wherein
$R^1$ is hydrogen, halogeno-lower alkyl, lower alkyl, or —O-lower alkyl,
$R^2$ is a group of the formula (II),
$R^3$ is lower alkylene-(cycloalkyl which may be substituted with halogen or —O-lower alkyl); lower alkylene-oxygen-containing saturated hetero ring; cycloalkyl which may be substituted with halogen or —O-lower alkyl; an oxygen-containing saturated hetero ring; or a monocyclic nitrogen-containing saturated hetero ring which may be substituted with lower alkyl, lower alkylene-aryl, or —CO-lower alkylene-O-lower alkyl,
$R^4$, $R^5$ and $R^6$ are hydrogen, and
$R^a$ and $R^b$ are combined with the adjacent nitrogen atom to form a monocyclic nitrogen-containing hetero ring, each of which may be substituted.

5. The compound or a pharmaceutically acceptable salt thereof as set forth in claim 4, wherein
the monocyclic nitrogen-containing hetero ring which may be substituted, formed by $R^a$ and $R^b$ which are combined with the adjacent nitrogen atom, is piperidyl or piperazinyl, each of which may be substituted.

6. The compound or a pharmaceutically acceptable salt thereof as set forth in claim 5, wherein
said piperidyl or piperazinyl, each of which may be substituted, formed by $R^a$ and $R^b$ which are combined with the adjacent nitrogen atom, may be substituted with 1 to 3 groups selected from the group consisting of:
—OH; halogeno-lower alkyl; —O-lower alkyl which may be substituted with 1 to 3 groups selected from the group consisting of halogen, halogeno-lower alkyl and cycloalkyl; aryl which may be substituted with a group selected from a group $G_1$; a hetero ring which may be substituted with a group selected from a group $G_2$; lower alkylene-O-cycloalkyl; —O-cycloalkyl; —O-(hetero ring which may be substituted with a group selected from a group $G_2$); lower alkyl which may be substituted with one or more groups selected from the group consisting of halogen, halogeno-lower alkyl, —O-cycloalkyl, —O-lower alkyl, and —O-halogeno-lower alkyl; and lower alkylene-O-lower alkyl which may be substituted with one or more groups selected from the group consisting of halogen, halogeno-lower alkyl and cycloalkyl.

7. The compound or a pharmaceutically acceptable salt thereof as set forth in claim 6, wherein
said piperidyl or piperazinyl, each of which may be substituted, formed by $R^a$ and $R^b$ which are combined with the adjacent nitrogen atom, may be substituted with 1 to 3 groups selected from the group consisting of:
—O-lower alkyl which may be substituted with 1 to 3 groups selected from halogen and cycloalkyl; lower alkylene-O-cycloalkyl; —O-cycloalkyl; lower alkyl which may be substituted with one or more groups selected from the group consisting of halogen, halogeno-lower alkyl, and —O-lower alkyl; or lower alkylene-O-lower alkyl.

8. The compound or a pharmaceutically acceptable salt thereof as set forth in any one of claims 1 or 4 to 7, wherein
$R^1$ is lower alkyl, and
$R^3$ is lower alkylene-cycloalkyl, lower alkylene-(cycloalkyl substituted with two halogen atoms), cycloalkyl, cycloalkyl substituted with two halogen atoms, an oxygen-containing saturated hetero ring, or a monocyclic nitrogen-containing saturated hetero ring substituted with lower alkyl.

9. The compound or a pharmaceutically acceptable salt thereof as set forth in any one of claims 1 or 4 to 7, wherein
$R^1$ is lower alkyl, and
$R^3$ is cycloalkyl or an oxygen-containing saturated hetero ring.

10. The compound or pharmaceutically acceptable salt thereof as set forth in claim 1, which is a compound selected from the group consisting of
8-[(4-{[(2S)-2-fluoropropyl]oxy}piperidin-1-yl)carbonyl]-7-methyl-1-(tetrahydro-2H-pyran-4-yl)-1,5-dihydro-4H-pyrazolo[4,3-c]quinolin-4-one, 7-methyl-1-(tetrahydro-2H-pyran-4-yl)-8-{[4-(3,3,3-trifluoropropyl)piperazin-1-yl]carbonyl}-1,5-dihydro-4H-pyrazolo[4,3-c]quinolin-4-one, 8-[(4-{[(2R)-2-fluoropropyl]oxy}piperidin-1-yl)carbonyl]-7-methyl-1-(tetrahydro-2H-pyran-4-yl)-1,5-dihydro-4H-pyrazolo[4,3-c]quinolin-4-one, 7-methyl-1-[(3S)-tetrahydrofuran-3-yl]-8-{[4-(3,3,3-trifluoropropyl)piperazin-1-yl]carbonyl}-1,5-dihydro-4H-pyrazolo[4,3-c]quinolin-4-one, 8-{[4-(2-methoxyethyl)piperidin-1-yl]carbonyl}-7-methyl-1-[(3S)-tetrahydrofuran-3-yl]-1,5-dihydro-4H-pyrazolo[4,3-c]quinolin-4-one, and 7-methyl-1-[(3S)-tetrahydrofuran-3-yl]-8-{[4-(2,2,2-trifluoroethyl)piperazin-1-yl]carbonyl}-1,5-dihydro-4H-pyrazolo[4,3-c]quinolin-4-one, or a pharmaceutically acceptable salt of said compound.

11. A pharmaceutical composition, comprising a compound or a pharmaceutically acceptable salt thereof as set forth in claim 1 and a pharmaceutically acceptable excipient.

12. A method for treating underactive bladder, voiding dysfunction in the underactive bladder, benign prostatic hyperplasia, and voiding dysfunction accompanying benign prostatic hyperplasia, comprising administering to a subject in need thereof an effective amount of a compound or a pharmaceutically acceptable salt thereof as set forth in claim 1.

13. The compound or pharmaceutically acceptable salt thereof as set forth in claim 10, which is 8-[(4-{[(2S)-2-fluoropropyl]oxy}piperidin-1-yl)carbonyl]-7-methyl-1-(tetrahydro-2H-pyran-4-yl)-1,5-dihydro-4H-pyrazolo[4,3-c]quinolin-4-one, or a pharmaceutically acceptable salt thereof.

14. The compound or pharmaceutically acceptable salt thereof as set forth in claim 10, which is 7-methyl-1-(tetrahydro-2H-pyran-4-yl)-8-{[4-(3,3,3-trifluoropropyl)piperazin-1-yl]carbonyl}-1,5-dihydro-4H-pyrazolo[4,3-c]quinolin-4-one, or a pharmaceutically acceptable salt thereof.

15. The compound or pharmaceutically acceptable salt thereof as set forth in claim 10, which is 8-[(4-{[(2R)-2-fluoropropyl]oxy}piperidin-1-yl)carbonyl]-7-methyl-1-(tetrahydro-2H-pyran-4-yl)-1,5-dihydro-4H-pyrazolo[4,3-c]quinolin-4-one, or a pharmaceutically acceptable salt thereof.

16. The compound or pharmaceutically acceptable salt thereof as set forth in claim 10, which is 7-methyl-1-[(3S)-tetrahydrofuran-3-yl]-8-{[4-(3,3,3-trifluoropropyl)piperazin-1-yl]carbonyl}-1,5-dihydro-4H-pyrazolo[4,3-c]quinolin-4-one, or a pharmaceutically acceptable salt thereof.

17. The compound or pharmaceutically acceptable salt thereof as set forth in claim 10, which is 8-{[4-(2-methoxyethyl)piperidin-1-yl]carbonyl}-7-methyl-1-[(3S)-tetrahydrofuran-3-yl]-1,5-dihydro-4H-pyrazolo[4,3-c]quinolin-4-one, or a pharmaceutically acceptable salt thereof.

18. The compound or pharmaceutically acceptable salt thereof as set forth in claim 10, which is 7-methyl-1-[(3S)-tetrahydrofuran-3-yl]-8-{[4-(2,2,2-trifluoroethyl)piperazin-1-yl]carbonyl}-1,5-dihydro-4H-pyrazolo [4,3-c]quinol-4-one, or a pharmaceutically acceptable salt thereof.

19. The compound or pharmaceutically acceptable salt thereof as set forth in claim 10, which is a compound selected from the group consisting of 7-methyl-1-(tetrahydro-2H-pyran-4-yl)-8-{[4-(3,3,3-trifluoropropyl)piperazin-1-yl]carbonyl}-1,5-dihydro-4H-pyrazolo[4,3-c]quinolin-4-one, 7-methyl-1-[(3S)-tetrahydrofuran-3-yl]-8-{[4-(3,3,3-trifluoropropyl)piperazin-1-yl]carbonyl}-1,5-dihydro-4H-pyrazolo[4,3-c]quinolin-4-one, and 7-methyl-1-[(3S)-tetrahydrofuran-3-yl]-8-{[4-(2,2,2-trifluoroethyl)piperazin-1-yl]carbonyl}-1,5-dihydro-4H-pyrazolo[4,3-c]quinolin-4-one, or a pharmaceutically acceptable salt thereof.

* * * * *